(12) United States Patent
Suh et al.

(10) Patent No.: US 11,396,494 B2
(45) Date of Patent: Jul. 26, 2022

(54) COMPOUND AND ORGANIC LIGHT EMITTING ELEMENT COMPRISING SAME

(71) Applicant: LG CHEM, LTD., Seoul (KR)

(72) Inventors: Sang Duk Suh, Daejeon (KR); Sung Kil Hong, Daejeon (KR); Seong So Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 406 days.

(21) Appl. No.: 16/624,554

(22) PCT Filed: Jul. 27, 2018

(86) PCT No.: PCT/KR2018/008545
§ 371 (c)(1),
(2) Date: Dec. 19, 2019

(87) PCT Pub. No.: WO2019/022562
PCT Pub. Date: Jan. 31, 2019

(65) Prior Publication Data
US 2020/0131124 A1  Apr. 30, 2020

(30) Foreign Application Priority Data

Jul. 28, 2017 (KR) .................... 10-2017-0096117

(51) Int. Cl.
| | | |
|---|---|---|
| *C07D 209/56* | (2006.01) | |
| *C07D 405/04* | (2006.01) | |
| *C07D 405/14* | (2006.01) | |
| *C07D 409/04* | (2006.01) | |
| *C07D 519/00* | (2006.01) | |
| *C07F 7/08* | (2006.01) | |
| *H01L 51/00* | (2006.01) | |
| *H01L 51/50* | (2006.01) | |

(52) U.S. Cl.
CPC ......... *C07D 209/56* (2013.01); *C07D 405/04* (2013.01); *C07D 405/14* (2013.01); *C07D 409/04* (2013.01); *C07D 519/00* (2013.01); *C07F 7/0812* (2013.01); *H01L 51/0052* (2013.01); *H01L 51/0061* (2013.01); *H01L 51/0072* (2013.01); *H01L 51/0073* (2013.01); *H01L 51/0074* (2013.01); *H01L 51/0094* (2013.01); *H01L 51/5056* (2013.01); *H01L 51/5072* (2013.01); *H01L 51/5092* (2013.01)

(58) Field of Classification Search
None
See application file for complete search history.

(56) References Cited

U.S. PATENT DOCUMENTS

| | | | |
|---|---|---|---|
| 2011/0297923 A1 | 12/2011 | Mizuki et al. | |
| 2012/0168734 A1* | 7/2012 | Park | H05B 33/14 257/40 |
| 2015/0307514 A1* | 10/2015 | Park | H01L 51/0071 544/212 |
| 2016/0149139 A1* | 5/2016 | Xia | H01L 51/0061 257/40 |
| 2016/0351816 A1* | 12/2016 | Kim | C09K 11/06 |
| 2016/0351817 A1* | 12/2016 | Kim | H01L 51/006 |
| 2016/0351818 A1* | 12/2016 | Kim | H01L 51/0052 |
| 2017/0110664 A1* | 4/2017 | Diev | C08G 61/12 |
| 2017/0148998 A1 | 5/2017 | Kang et al. | |
| 2017/0155049 A1* | 6/2017 | Kim | H01L 51/0059 |
| 2017/0294590 A1 | 10/2017 | Moon et al. | |
| 2018/0022991 A1 | 1/2018 | Kang et al. | |
| 2018/0033975 A1 | 2/2018 | Kim et al. | |
| 2018/0138373 A1* | 5/2018 | Han | H01L 33/48 |
| 2018/0182973 A1 | 6/2018 | Kim et al. | |
| 2020/0216428 A1* | 7/2020 | Takeda | H01L 51/0059 |

FOREIGN PATENT DOCUMENTS

| | | | | |
|---|---|---|---|---|
| KR | 10-20100108924 | 10/2010 | | |
| KR | 10-20110103974 | 9/2011 | | |
| KR | 10-20130030908 | 3/2013 | | |
| KR | 1020140128892 | * 11/2014 | ........... | C07D 209/82 |
| KR | 10-20150135109 | 12/2015 | | |
| KR | 10-20160037107 | 4/2016 | | |
| KR | 10-20160099471 | 8/2016 | | |
| KR | 10-20160110078 | 9/2016 | | |
| KR | 10-20160149994 | 12/2016 | | |
| KR | 10-1740858 | 5/2017 | | |
| WO | 2010114264 | 10/2010 | | |

* cited by examiner

*Primary Examiner* — Robert S Loewe
(74) *Attorney, Agent, or Firm* — Dentons US LLP

(57) ABSTRACT

Provided is a compound of Chemical Formula 1:

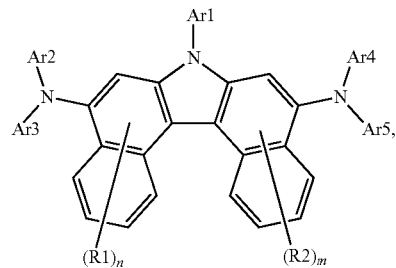

and an organic light emitting device including the same.

15 Claims, 1 Drawing Sheet

【FIG. 1】
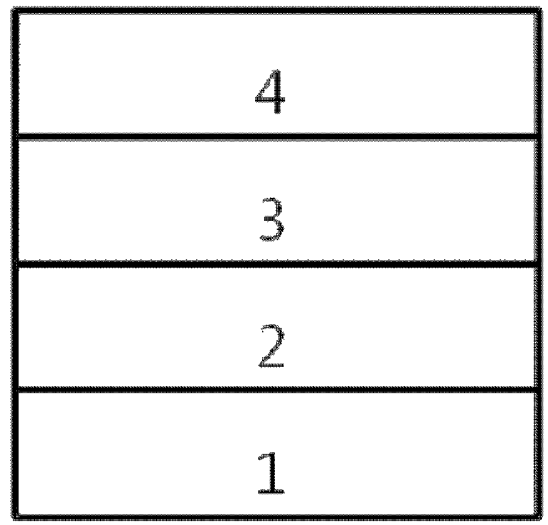
【FIG. 2】
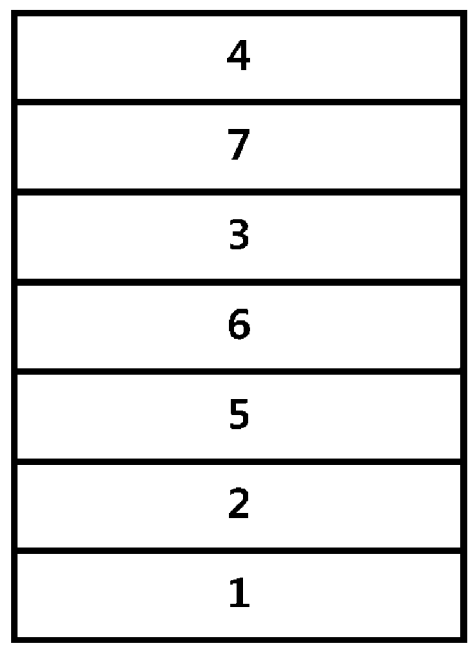

COMPOUND AND ORGANIC LIGHT EMITTING ELEMENT COMPRISING SAME

CROSS-REFERENCE TO RELATED APPLICATIONS

The present specification is a National Stage Application of International Application No. PCT/KR2018/008545, filed on Jul. 27, 2018, which claims priority to and the benefit of Korean Patent Application No. 10-2017-0096117, filed with the Korean Intellectual Property Office on Jul. 28, 2017, the entire contents of which are incorporated herein by reference.

TECHNICAL FIELD

The present specification relates to a compound and an organic light emitting device including the same.

BACKGROUND

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film can be formed in a single layer or a multilayer as necessary.

A material of the organic thin film can have a light emitting function as necessary. For example, as a material of the organic thin film, compounds capable of forming a light emitting layer themselves alone can be used, or compounds capable of performing a role of a host or a dopant of a host-dopant-based light emitting layer can also be used. In addition thereto, compounds capable of performing roles of hole injection, hole transfer, electron blocking, hole blocking, electron transfer, electron injection and the like can also be used as a material of the organic thin film.

Development of an organic thin film material has been continuously required for enhancing performance, lifetime or efficiency of an organic light emitting device.

Technical Problem

The present specification is directed to providing a compound and an organic light emitting device including the same.

Technical Solution

One embodiment of the present specification provides a compound of Chemical Formula 1:

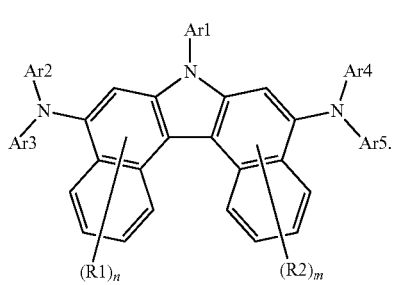

Chemical Formula 1

In Chemical Formula 1:

Ar1 is a substituted or unsubstituted aryl group having 6 to 30 carbon atoms, or a substituted or unsubstituted heterocyclic group having 2 to 30 carbon atoms;

Ar2 and Ar4 are the same as each other, and Ar3 and Ar5 are the same as each other;

Ar2 to Ar5 are each a substituted or unsubstituted aryl group, or a substituted or unsubstituted heterocyclic group;

R1 and R2 are the same as or different from each other, and each independently is hydrogen, deuterium, a halogen group, a cyano group, a substituted or unsubstituted alkyl group, a substituted or unsubstituted alkoxy group, a substituted or unsubstituted aryl group, or a substituted or unsubstituted heterocyclic group; and n and m are each an integer of 0 to 5, and when n is 2 or greater, the R1s are the same as or different from each other, and when m is 2 or greater, the R2s are the same as or different from each other.

Another embodiment of the present application provides an organic light emitting device including a first electrode; a second electrode provided opposite to the first electrode; and one or more organic material layers provided between the first electrode and the second electrode, wherein one or more layers of the organic material layers include the compound described above.

Advantageous Effects

A compound according to one embodiment of the present application is, by being used in an organic light emitting device, capable of lowering a driving voltage of an organic light emitting device, enhancing light efficiency, and enhancing device lifetime properties by thermal stability of the compound.

DESCRIPTION OF DRAWINGS

FIG. 1 illustrates an example of an organic light emitting device in which a substrate (1), an anode (2), a light emitting layer (3) and a cathode (4) are consecutively laminated.

FIG. 2 illustrates an example of an organic light emitting device in which a substrate (1), an anode (2), a hole injection layer (5), a hole transfer layer (6), a light emitting layer (3), an electron transfer layer (7) and a cathode (4) are consecutively laminated.

REFERENCE NUMERAL

1: Substrate
2: Anode
3: Light Emitting Layer
4: Cathode
5: Hole Injection Layer
6: Hole Transfer Layer
7: Electron Transfer Layer

MODE FOR DISCLOSURE

Hereinafter, the present specification will be described in more detail.

One embodiment of the present specification provides a compound of Chemical Formula 1.

The compound of Chemical Formula 1 employs a structure in which an arylamine group, a heteroarylamine group or an arylheteroarylamine group is linked to a dibenzo[c,g] carbazole group in an N-meta direction as a basic skeleton.

The N-meta direction is a direction in which conjugation continues, and when an amine group is linked to parts other than the N-meta direction, the conjugation length increases emitting light with a longer wavelength than blue. In addition, a carbazole group or benzocarbazole group structure has low electron density and thereby emits light with a short wavelength, whereas a dibenzocarbazole group has higher electron density and is capable of satisfying a blue light emission wavelength required for an organic light emitting device.

In addition, when hydrogen atoms are present on Nos. 4 and 10 of dibenzo[c,g]carbazole as follows, the hydrogen atoms generate repulsive force with an aryl group or a heterocyclic group linked to an amine group, and thereby interfere with the rotation of the amine group. As a result, when using a compound having the following structure as a blue fluorescent dopant, a half width decreases, and when used in an organic light emitting device, a device with higher color purity can be obtained:

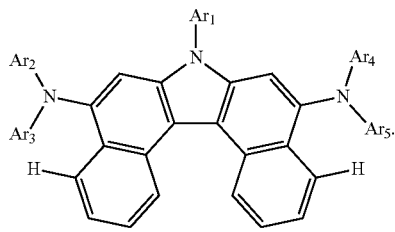

Examples of substituents in the present specification will be described below, however, the substituents are not limited thereto.

In the present specification,  and a dotted line mean a site bonding to other substituents or bonding sites.

The team "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents can be the same as or different from each other.

In the present specification, the term "substituted or unsubstituted" means being substituted with one, two or more substituents selected from the group consisting of deuterium, a halogen group, a cyano group, a nitro group, a hydroxyl group, an alkyl group, a cycloalkyl group, an alkenyl group, an alkoxy group, a substituted or unsubstituted phosphine oxide group, an aryl group, and a heteroaryl group, or being substituted with a substituent linking two or more substituents of the above-illustrated substituents, or having no substituents. For example, a "substituent linking two or more substituents" can include a biphenyl group. In other words, a biphenyl group can be an aryl group, or can be interpreted as a substituent linking two phenyl groups.

In the present specification, examples of the halogen group include fluorine, chlorine, bromine or iodine.

In the present specification, the alkyl group can be linear or branched, and although not particularly limited thereto, the number of carbon atoms is preferably from 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 2-methylpentyl, 4-methylhexyl, 5-methylhexyl and the like, but are not limited thereto.

In the present specification, the cycloalkyl group is not particularly limited, but preferably has 3 to 60 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethyl-cyclohexyl, 3,4,5-trimethylcyclohexyl, 4-tert-butylcyclohexyl, cycloheptyl, cyclooctyl and the like, but are not limited thereto.

In the present specification, the alkoxy group can be linear, branched or cyclic. The number of carbon atoms of the alkoxy group is not particularly limited, but is preferably from 1 to 20. Specific examples thereof include methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the alkenyl group can be linear or branched, and although not particularly limited thereto, the number of carbon atoms is preferably from 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, specific examples of the phosphine oxide group include a diphenylphosphine oxide group, a dinaphthylphosphine oxide group and the like, but are not limited thereto.

In the present specification, when the aryl group is a monocyclic aryl group, the number of carbon atoms is not particularly limited, but is preferably from 6 to 30. Specific examples of the monocyclic aryl group include a phenyl group, a biphenyl group, a terphenyl group and the like, but are not limited thereto.

When the aryl group is a polycyclic aryl group, the number of carbon atoms is not particularly limited, but is preferably from 10 to 24. Specific examples of the polycyclic aryl group include a naphthyl group, an anthracenyl group, a phenanthryl group, a pyrenyl group, a perylenyl group, a chrysenyl group, a fluorenyl group and the like, but are not limited thereto.

In the present specification, the fluorenyl group can be substituted, and adjacent substituents can bond to each other to form a ring.

When the fluorenyl group is substituted,

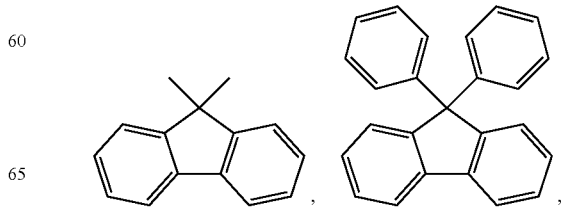

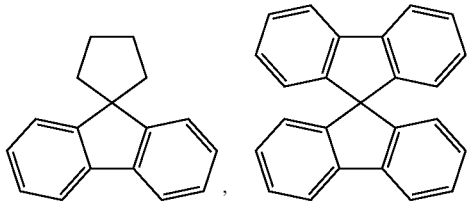

and the like can be included. However, the structure is not limited thereto.

In the present specification, the "adjacent" group can mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring can be interpreted as groups "adjacent" to each other.

In the present specification, the heterocyclic group is a group including one or more atoms that are not carbon, that is, heteroatoms, and specifically, the heteroatom can include one or more atoms selected from the group consisting of O, N, Se, Si, S and the like. The number of carbon atoms of the heterocyclic group is not particularly limited, but is preferably from 2 to 60 or 2 to 30. Examples of the heterocyclic group include a thiophene group, a furan group, a pyrrole group, an imidazolyl group, a triazole group, an oxazole group, an oxadiazole group, a triazole group, a pyridyl group, a bipyridyl group, a pyrimidyl group, a triazine group, an acridine group, a hydroacridyl group (for example,

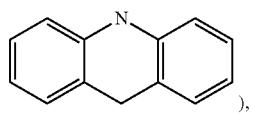 [SMILES: c1ccc2c(c1)Cc1ccccc1N2]

a pyridazinyl group, a pyrazinyl group, a quinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indole group, a carbazole group, a benzoxazole group, a benzimidazole group, a benzothiazole group, a benzocarbazole group, a dibenzocarbazole group, a benzothiophene group, a dibenzothiophene group, a benzofuran group, a dibenzofuran group, a benzosilole group, a dibenzosilole group, a phenanthrolinyl group, an isoxazole group, a thiadiazole group, a benzothiazole group, a phenothiazine group, a phenoxazine group, fused structures thereof, and the like, but are not limited thereto. In addition thereto, examples of the heterocyclic group include a sulfonyl group-including heterocyclic structure such as

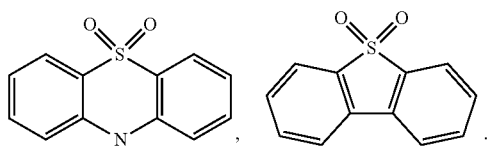

In the present specification, descriptions on the aryl group provided above can be applied to arylene except for being divalent.

In the present specification, the meaning of, among the substituents, "adjacent two bond to each other to form a ring" means forming a substituted or unsubstituted hydrocarbon ring; or a substituted or unsubstituted heteroring by bonding with an adjacent group.

In the present specification, the ring means a substituted or unsubstituted hydrocarbon ring; or a substituted or unsubstituted heteroring.

In the present specification, the hydrocarbon ring can be aromatic, aliphatic or a fused ring of aromatic and aliphatic, and can be selected from among the examples of the cycloalkyl group or the aryl group except for those that are not monovalent.

In the present specification, the aromatic ring can be monocyclic or polycyclic, and can be selected from among the examples of the aryl group except for those that are not monovalent.

In one embodiment of the present specification, Ar1 is a substituted or unsubstituted phenyl group, a substituted or unsubstituted biphenyl group, a substituted or unsubstituted naphthyl group, a substituted or unsubstituted phenanthrene group, a substituted or unsubstituted dibenzofuran group, or a substituted or unsubstituted dibenzothiophene group.

In one embodiment of the present specification, Ar1 is a phenyl group unsubstituted or substituted with an alkyl group or a silyl group; a biphenyl group unsubstituted or substituted with an alkyl group or a silyl group; a naphthyl group unsubstituted or substituted with an alkyl group or a silyl group; a phenanthrene group unsubstituted or substituted with an alkyl group or a silyl group; a dibenzofuran group unsubstituted or substituted with an alkyl group or a silyl group; or a dibenzothiophene group unsubstituted or substituted with an alkyl group or a silyl group.

In one embodiment of the present specification, Ar1 is a phenyl group unsubstituted or substituted with a methyl group, an ethyl group, a propyl group, a butyl group or a trimethylsilyl group; a biphenyl group unsubstituted or substituted with a methyl group, an ethyl group, a propyl group, a butyl group or a trimethylsilyl group; a naphthyl group unsubstituted or substituted with a methyl group, an ethyl group, a propyl group, a butyl group or a trimethylsilyl group; a phenanthrene group unsubstituted or substituted with a methyl group, an ethyl group, a propyl group, a butyl group or a trimethylsilyl group; a dibenzofuran group unsubstituted or substituted with a methyl group, an ethyl group, a propyl group, a butyl group or a trimethylsilyl group; or a dibenzothiophene group unsubstituted or substituted with a methyl group, an ethyl group, a propyl group, a butyl group or a trimethylsilyl group.

In one embodiment of the present specification, Ar1 is a phenyl group unsubstituted or substituted with a methyl group, a propyl group, a butyl group or a trimethylsilyl group; a biphenyl group unsubstituted or substituted with a methyl group, a propyl group, a butyl group or a trimethylsilyl group; a naphthyl group unsubstituted or substituted with a methyl group, a propyl group, a butyl group or a trimethylsilyl group; a phenanthrene group unsubstituted or substituted with a methyl group, a propyl group, a butyl group or a trimethylsilyl group; a dibenzofuran group unsubstituted or substituted with a methyl group, a propyl group, a butyl group or a trimethylsilyl group; or a dibenzothiophene group unsubstituted or substituted with a methyl group, a propyl group, a butyl group or a trimethylsilyl group.

In one embodiment of the present specification, Ar1 is a phenyl group unsubstituted or substituted with a methyl group, a propyl group, a butyl group or a trimethylsilyl group; a biphenyl group; a naphthyl group; a phenanthrene group; a dibenzofuran group; or a dibenzothiophene group.

In one embodiment of the present specification, Ar1 is a phenyl group, a biphenyl group, a naphthyl group, a phenanthrene group, a dibenzofuran group or a dibenzothiophene group.

In one embodiment of the present specification, Ar2 to Ar5 are each a substituted or unsubstituted phenyl group, a substituted or unsubstituted biphenyl group, or a substituted or unsubstituted dibenzofuran group.

In one embodiment of the present specification, Ar2 to Ar5 are each a phenyl group unsubstituted or substituted with a substituent selected from the group consisting of an alkyl group, a silyl group and an aryl group; a biphenyl group unsubstituted or substituted with a substituent selected from the group consisting of an alkyl group, a silyl group and an aryl group; or a dibenzofuran group unsubstituted or substituted with a substituent selected from the group consisting of an alkyl group, a silyl group and an aryl group.

In one embodiment of the present specification, Ar2 to Ar5 are each a phenyl group unsubstituted or substituted with a substituent selected from the group consisting of a methyl group, an ethyl group, a propyl group, a butyl group, a trimethylsilyl group and a phenyl group; a biphenyl group unsubstituted or substituted with a substituent selected from the group consisting of a methyl group, an ethyl group, a propyl group, a butyl group, a trimethylsilyl group and a phenyl group; or a dibenzofuran group unsubstituted or substituted with a methyl group, an ethyl group, a propyl group, a butyl group, a trimethylsilyl group and a phenyl group.

In one embodiment of the present specification, Ar2 to Ar5 are each a phenyl group unsubstituted or substituted with a substituent selected from the group consisting of a methyl group, an ethyl group, a propyl group, a butyl group and a trimethylsilyl group; a biphenyl group unsubstituted or substituted with a substituent selected from the group consisting of a methyl group, an ethyl group, a propyl group, a butyl group and a trimethylsilyl group; or a dibenzofuran group unsubstituted or substituted with a methyl group, an ethyl group, a propyl group, a butyl group and a trimethylsilyl group.

In one embodiment of the present specification, R1 and R2 are hydrogen.

In one embodiment of the present specification, the compound of Chemical Formula 1 is selected from among the following compounds:

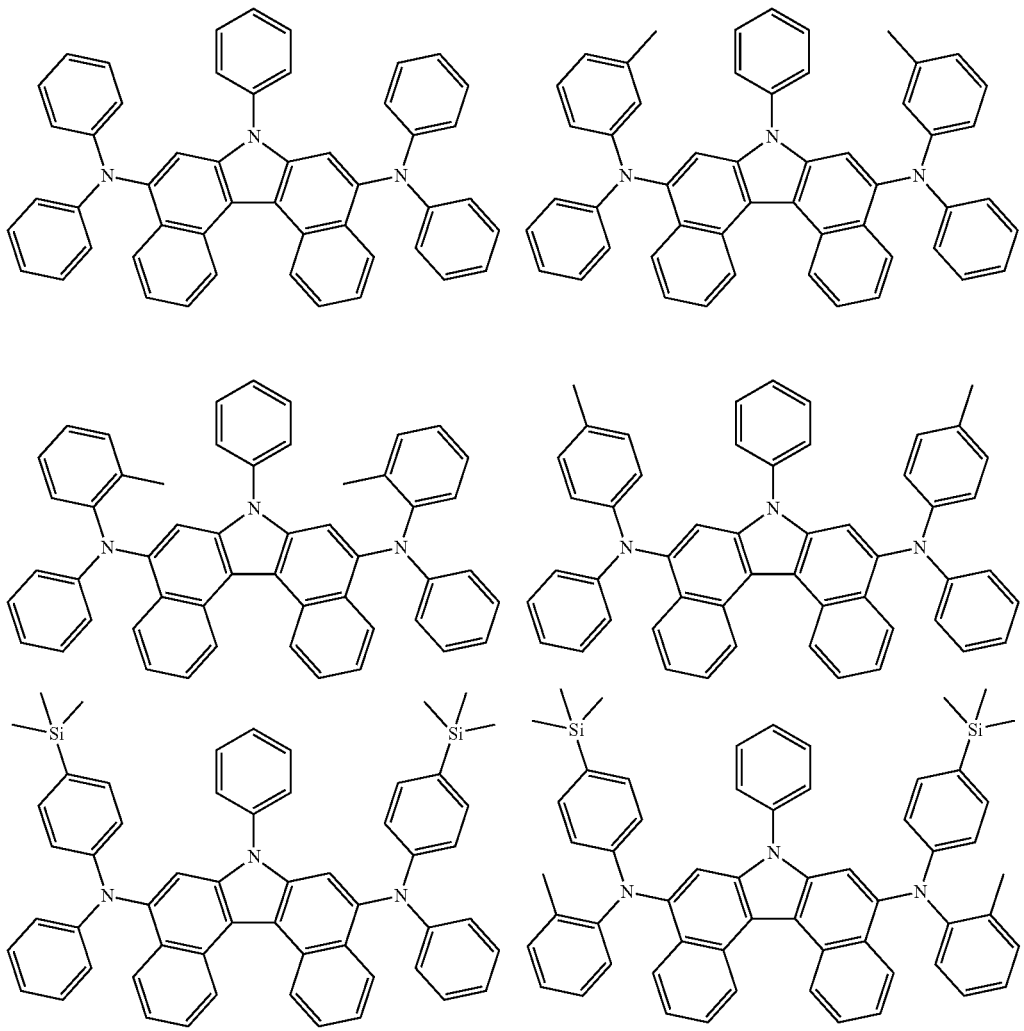

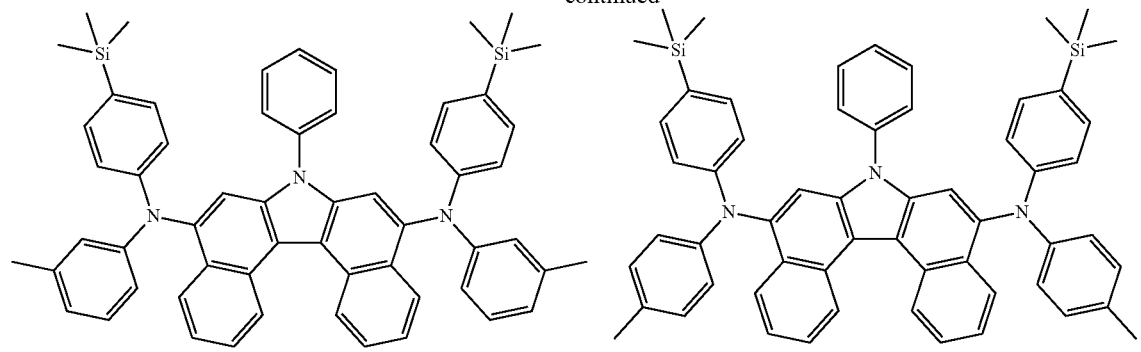
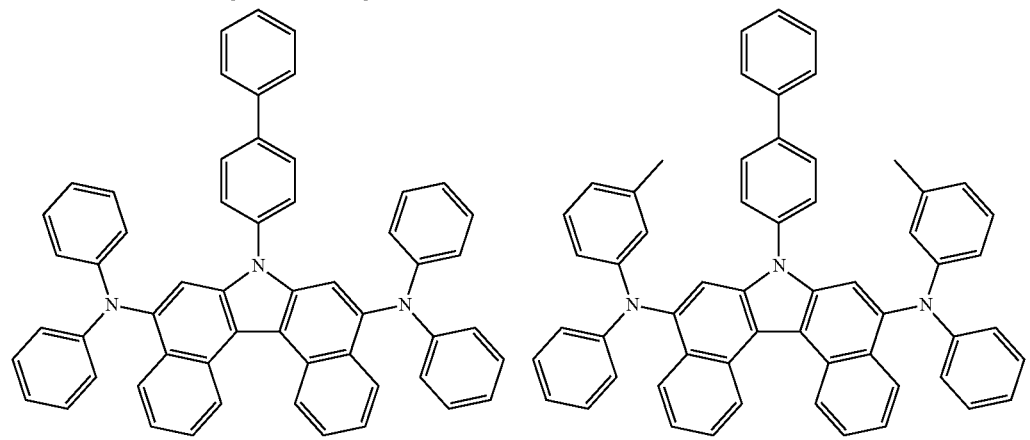
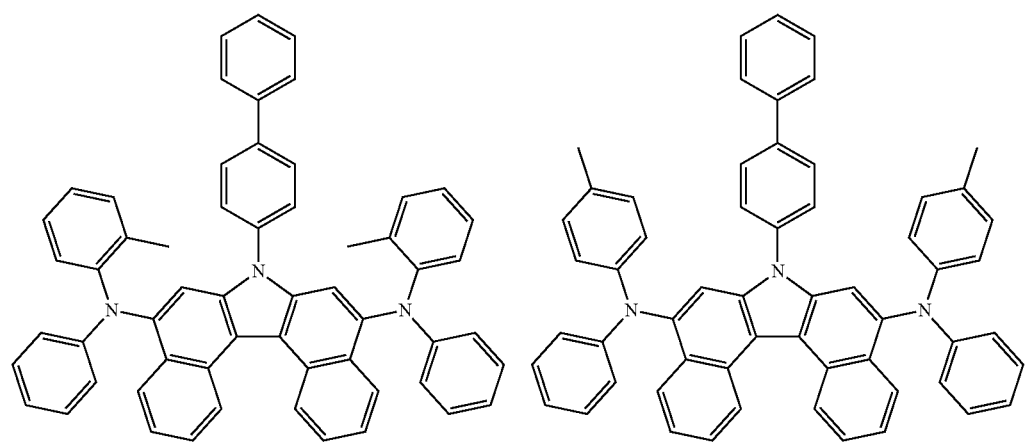
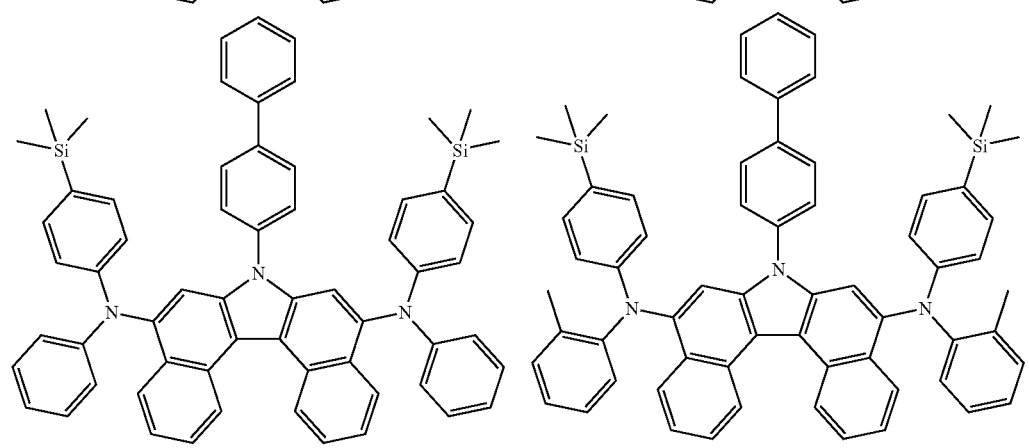

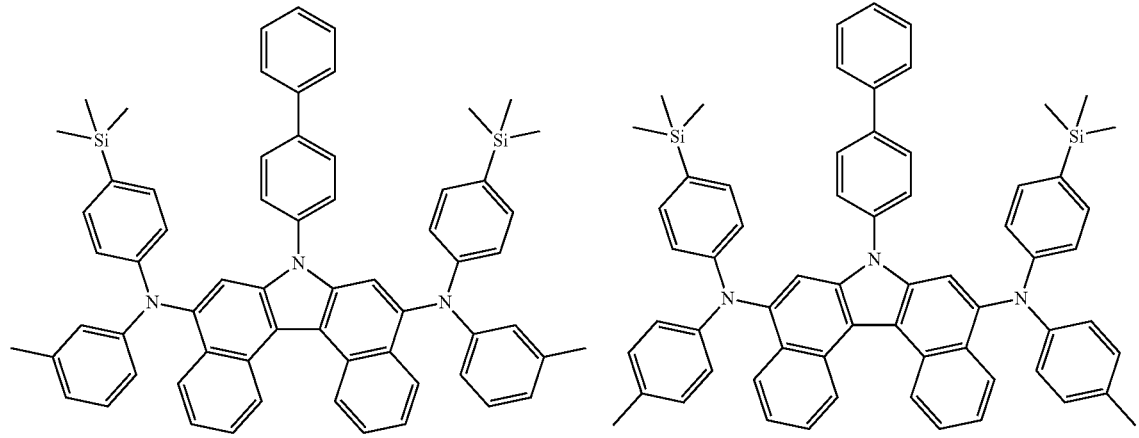
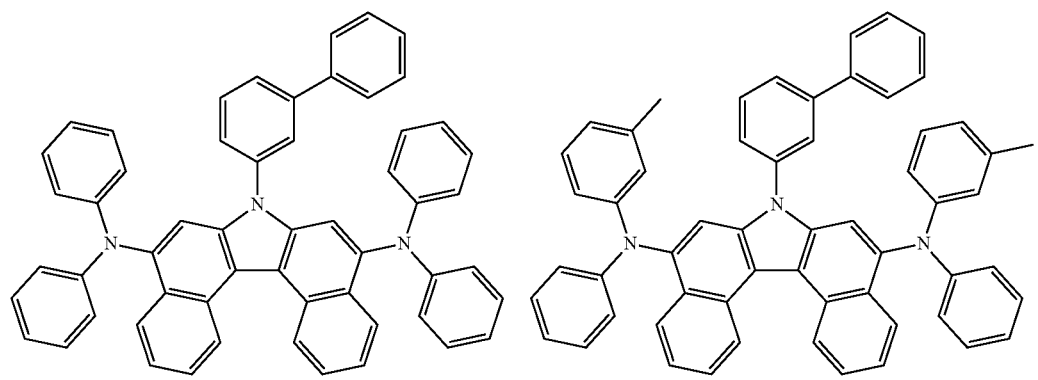
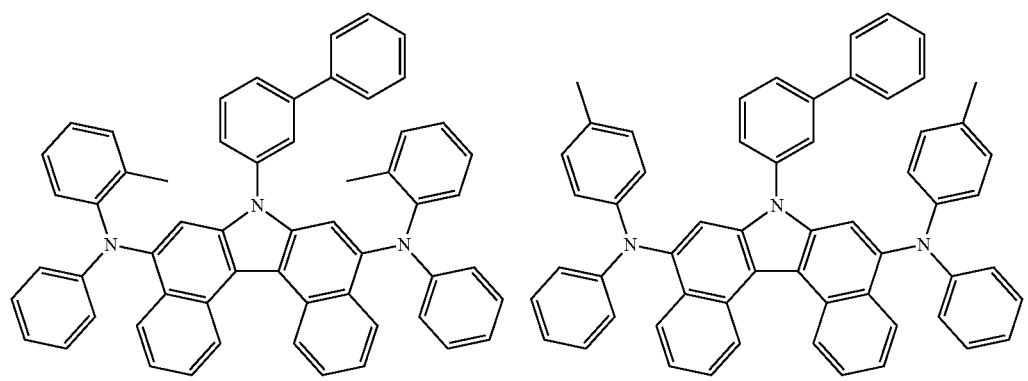
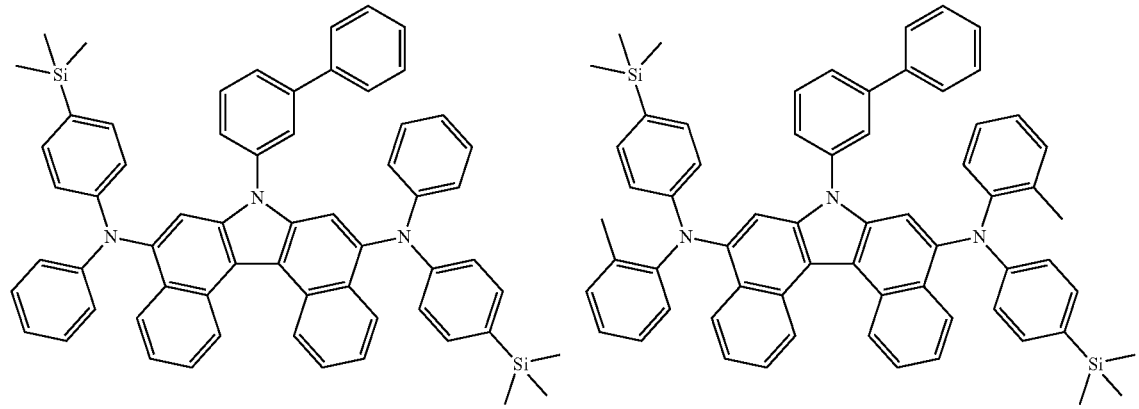

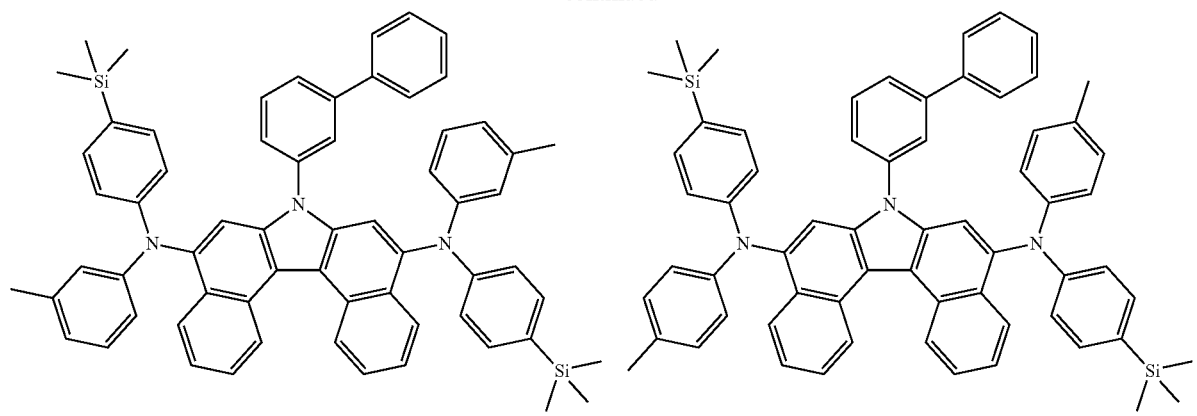
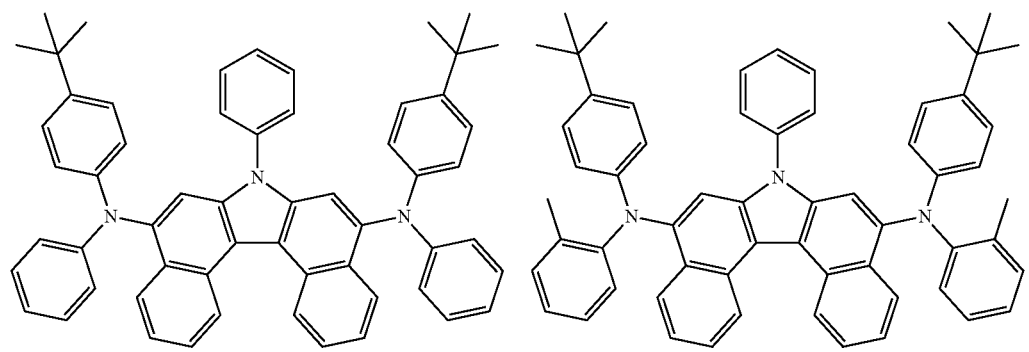
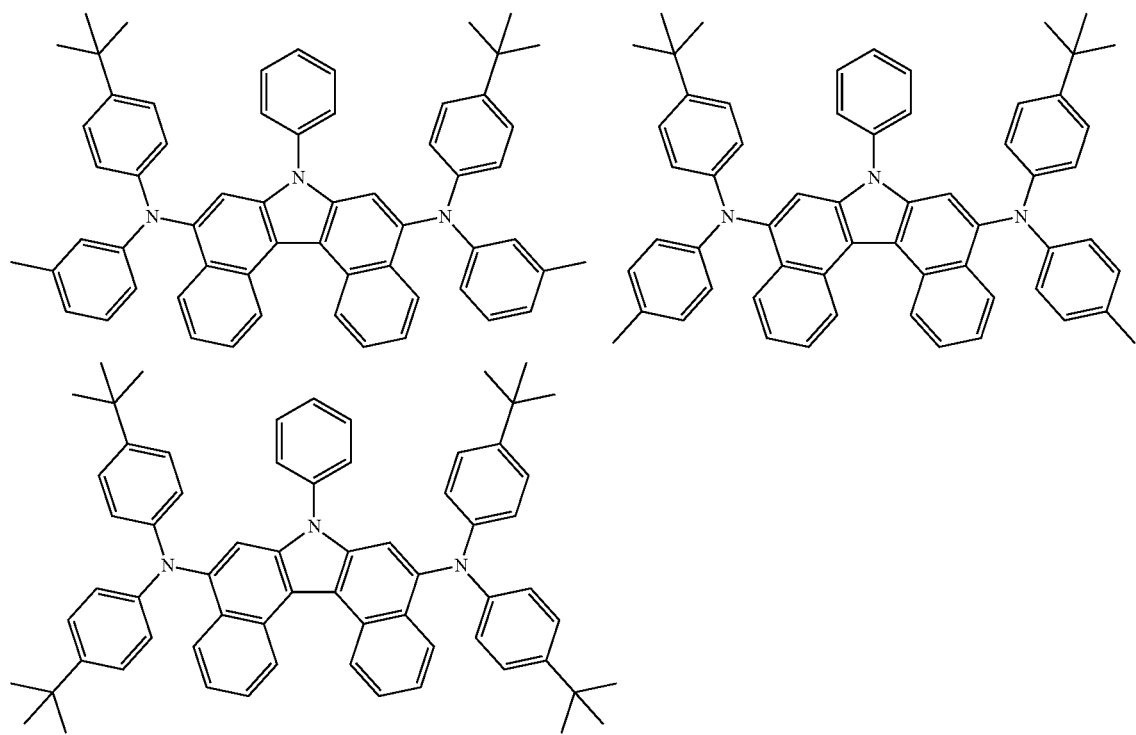

-continued
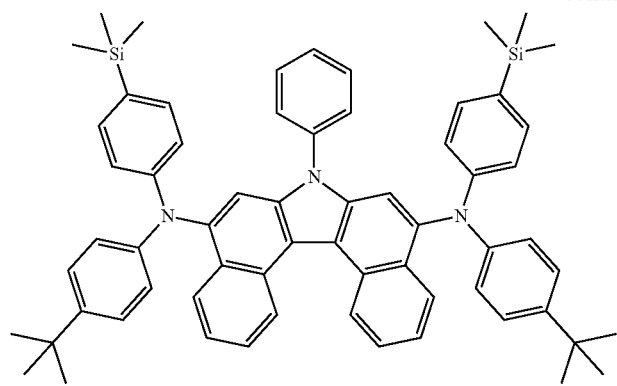
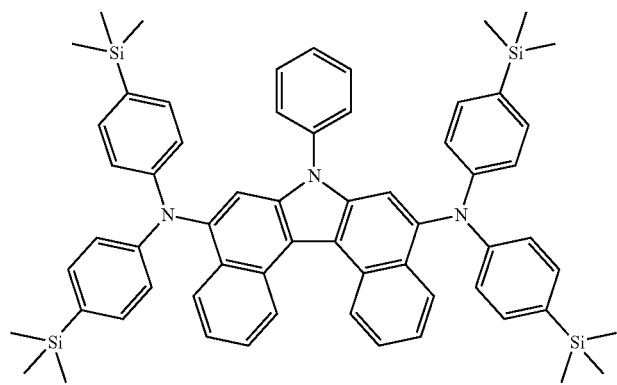
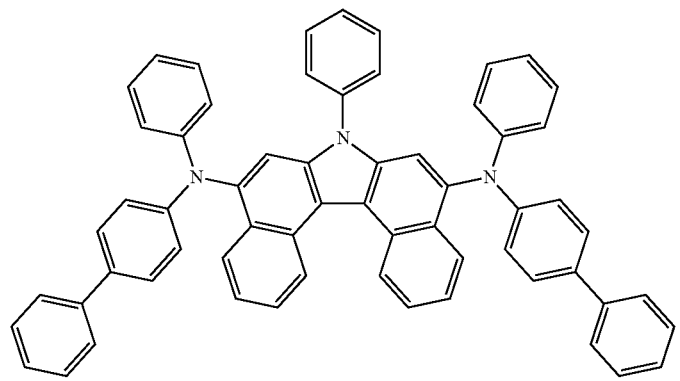
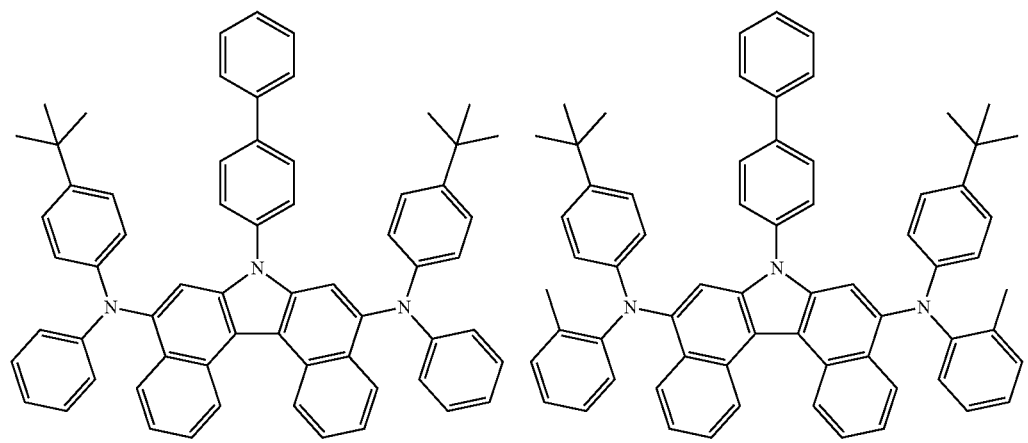

17 18
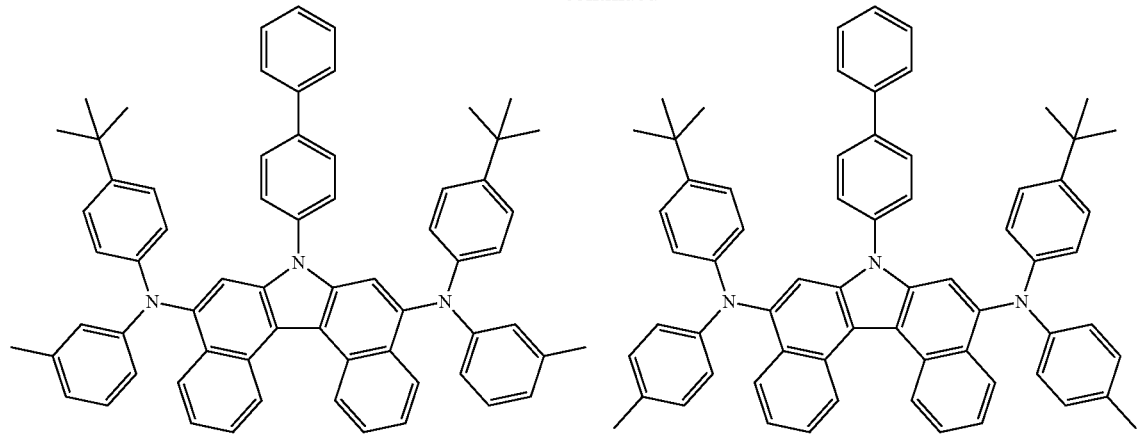
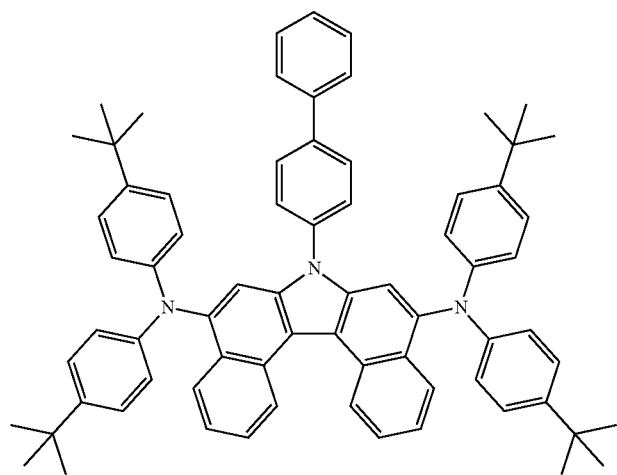
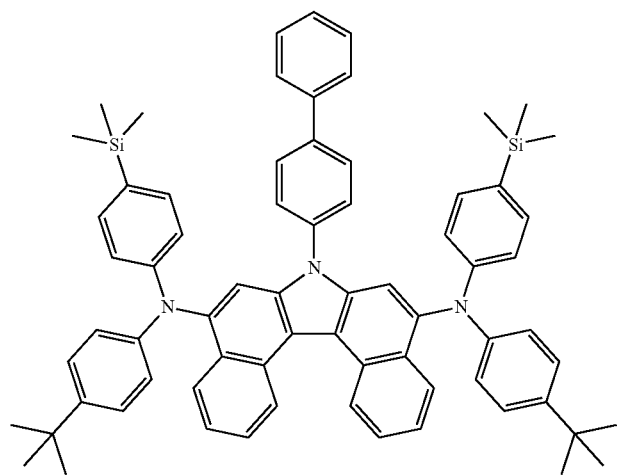

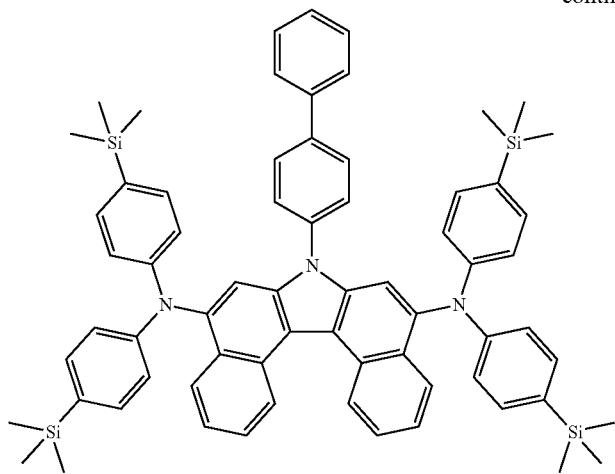
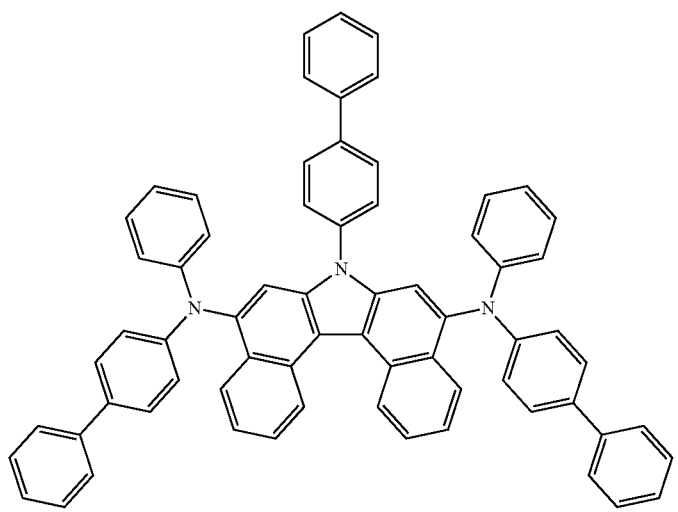
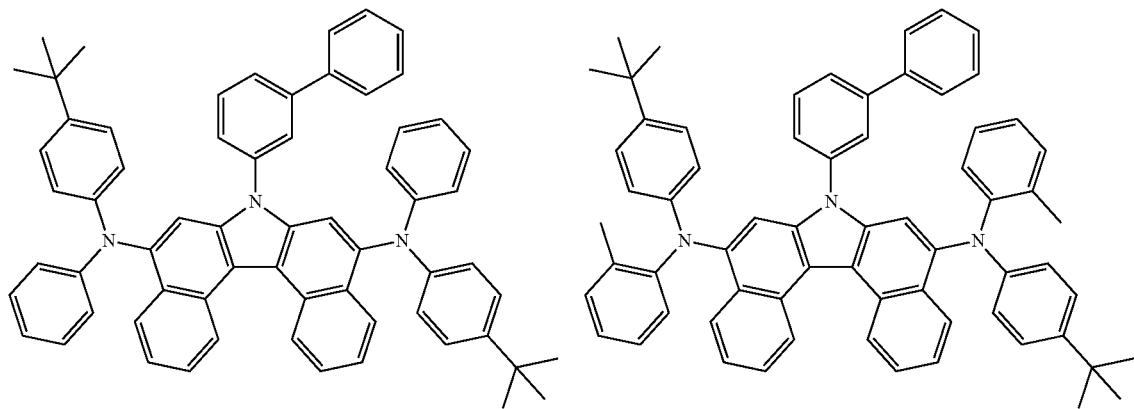

-continued
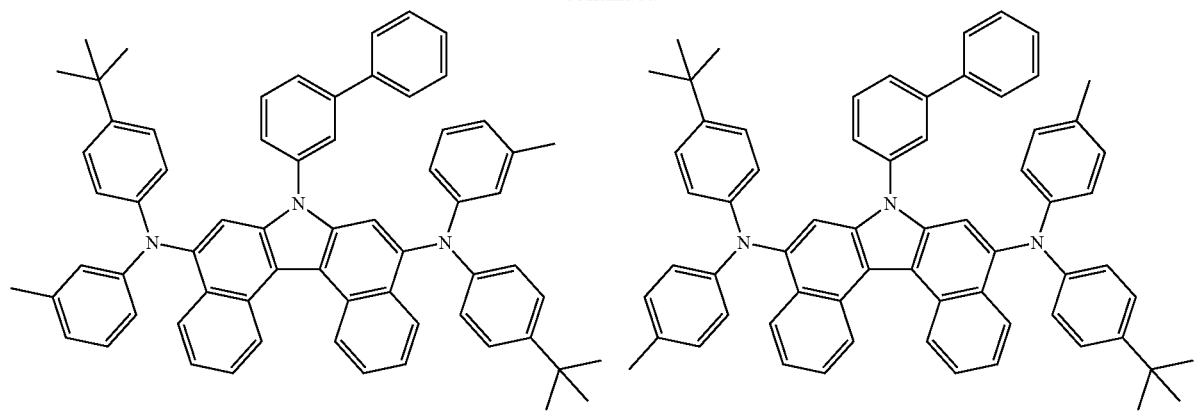
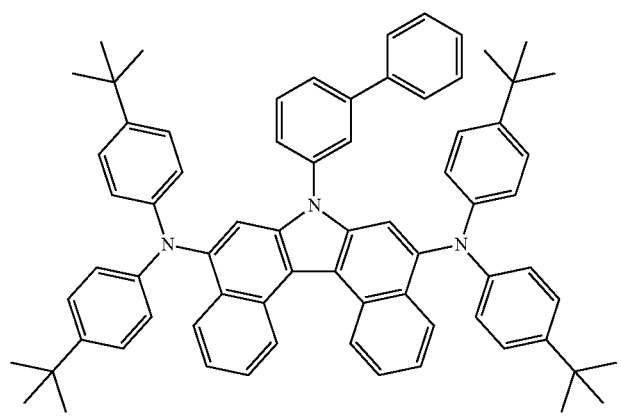
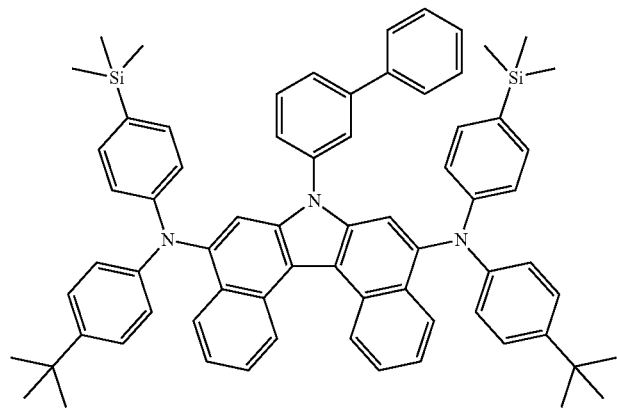
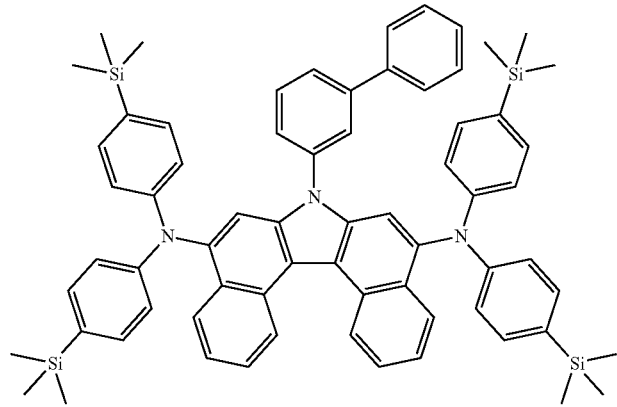

-continued
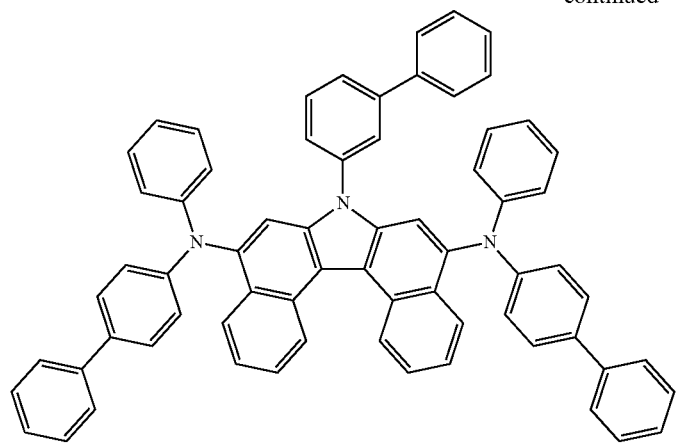
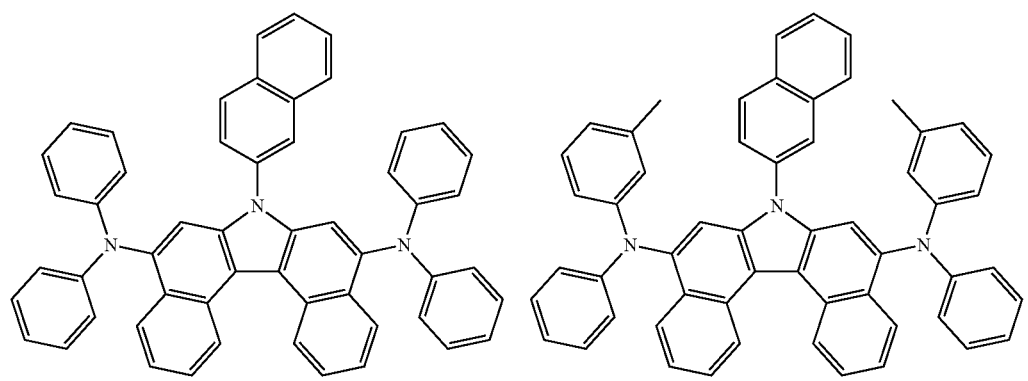
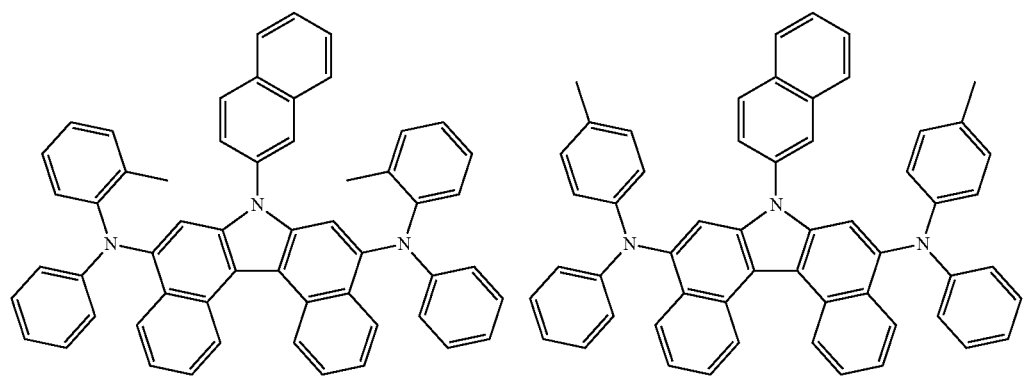
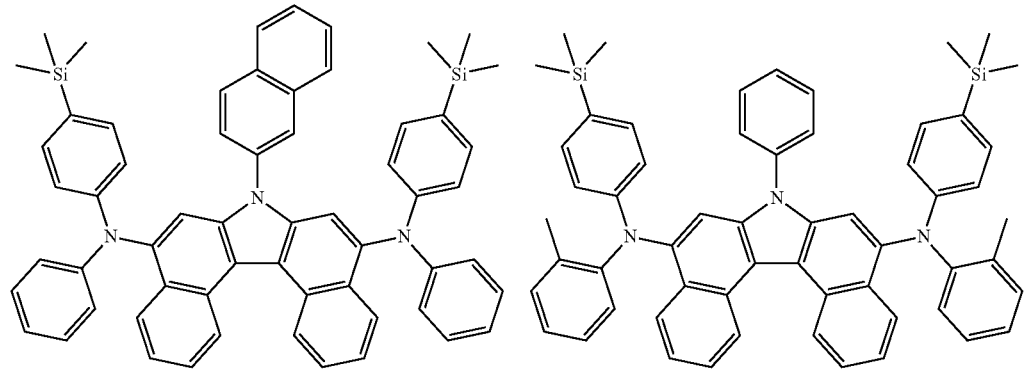

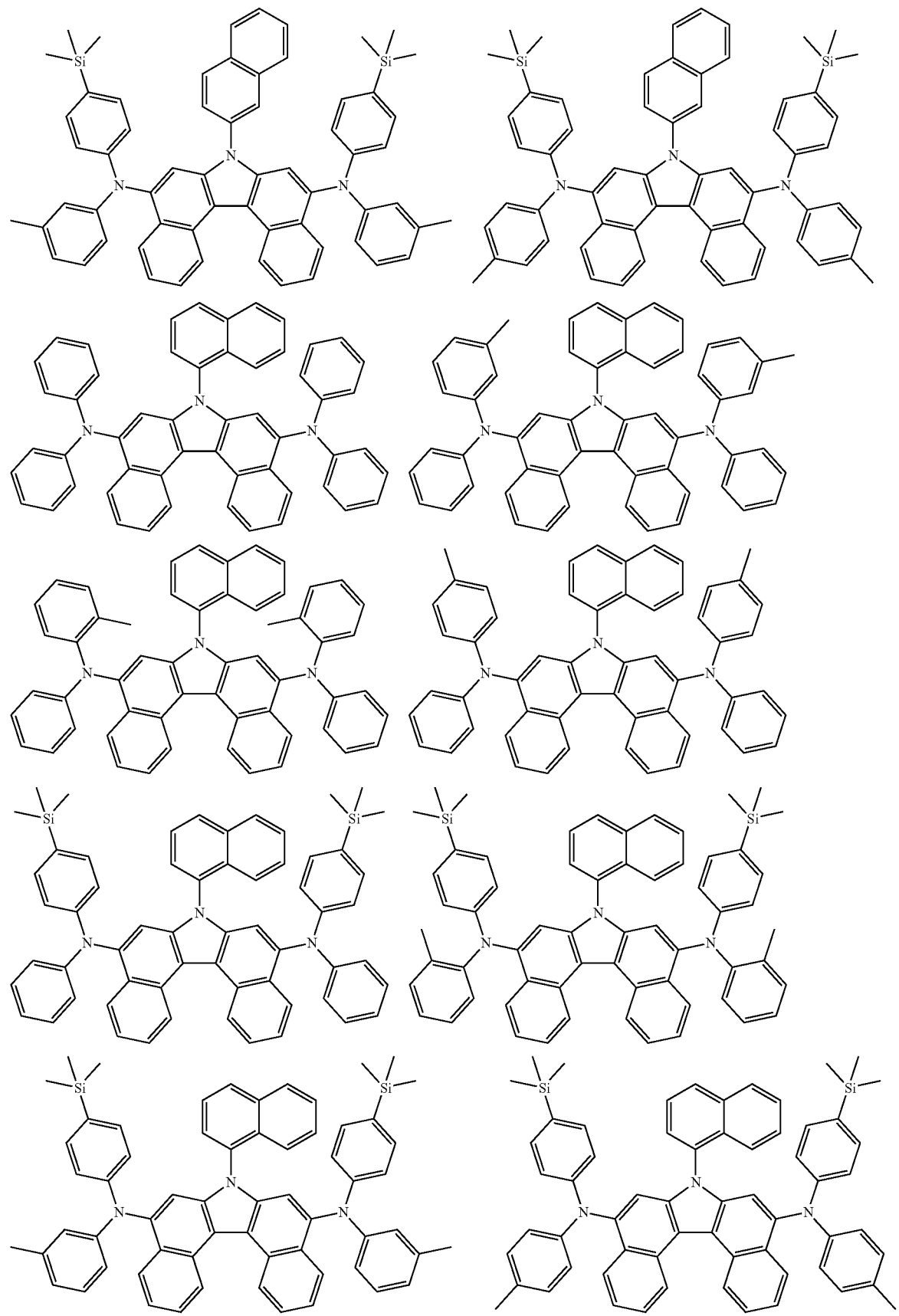

-continued
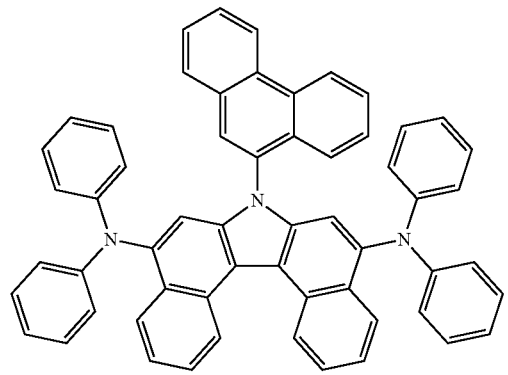 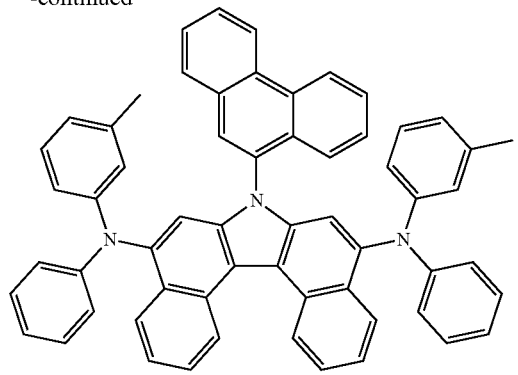
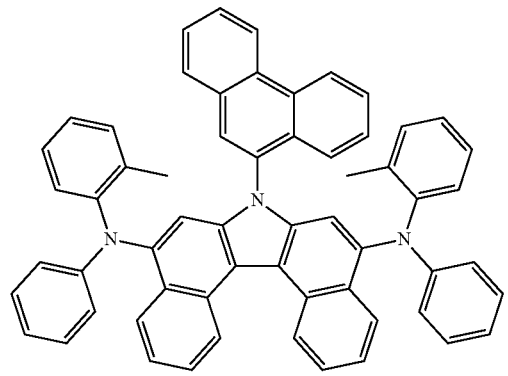 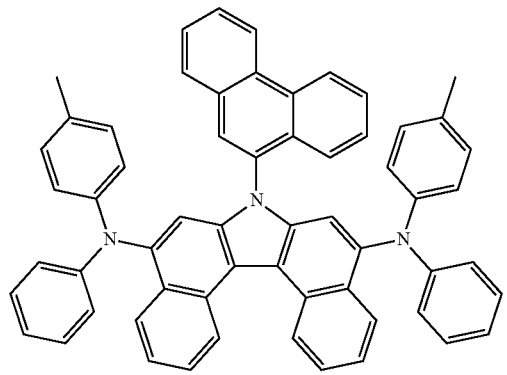
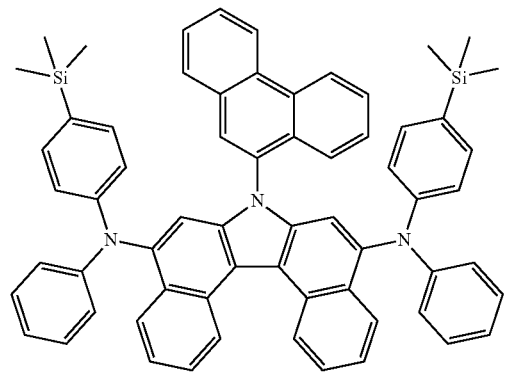 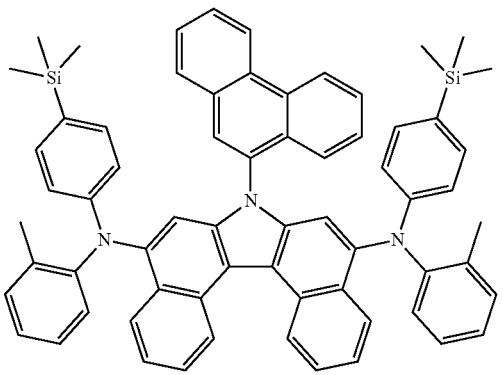
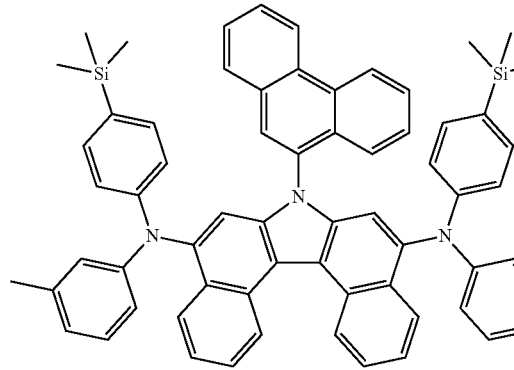 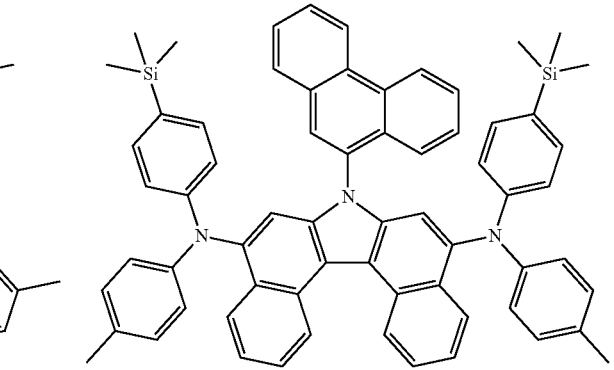

-continued
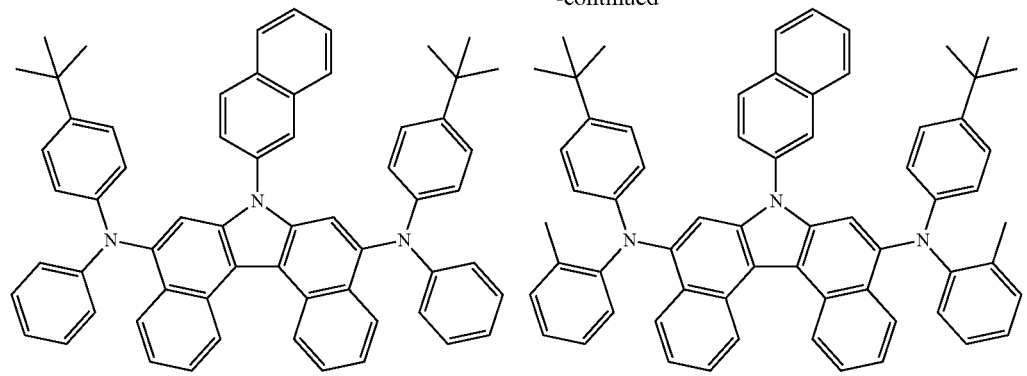
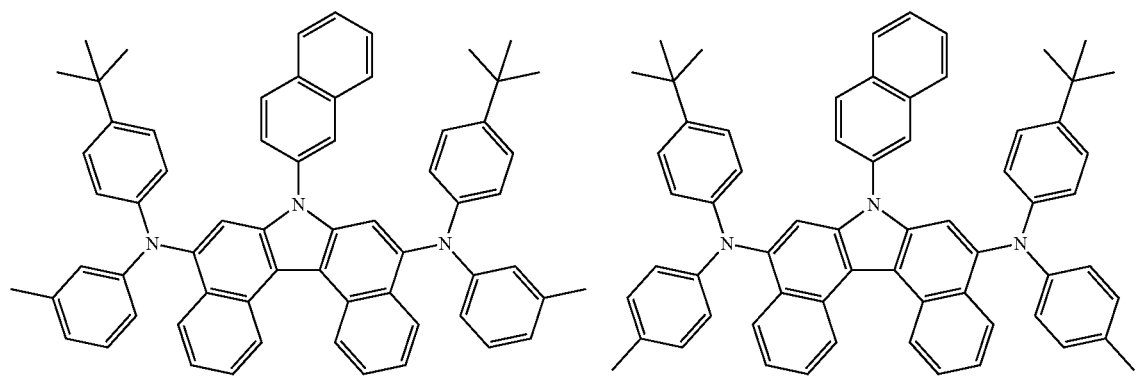
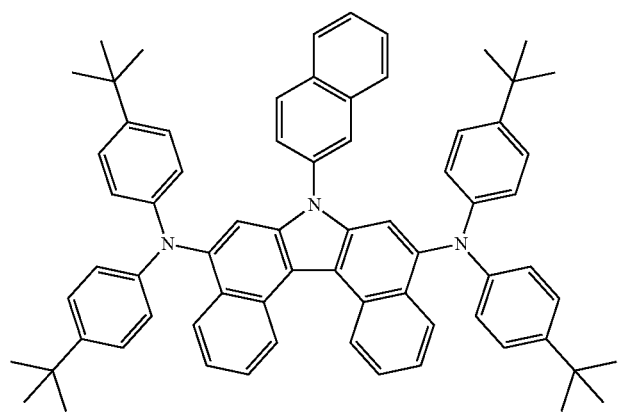
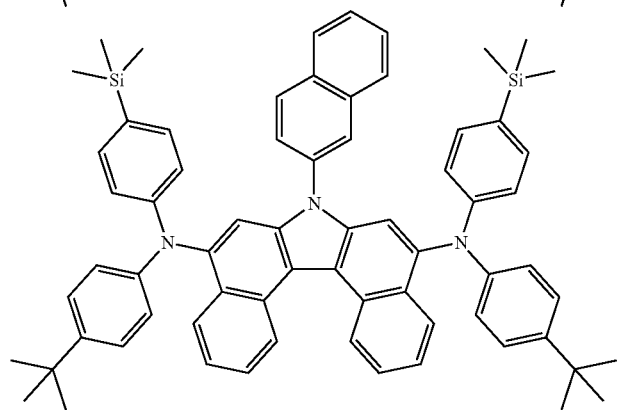

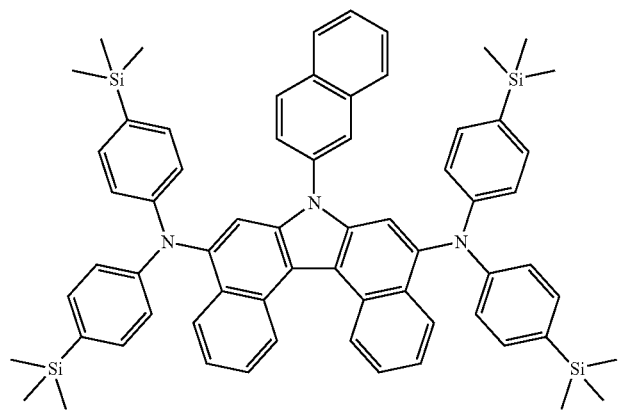
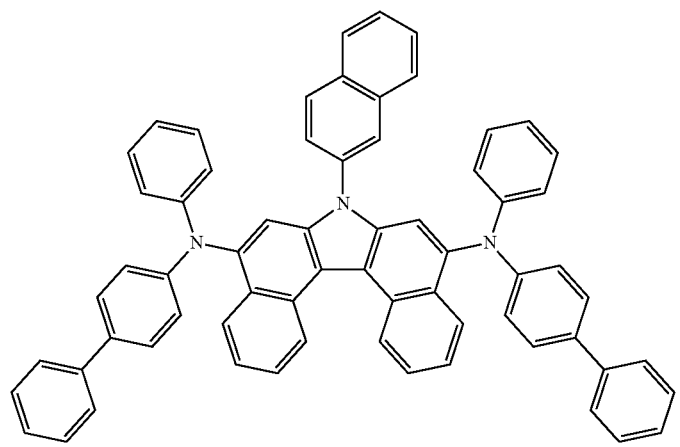
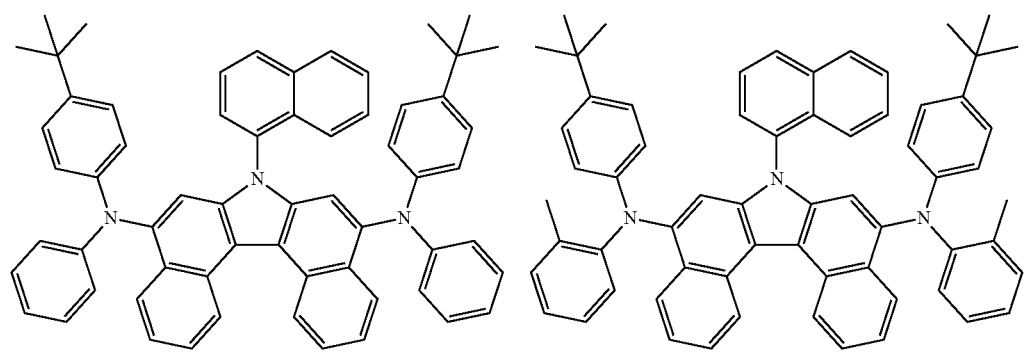
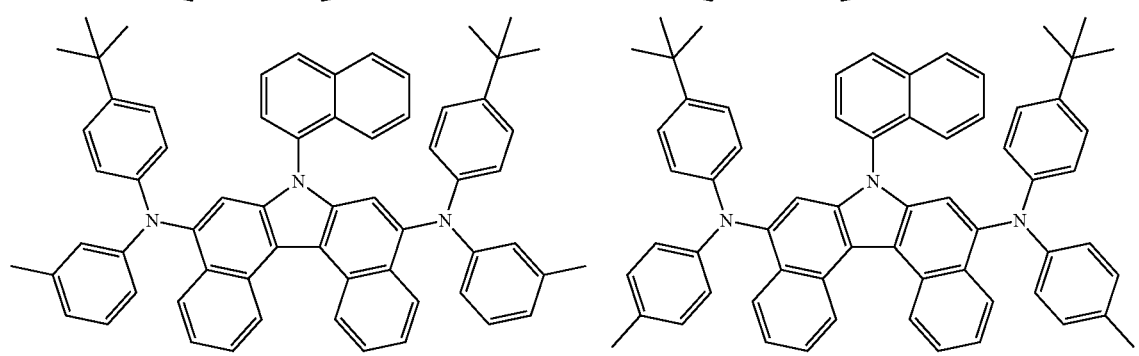

-continued
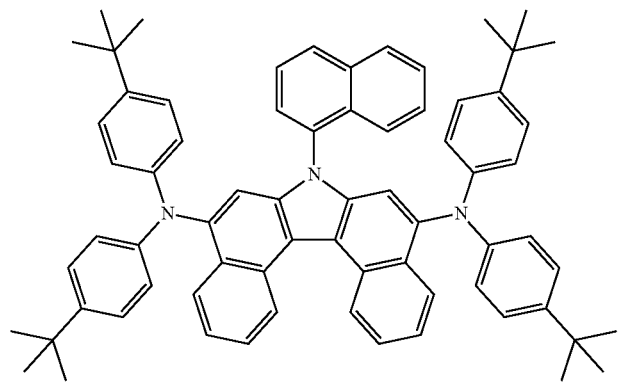
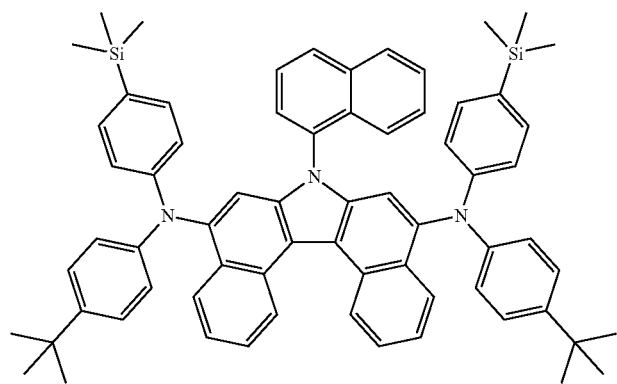
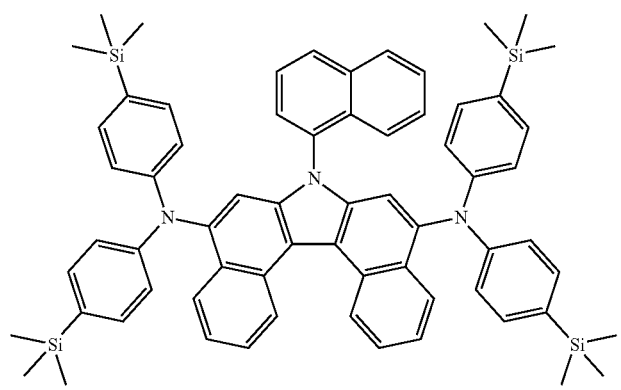
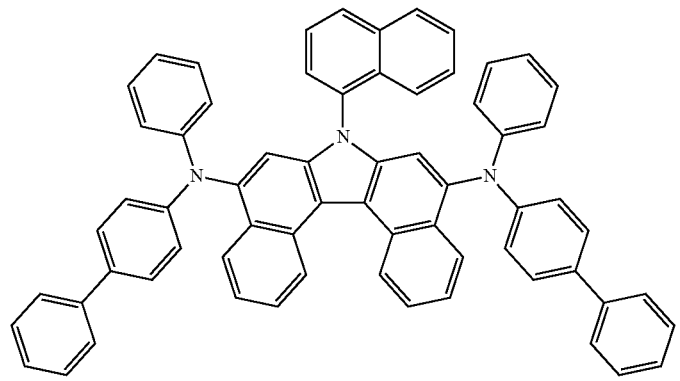

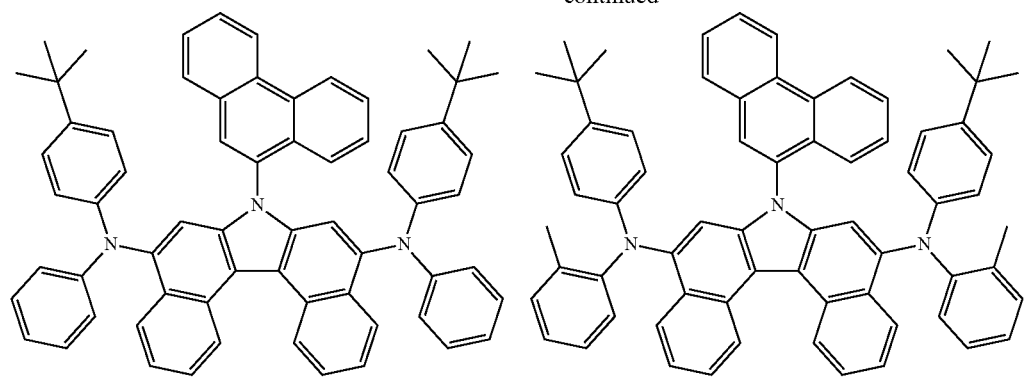
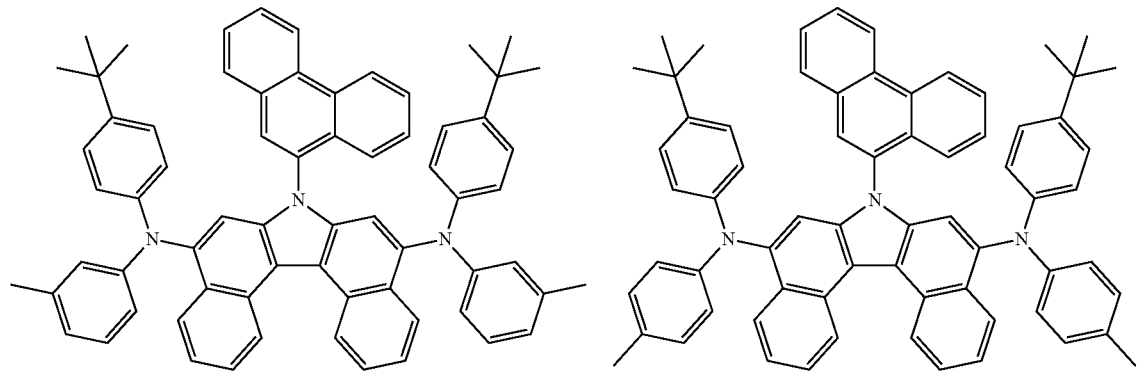
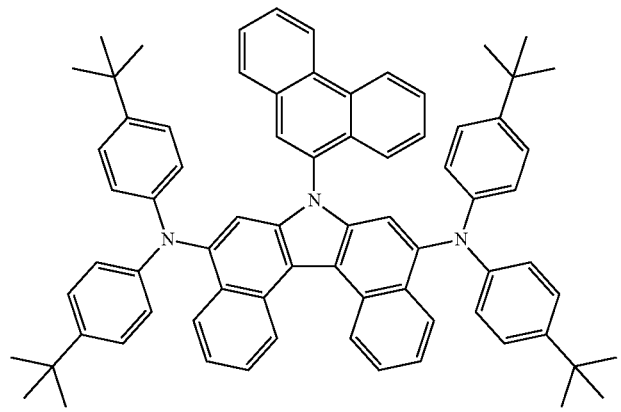
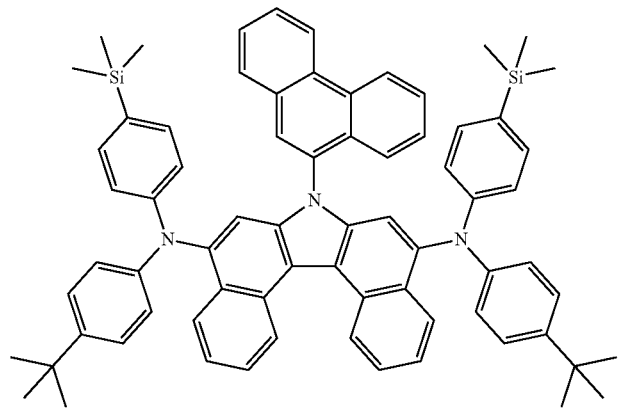

-continued
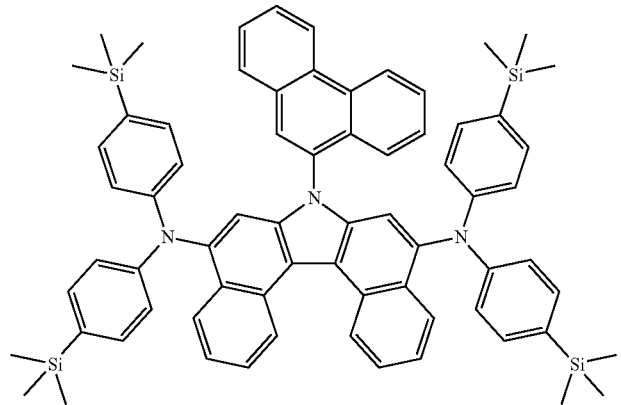
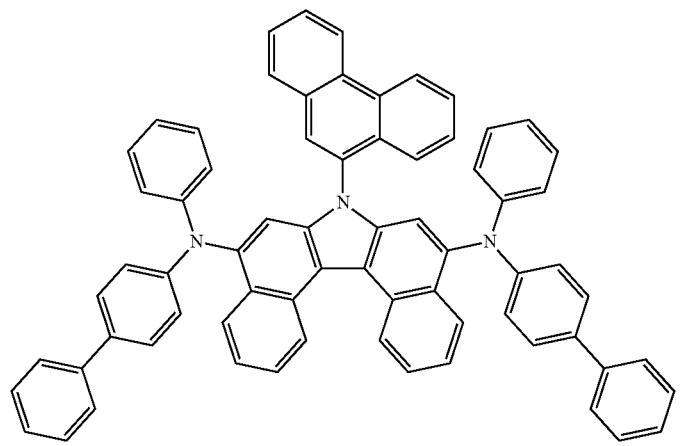
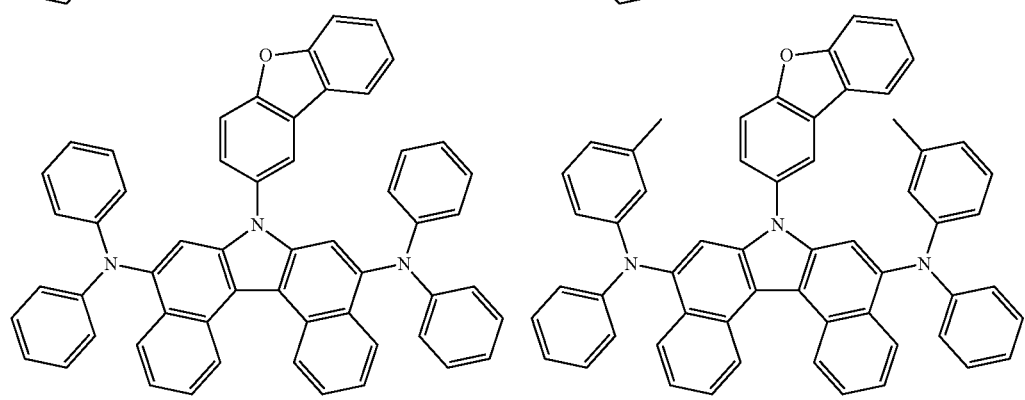
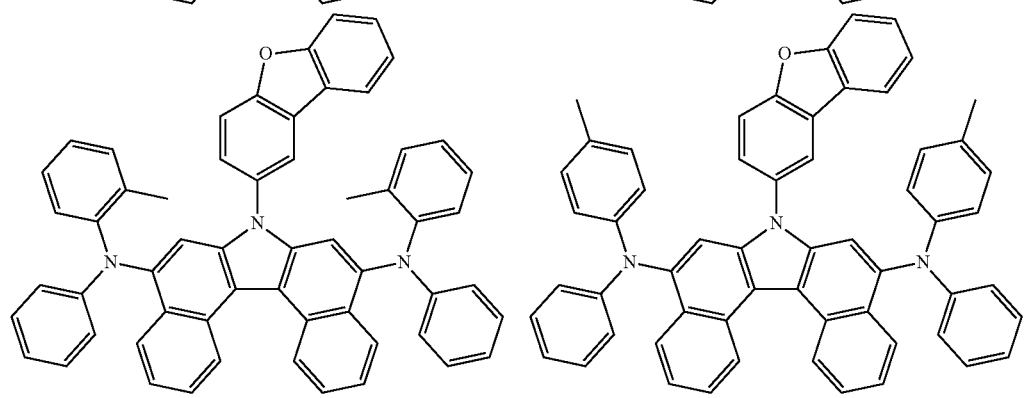

-continued
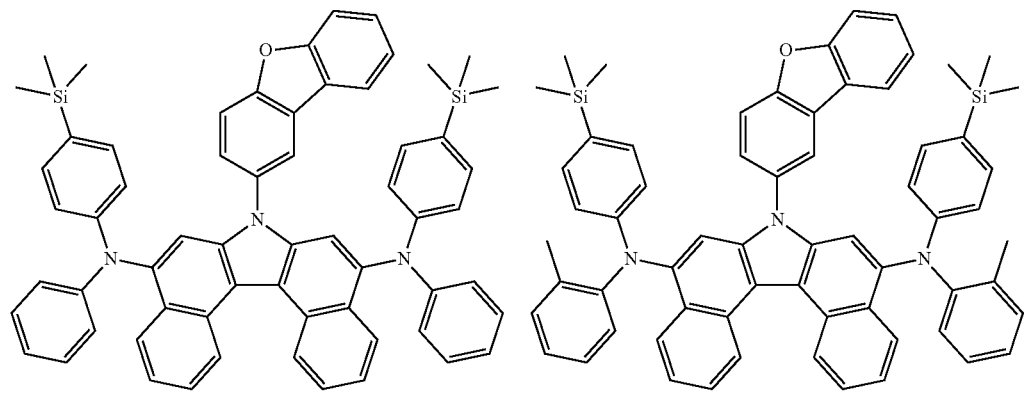
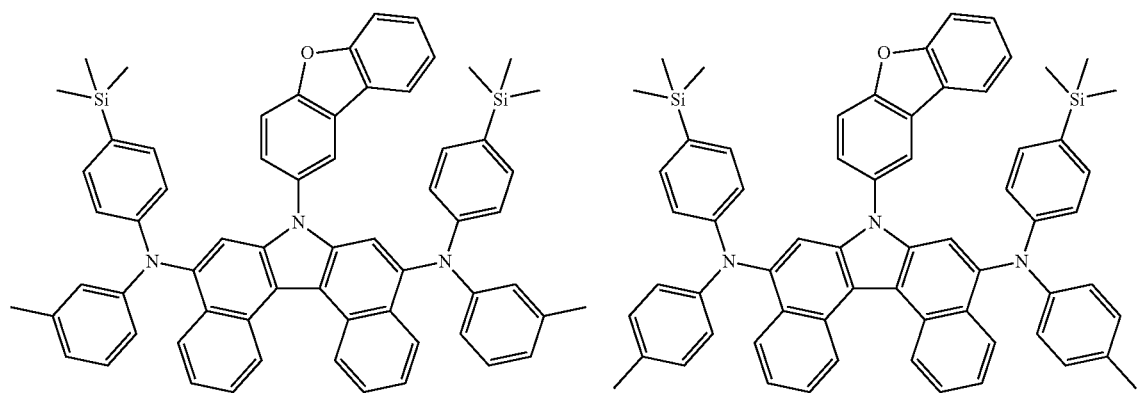
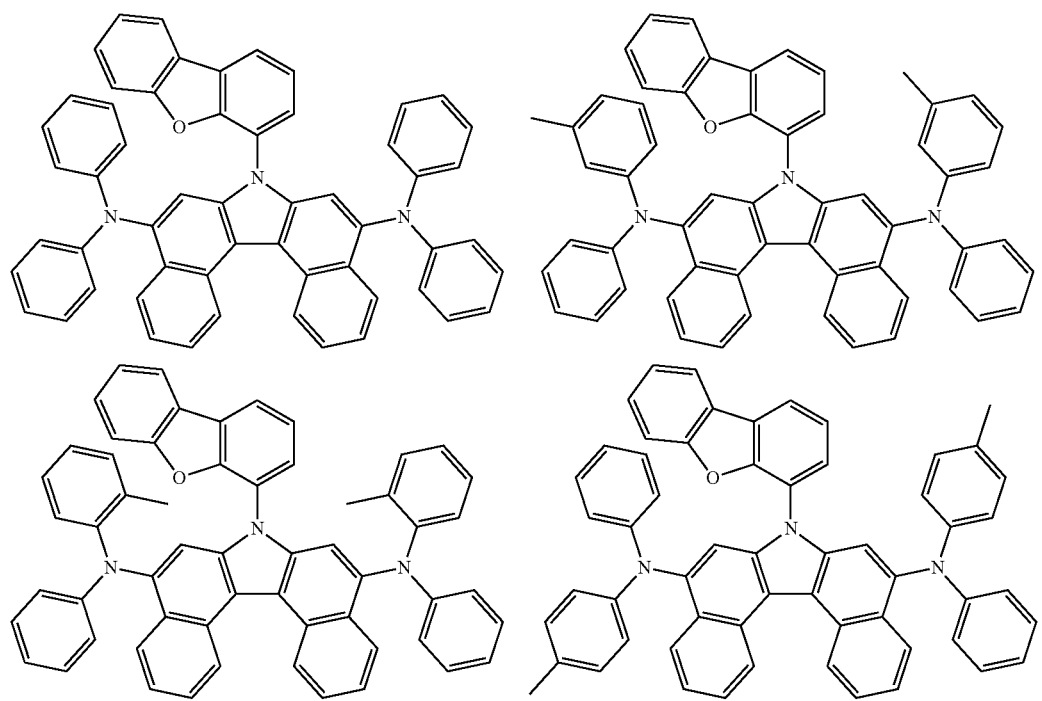

-continued
41
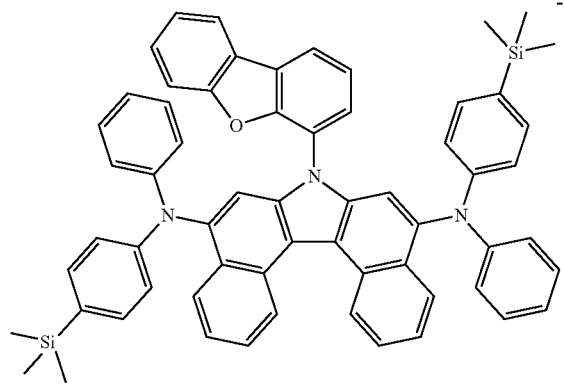
42
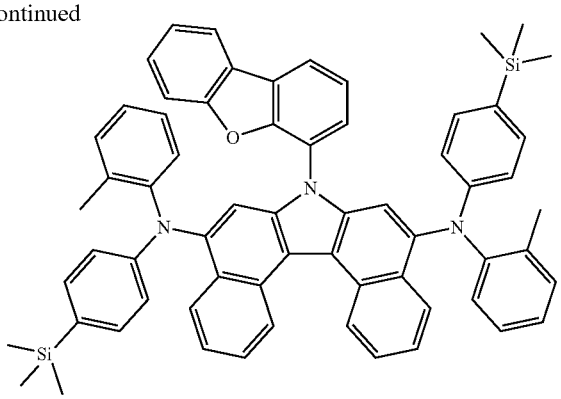
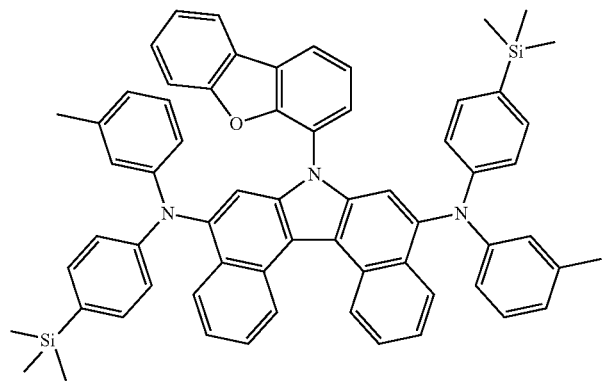
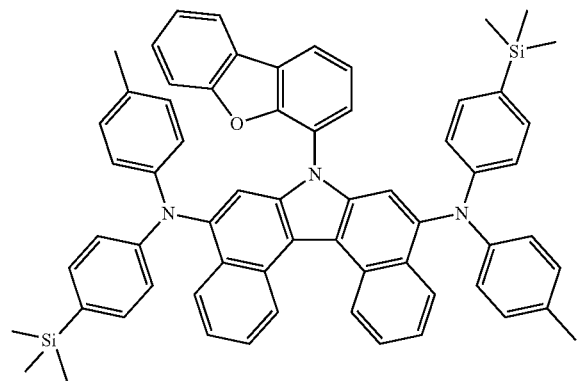
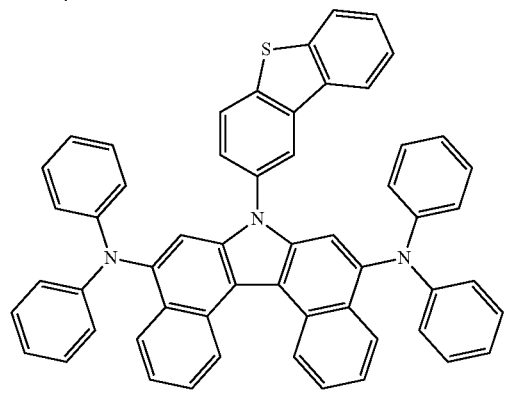
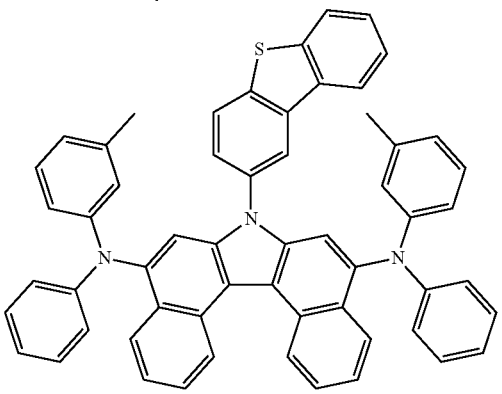
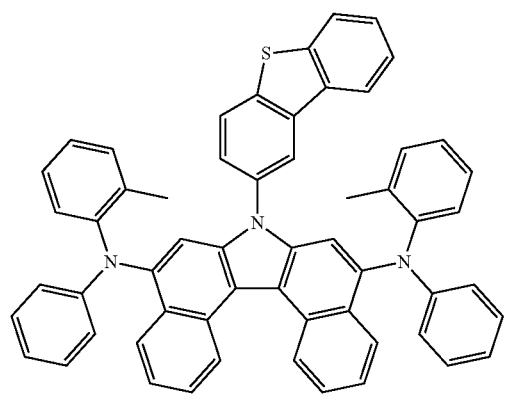
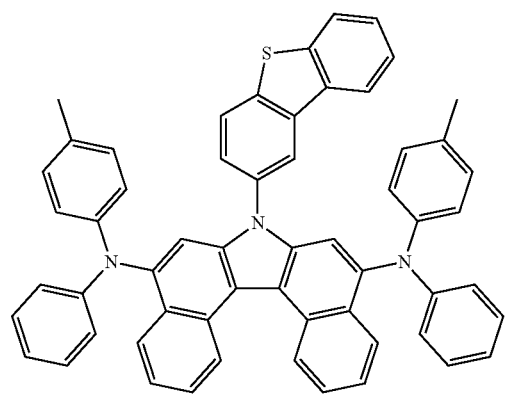

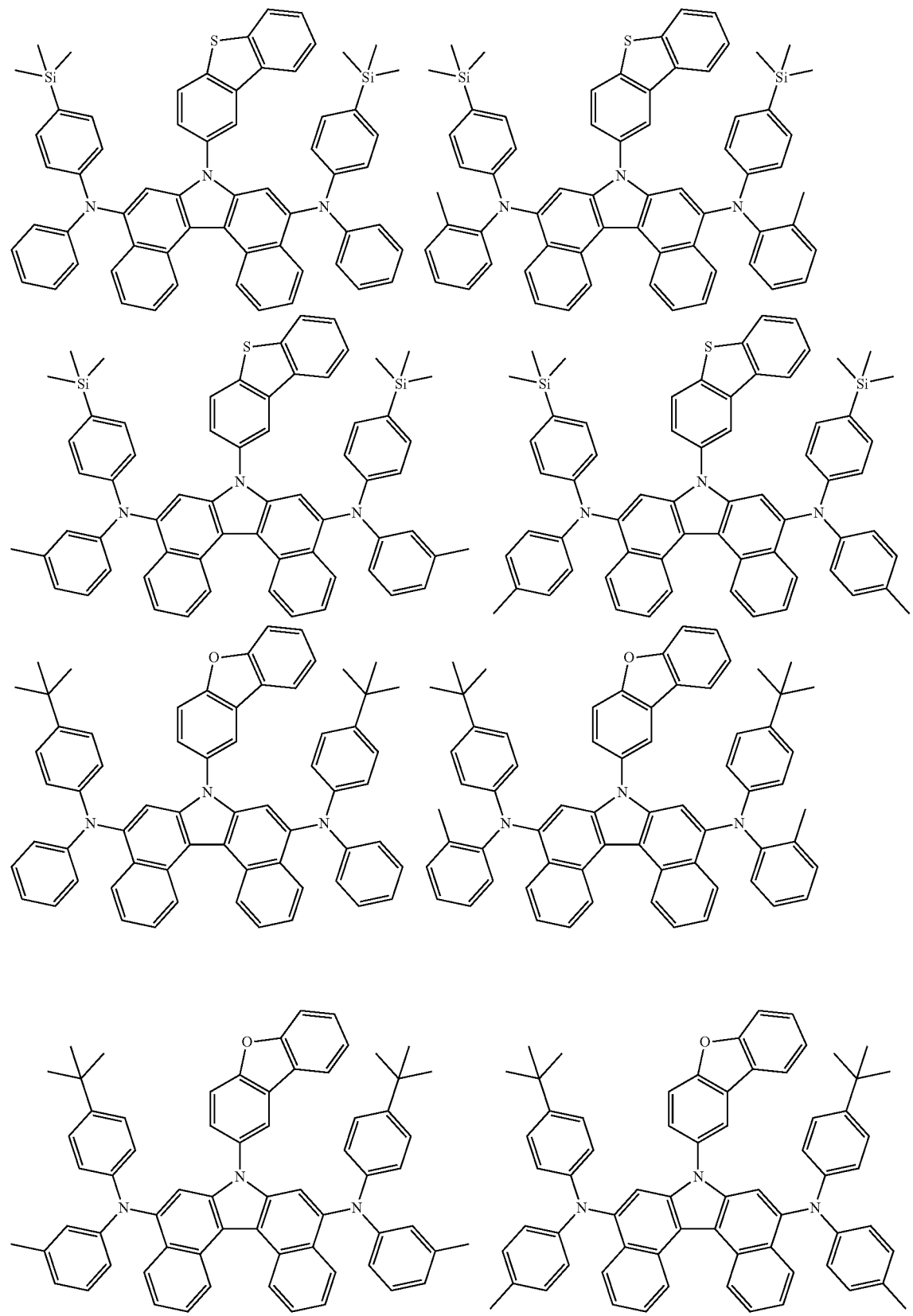

-continued
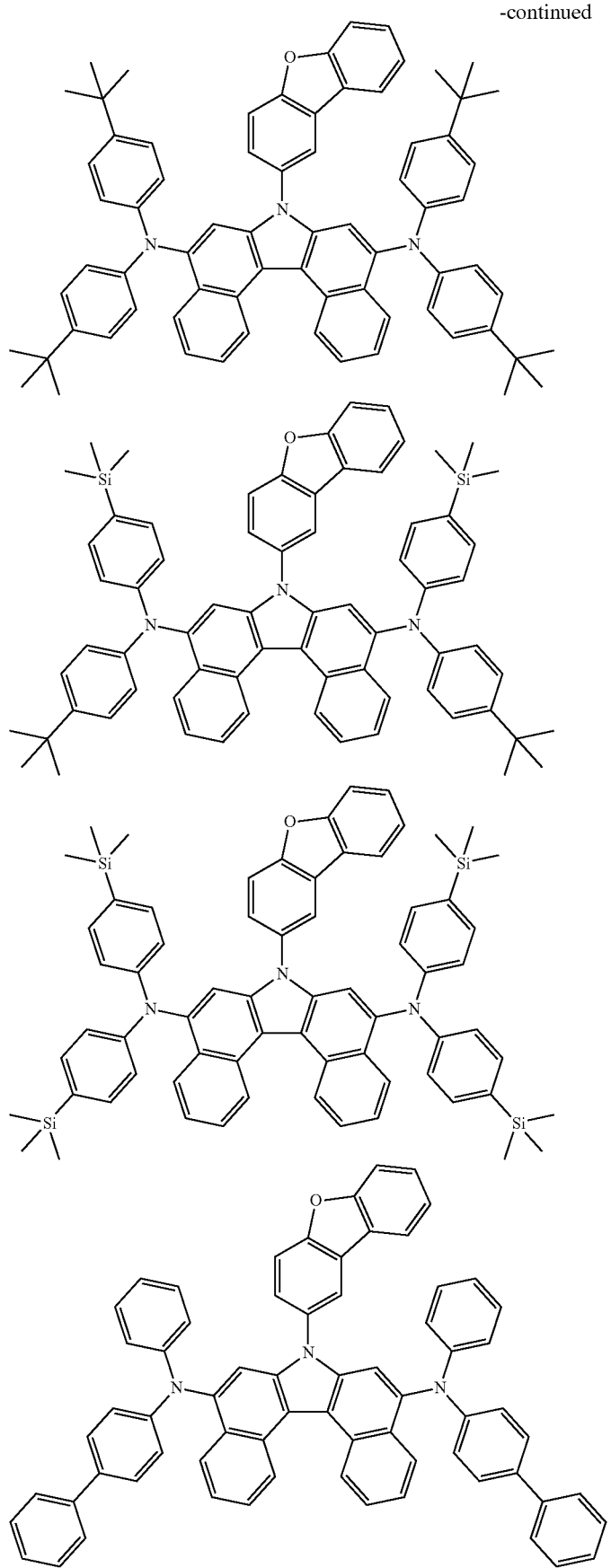

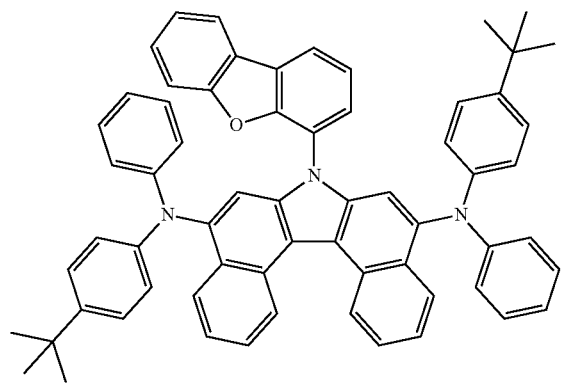
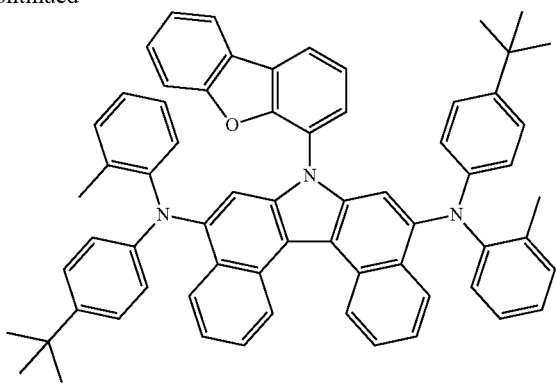
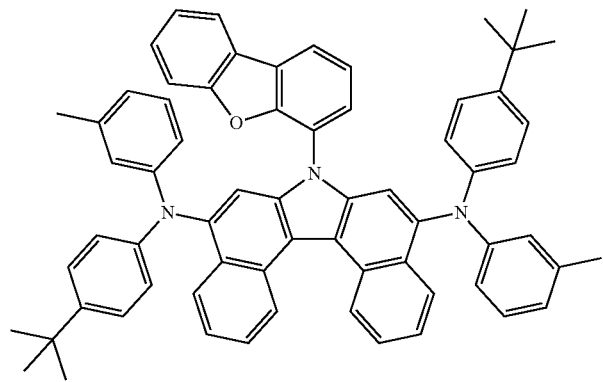
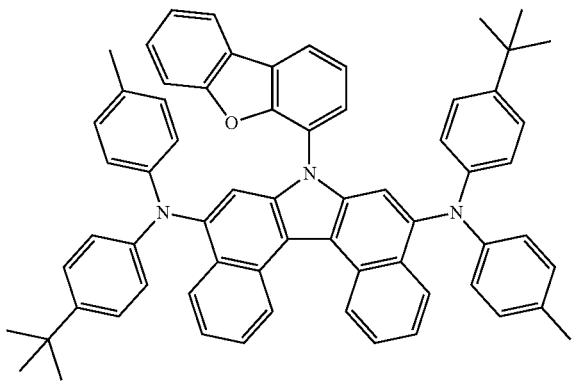
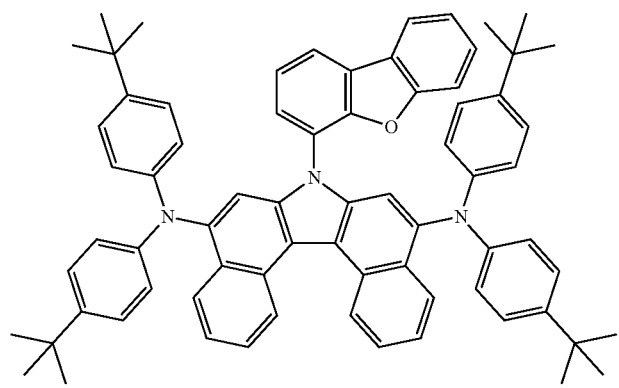
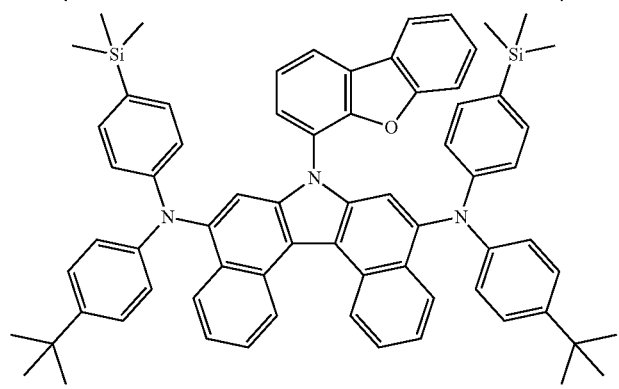

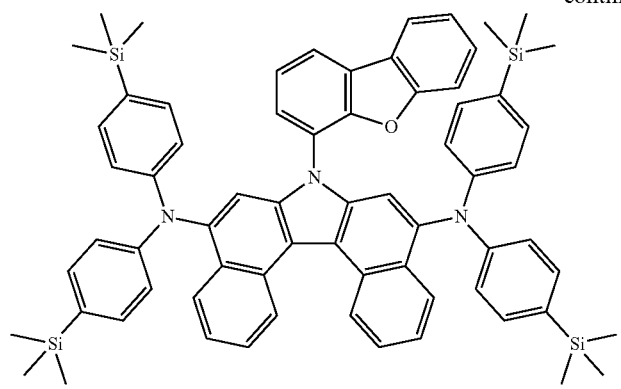
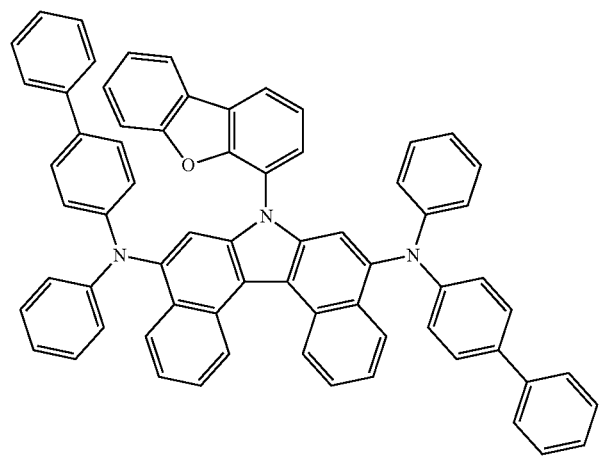
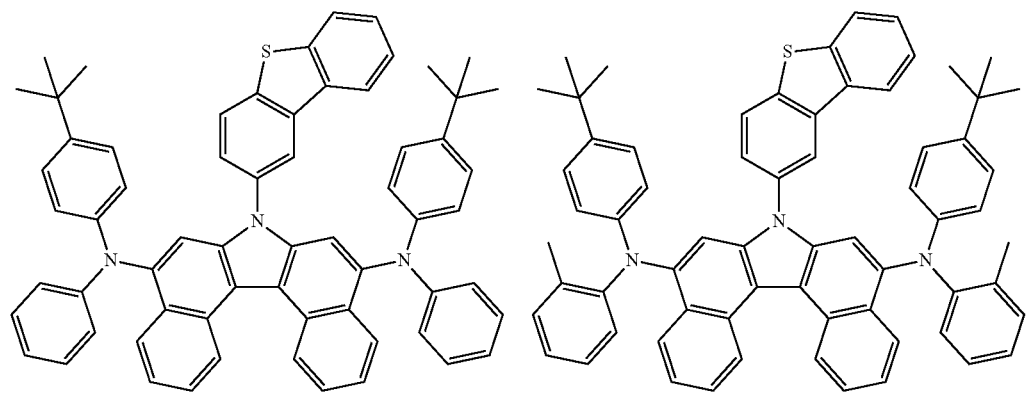
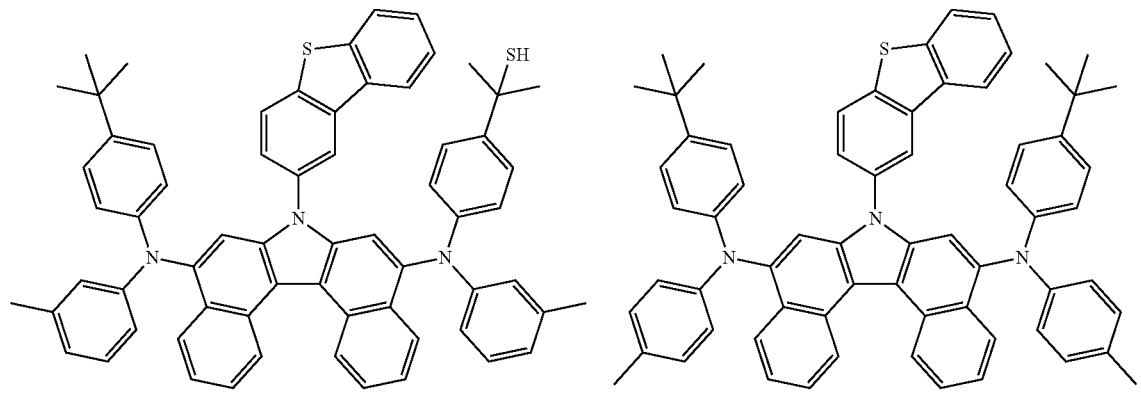

-continued
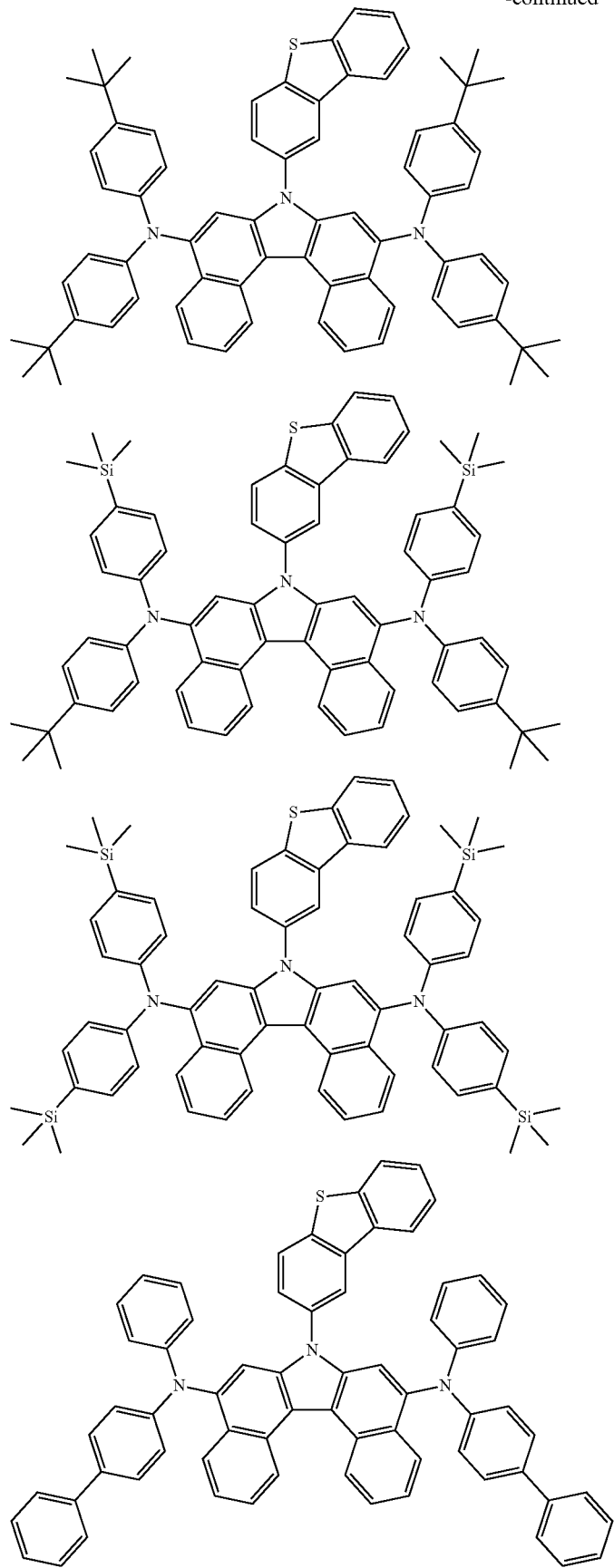

-continued
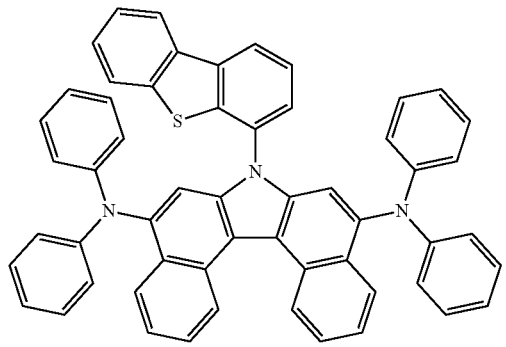
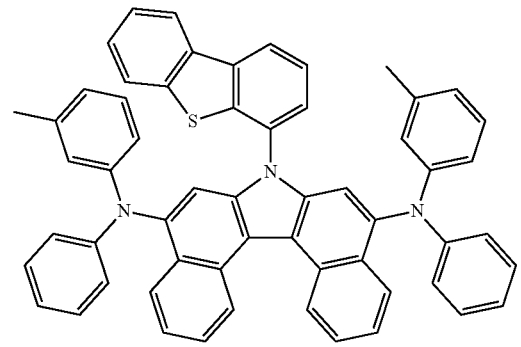
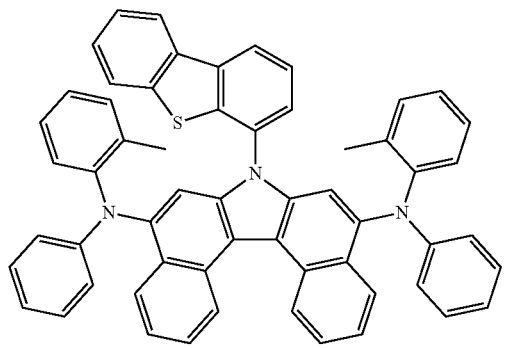
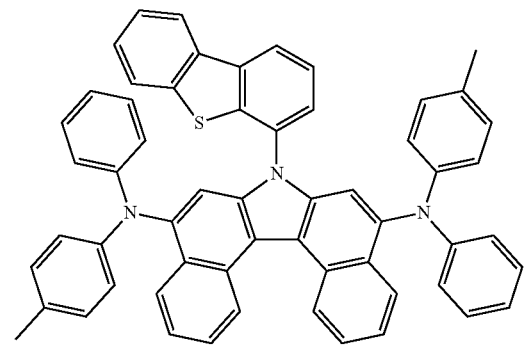
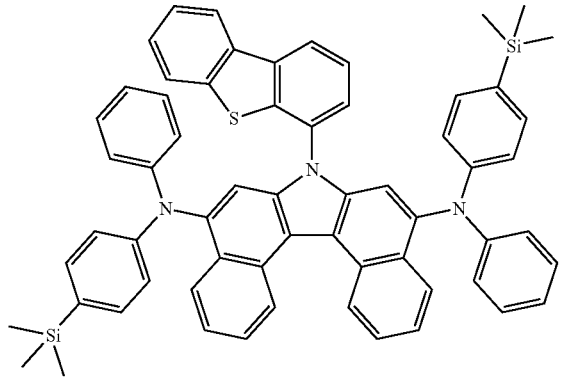
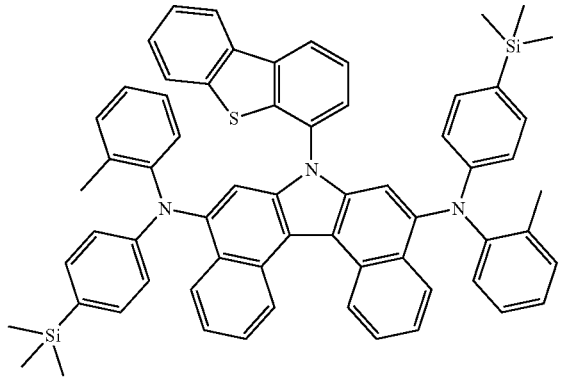
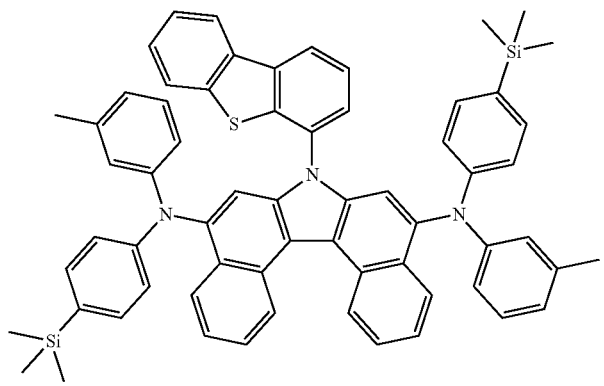
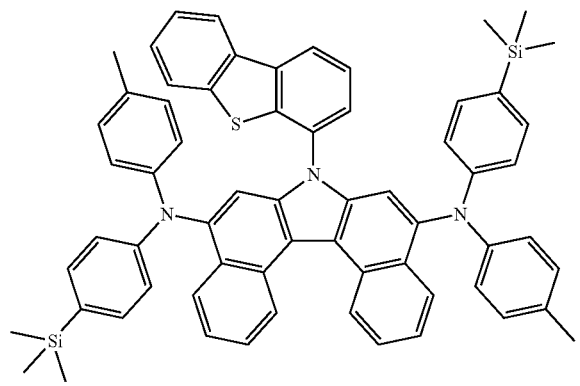

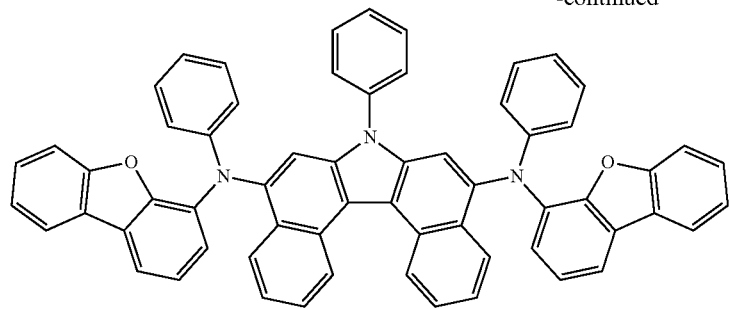
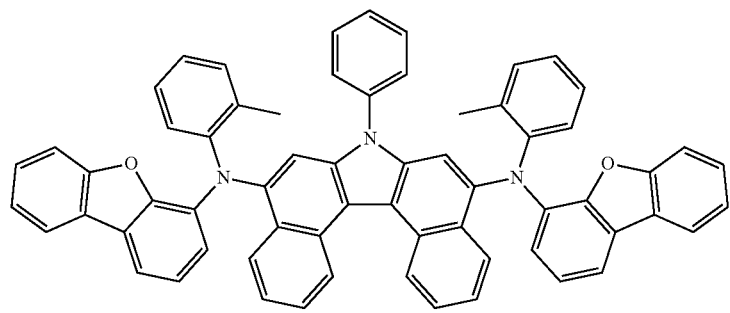
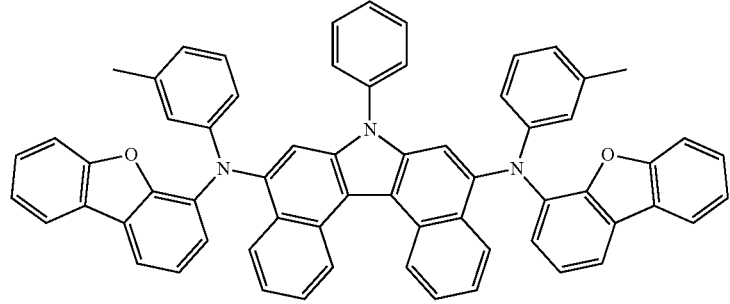
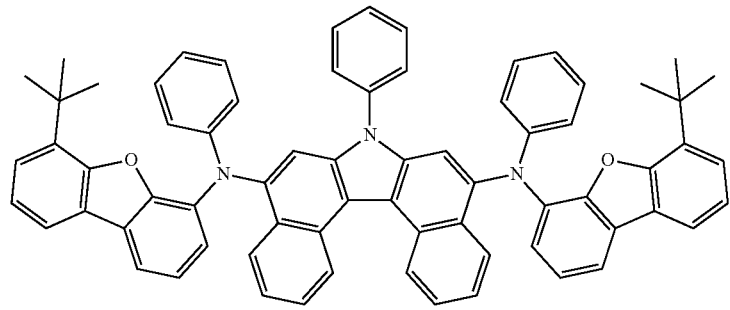
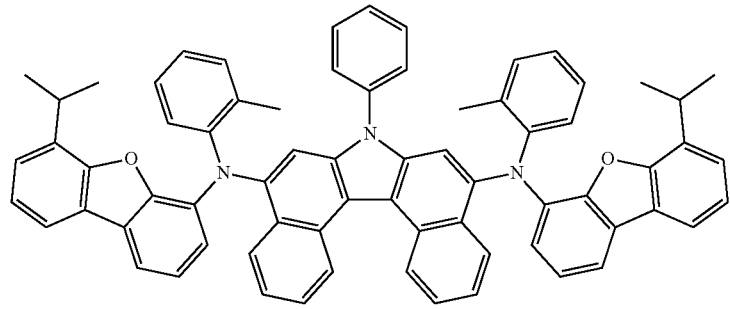

-continued
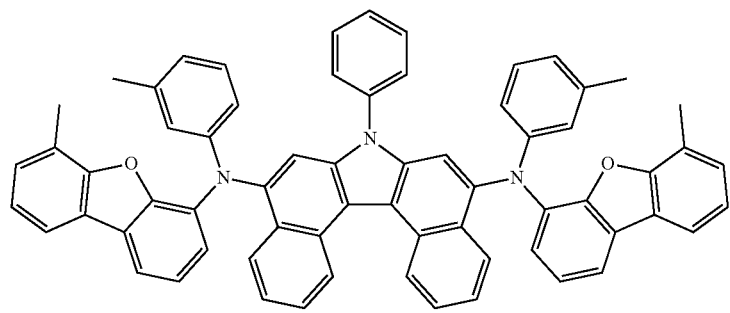
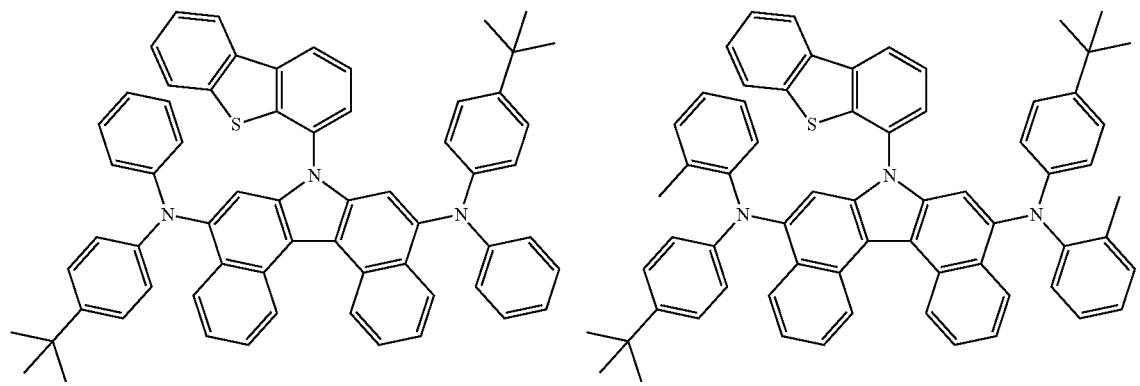
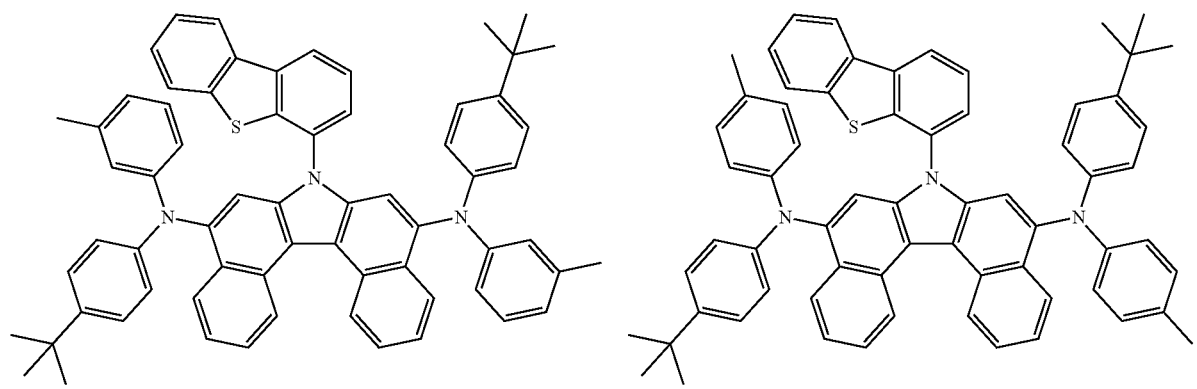
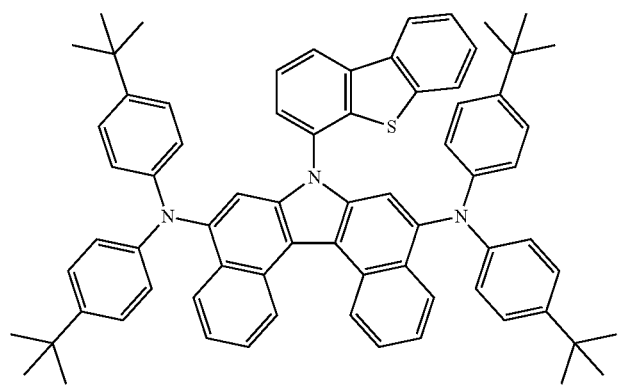

-continued
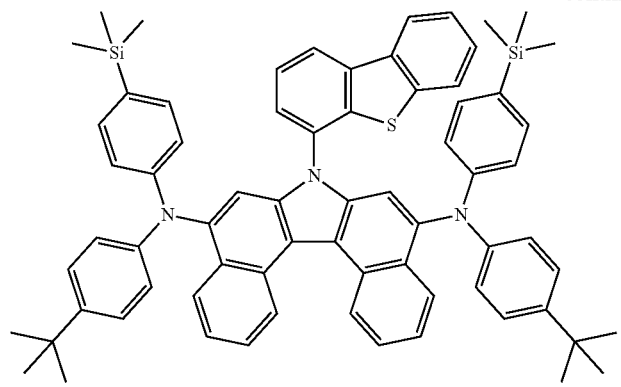
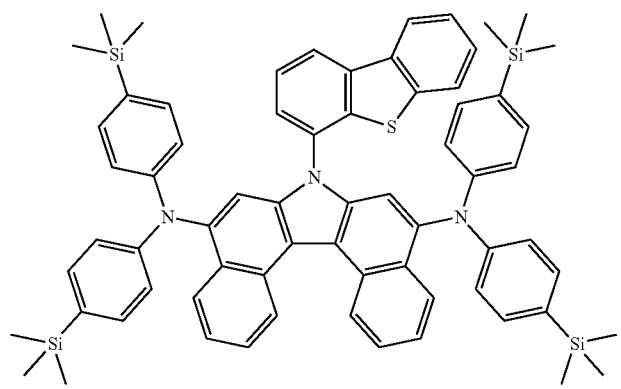
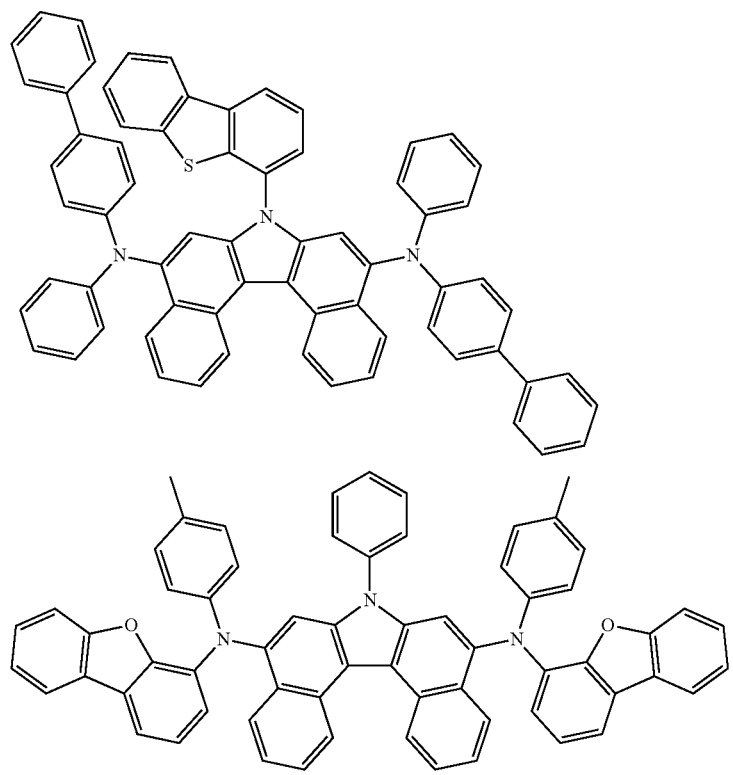

-continued
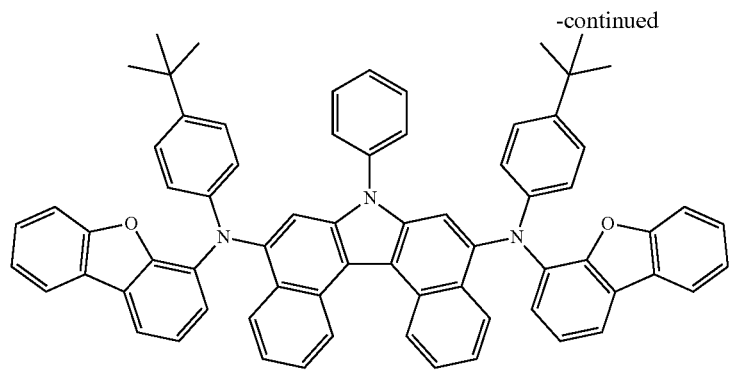
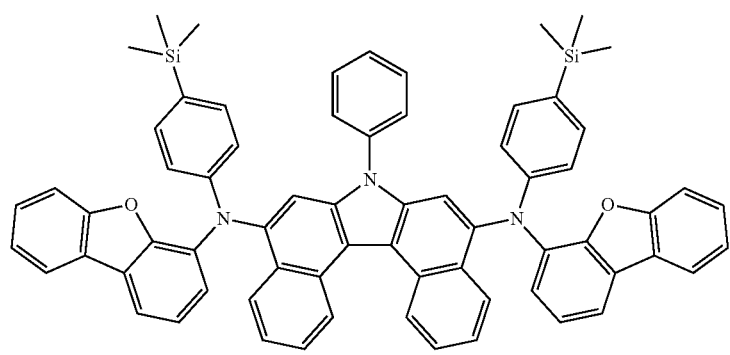
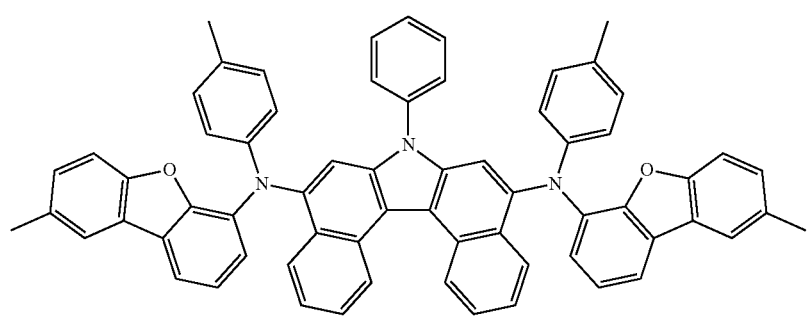
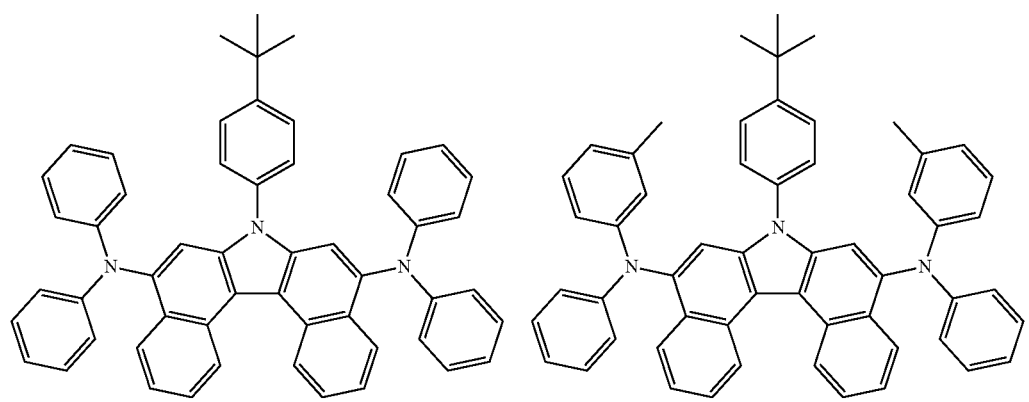

-continued
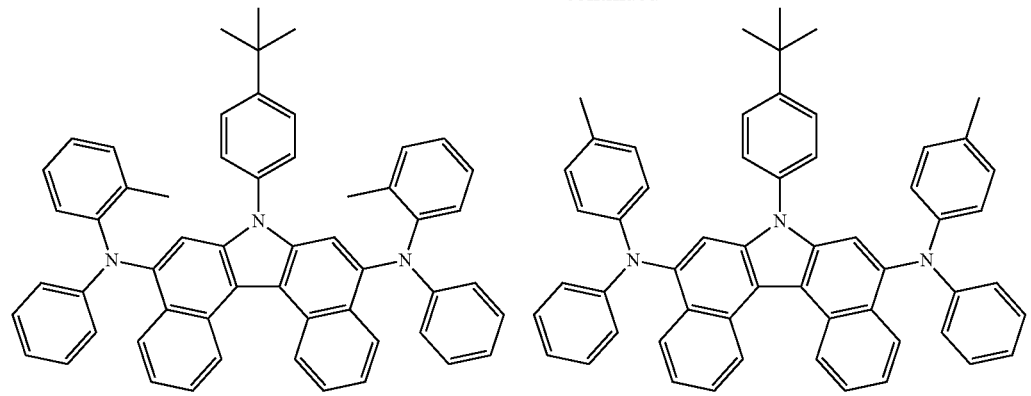
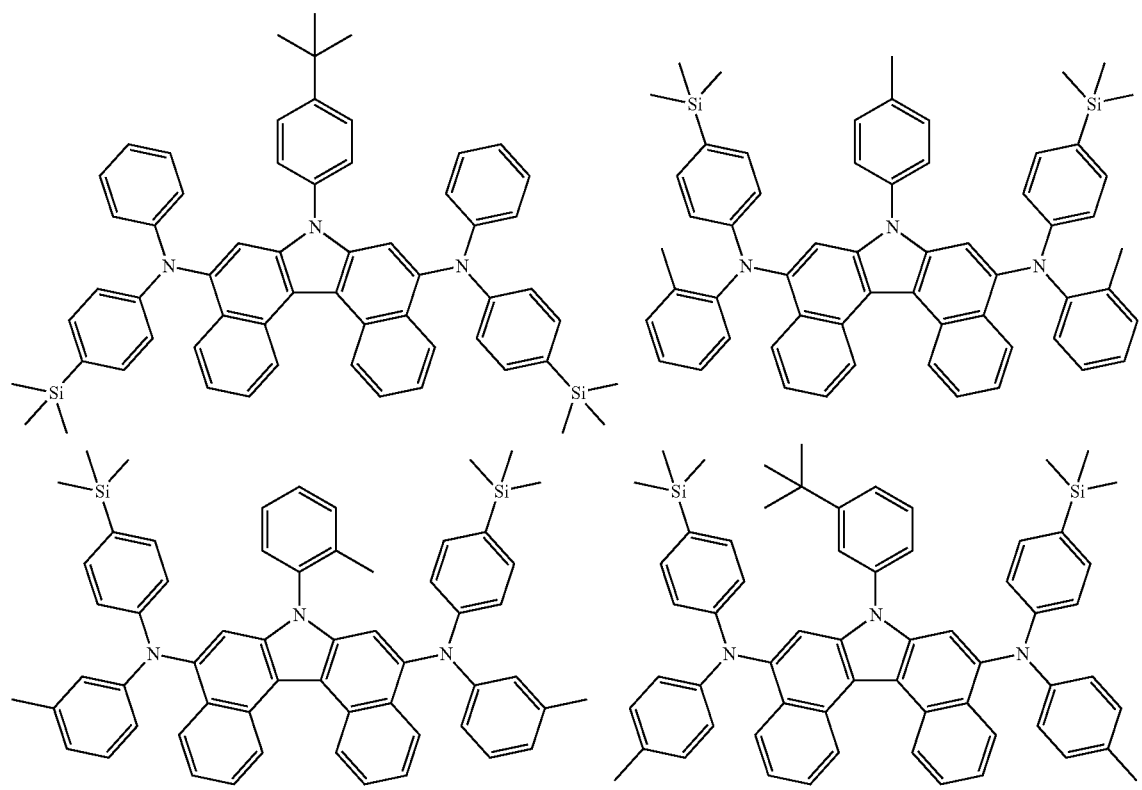
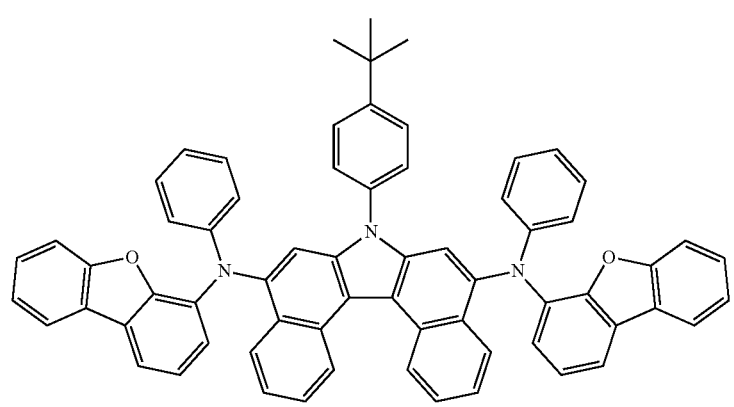

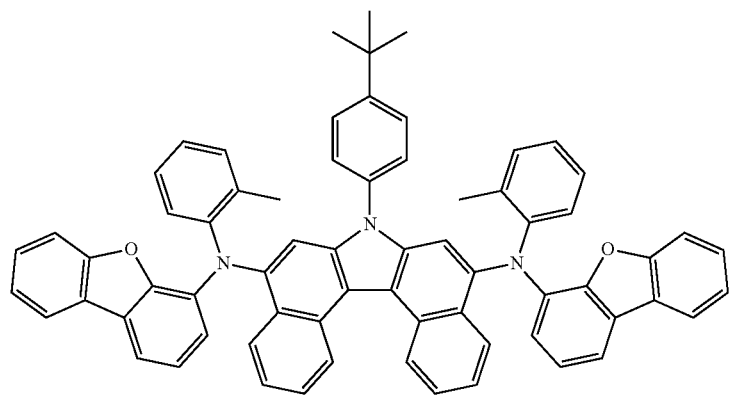
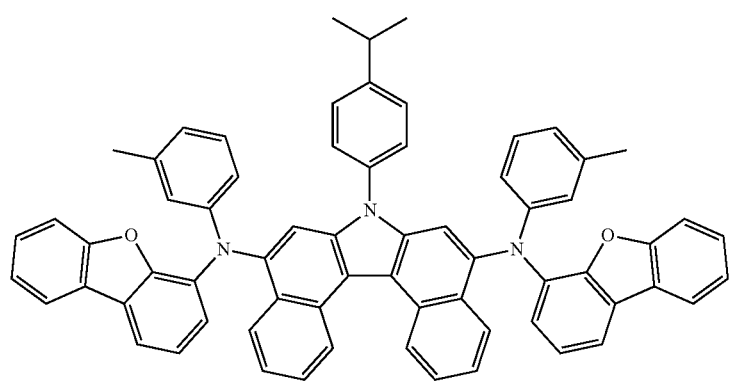
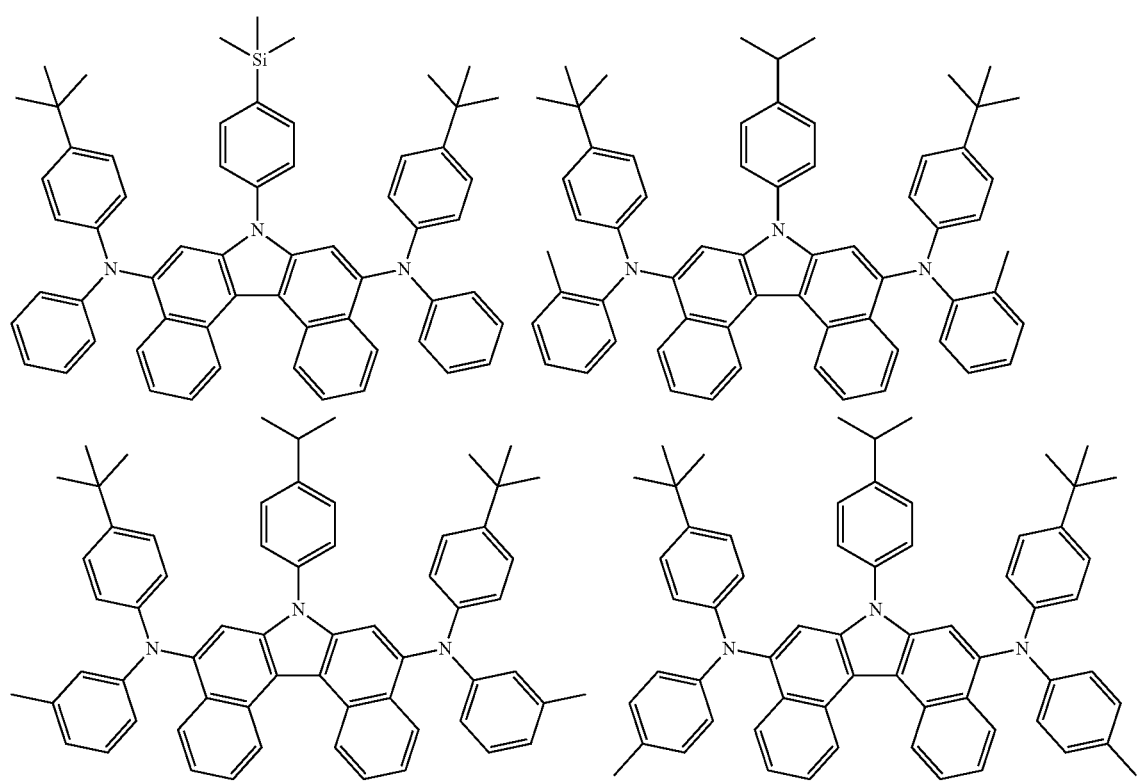

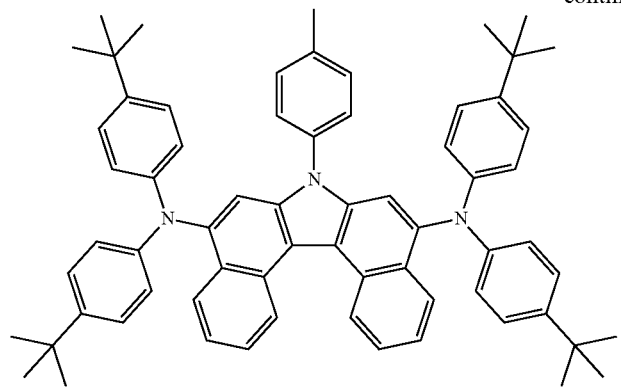
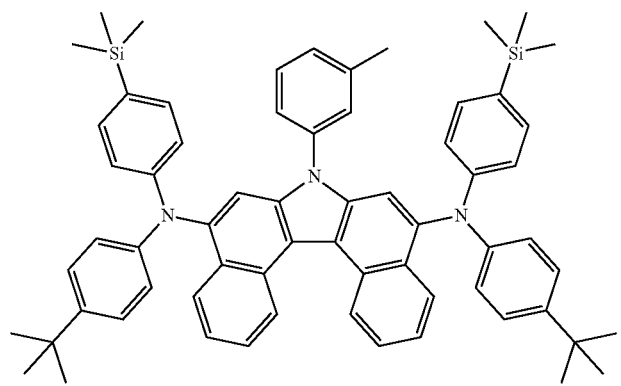
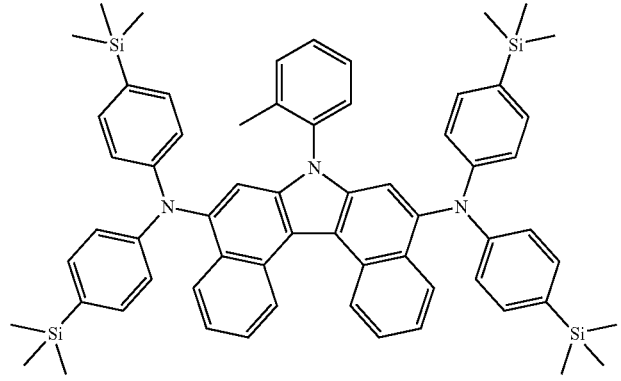
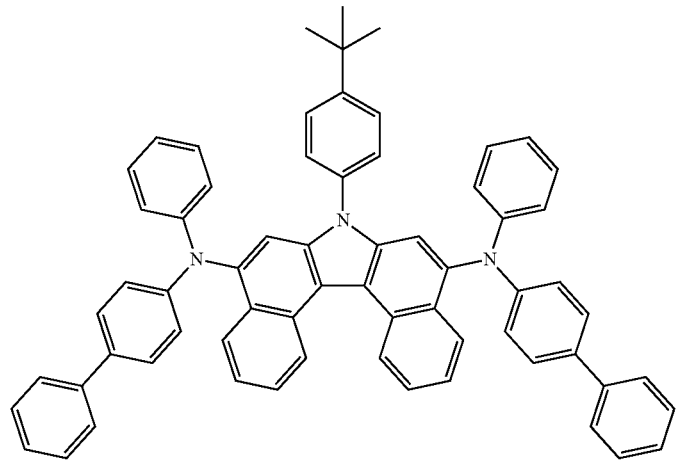

-continued

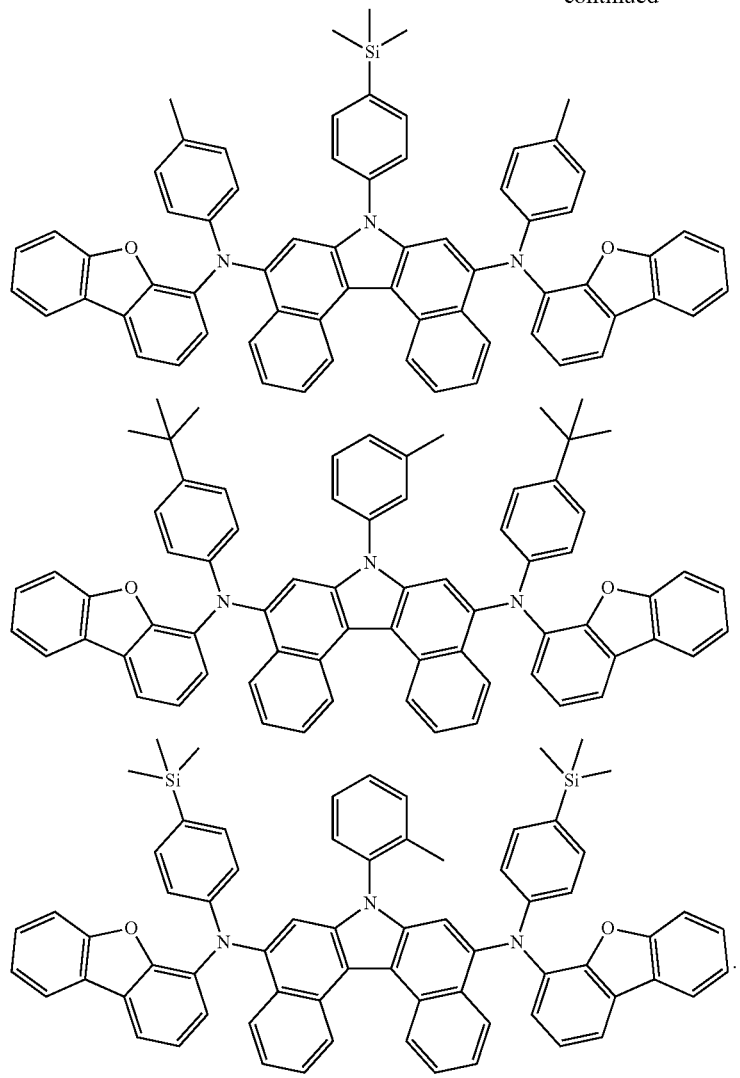

The compound according to one embodiment of the present application can be prepared using a preparation method to describe later.

For example, the compound of Chemical Formula 1 can have its core structure prepared from [Intermediate A] using a Buchwald-Hartwig coupling reaction, a method well known in the art, as in the following Reaction Formula 1 and Reaction Formula 2. Substituents can bond using methods known in the art, and types, positions or the number of the substituents can vary depending on technologies known in the art.

[Reaction Formula 1]

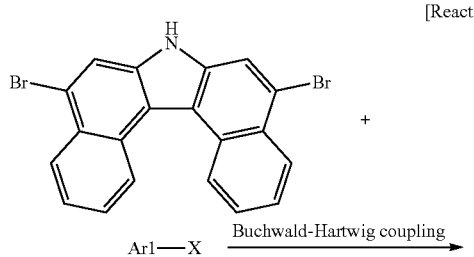

[Reaction Formula 2]

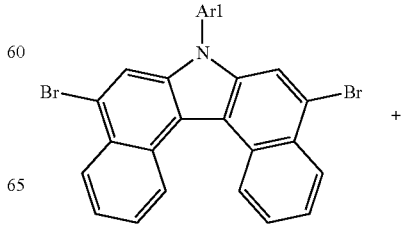

-continued

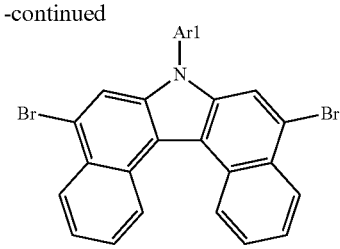

-continued

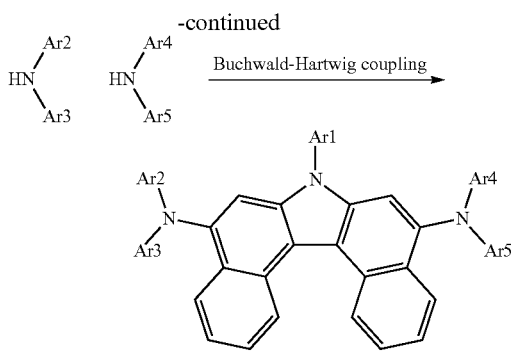

Ar1 to Ar5 of the reaction formulae are as described above.

One embodiment of the present application provides an organic light emitting device including a first electrode; a second electrode provided opposite to the first electrode; and one or more organic material layers provided between the first electrode and the second electrode, wherein one or more layers of the organic material layers include the compound.

In the present specification, a description of one member being placed "on" another member includes not only a case of the one member adjoining the another member but a case of still another member being present between the two members.

In the present specification, a description of a certain part "including" certain constituents means capable of further including other constituents, and does not exclude other constituents unless particularly stated on the contrary.

The organic material layer of the organic light emitting device of the present application can be famed in a single layer structure, but can be formed in a multilayer structure in which two or more organic material layers are laminated. For example, as a typical example of the organic light emitting device of the present disclosure, the organic light emitting device can have a structure including, as the organic material layer, a hole injection layer, a hole transfer layer, a light emitting layer, an electron transfer layer, an electron injection layer and the like. However, the structure of the organic light emitting device is not limited thereto, and can include less numbers of organic material layers.

In one embodiment of the present application, the organic material layer includes a light emitting layer, and the light emitting layer includes the compound.

In one embodiment of the present application, the organic material layer includes a hole injection layer or a hole transfer layer, and the hole injection layer or the hole transfer layer includes the compound.

In another embodiment, the organic material layer includes a light emitting layer, and the light emitting layer includes the compound.

In one embodiment of the present application, the organic material layer includes an electron transfer layer or an electron injection layer, and the electron transfer layer or the electron injection layer includes the compound.

In one embodiment of the present application, the organic material layer includes an electron injection layer, an electron transfer layer, or an electron injection and transfer layer, and the electron injection layer, the electron transfer layer, or the electron injection and transfer layer includes the compound.

In one embodiment of the present application, the organic material layer includes an electron blocking layer or a hole blocking layer, and the electron blocking layer or the hole blocking layer includes the compound.

In one embodiment of the present application, the organic material layer includes a hole injection layer, a hole transfer layer, or a hole injection and transfer layer, and the hole injection layer, the hole transfer layer, or the hole injection and transfer layer includes the compound.

In one embodiment of the present application, the organic material layer includes a light emitting layer, and the light emitting layer includes the compound as a blue dopant.

In one embodiment of the present application, the light emitting layer further includes a compound including anthracene as a host.

In one embodiment of the present application, the host is the following Chemical Formula A:

[Chemical Formula A]

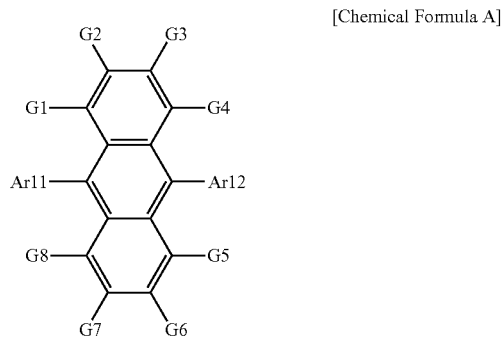

In Chemical Formula A:

Ar11 and Ar12 are the same as or different from each other, and each independently is a substituted or unsubstituted aryl group, or a substituted or unsubstituted heterocyclic group; and G1 to G8 are the same as or different from each other, and each independently is hydrogen, a substituted or unsubstituted monocyclic aryl group, or a substituted or unsubstituted polycyclic aryl group.

In one embodiment of the present specification, G1 to G8 are hydrogen.

In one embodiment of the present specification, Ar11 and Ar12 are the same as or different from each other, and each independently is a substituted or unsubstituted phenyl group, a substituted or unsubstituted naphthyl group, a substituted or unsubstituted biphenyl group, a substituted or unsubstituted a phenanthrene group, a substituted or unsubstituted dibenzofuran group, or a substituted or unsubstituted benzonaphthofuran group.

In one embodiment of the present specification, Ar11 and Ar12 are the same as or different from each other, and each independently is a phenyl group unsubstituted or substituted with a phenyl group or a naphthyl group; a naphthyl group unsubstituted or substituted with a phenyl group or a naphthyl group; a biphenyl group unsubstituted or substituted with a phenyl group or a naphthyl group; a phenanthrene group unsubstituted or substituted with a phenyl group or a naphthyl group; a dibenzofuran group unsubstituted or substituted with a phenyl group or a naphthyl group; or a benzonaphthofuran group unsubstituted or substituted with a phenyl group or a naphthyl group.

In one embodiment of the present specification, Ar11 and Ar12 are the same as or different from each other, and each independently is a phenyl group unsubstituted or substituted with a naphthyl group, a naphthyl group unsubstituted or substituted with a phenyl group, a biphenyl group, a phenanthrene group, a dibenzofuran group, or a benzonaphthofuran group.

In one embodiment of the present specification, Chemical Formula A is the following Chemical Formula A-1:

[Chemical Formula A-1]

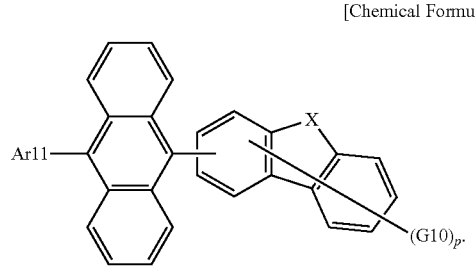

In Chemical Formula A-1:

Ar11 is a substituted or unsubstituted aryl group;

X is O or S;

G10 is hydrogen, a substituted or unsubstituted aryl group, or a substituted or unsubstituted heterocyclic group, or adjacent two or more G10s bond to each other to form a substituted or unsubstituted ring; and p is an integer of 0 to 4, and when p is 2 or greater, the G10s are the same as or different from each other.

In one embodiment of the present specification, Chemical Formula A is selected from among the following compounds:

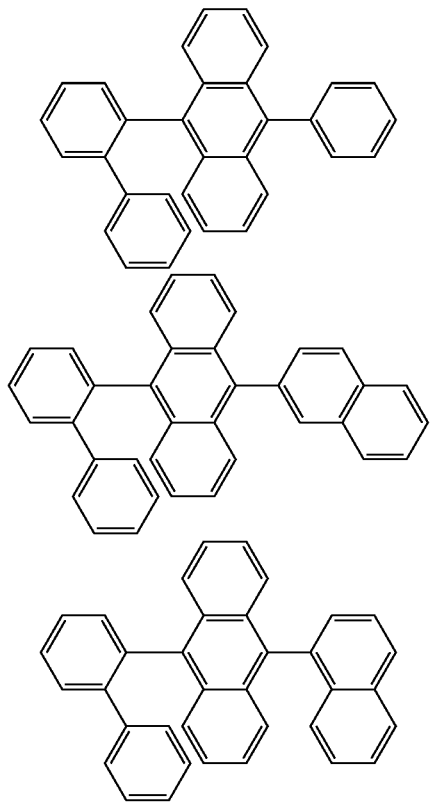

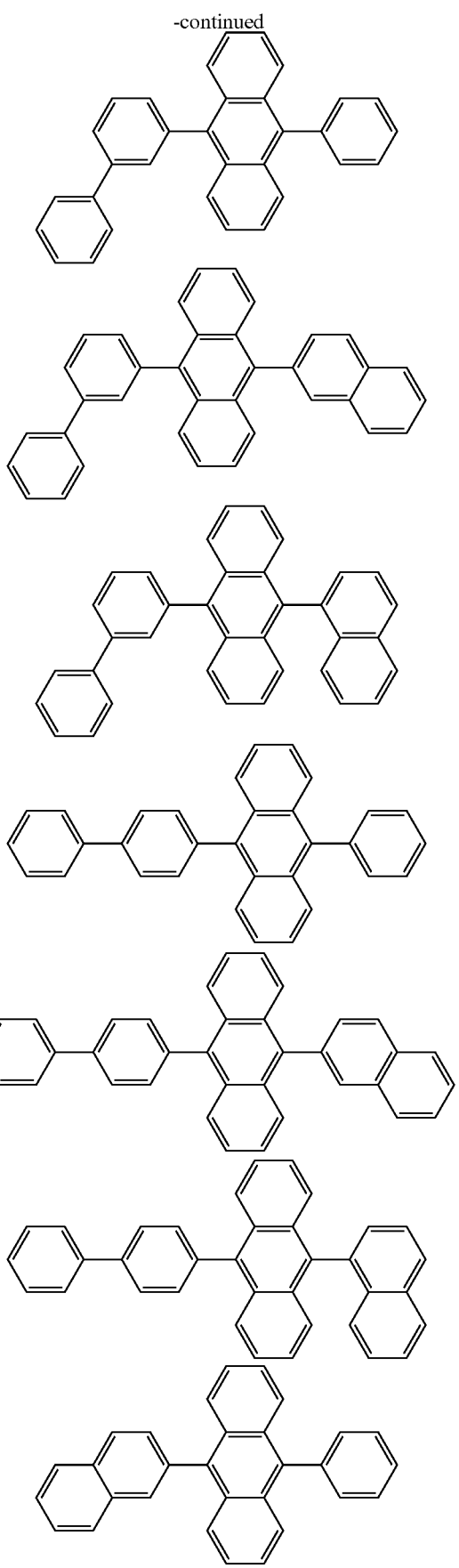

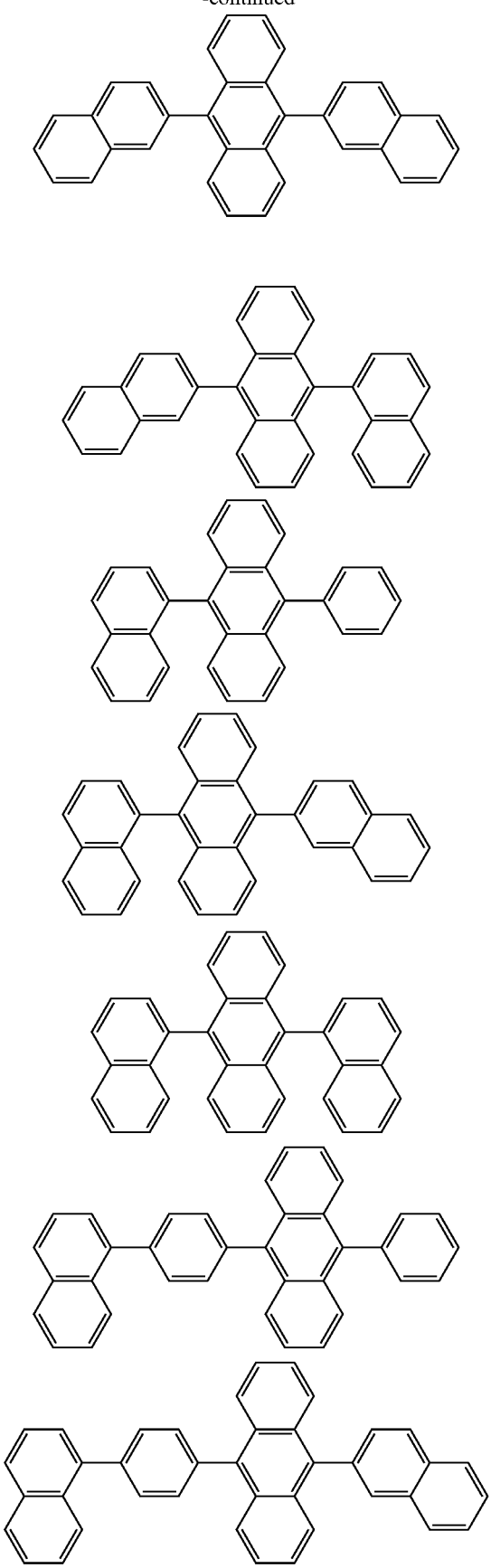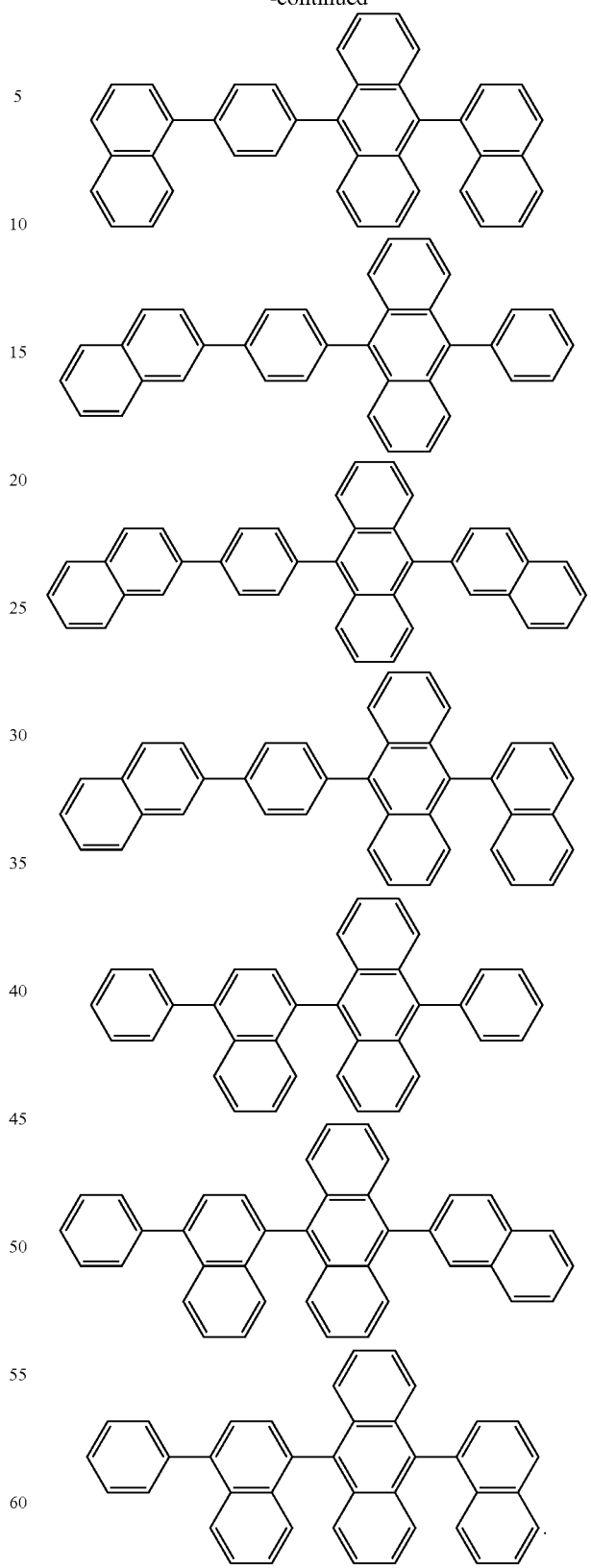
In one embodiment of the present specification, in Chemical Formula A-1, Ar11 is a substituted or unsubstituted phenyl group, a substituted or unsubstituted naphthyl group, a substituted or unsubstituted biphenyl group, or a substituted or unsubstituted a phenanthrene group.

In one embodiment of the present specification, in Chemical Formula A-1, Ar11 is a phenyl group unsubstituted or substituted with an aryl group, a naphthyl group unsubstituted or substituted with an aryl group, a biphenyl group unsubstituted or substituted with an aryl group, or a phenanthrene group unsubstituted or substituted with an aryl group.

In one embodiment of the present specification, in Chemical Formula A-1, Ar11 is a phenyl group unsubstituted or substituted with a naphthyl group, a naphthyl group unsubstituted or substituted with a phenyl group, a biphenyl group, or a phenanthrene group.

In one embodiment of the present specification, in Chemical Formula A-1, G11 is hydrogen, or two or more adjacent G11s bond to each other to form a substituted or unsubstituted aromatic ring.

In one embodiment of the present specification, in Chemical Formula A-1, G11 is hydrogen, or two or more adjacent G11s bond to each other to form a substituted or unsubstituted benzene ring.

In one embodiment of the present specification, in Chemical Formula A-1, G11 is hydrogen, or two or more adjacent G11s bond to each other to form an aromatic ring.

In one embodiment of the present specification, in Chemical Formula A-1, G11 is hydrogen, or two or more adjacent G11s bond to each other to form a benzene ring.

In one embodiment of the present specification, Chemical Formula A-1 is selected from among the following compounds:

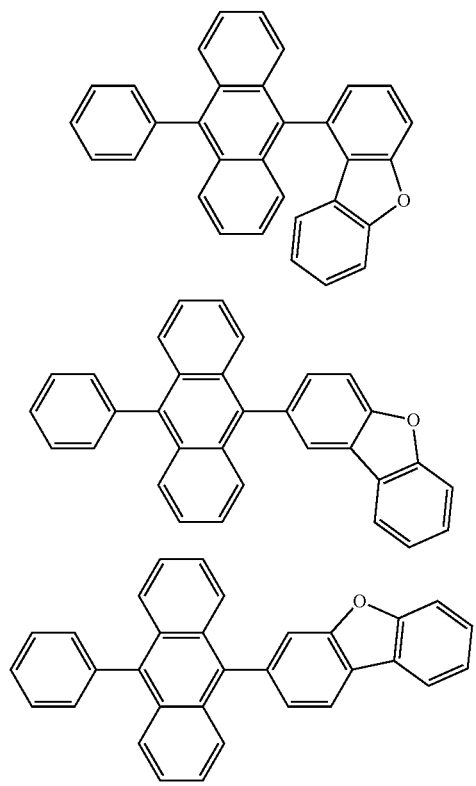

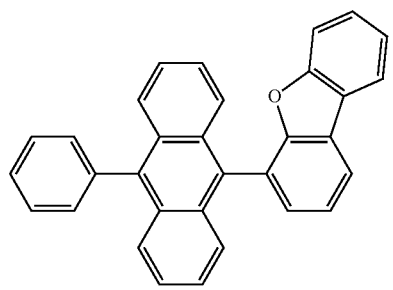

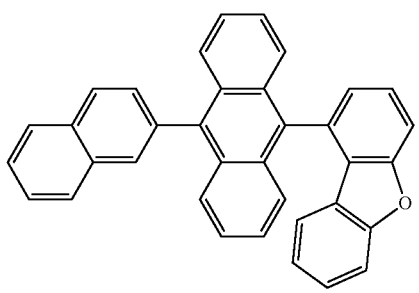

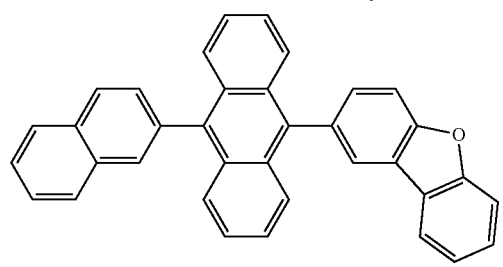

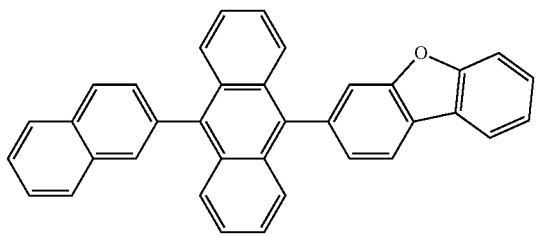

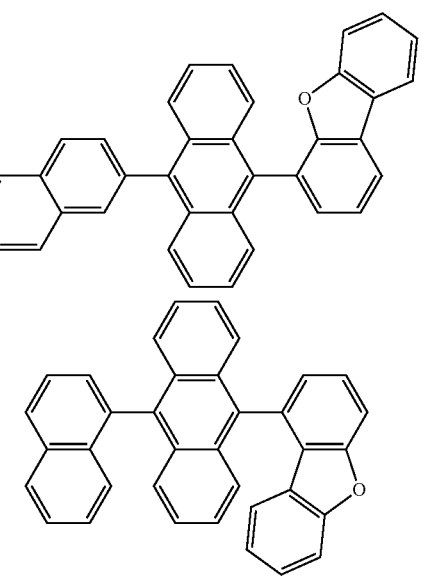

-continued
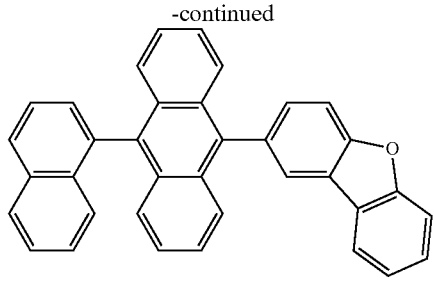
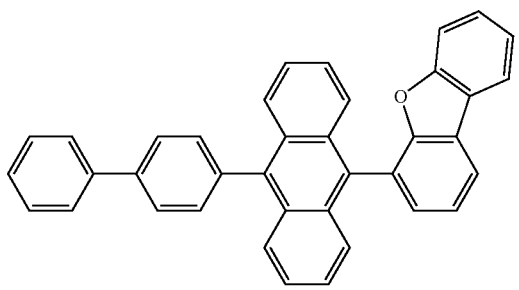
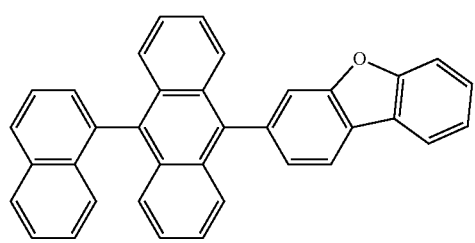
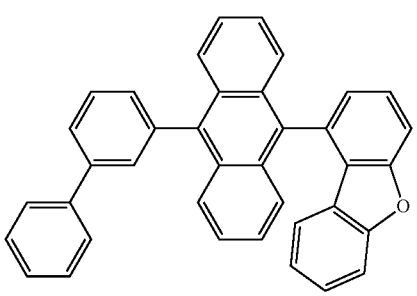
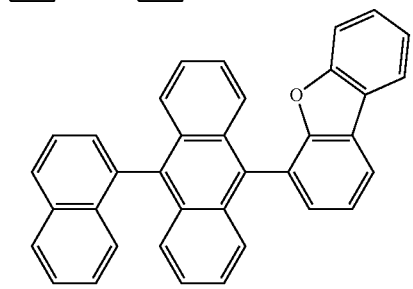
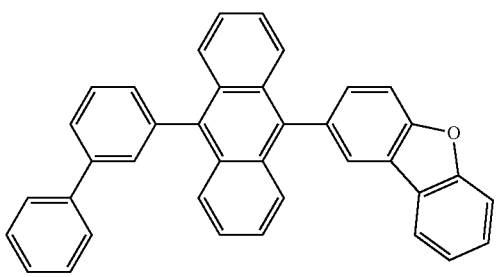
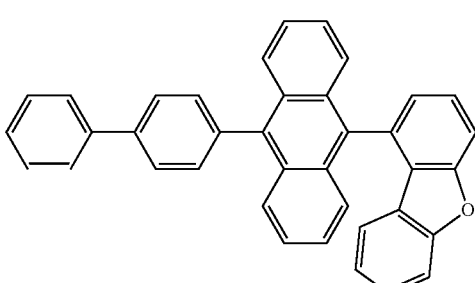
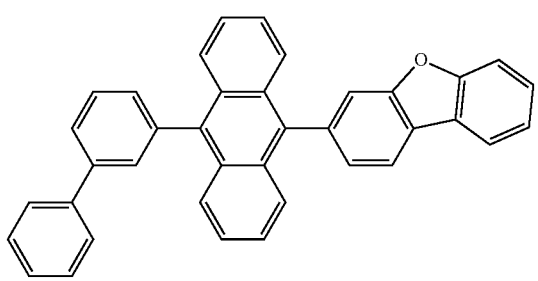
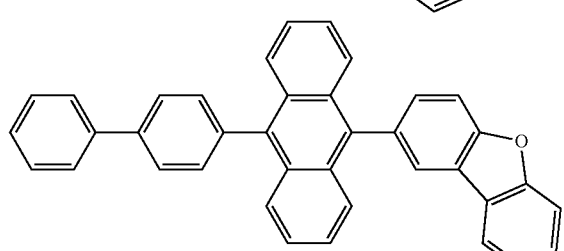
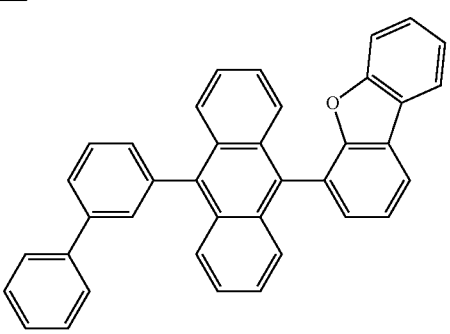
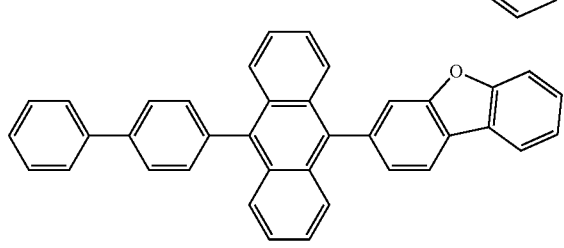

81
-continued
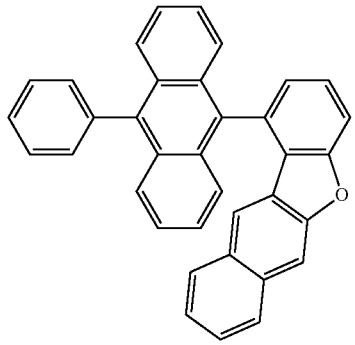
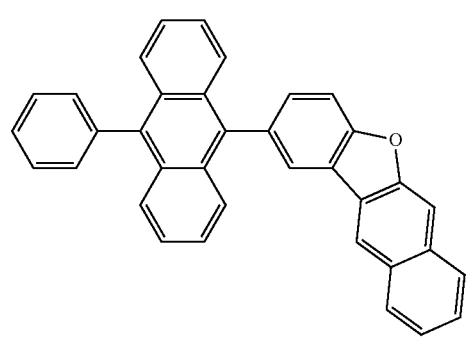
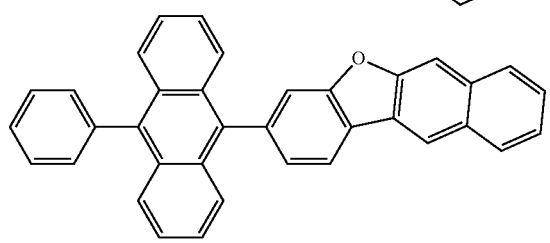
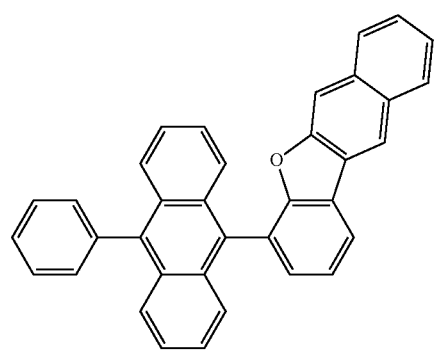
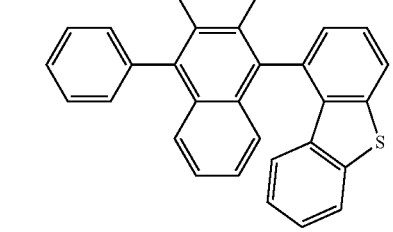
82
-continued
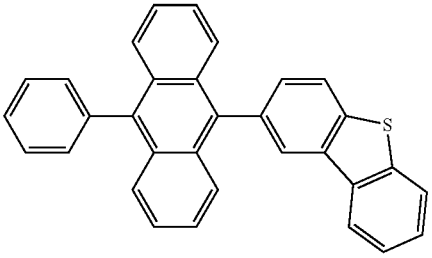
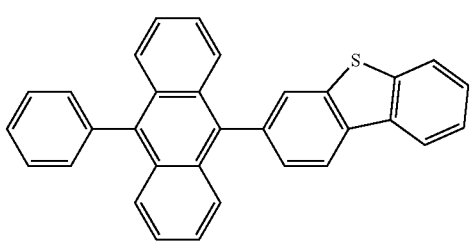
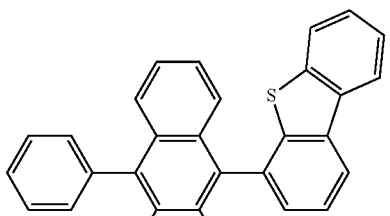
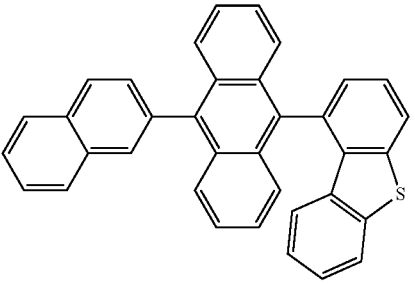
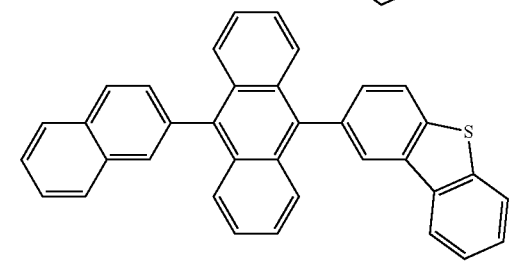
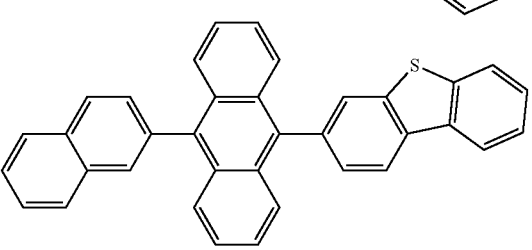

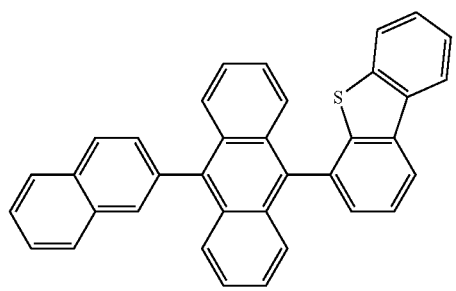
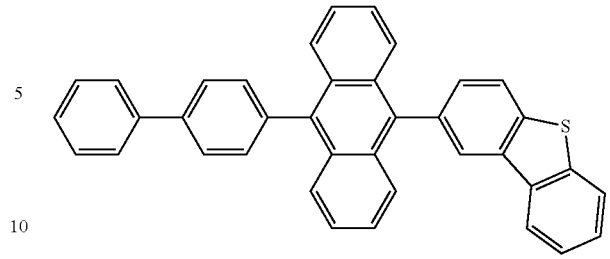
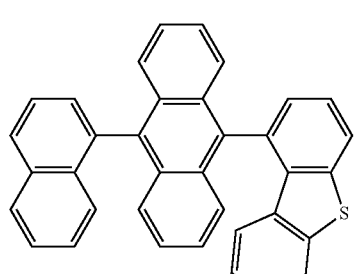
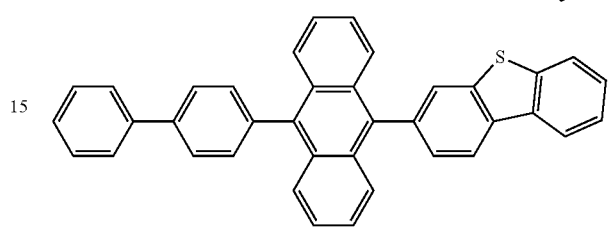
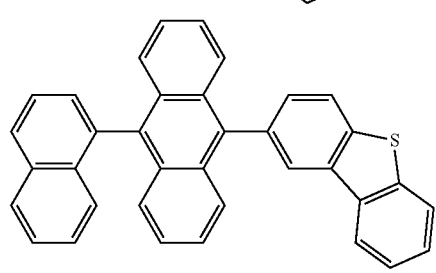
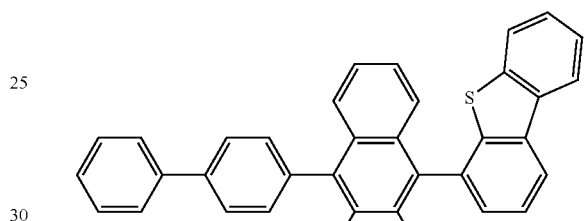
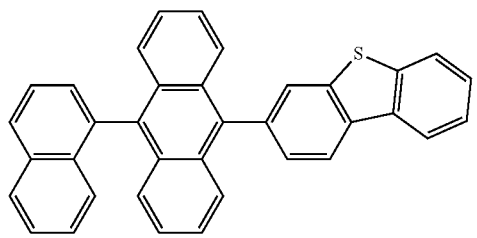
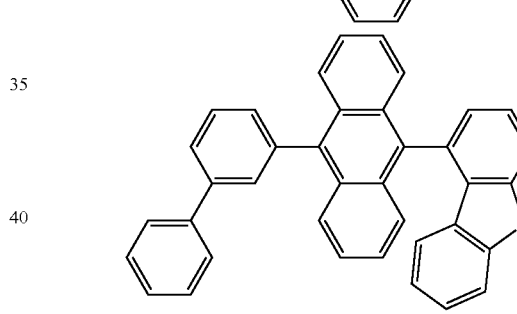
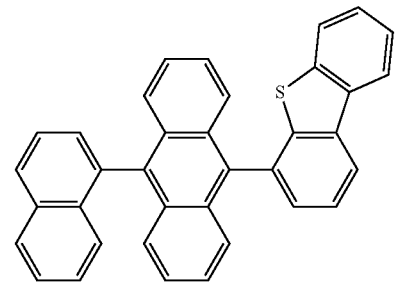
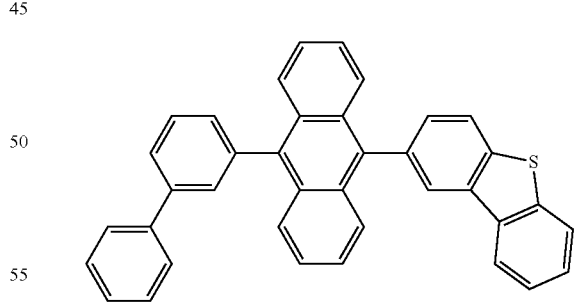
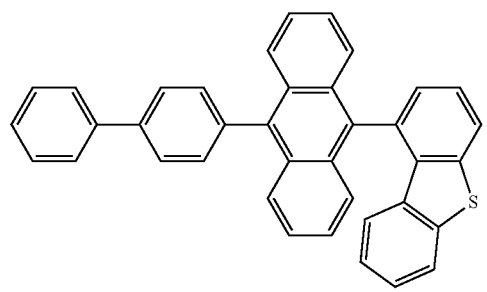
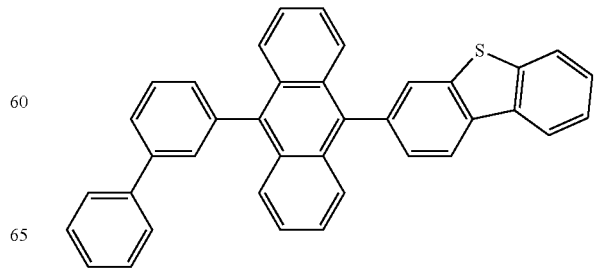

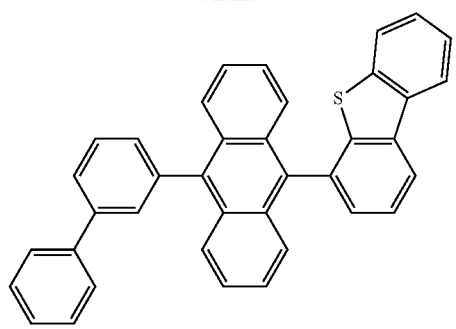
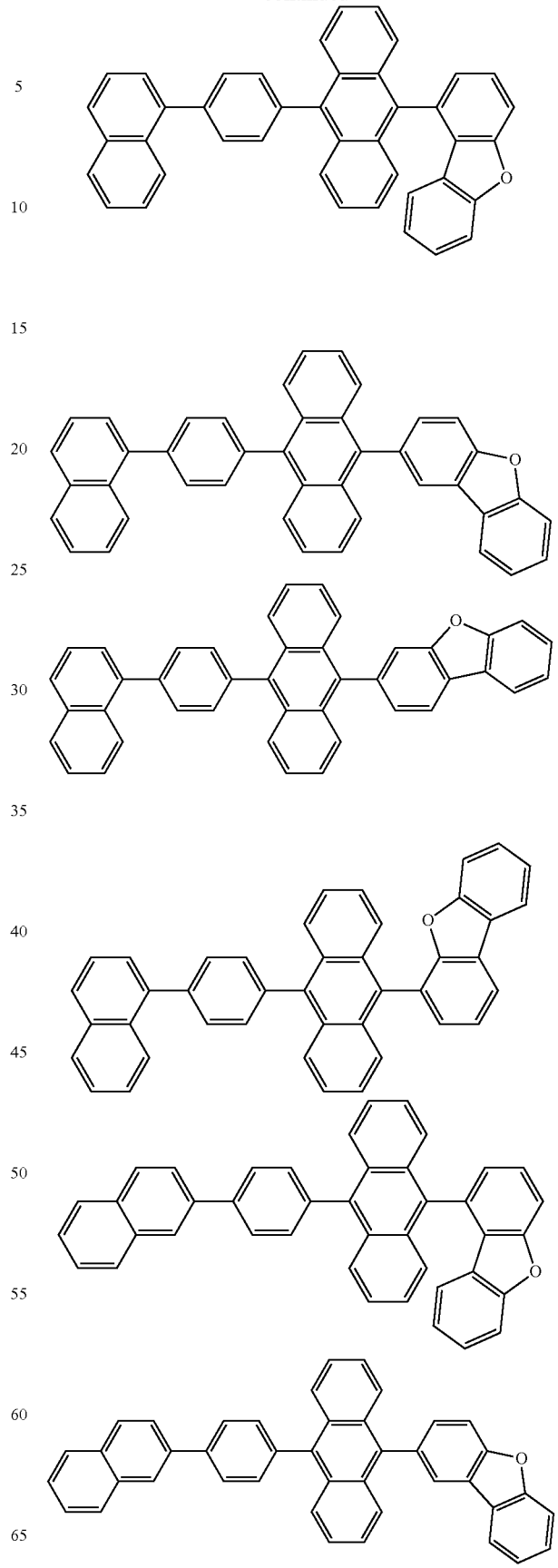

-continued
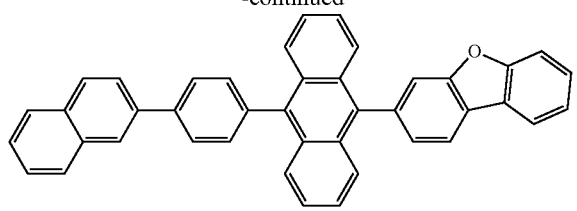
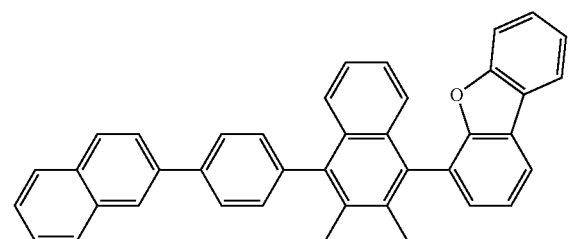
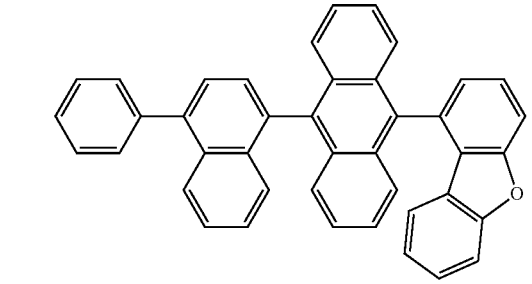
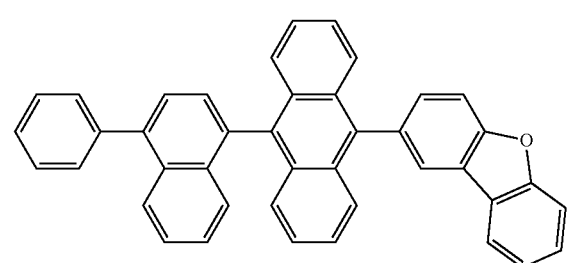
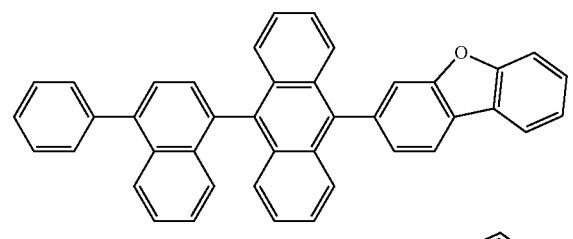
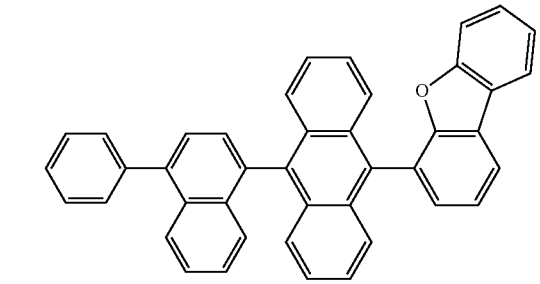
-continued
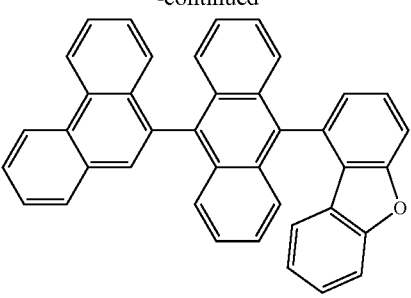
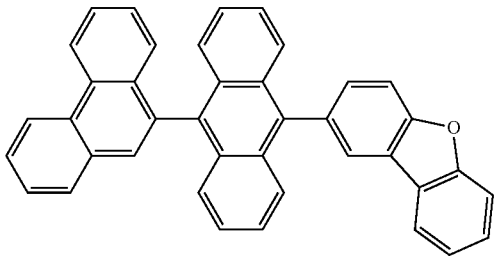
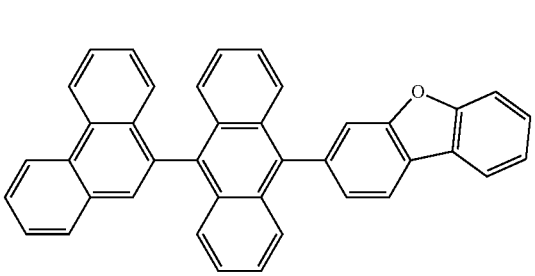
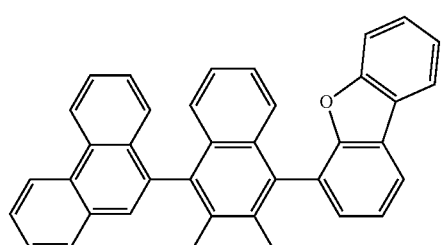
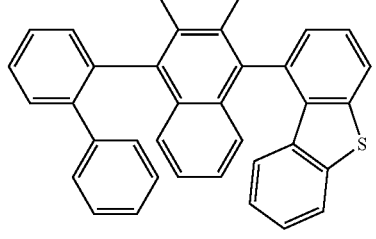
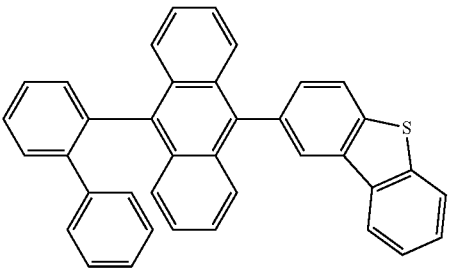

-continued
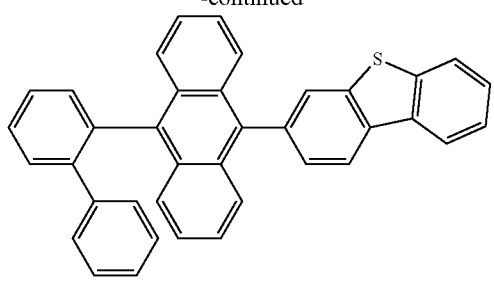
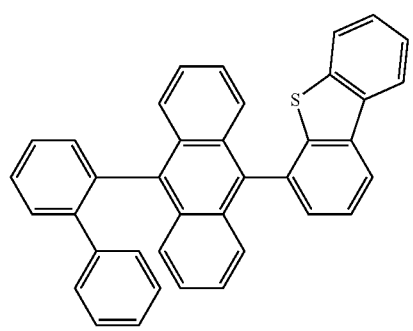
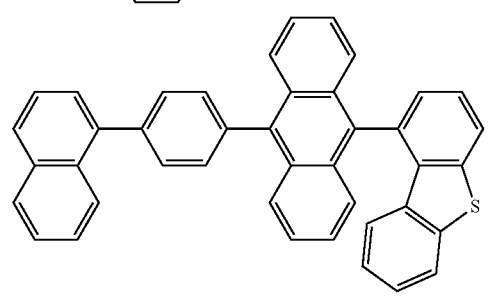
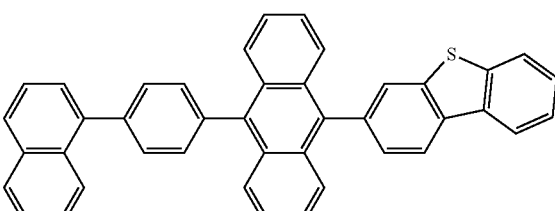
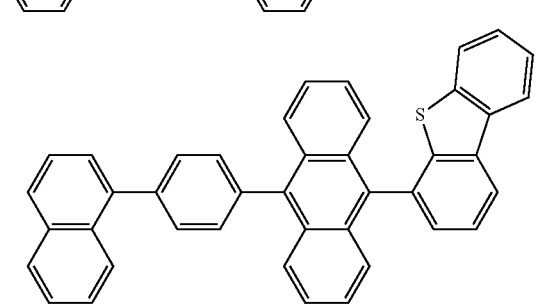
-continued
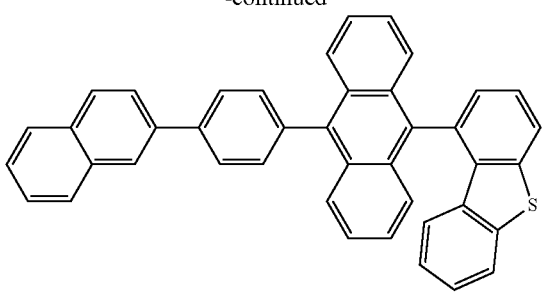
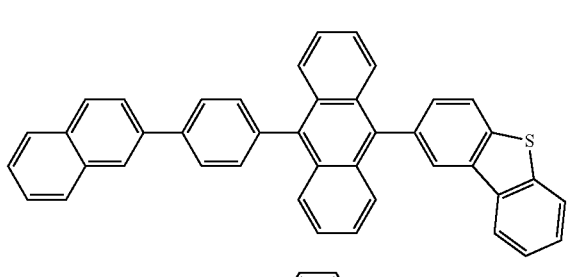
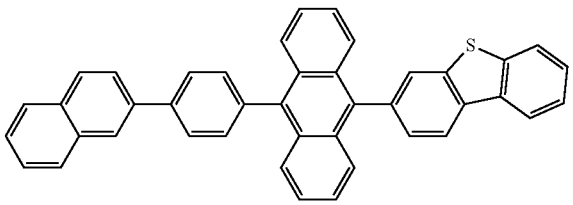
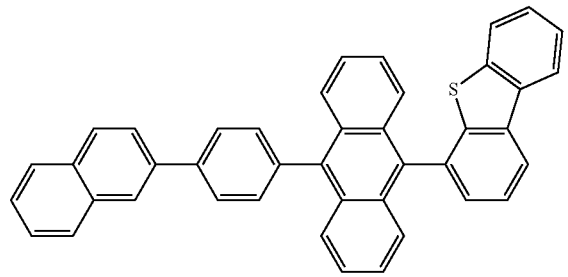
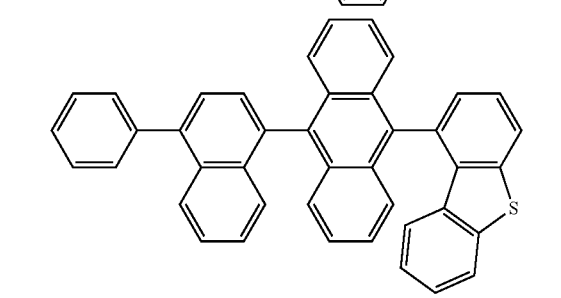
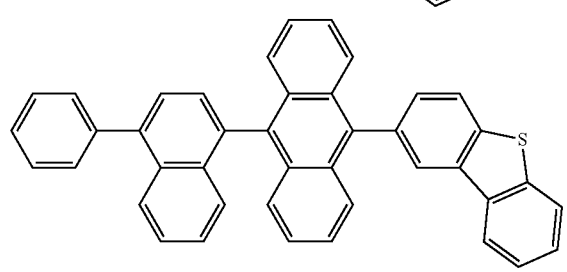

-continued

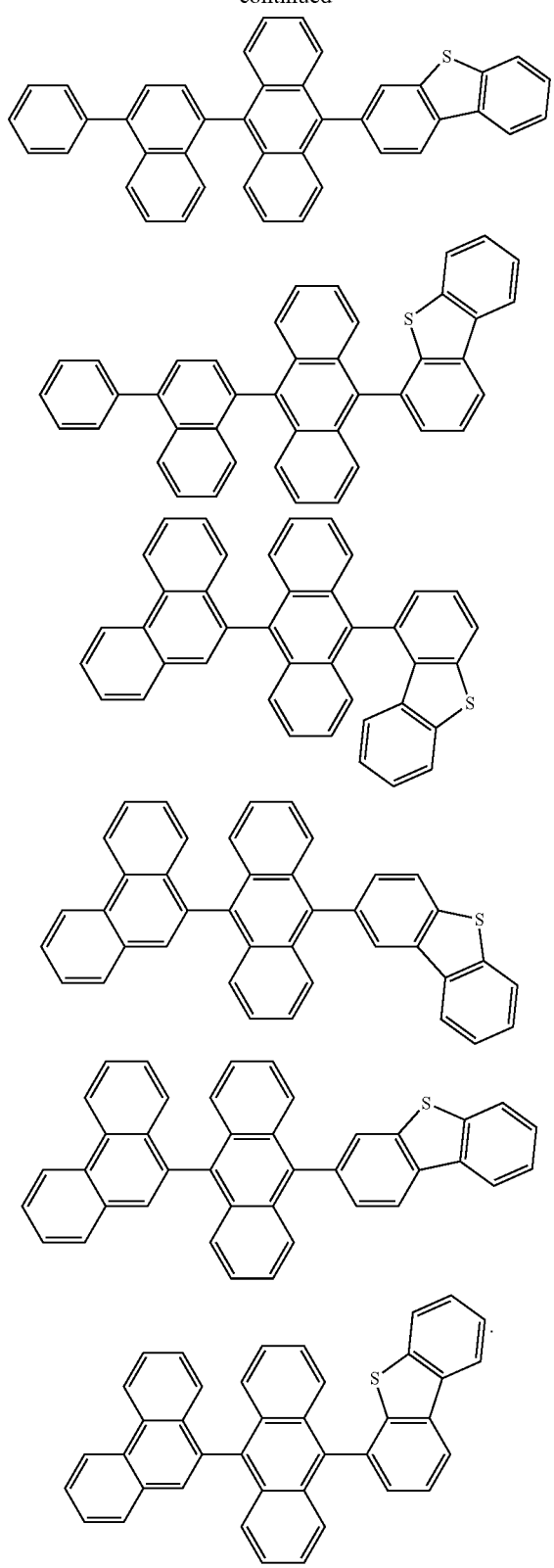

In one embodiment of the present application, the compound of Chemical Formula 1 and the host compound of Chemical Formula A have a weight ratio of from 1:2 to 1:100.

In one embodiment of the present application, the organic material layer including the compound of Chemical Formula 1 has a thickness of from 10 Å to 500 Å.

The organic light emitting device includes a first electrode; a second electrode provided opposite to the first electrode; a light emitting layer provided between the first electrode and the second electrode; and two or more organic material layers provided between the light emitting layer and the first electrode, or between the light emitting layer and the second electrode, and at least one of the two or more organic material layers includes the compound.

In one embodiment of the present application, as the two or more organic material layers, two or more can be selected from the group consisting of an electron transfer layer, an electron injection layer, a layer carrying out electron transfer and electron injection at the same time, and a hole blocking layer.

In one embodiment of the present application, the organic material layer includes two or more electron transfer layers, and at least one of the two or more electron transfer layers includes the compound. Specifically, in one embodiment of the present specification, the compound can be included in one of the two or more electron transfer layers, or can be included in each of the two or more electron transfer layers.

In addition, in one embodiment of the present application, when the compound is included in each of the two or more electron transfer layers, materials other than the compound can be the same as or different from each other.

In one embodiment of the present application, the organic material layer further includes, in addition to the organic material layer including the compound, a hole injection layer or a hole transfer layer including a compound including an arylamino group, a carbazolyl group or a benzocarbazolyl group.

In another embodiment, the organic light emitting device can be an organic light emitting device having a structure in which an anode, one or more organic material layers and a cathode are consecutively laminated on a substrate (normal type).

In another embodiment, the organic light emitting device can be an organic light emitting device having a structure in a reverse direction in which a cathode, one or more organic material layers and an anode are consecutively laminated on a substrate (inverted type).

For example, a structure of the organic light emitting device according to one embodiment of the present application is illustrated in FIGS. 1 and 2.

FIG. 1 illustrates a structure of the organic light emitting device in which a substrate (1), an anode (2), a light emitting layer (3) and a cathode (4) are consecutively laminated. In such a structure, the compound can be included in the light emitting layer (3).

FIG. 2 illustrates a structure of the organic light emitting device in which a substrate (1), an anode (2), a hole injection layer (5), a hole transfer layer (6), a light emitting layer (3), an electron transfer layer (7) and a cathode (4) are consecutively laminated. In such a structure, the compound can be included in one or more layers of the hole injection layer (5), the hole transfer layer (6), the light emitting layer (3) and the electron transfer layer (7).

In such a structure, the compound can be included in one or more layers of the hole injection layer, the hole transfer layer, the light emitting layer and the electron transfer layer.

The organic light emitting device of the present application can be manufactured using materials and methods known in the art, except that one or more layers of the organic material layers include the compound of the present application, that is, the above-described compound.

When the organic light emitting device includes a plurality of organic material layers, the organic material layers can be formed with materials the same as or different from each other.

The organic light emitting device of the present application can be manufactured using materials and methods known in the art, except that one or more layers of the organic material layers include the above-described compound, that is, the compound of Chemical Formula 1.

For example, the organic light emitting device of the present application can be manufactured by consecutively laminating a first electrode, an organic material layer and a second electrode on a substrate. Herein, the organic light emitting device can be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a cathode thereon. In addition to such a method, the organic light emitting device can also be manufactured by consecutively depositing a cathode material, an organic material layer and an anode material on a substrate.

In addition, the compound of Chemical Formula 1 can be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such as method, the organic light emitting device can also be manufactured by consecutively laminating a cathode material, an organic material layer and an anode material on a substrate (International Patent Application Laid-Open Publication No. WO2003/012890). However, the manufacturing method is not limited thereto.

In one embodiment of the present application, the first electrode is an anode, and the second electrode is a cathode.

In another embodiment, the first electrode is a cathode, and the second electrode is an anode.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; and multilayer structure materials such as LiF/Al or $LiO_2$/Al, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$), carbazole series compounds, dimerized styryl compounds, BAlq, 10-hydroxybenzo quinoline-metal compounds, benzoxazole, benzothiazole and benzimidazole series compounds, poly(p-phenylenevinylene) (PPV) series polymers, spiro compounds, polyfluorene, rubrene, and the like, but are not limited thereto.

The light emitting layer can include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes compounds, dibenzofuran derivatives, ladder-type furan compounds, pyrimidine derivatives and the like, but the material is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline, complexes including $Alq_3$, organic radical compounds, hydroxyflavon-metal complexes, and the like, but are not limited thereto. The electron transfer layer can be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)berylium, bis(10-hydroxybenzo[h]-quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)-(2-naphtholato)gallium and the like, but is not limited thereto.

The hole blocking layer is a layer blocking holes from reaching a cathode and can be generally formed under the same condition as the hole injection layer. Specifically, oxadiazole derivatives, triazole derivatives, phenanthroline derivatives, BCP, aluminum complexes and the like are included, however, the hole blocking layer is not limited thereto.

The organic light emitting device according to the present specification can be a top-emission type, a bottom-emission type or a dual-emission type depending on the materials used.

Methods for preparing the compound of Chemical Formula 1 and manufacturing an organic light emitting device including the same will be specifically described in the following examples. However, the following examples are for illustrative purposes only, and the scope of the present specification is not limited thereby.

SYNTHESIS EXAMPLES

<Synthesis Example 1> Synthesis of Intermediate A (Synthesis Example 1-1) Synthesis of Intermediate A-1

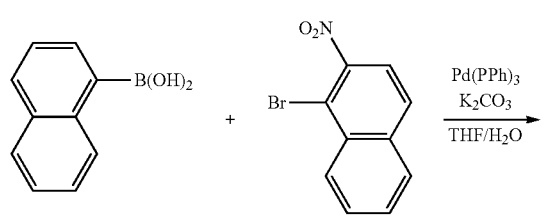

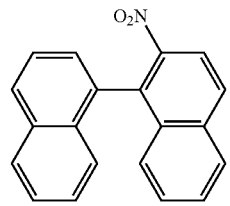

Intermediate A-1

In a 3-neck flask, naphthalen-1-yl-boronic acid (15.0 g, 87.2 mmol) and 1-bromo-2-nitronaphthalene (23.1 g, 91.6 mmol) were dissolved in tetrahydrofuran (THF) (225 ml), and $K_2CO_3$ (48.2 g, 348.9 mmol) dissolved in $H_2O$ (113 ml) was introduced thereto. $Pd(PPh_3)_4$ (3.0 g, 2.6 mmol) was introduced thereto, and the result was stirred for 8 hours under an argon atmosphere reflux condition. When the reaction was terminated, the result was cooled to room temperature, and the reaction solution was transferred to a separatory funnel and then extracted with ethyl acetate. The extract was dried with $MgSO_4$, then filtered and concentrated, and the sample was purified using silica gel column chromatography to obtain Intermediate A-1 (22.2 g, yield 85%). (MS[M+H]$^+$=299)

(Synthesis Example 1-2) Synthesis of Intermediate A-2

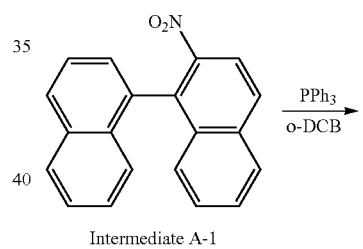

Intermediate A-1

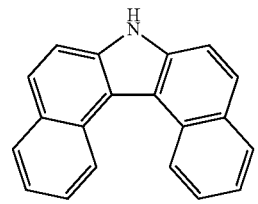

Intermediate A-2

To a 2-neck flask, Intermediate A-1 (20.0 g, 66.8 mmol), triphenylphosphine (13.9 g, 100.2 mmol) and o-dichlorobenzene (200 ml) were introduced, and the result was stirred for 12 hours under a reflux condition. When the reaction was terminated, the result was cooled to room temperature, then vacuum distilled to remove the solvent, and extracted with water and $CH_2Cl_2$. The extract was dried with $MgSO_4$, filtered and concentrated, and the sample was purified using silica gel column chromatography to obtain Intermediate A-2 (12.7 g, yield 71%). (MS[M+H]$^+$=267)

(Synthesis Example 1-3) Synthesis of Intermediate A

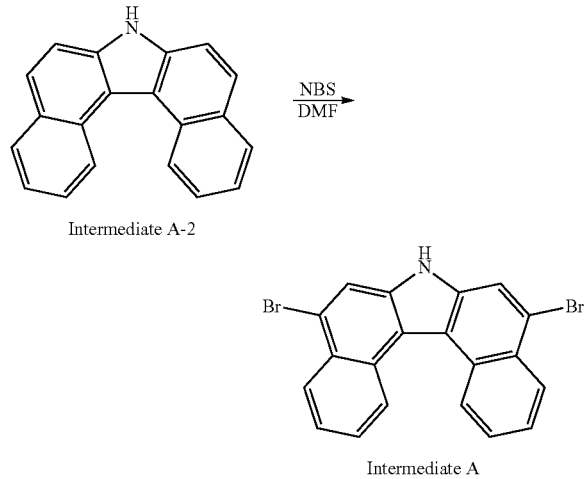

Intermediate A-2

Intermediate A

To a 2-neck flask, Intermediate A-2 (12.5 g, 46.8 mmol), N-bromosuccinimide (NBS) (18.3 g, 102.9 mmol) and dimethylformamide (DMF) (450 mL) were introduced, and the result was stirred for 5 hours at room temperature under the argon atmosphere. After the reaction was terminated, the reaction solution was transferred to a separatory funnel, water (300 mL) was added thereto, and the result was extracted with ethyl acetate. The sample was purified using silica gel column chromatography to obtain Intermediate A (9.5 g, yield 48%). (MS[M+H]$^+$=425)

When substituents bond to naphthalen-1-ylboronic acid or 1-bromo-2-nitronaphthalene in Synthesis Example 1-1, compounds of Chemical Formula 1 in which R1 and R2 bond can be synthesized.

<Synthesis Example 2> Synthesis of Compound 1

(Synthesis Example 2-1) Synthesis of Compound 1-1

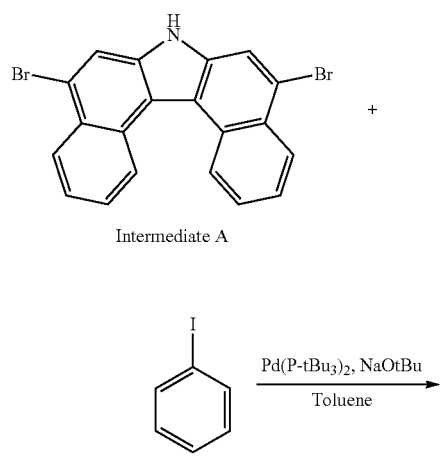

Intermediate A

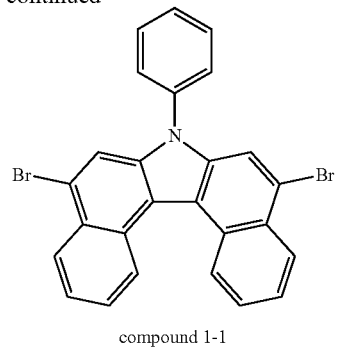

compound 1-1

In a 3-neck flask, Intermediate A (9.0 g, 21.2 mmol) and iodobenzene (4.5 g, 22.2 mmol) were dissolved in toluene (180 ml), and after introducing sodium tert-butoxide (3.1 g, 31.8 mmol) and bis(tri-tert-butylphosphine)palladium(0) (0.2 g, 0.4 mmol) thereto, the result was stirred for 6 hours under an argon atmosphere reflux condition. When the reaction was terminated, the result was cooled to room temperature, H$_2$O (200 ml) was introduced thereto, and the reaction solution was transferred to a separatory funnel and extracted. The extract was dried with MgSO$_4$, then filtered and concentrated, and the sample was purified using silica gel column chromatography to obtain Compound 1-1 (9.5 g, yield 90%). (MS[M+H]$^+$=501)

In Synthesis Example 2-1, compounds with different Ar1 can be synthesized using a compound such as an aryl group having 6 to 30 carbon atoms or a heterocyclic group having 2 to 30 carbon atoms, which can correspond to Ar1, instead of a phenyl group of the iodobenzene.

(Synthesis Example 2-2) Synthesis of Compound 1

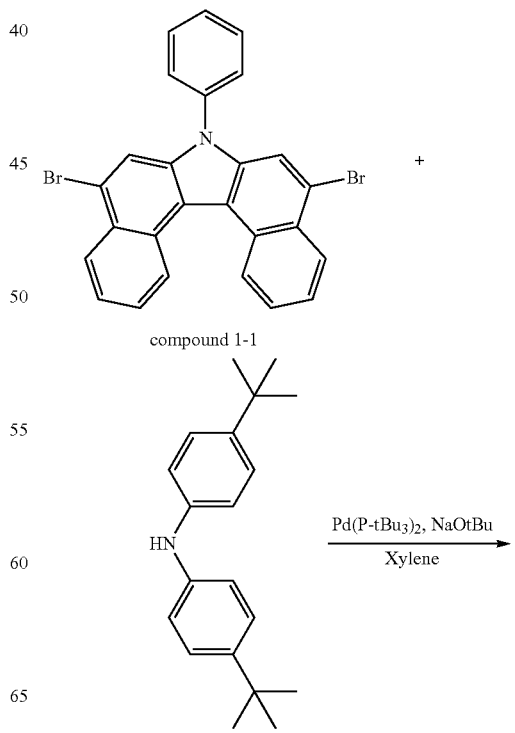

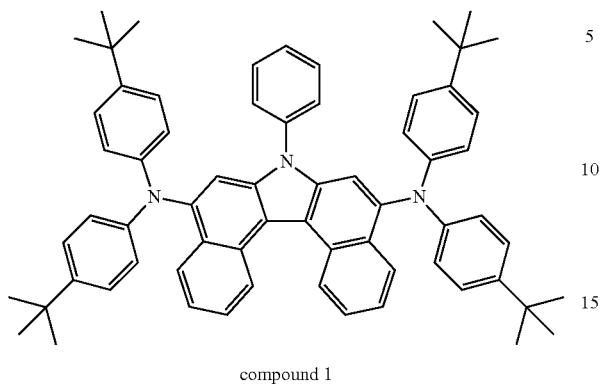

compound 1

In a 3-neck flask, Compound 1-1 (9.5 g, 19.0 mmol) and bis(4-(tert-butyl)phenyl)amine (11.7 g, 41.7 mmol) were dissolved in xylene (190 ml), and after introducing sodium tert-butoxide (2.7 g, 28.4 mmol) and bis(tri-tert-butylphosphine)palladium(0) (0.2 g, 0.4 mmol) thereto, the result was stirred for 6 hours under an argon atmosphere reflux condition. When the reaction was terminated, the result was cooled to room temperature, $H_2O$ (200 ml) was introduced thereto, and the reaction solution was transferred to a separatory funnel and extracted. The extract was dried with $MgSO_4$ and concentrated, and the sample was purified using silica gel column chromatography, and then sublimation purified to obtain Compound 1 (5.8 g, yield 34%). ($MS[M+H]^+$=902)

<Synthesis Example 3> Synthesis of Compound 2

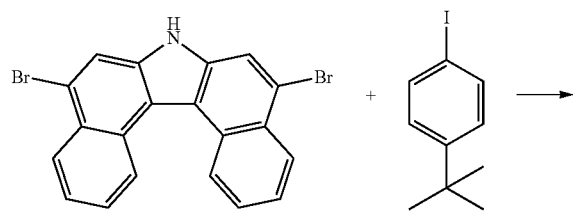

compound 2

Compound 2 was synthesized using the same method as the synthesis of Compound 1 except that, in <Synthesis Example 2>, iodobenzene was changed to 1-(tert-butyl)-4-iodobenzene, and bis(4-(tert-butyl)phenyl)amine was changed to N-phenyl-4-(trimethylsilyl)aniline. ($MS[M+H]^+$=878)

<Synthesis Example 4> Synthesis of Compound 3

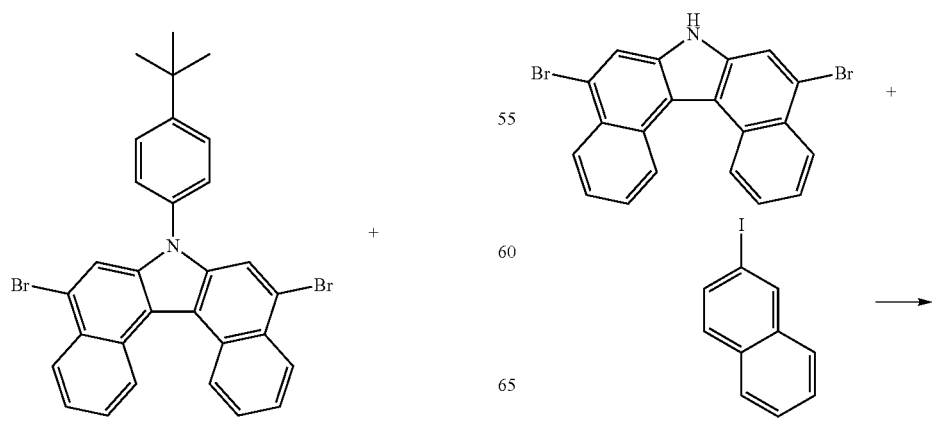

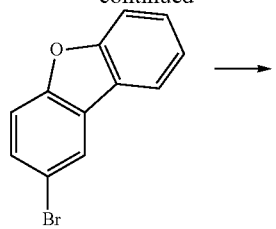

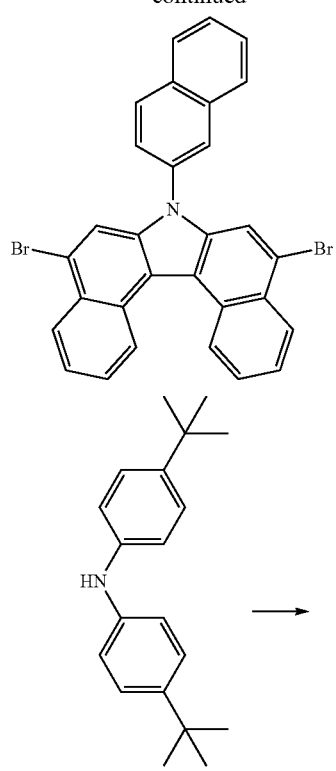

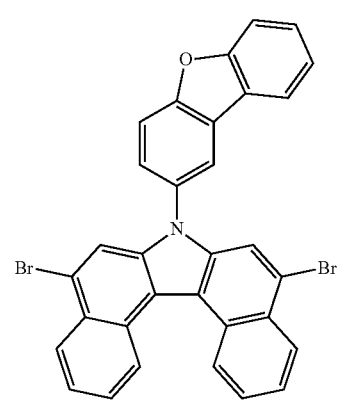

compound 3

Compound 3 was synthesized using the same method as the synthesis of Compound 1 except that, in <Synthesis Example 2>, iodobenzene was changed to 2-iodonaphthalene. (MS[M+H]⁺=952)

<Synthesis Example 5> Synthesis of Compound 4

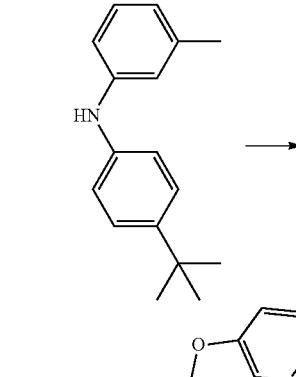

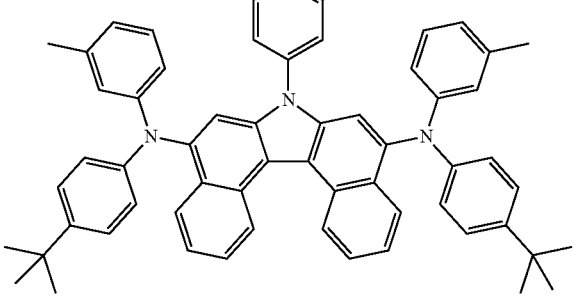

compound 4

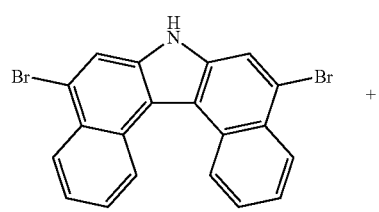

Compound 4 was synthesized using the same method as the synthesis of Compound 1 except that, in <Synthesis Example 2>, iodobenzene was changed to 2-bromodibenzo[b,d]furan, and bis(4-(tert-butyl)phenyl)amine was changed to N-(4-(tert-butyl)phenyl)-3-methylaniline. (MS[M+H]⁺=908)

<Synthesis Example 6> Synthesis of Compound 5

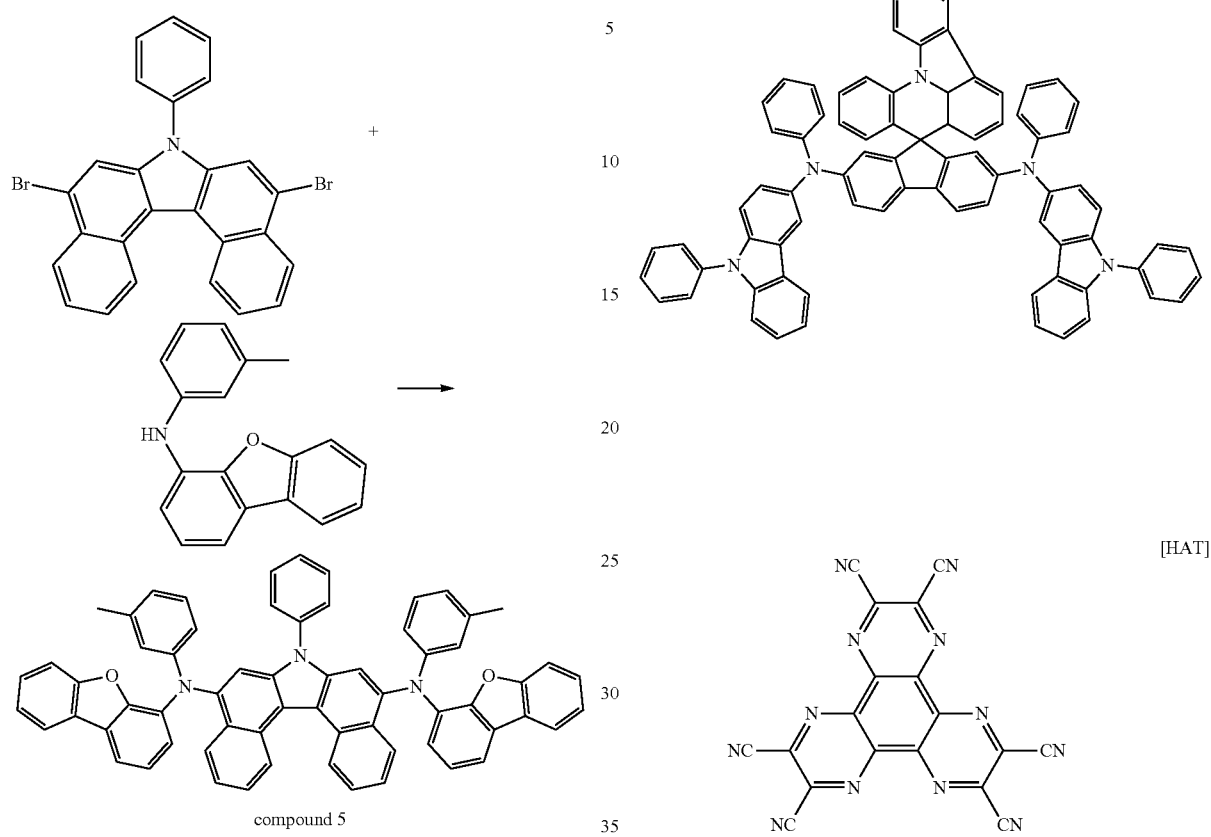

Compound 5 was synthesized using the same method as the synthesis of Compound 1 except that, in <Synthesis Example 2-2>, bis(4-(tert-butyl)phenyl)amine was changed to N-(m-tolyl)dibenzo[b,d]furan-4-amine. (MS[M+H]⁺= 886)

EXAMPLE

Example 1

A glass substrate on which indium tin oxide (ITO) was coated as a thin film to a thickness of 1,400 Å was placed in distilled water containing dissolved detergent and ultrasonically cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by consecutively thermal vacuum depositing the following [HI-A] and hexanitrile hexaazatriphenylene (HAT) to a thickness of 650 Å and 50 Å*, respectively.

A hole transfer layer was formed thereon by vacuum depositing the following [HT-A] to a thickness of 600 Å, and then the following [HT-B] was thermal vacuum deposited to a thickness of 50 Å as an electron blocking layer.

-continued

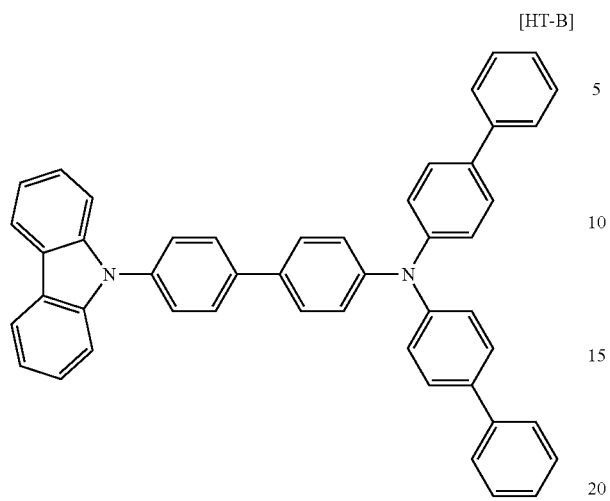

[HT-B]

Subsequently, the following host [BH-A] and 4 wt % dopant [Compound 1] were vacuum deposited to a thickness of 200 Å as a light emitting layer.

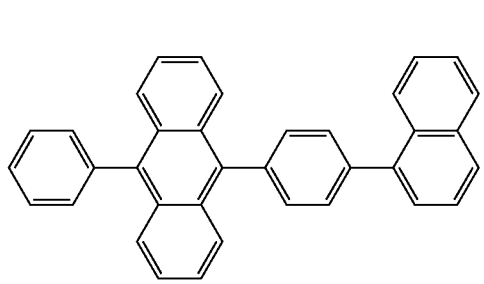

[BH-A]

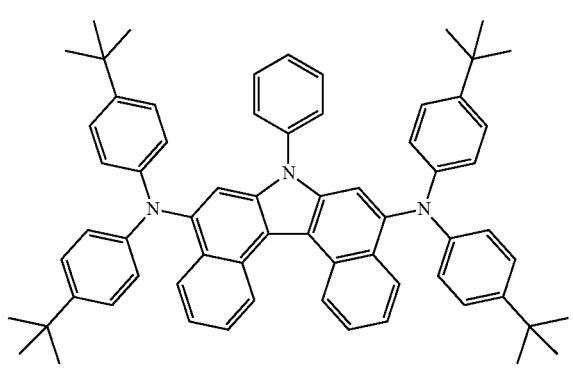

compound 1

Next, as an electron transfer layer and an electron injection layer, the following [ET-A] and [Liq] were thermal vacuum deposited to a thickness of 360 Å in a ratio of 1:1, and then [Liq] was vacuum deposited to a thickness of 5 Å.

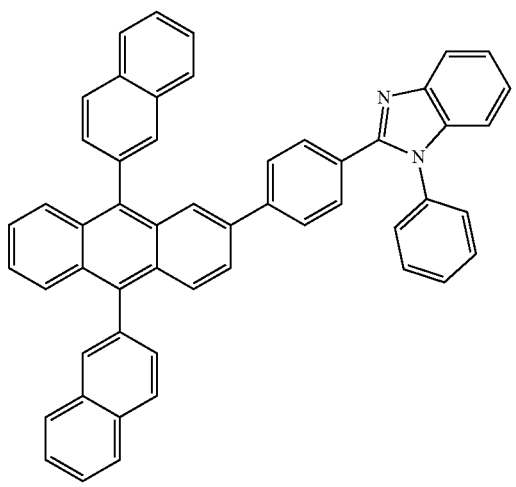

[ET-A]

[Liq]

On the electron injection layer, a cathode was formed by consecutively depositing magnesium and silver to a thickness of 220 Å in a ratio of 10:1, and depositing aluminum to a thickness of 1000 Å, and an organic light emitting device was manufactured.

Example 2

An organic light emitting device was manufactured in the same manner as in Example 1 except that Compound 2 was used instead of Compound 1 as the dopant material in Example 1.

Example 3

An organic light emitting device was manufactured in the same manner as in Example 1 except that Compound 3 was used instead of Compound 1 as the dopant material in Example 1.

Example 4

An organic light emitting device was manufactured in the same manner as in Example 1 except that Compound 4 was used instead of Compound 1 as the dopant material in Example 1.

Example 5

An organic light emitting device was manufactured in the same manner as in Example 1 except that Compound 5 was used instead of Compound 1 as the dopant material in Example 1.

Example 6

An organic light emitting device was manufactured in the same manner as in Example 1 except that BH-B was used instead of BH-A as the host material in Example 1.

[BH-B]

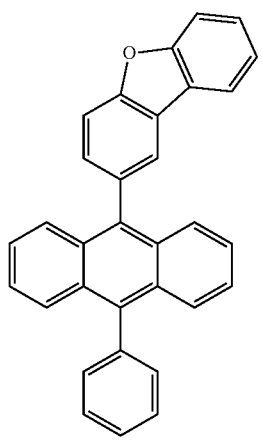

Example 7

An organic light emitting device was manufactured in the same manner as in Example 1 except that Compound 3 was used instead of Compound 1 as the dopant material, and BH-B was used instead of BH-A as the host material in Example 1.

Example 8

An organic light emitting device was manufactured in the same manner as in Example 1 except that Compound 5 was used instead of Compound 1 as the dopant material, and BH-C was used instead of BH-A as the host material in Example 1.

[BH-C]

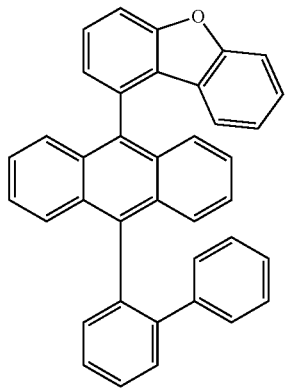

Example 9

An organic light emitting device was manufactured in the same manner as in Example 1 except that Compound 2 was used instead of Compound 1 as the dopant material, and BH-C was used instead of BH-A as the host material in Example 1.

Example 10

An organic light emitting device was manufactured in the same manner as in Example 1 except that Compound 4 was used instead of Compound 1 as the dopant material, and BH-D was used instead of BH-A as the host material in Example 1.

[BH-D]

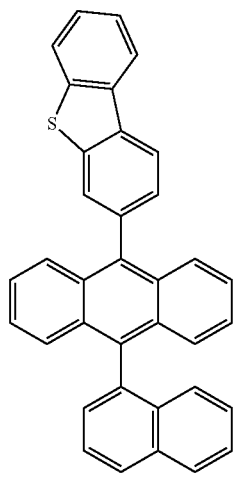

Comparative Example 1

An organic light emitting device was manufactured in the same manner as in Example 1 except that the following BD-A was used instead of Compound 1 as the dopant material in Example 1.

Comparative Example 2

An organic light emitting device was manufactured in the same manner as in Example 1 except that the following BD-B was used instead of Compound 1 as the dopant material in Example 1.

Comparative Example 3

An organic light emitting device was manufactured in the same manner as in Example 1 except that the following BD-C was used instead of Compound 1 as the dopant material in Example 1.

Comparative Example 4

An organic light emitting device was manufactured in the same manner as in Example 1 except that the following BD-D was used instead of Compound 1 as the dopant material in Example 1.

Comparative Example 5

An organic light emitting device was manufactured in the same manner as in Example 1 except that the following BD-E was used instead of Compound 1 as the dopant material in Example 1.

Comparative Example 6

An organic light emitting device was manufactured in the same manner as in Example 1 except that the following BD-B was used instead of Compound 1 as the dopant material, and BH-B was used instead of BH-A as the host material in Example 1.

Device performance was measured when applying current density of 10 mA/cm² to the organic light emitting devices manufactured in Examples 1 to 10 and Comparative Examples 1 to 6, and the results are shown in Table 1.

[BD-A]

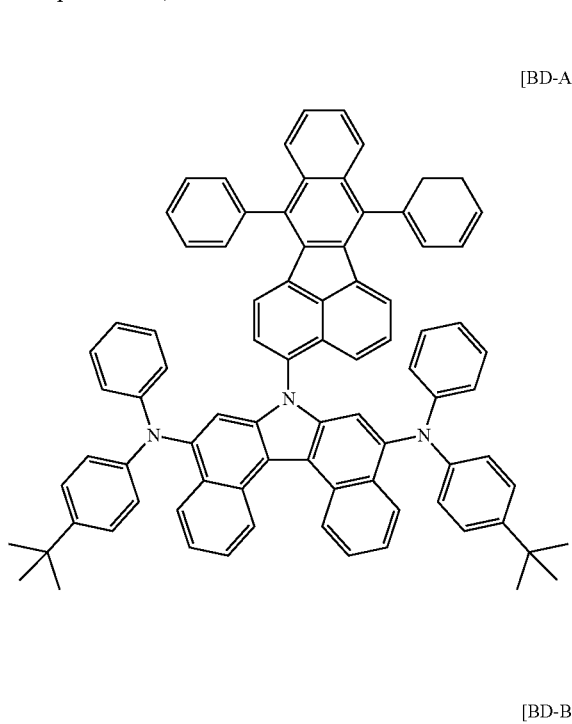

[BD-B]

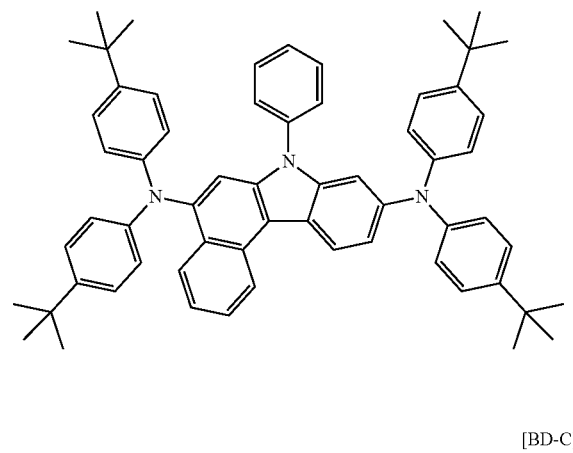

[BD-C]

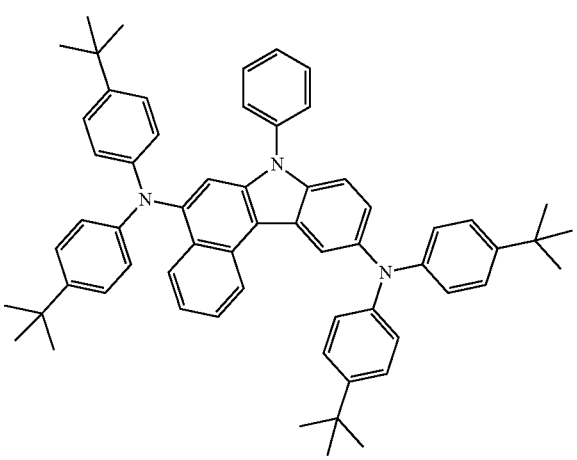

[BD-D]

[BD-E]

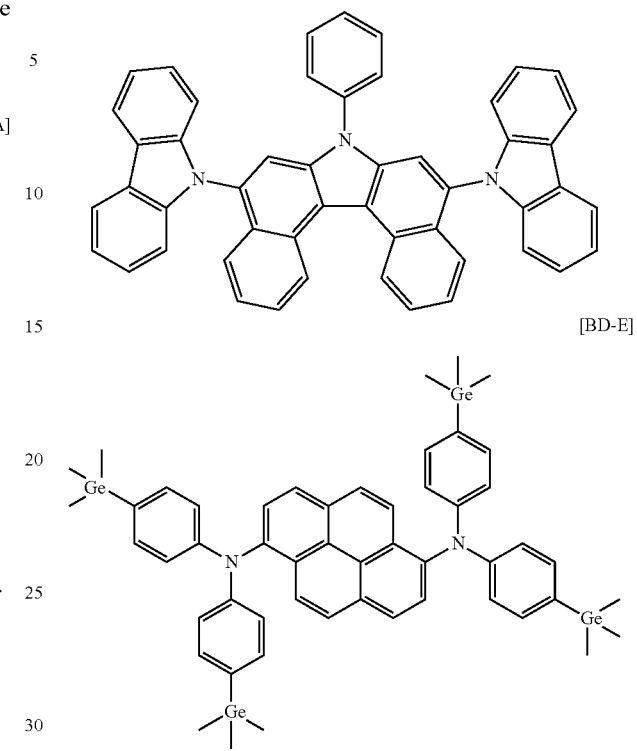

TABLE 1

| | Dopant | Host | Voltage (V) | Efficiency (cd/A) | CIE-x | CIE-y |
|---|---|---|---|---|---|---|
| | | | @10 mA/cm² | | | |
| Example 1 | Compound 1 | BH-A | 3.71 | 6.53 | 0.138 | 0.071 |
| Example 2 | Compound 2 | BH-A | 3.81 | 6.81 | 0.139 | 0.073 |
| Example 3 | Compound 3 | BH-A | 3.75 | 6.82 | 0.138 | 0.072 |
| Example 4 | Compound 4 | BH-A | 3.80 | 6.38 | 0.140 | 0.072 |
| Example 5 | Compound 5 | BH-A | 3.78 | 6.67 | 0.138 | 0.071 |
| Example 6 | Compound 1 | BH-B | 3.65 | 6.62 | 0.137 | 0.071 |
| Example 7 | Compound 3 | BH-B | 3.63 | 6.90 | 0.138 | 0.073 |
| Example 8 | Compound 5 | BH-C | 3.61 | 6.89 | 0.138 | 0.072 |
| Example 9 | Compound 2 | BH-C | 3.68 | 6.52 | 0.139 | 0.072 |
| Example 10 | Compound 4 | BH-D | 3.69 | 6.75 | 0.137 | 0.071 |
| Comparative Example 1 | BD-A | BH-A | 4.25 | 6.53 | 0.138 | 0.075 |
| Comparative Example 2 | BD-B | BH-A | 4.18 | 5.86 | 0.141 | 0.112 |
| Comparative Example 3 | BD-C | BH-A | 5.89 | 1.28 | 0.147 | 0.121 |
| Comparative Example 4 | BD-D | BH-A | 6.12 | 0.82 | 0.150 | 0.128 |
| Comparative Example 5 | BD-E | BH-A | 3.91 | 5.81 | 0.138 | 0.094 |
| Comparative Example 6 | BD-B | BH-B | 4.38 | 5.65 | 0.142 | 0.115 |

As identified in Comparative Example 1 of Table 1, device efficiency significantly decreased when introducing a high molecular weight substituent to Ar1. BD-B of Comparative Example 2 was a benzocarbazole compound and was identified to have decreased color purity compared to the dibenzocarbazole compounds of [Chemical Formula 1]. Particularly, it was identified that, when using a BD-C structure of the benzocarbazole compound as in Comparative Example 3, a voltage increased and efficiency decreased. This indicates that a structure having two amine groups and a carbazole skeleton positioned therebetween is capable of functioning as a dopant when the amine groups are positioned in a meta direction of N. In dibenzocarbazole, various skeletons can be obtained depending on the substituted position of benzene, and the structure having both amine structures positioned in a meta direction of N is dibenzo[c,g]carbazole only. The structure such as BD-D introducing a carbazole group having a lower electron donating ability than the amine group reduces electron density inside the skeleton, and performance declined when used in the organic light emitting device. Accordingly, it was seen that substituents having a lower electron donating ability than the amine group was difficult to be used as a blue light emitting dopant even when linked to the dibenzo[c,g] carbazole group. Particularly, the compound of [Chemical Formula 1] exhibited properties of lower voltage and higher efficiency when forming a light emitting layer with a host material having the structure of [Chemical Formula A-1].

As a result, it was identified that using the compound of [Chemical Formula 1] of the present disclosure as a dopant in a light emitting layer of an organic light emitting device was significantly effective in increasing efficiency while having high color purity.

The invention claimed is:

1. A compound of Chemical Formula 1:

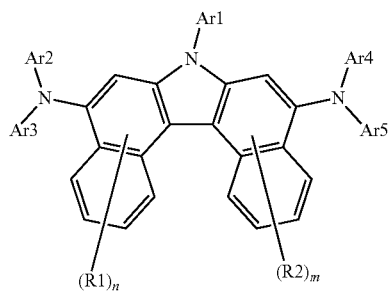

Chemical Formula 1 wherein, in Chemical Formula 1:
Ar1 is a substituted or unsubstituted aryl group having 6 to 30 carbon atoms, or a substituted or unsubstituted heterocyclic group having 2 to 30 carbon atoms;
Ar2 and Ar4 are the same as each other, and Ar3 and Ar5 are the same as each other;
Ar2 to Ar5 are each a substituted or unsubstituted aryl group, or a substituted or unsubstituted heterocyclic group;
R1 and R2 are the same as or different from each other, and each independently is hydrogen, deuterium, a halogen group, a cyano group, a substituted or unsubstituted alkyl group, a substituted or unsubstituted alkoxy group, a substituted or unsubstituted aryl group, or a substituted or unsubstituted heterocyclic group; and
n and m are each an integer of 0 to 5, and when n is 2 or greater, the R1s are the same as or different from each other, and when m is 2 or greater, the R2s are the same as or different from each other.

2. The compound of claim 1, wherein Ar1 is a phenyl group unsubstituted or substituted with an alkyl group or a silyl group, a biphenyl group unsubstituted or substituted with an alkyl group or a silyl group, a naphthyl group unsubstituted or substituted with an alkyl group or a silyl group, a phenanthrene group unsubstituted or substituted with an alkyl group or a silyl group, a dibenzofuran group unsubstituted or substituted with an alkyl group or a silyl group, or a dibenzothiophene group unsubstituted or substituted with an alkyl group or a silyl group.

3. The compound of claim 1, wherein Ar2 to Ar5 are each a phenyl group unsubstituted or substituted with a substituent selected from the group consisting of an alkyl group, a silyl group and an aryl group; a biphenyl group unsubstituted or substituted with a substituent selected from the group consisting of an alkyl group, a silyl group and an aryl group; or a dibenzofuran group unsubstituted or substituted with a substituent selected from the group consisting of an alkyl group, a silyl group and an aryl group.

4. The compound of claim 1, wherein R1 and R2 are hydrogen.

5. The compound of claim 1, wherein the compound of Chemical Formula 1 is selected from among the following compounds:

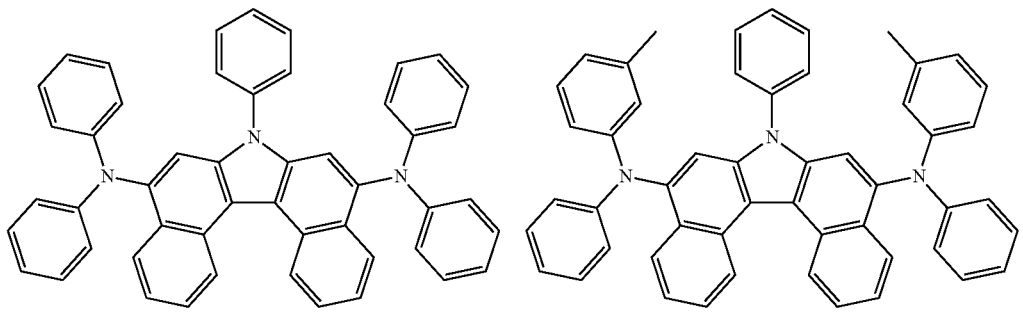

113 114
-continued
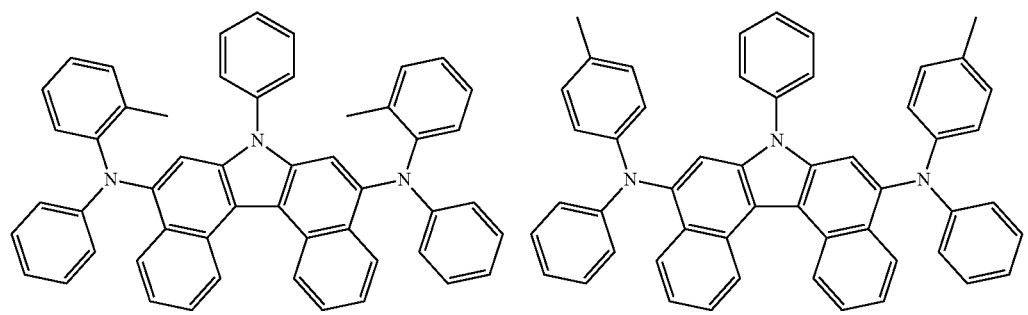
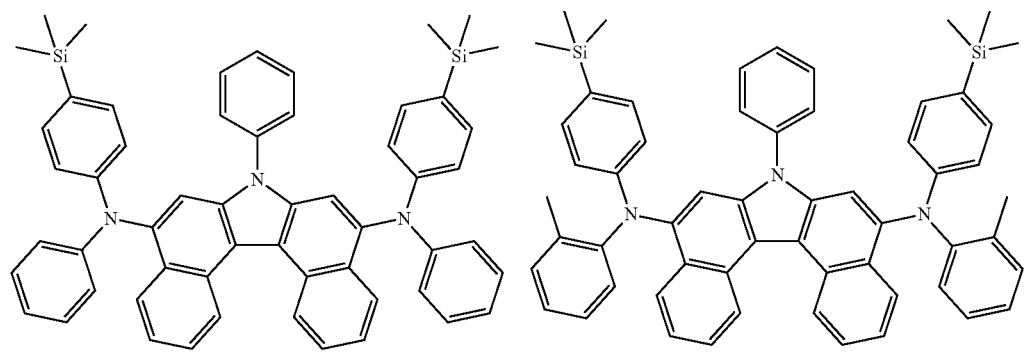
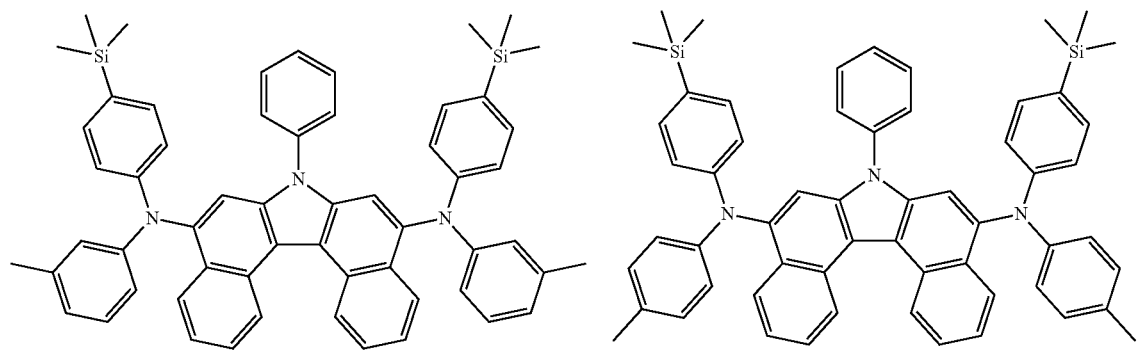
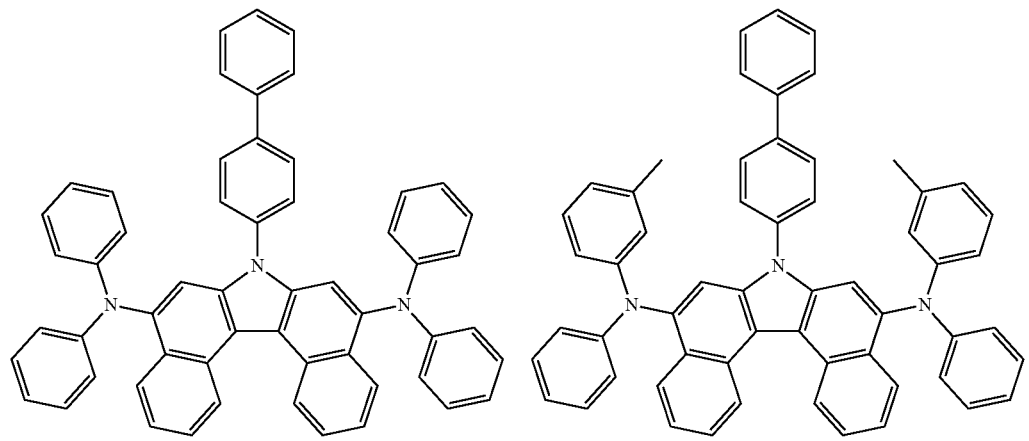

-continued
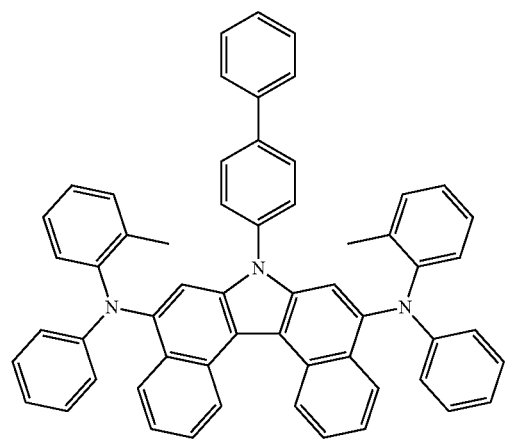
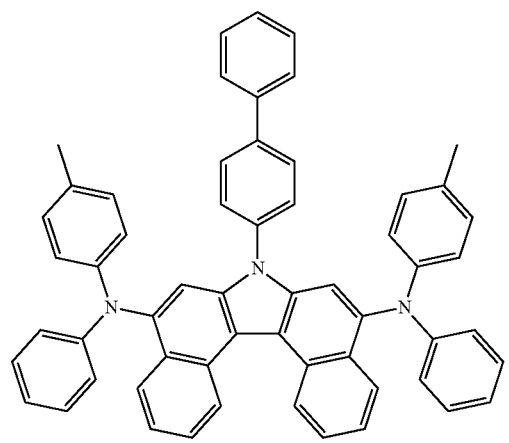
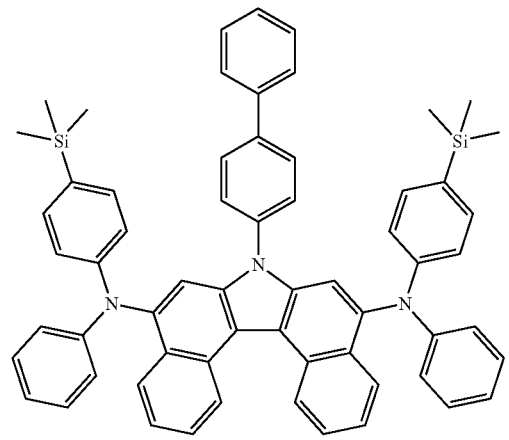
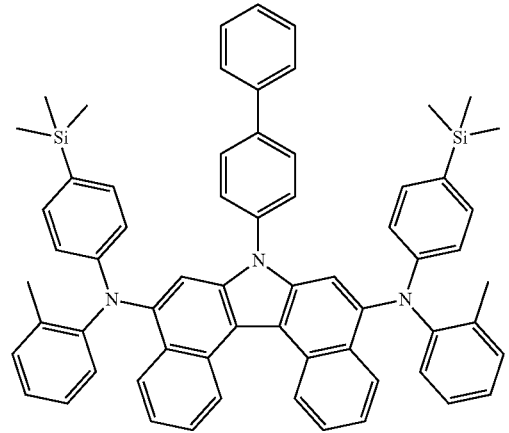
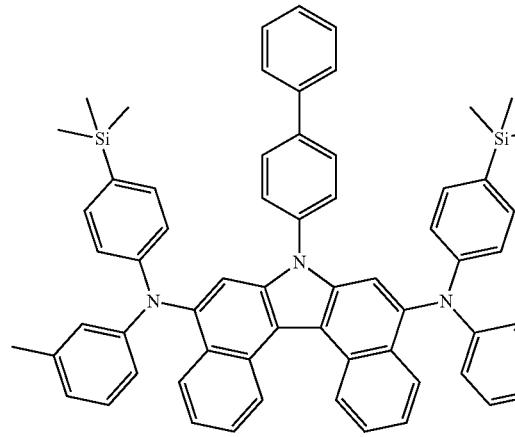
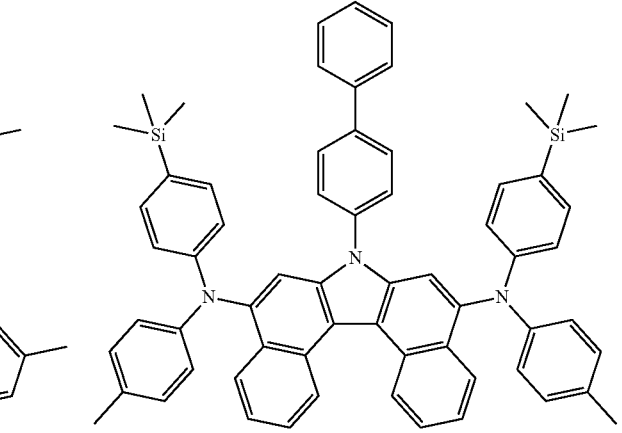
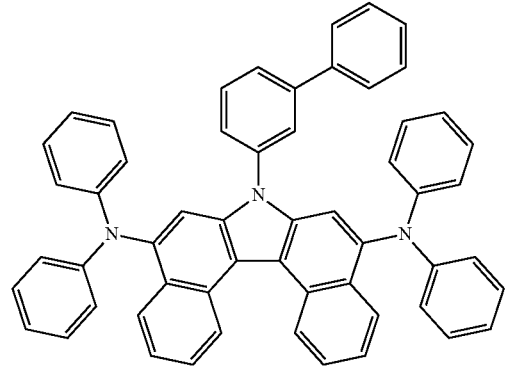
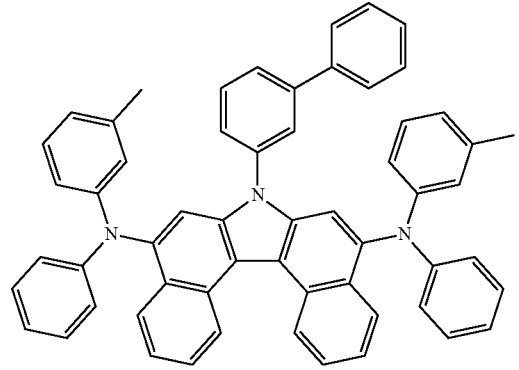

117 118
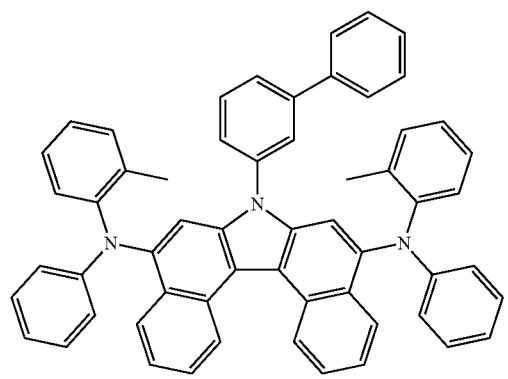 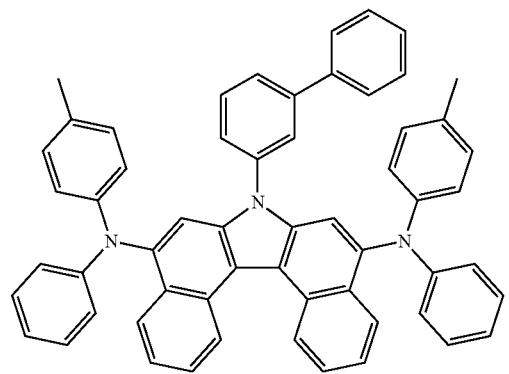
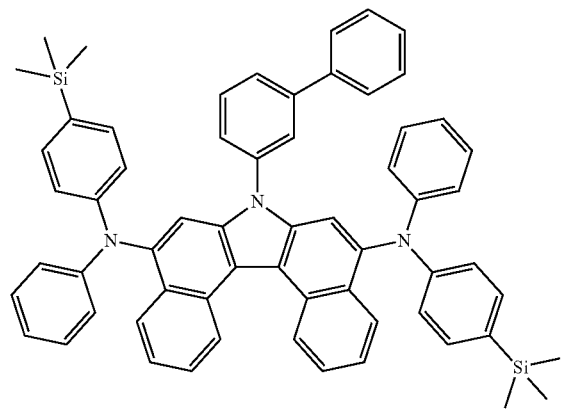 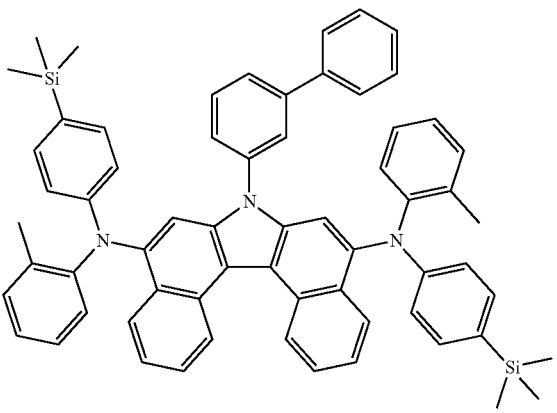
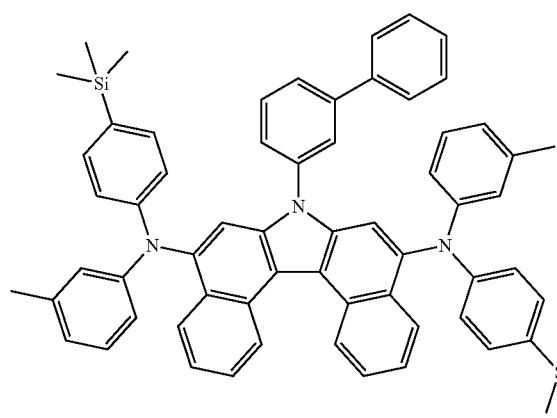 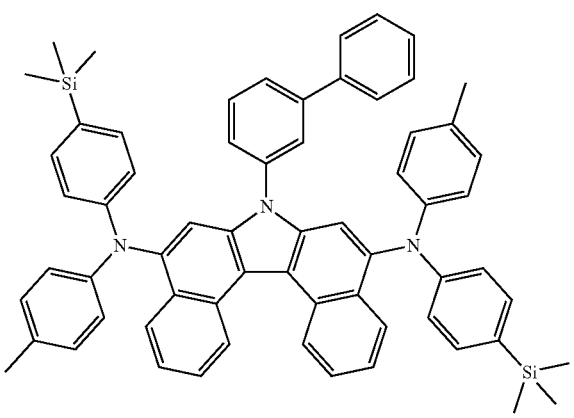
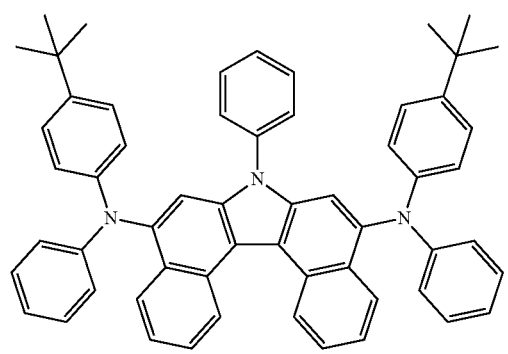 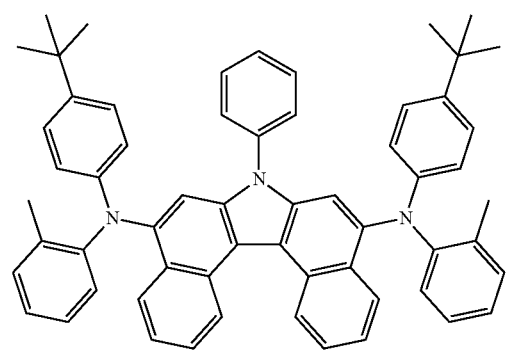

-continued
| 119 | 120 |
|---|---|
| 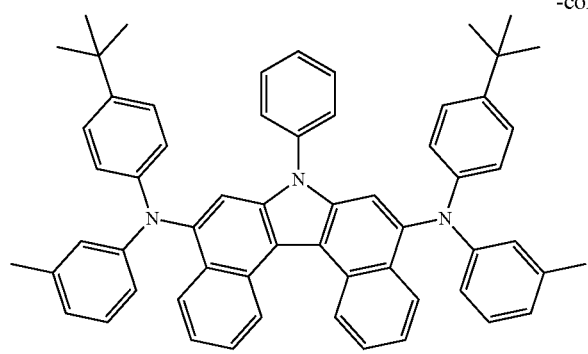 | 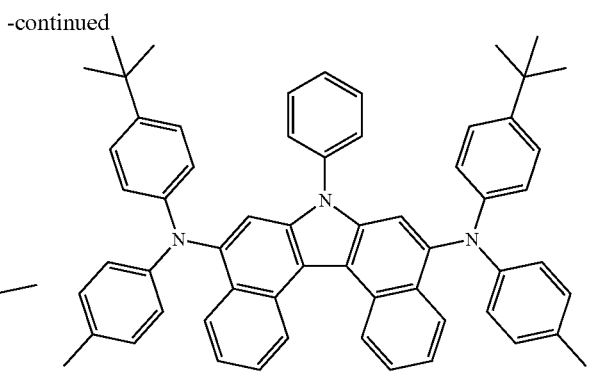 |
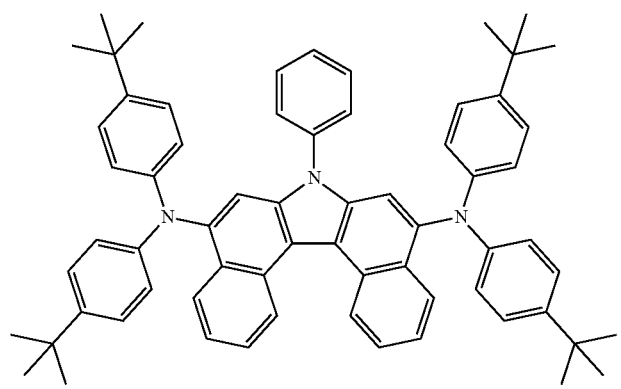
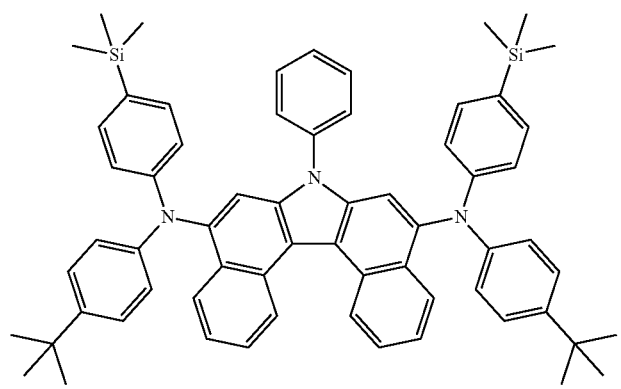
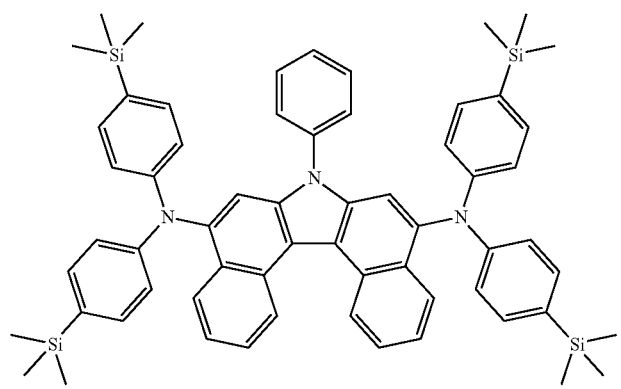

-continued
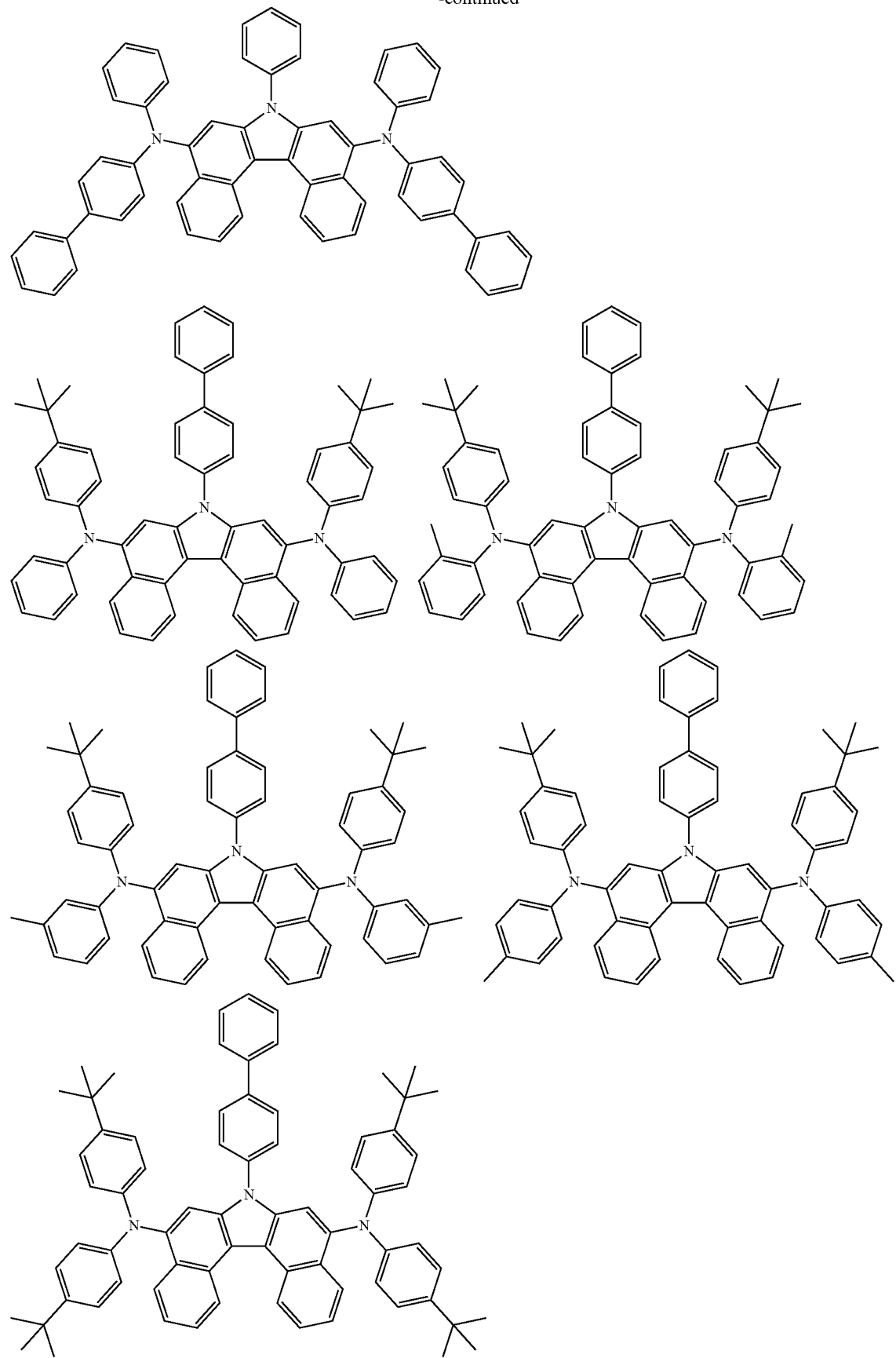

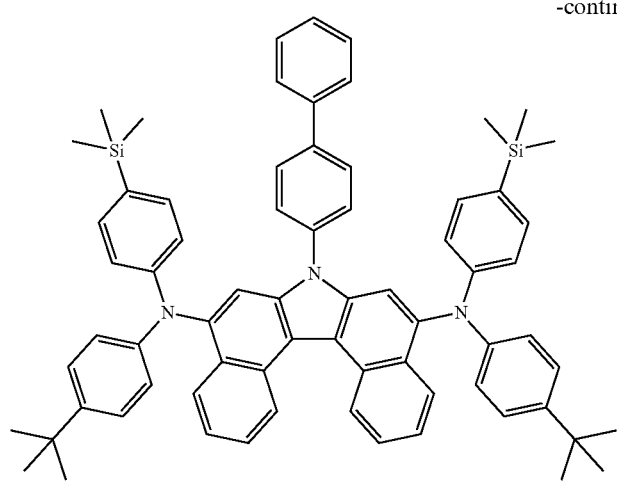
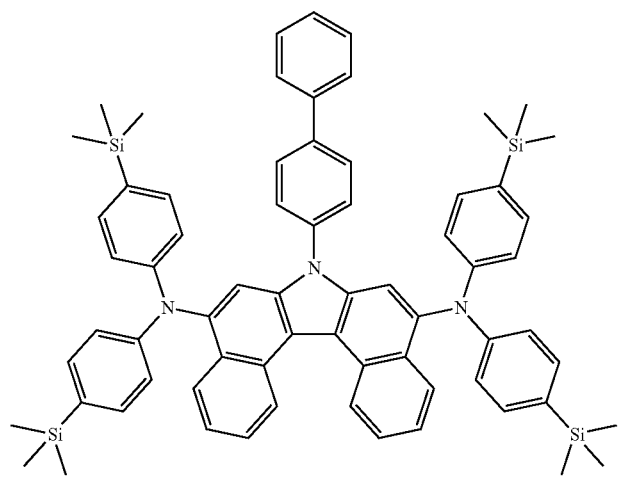
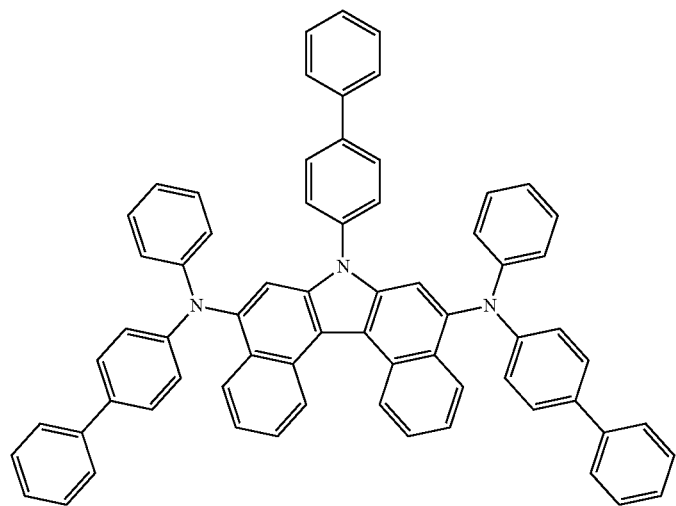

-continued
125 126
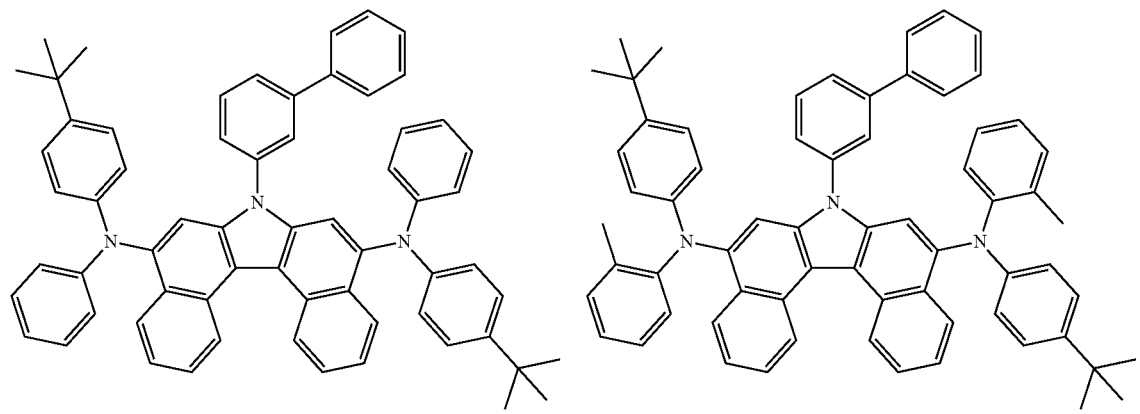
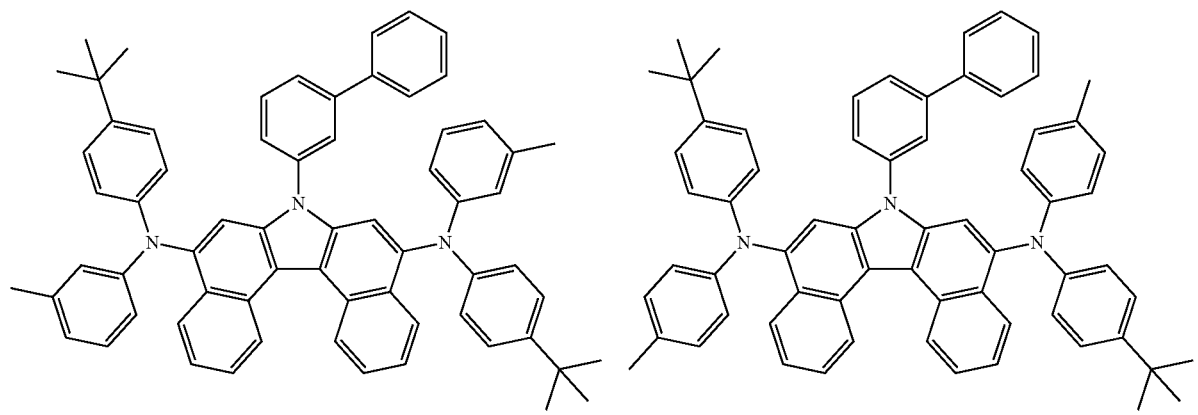
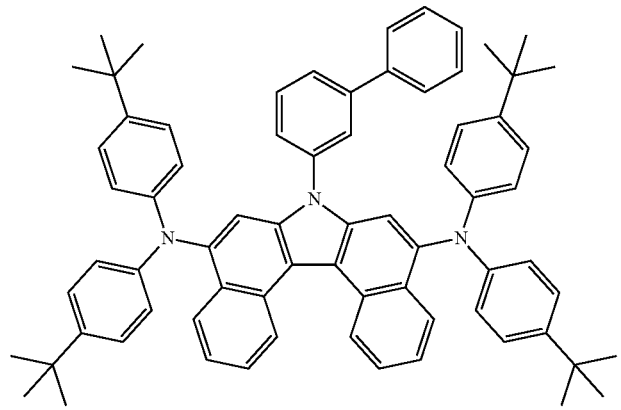
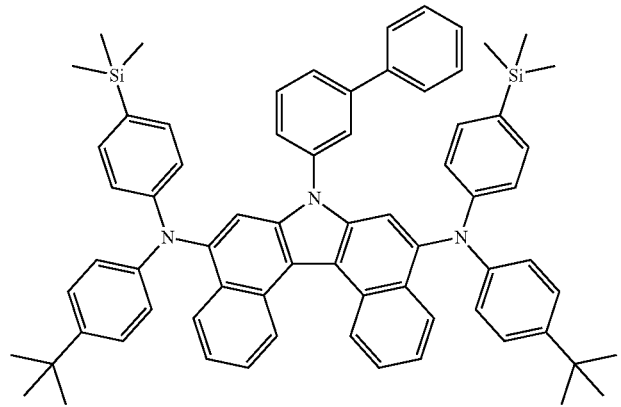

-continued
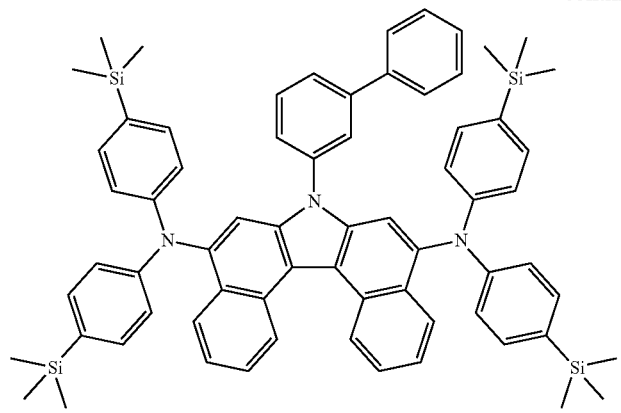
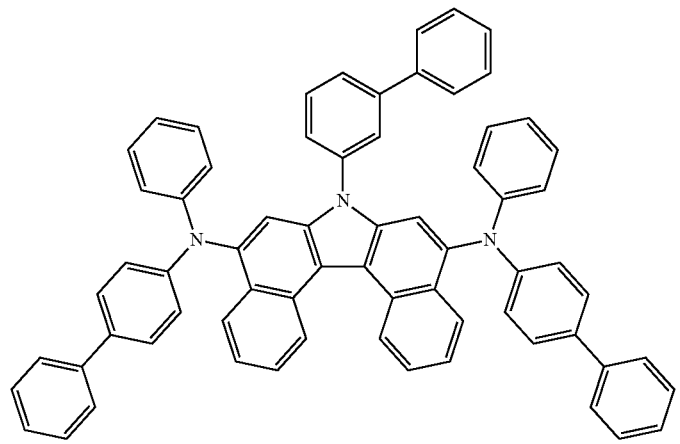
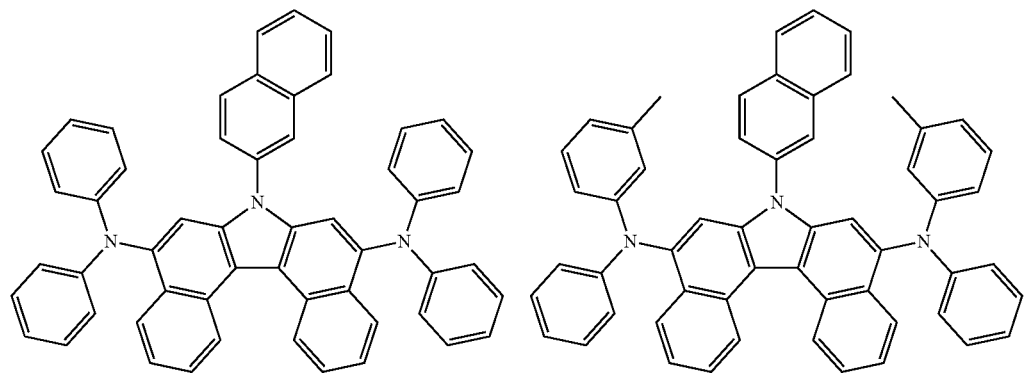
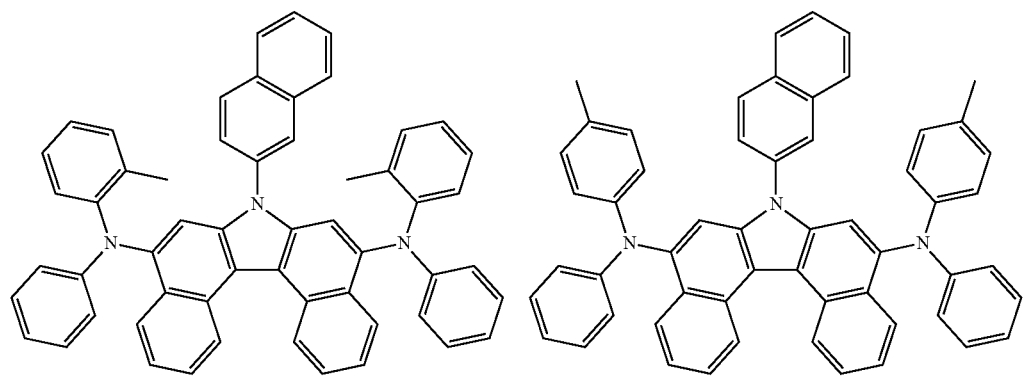

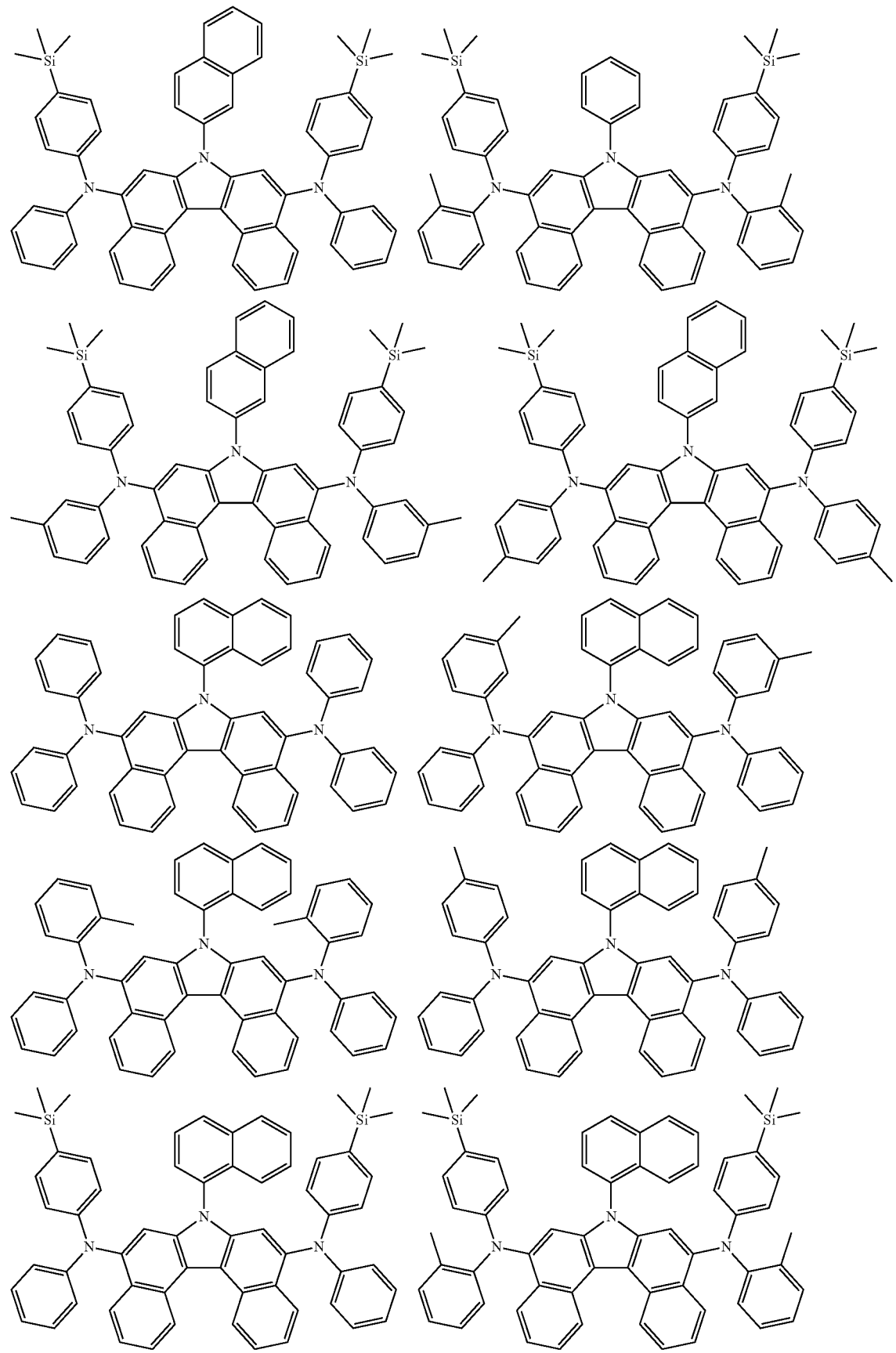

-continued
131
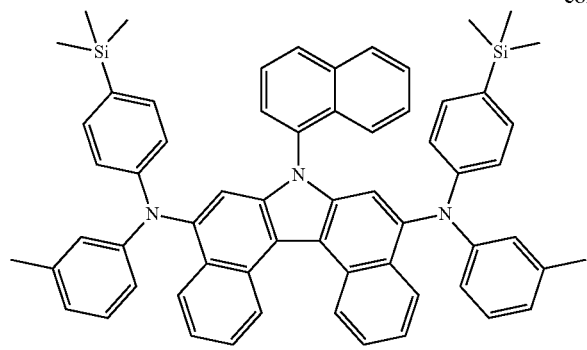
132
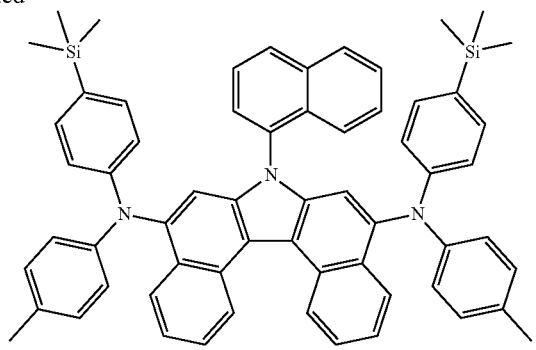
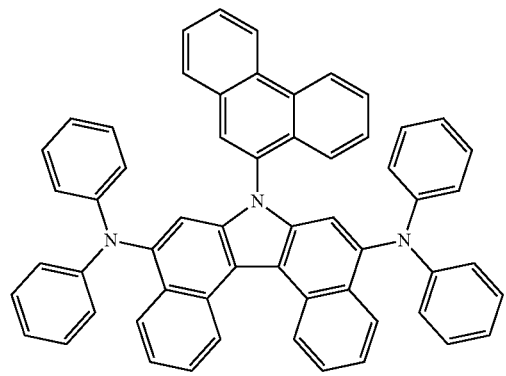
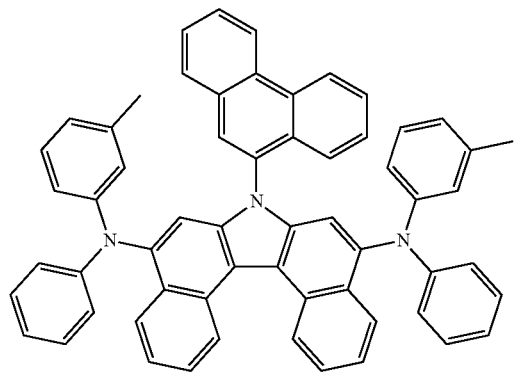
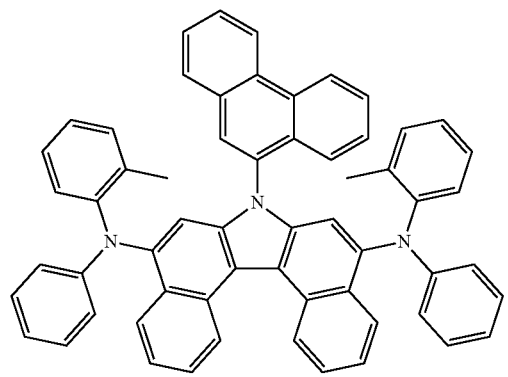
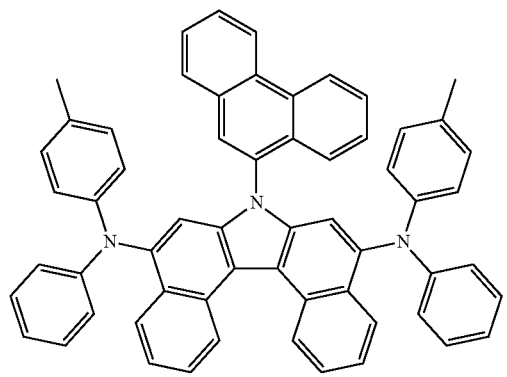
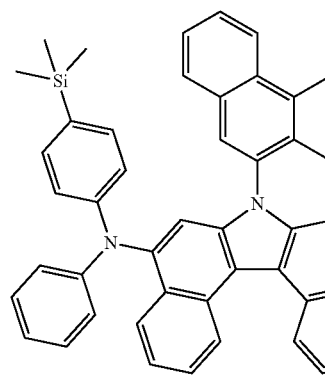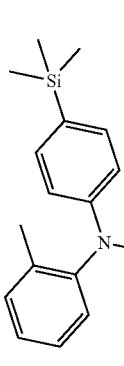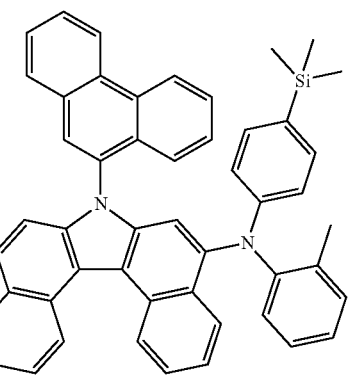

133
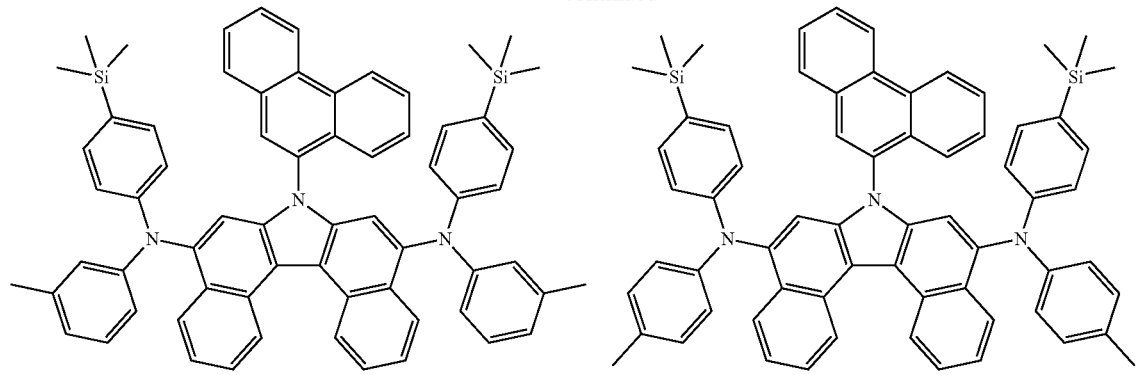
134
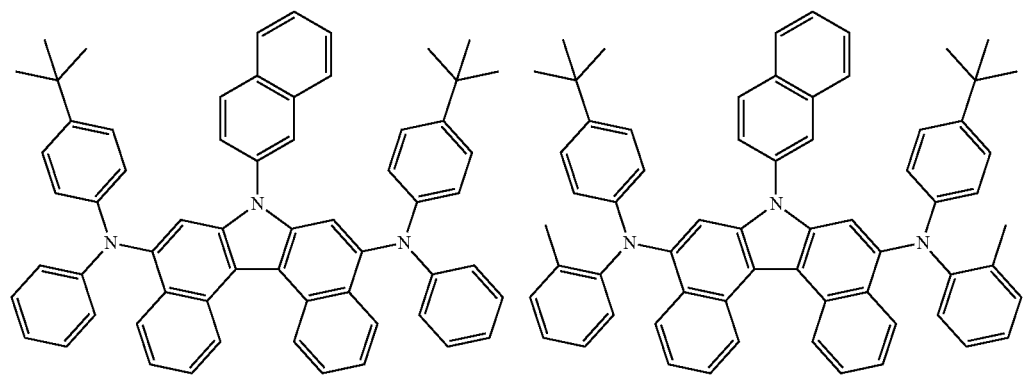
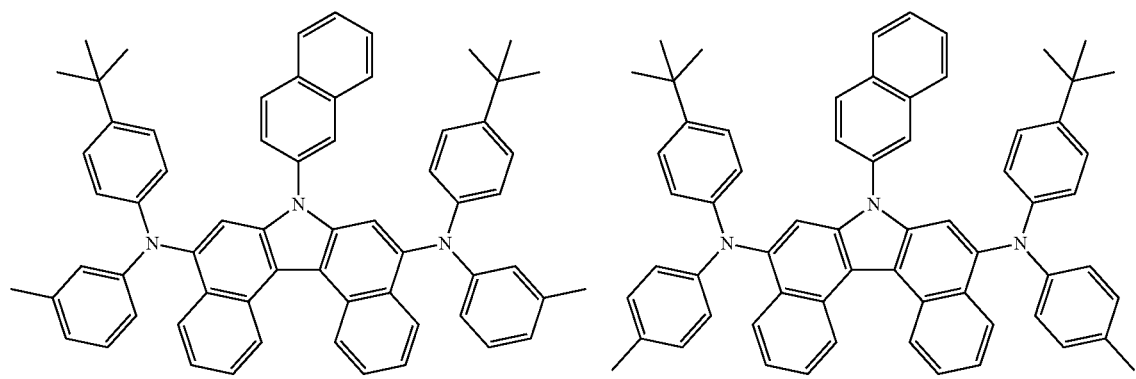
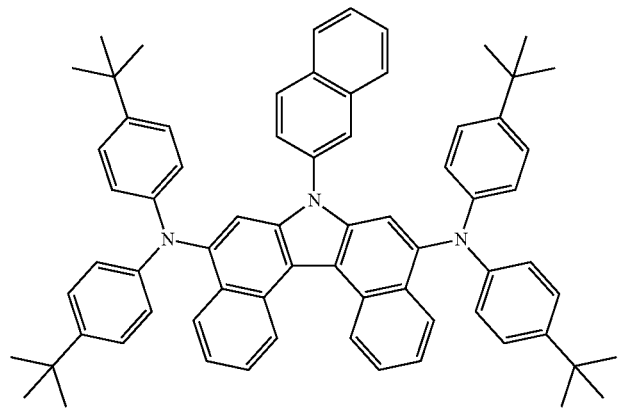

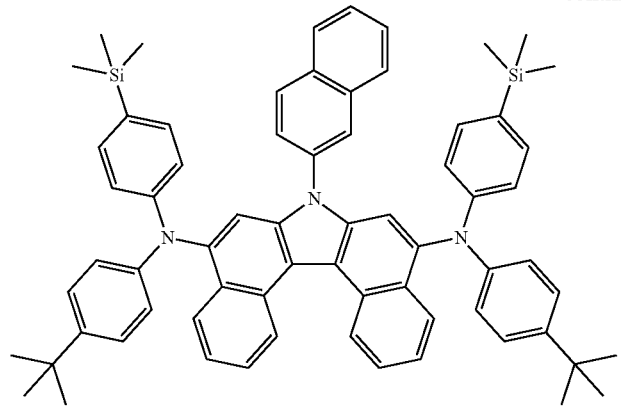
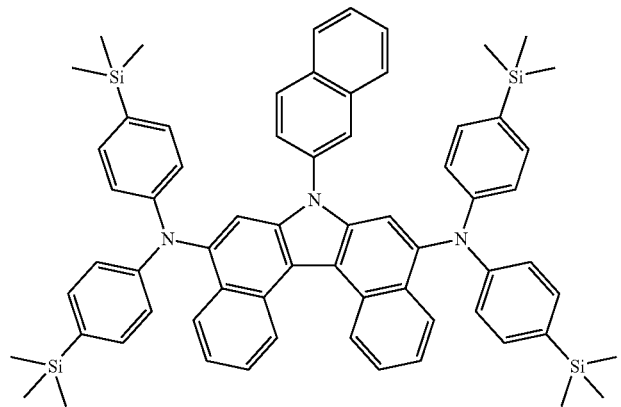
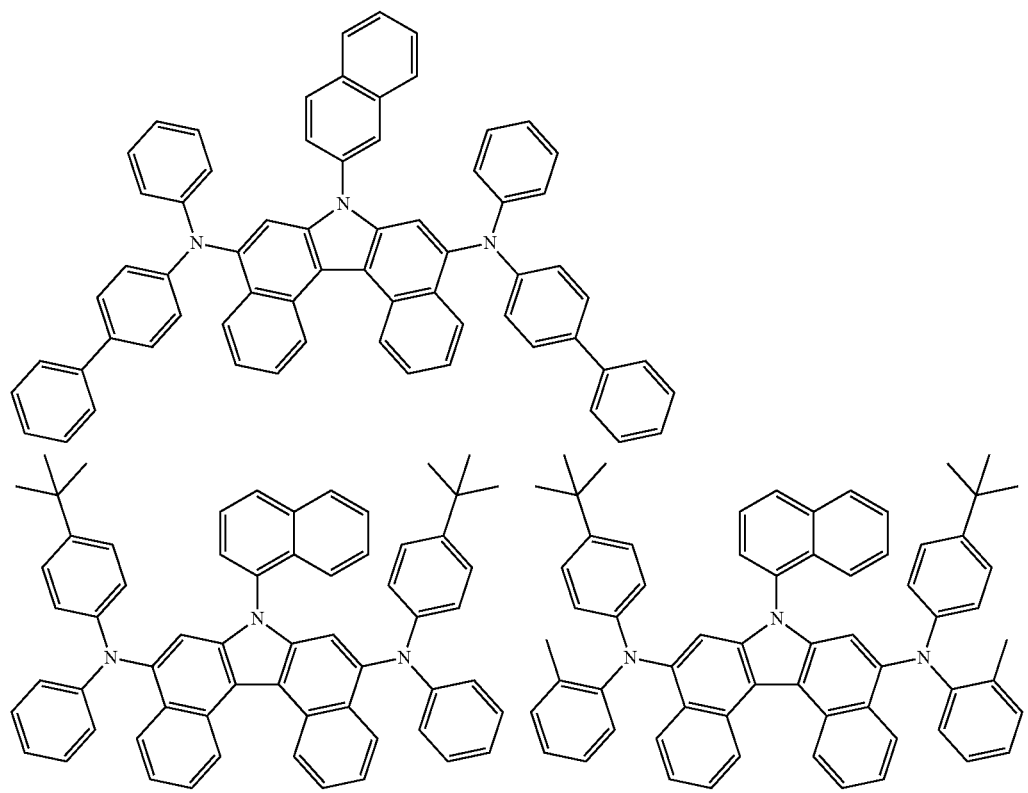

-continued
137 138
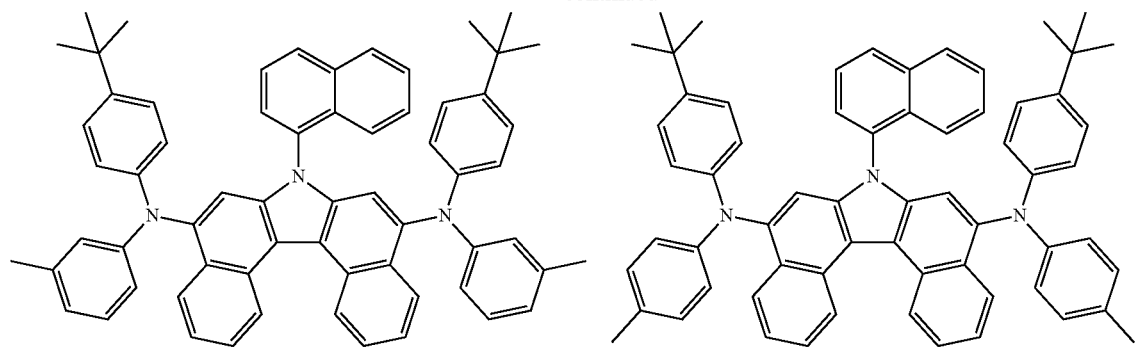
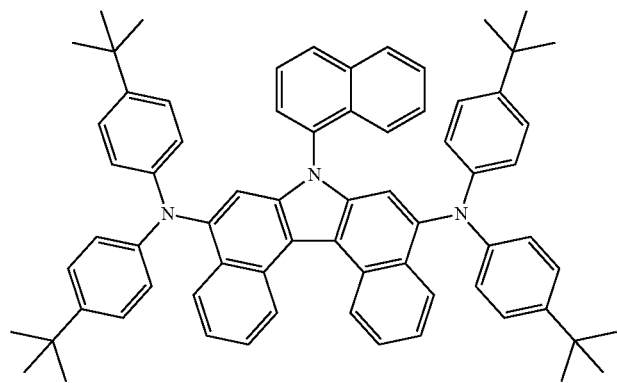
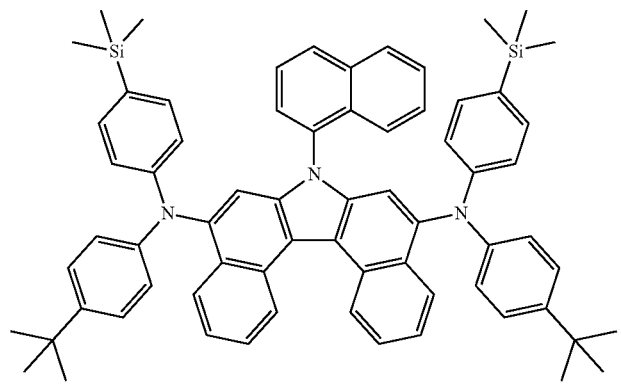
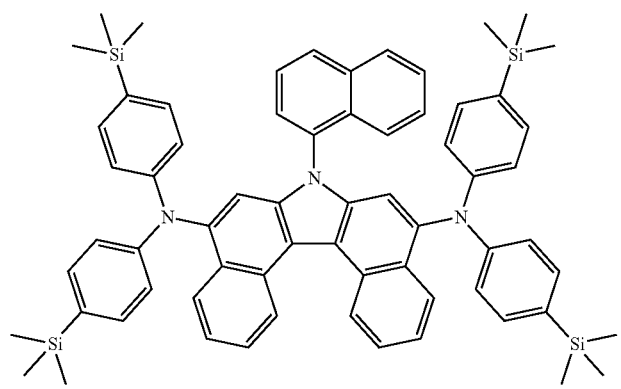

-continued
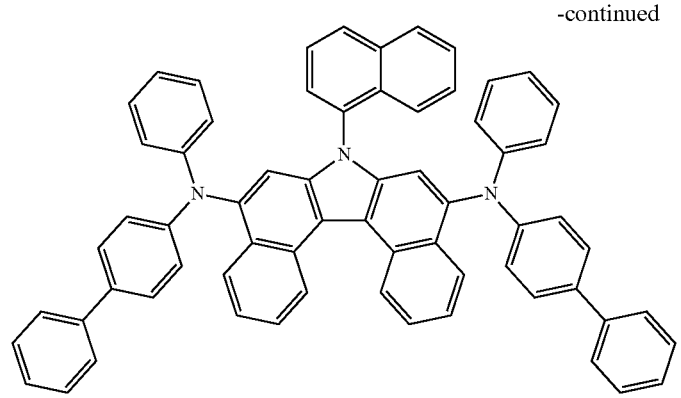
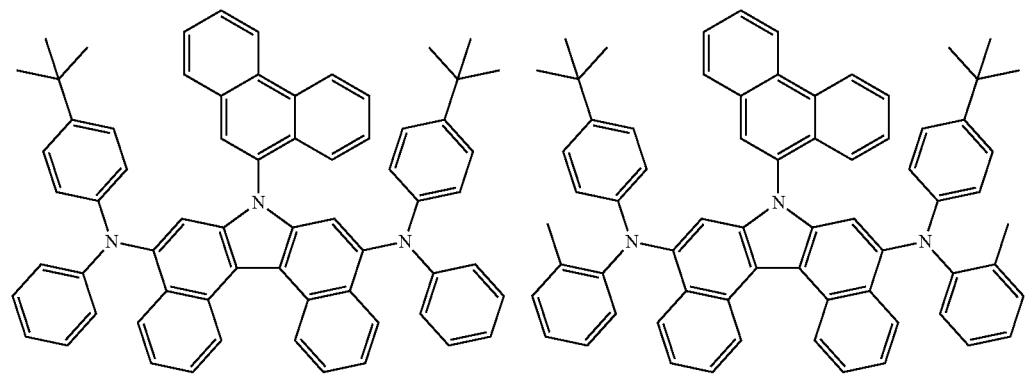
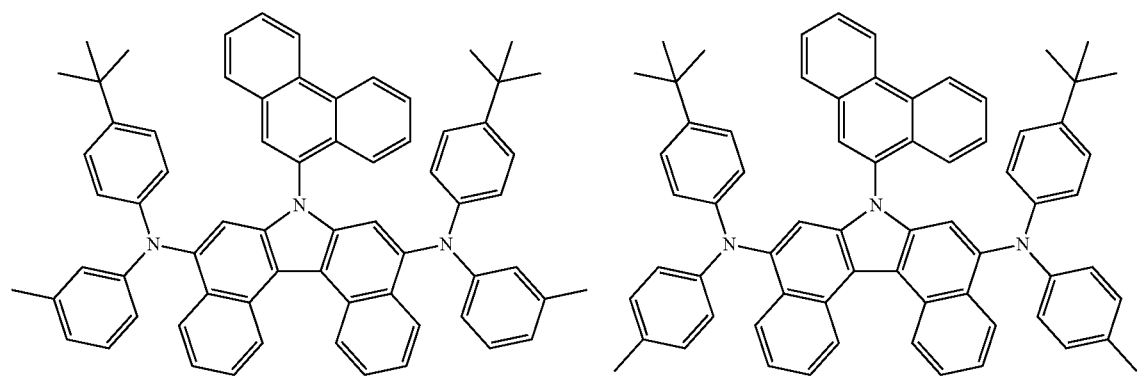
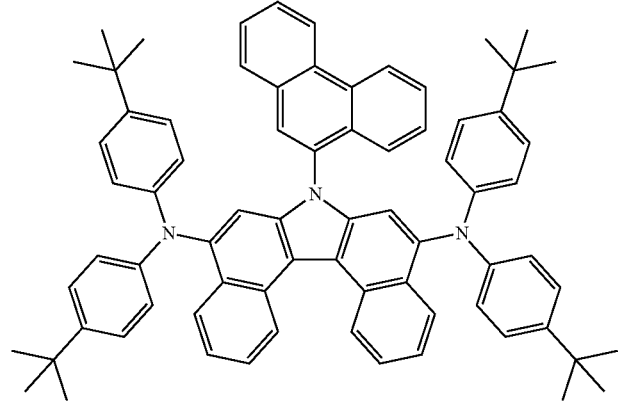

-continued
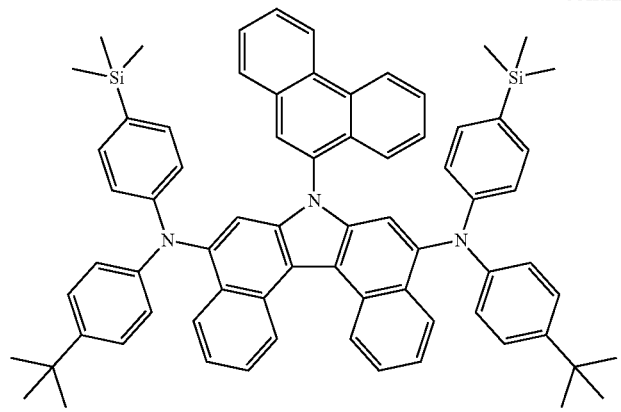
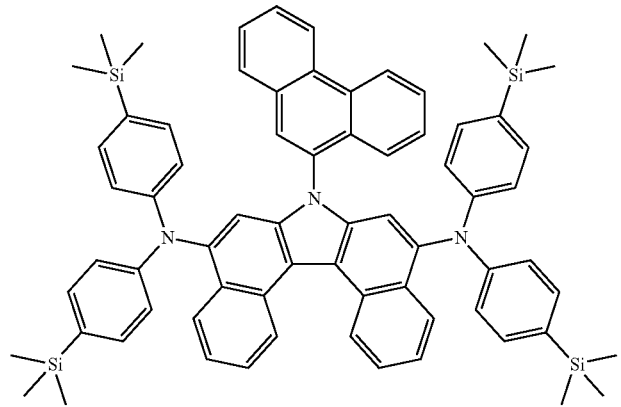
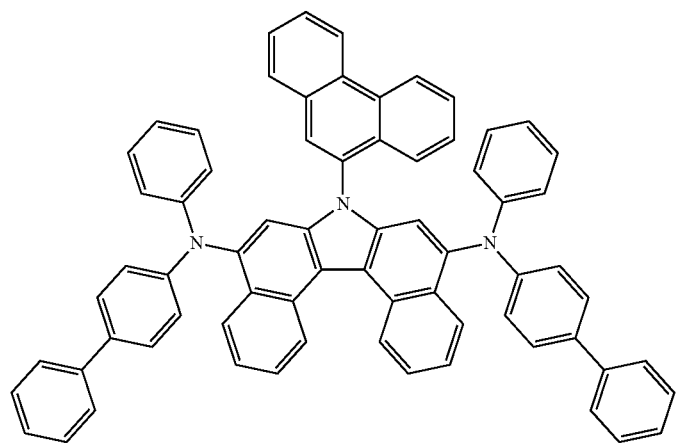
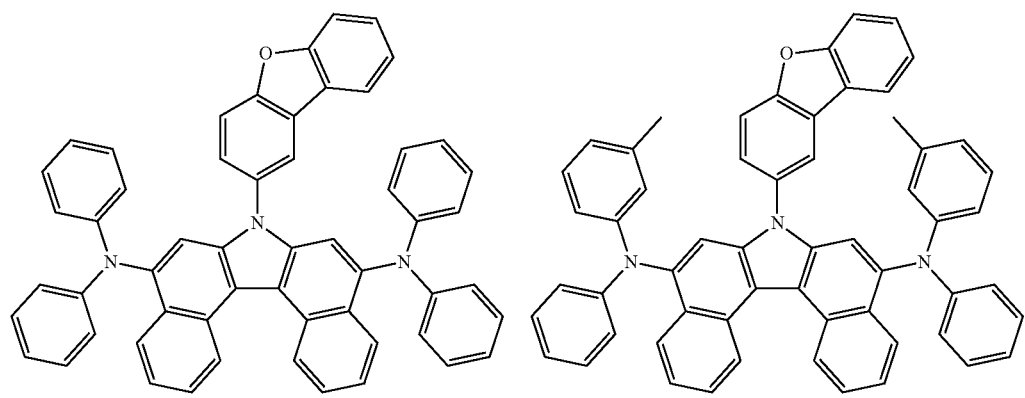

143 144
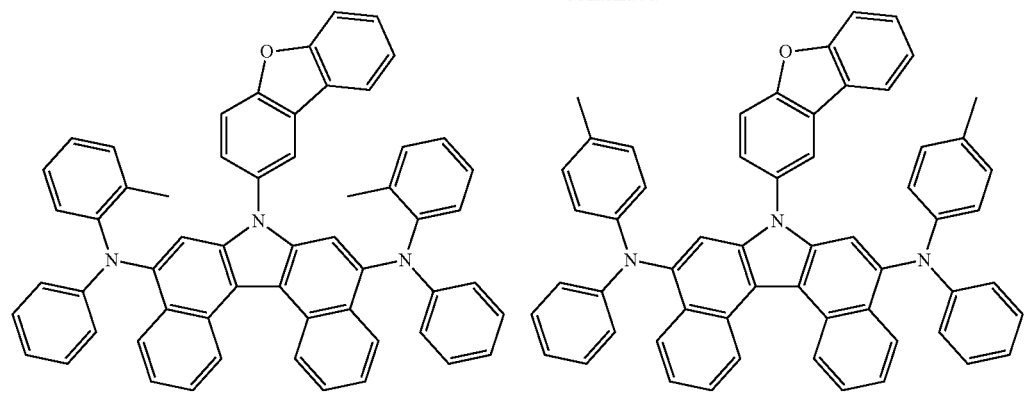
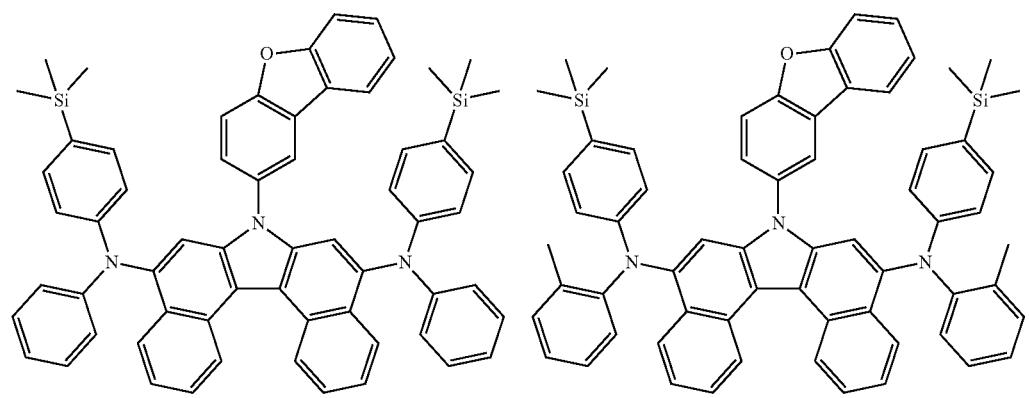
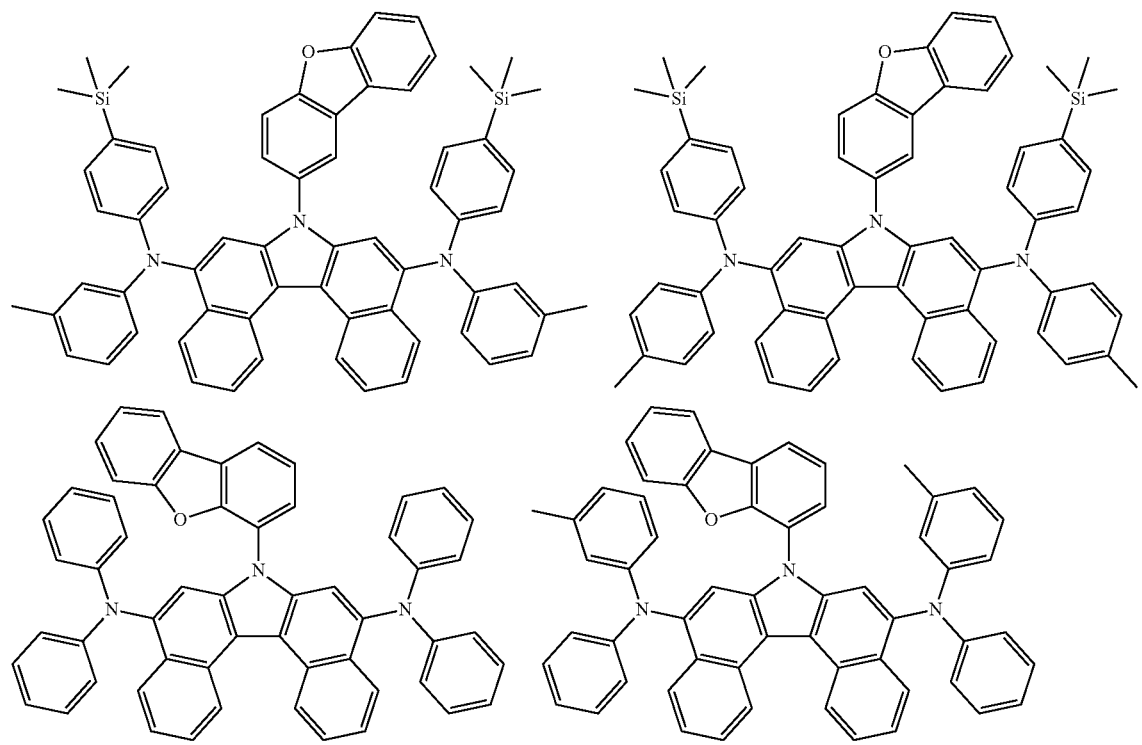

145
146
-continued
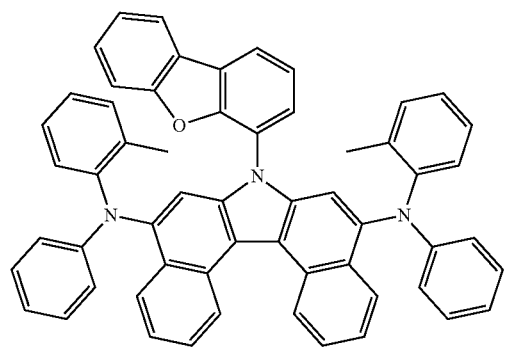
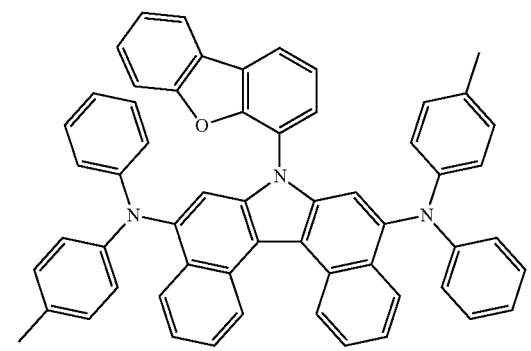
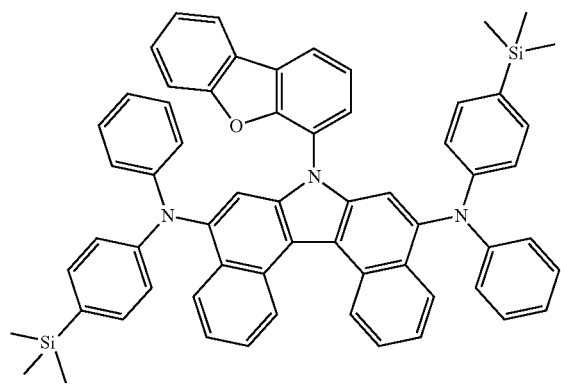
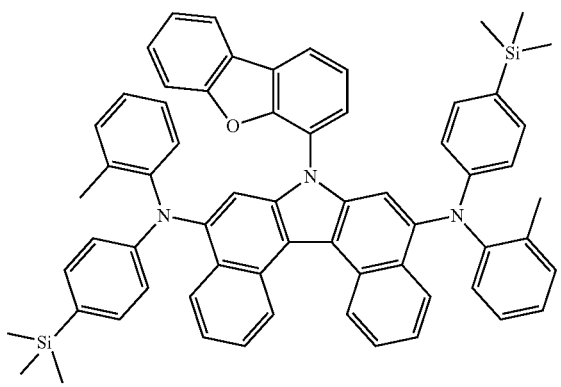
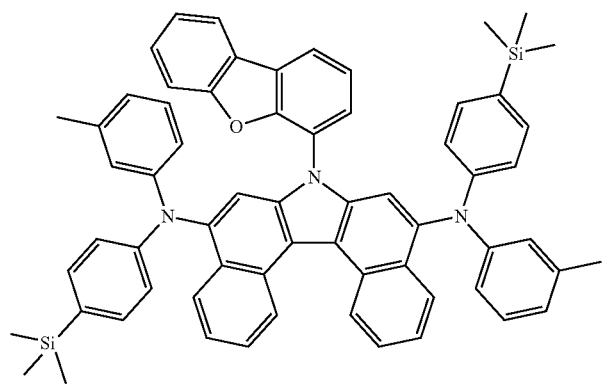
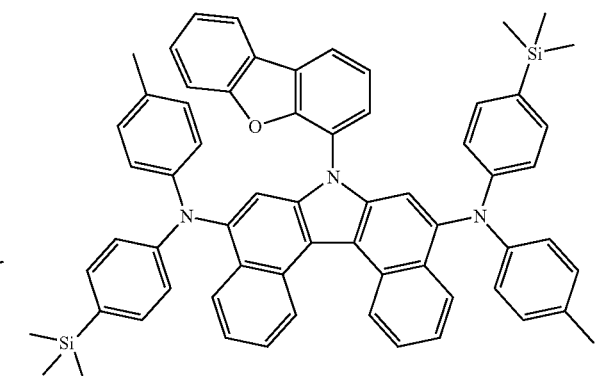
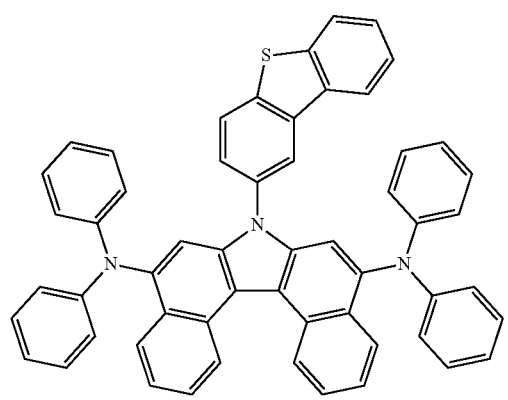
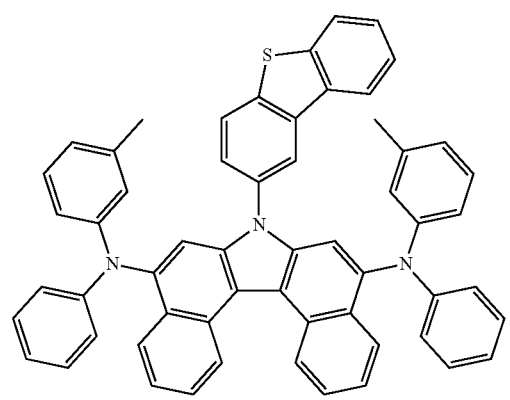

-continued
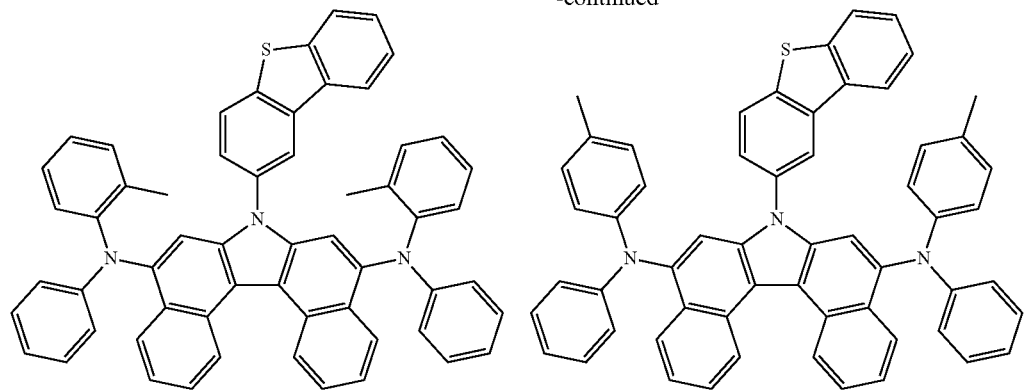
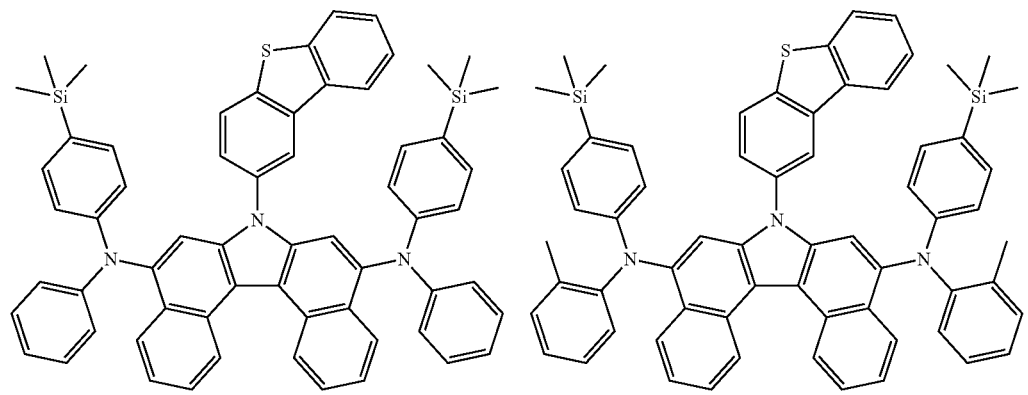
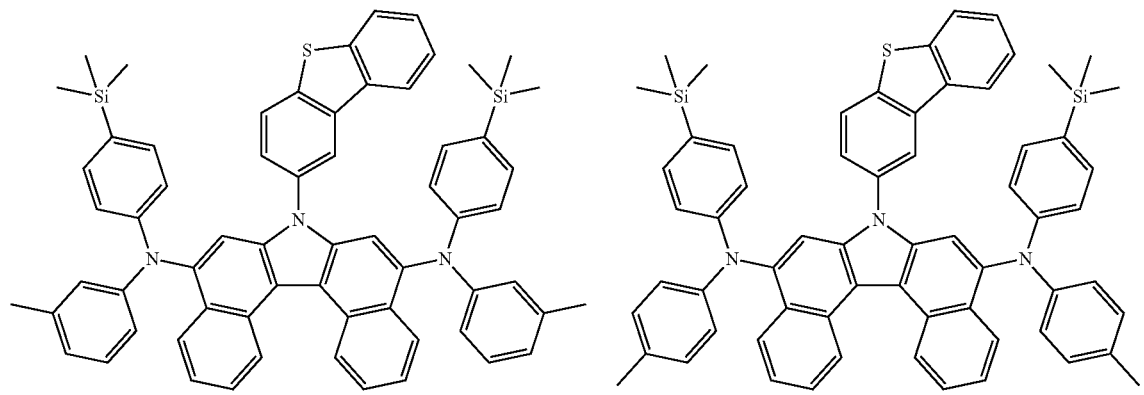
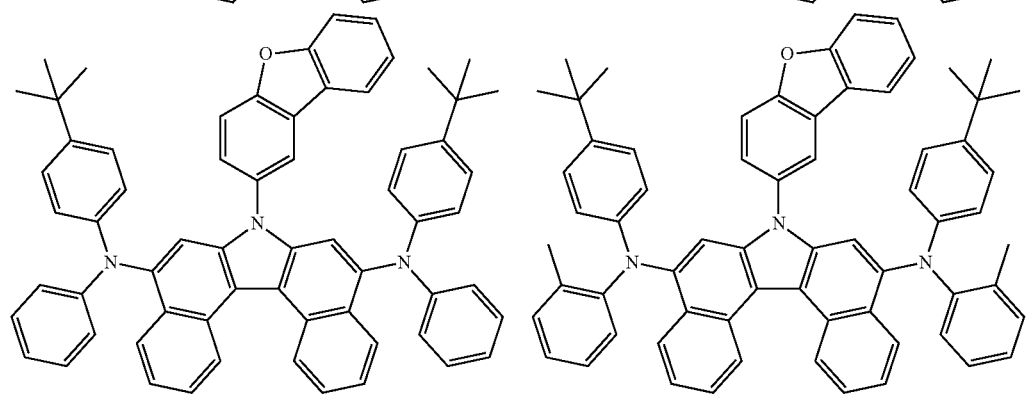

149
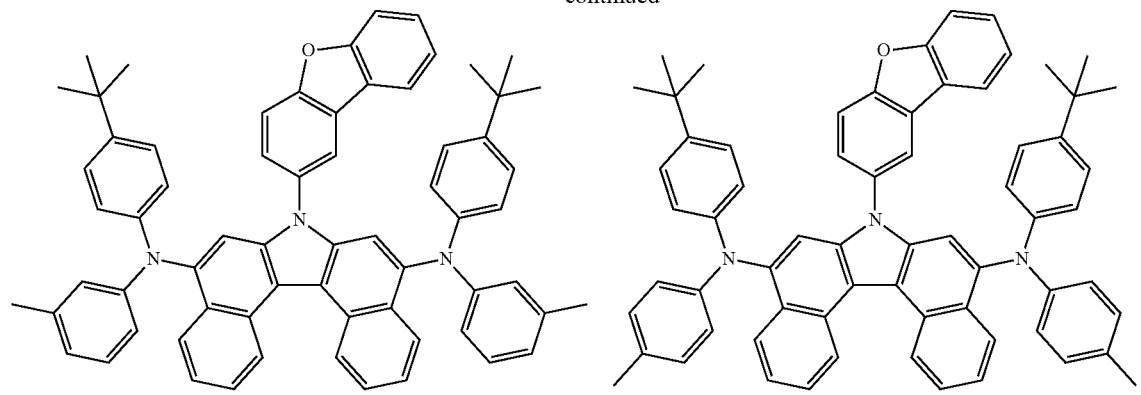
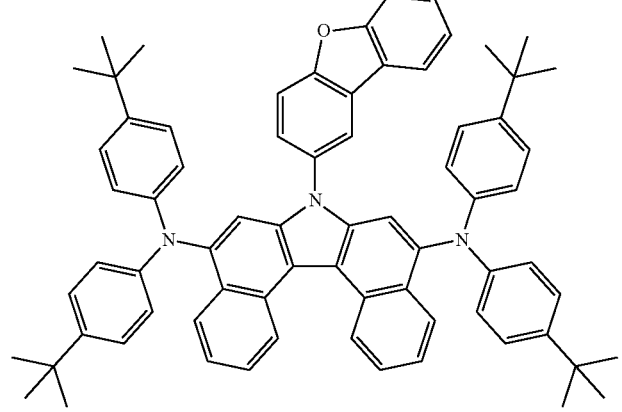
150
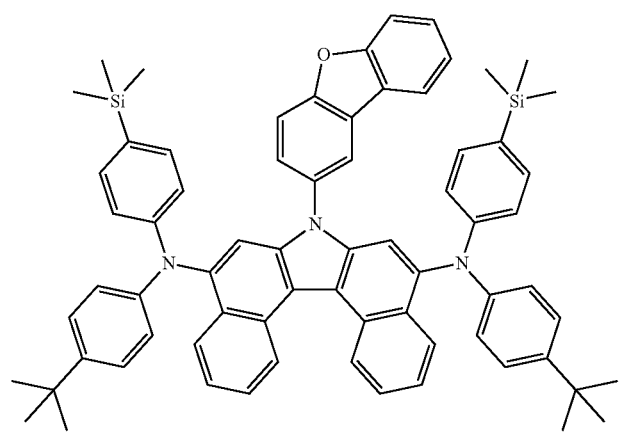
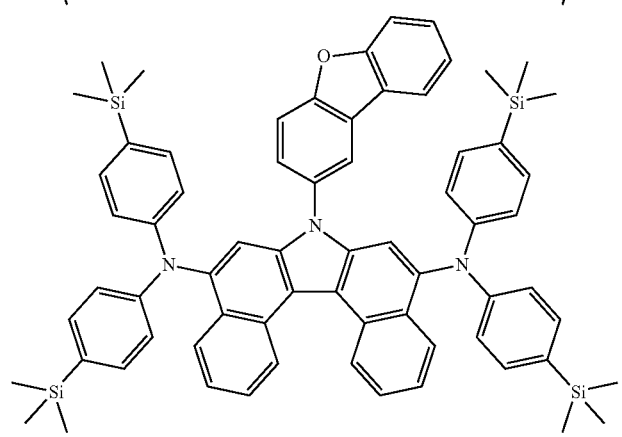

151
152
-continued
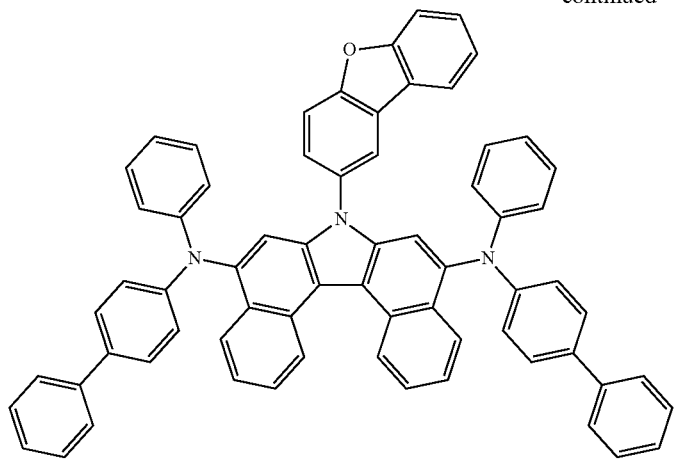
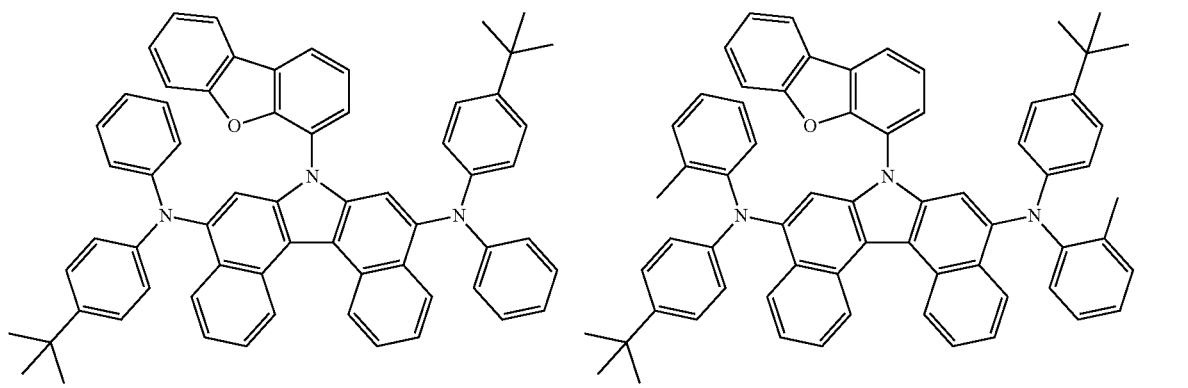
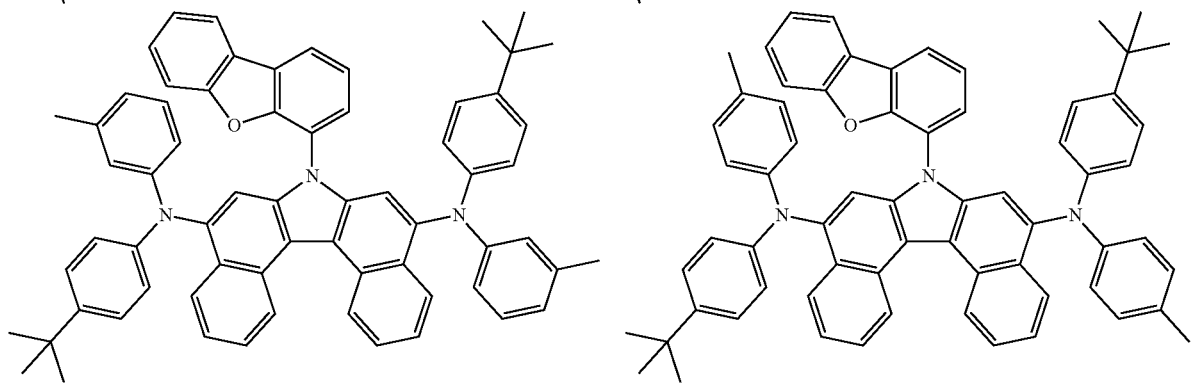
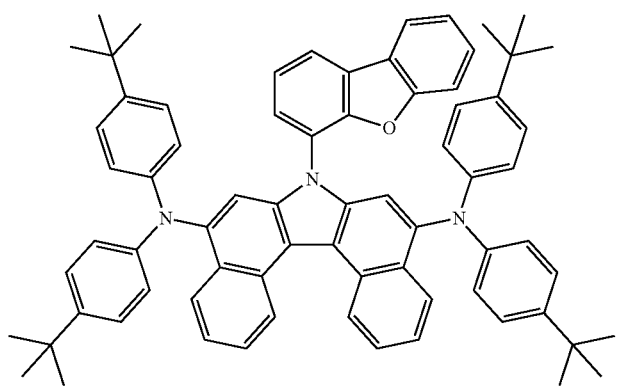

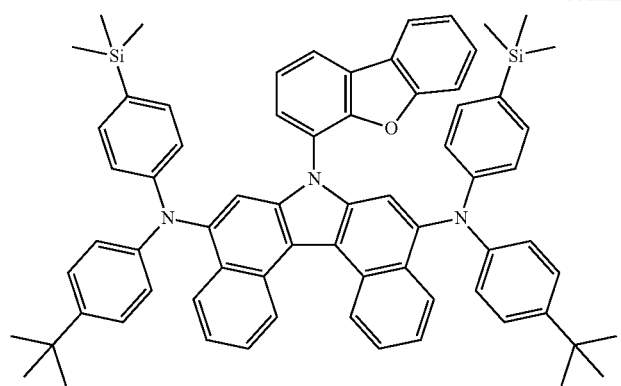
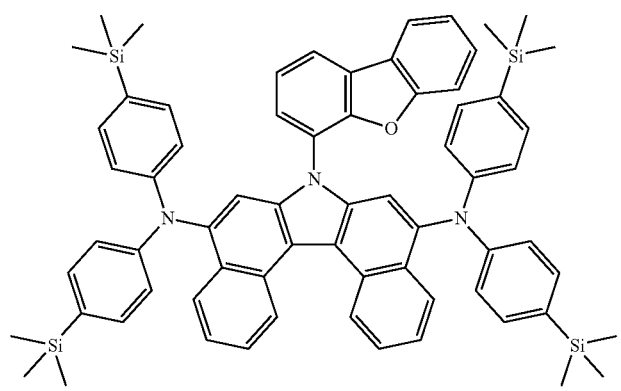
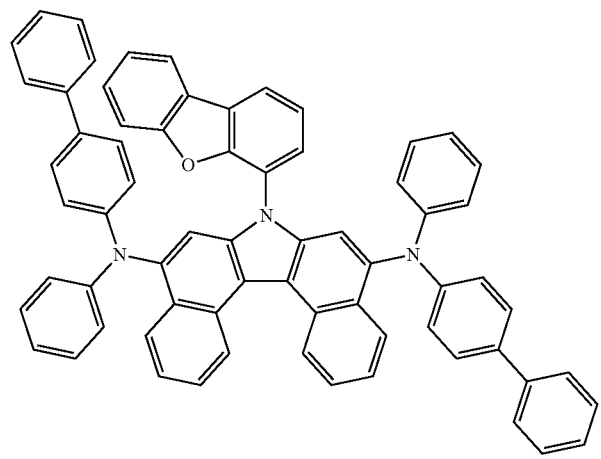
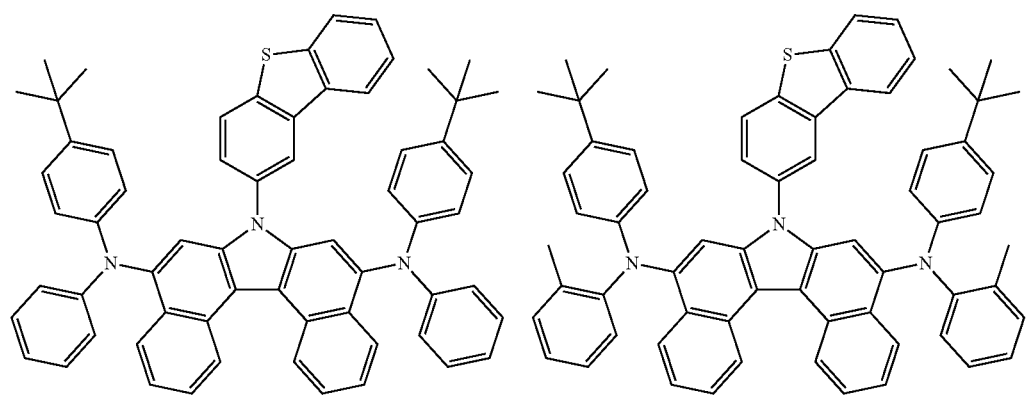

-continued
155 156
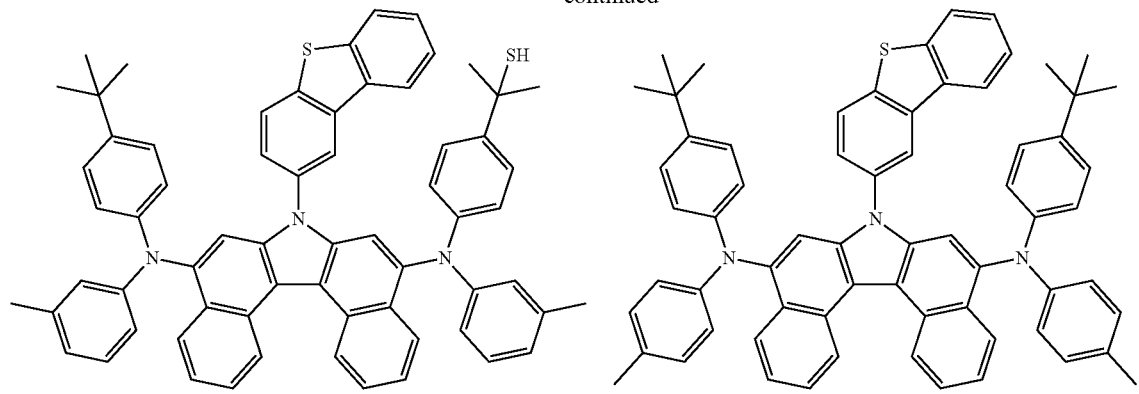
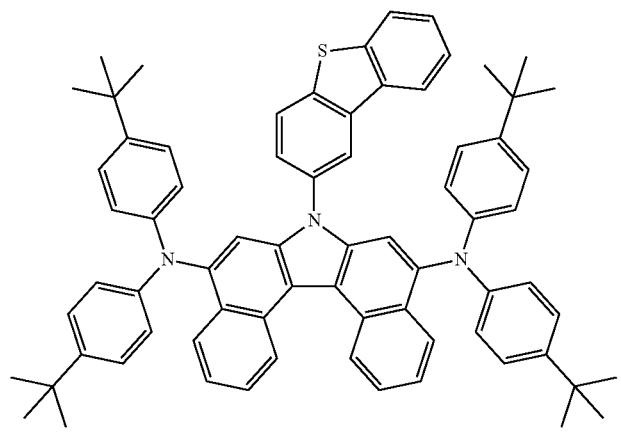
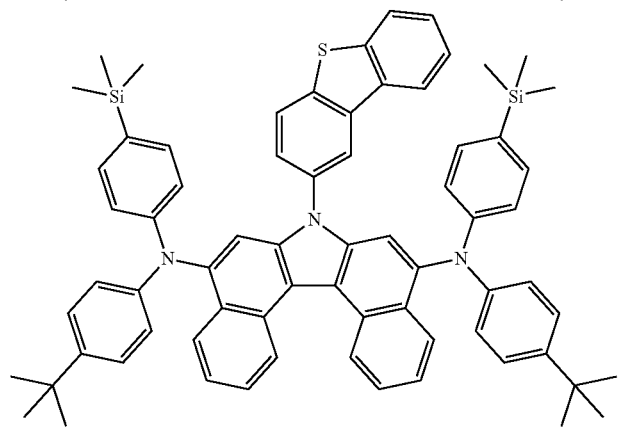
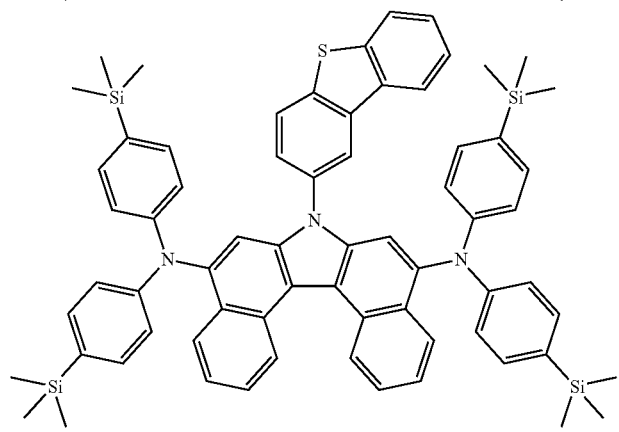

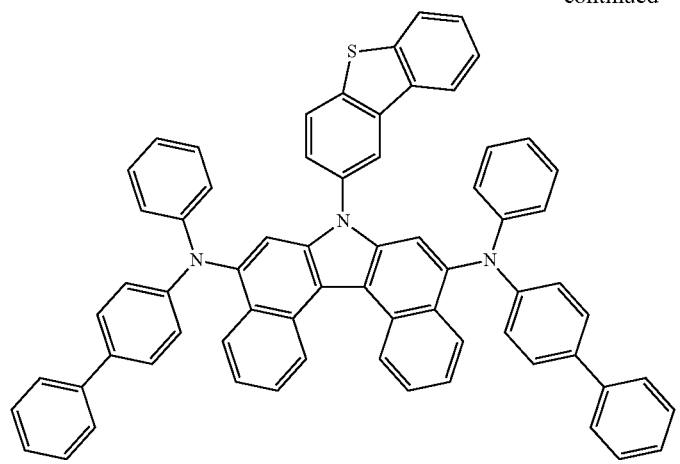
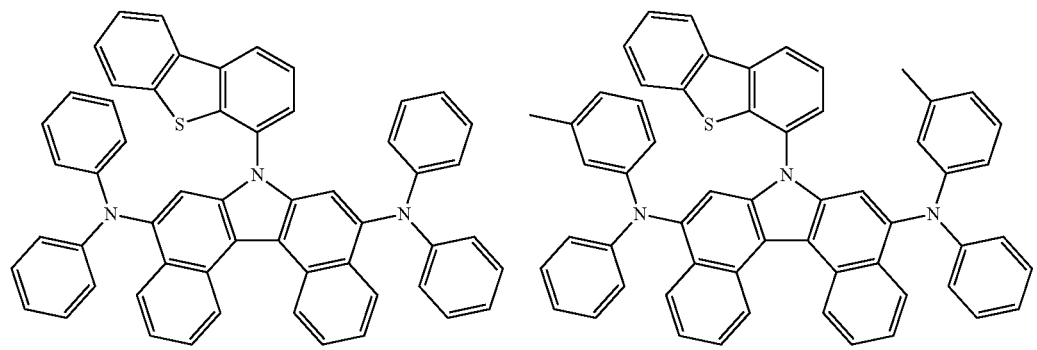
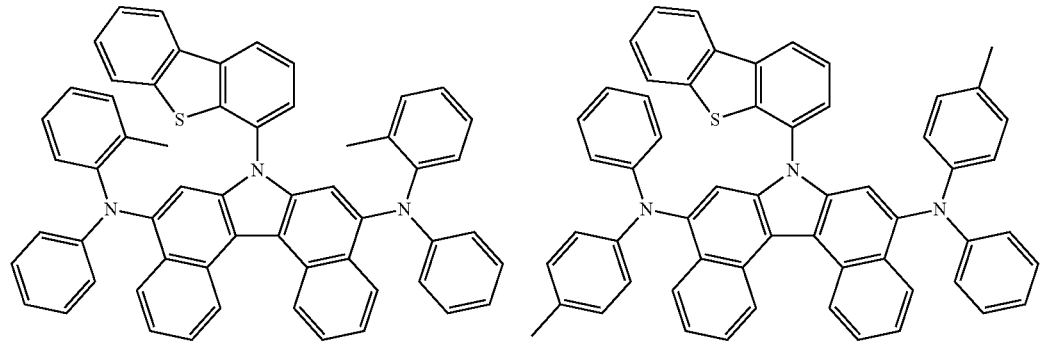
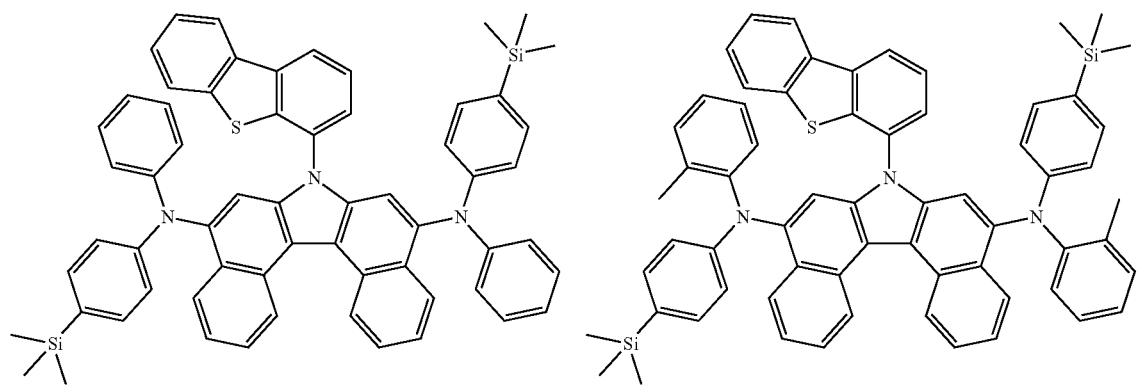

-continued
159 160
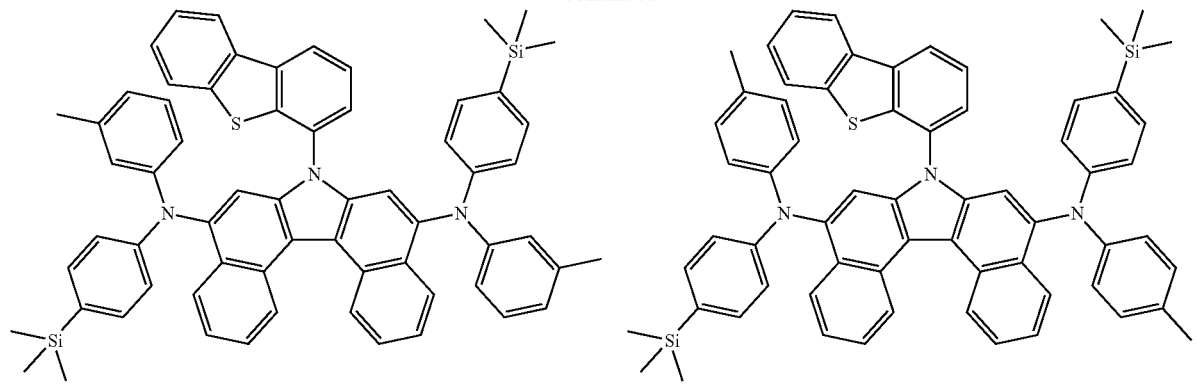
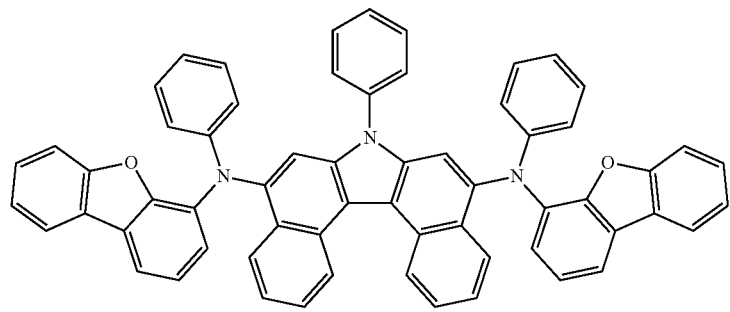
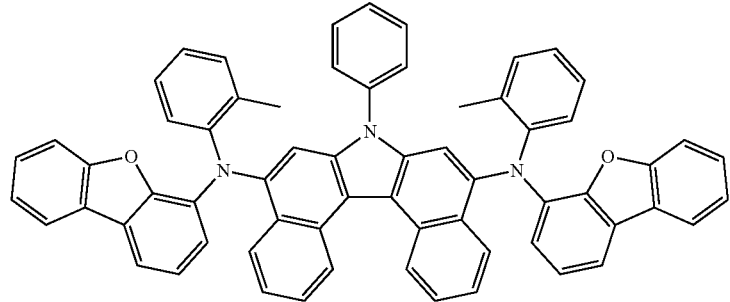
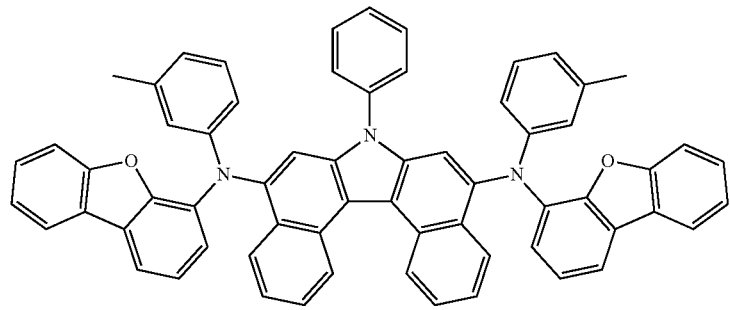
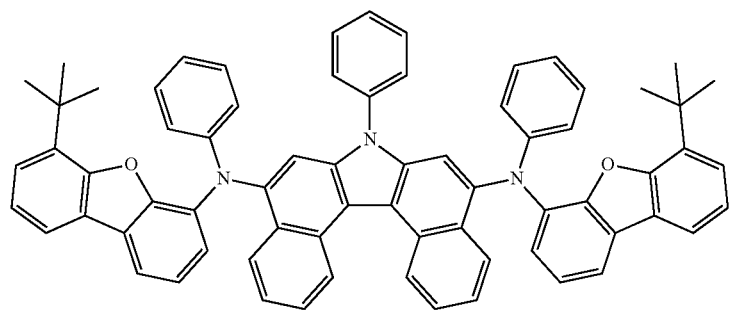

161 162
-continued
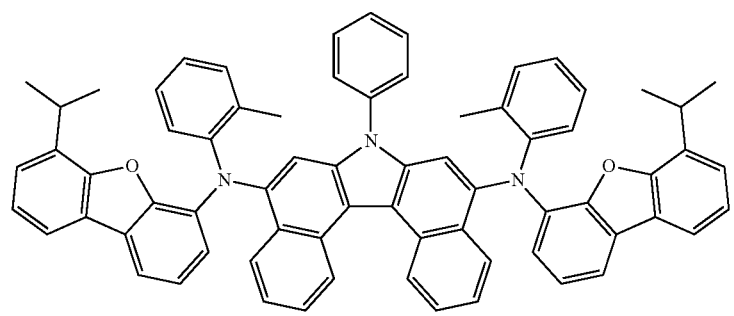
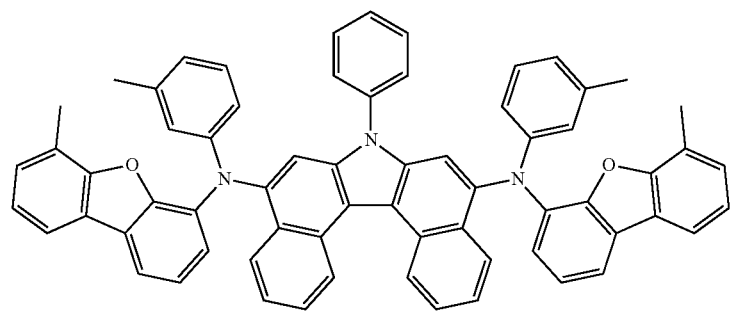
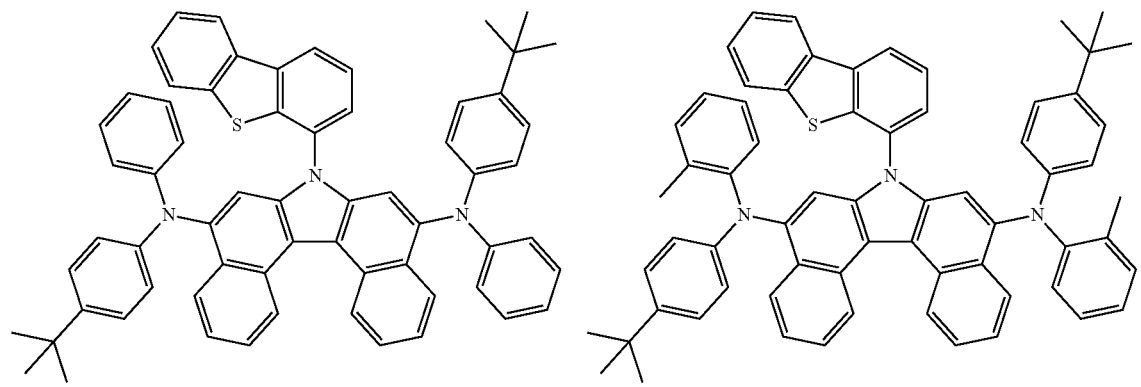
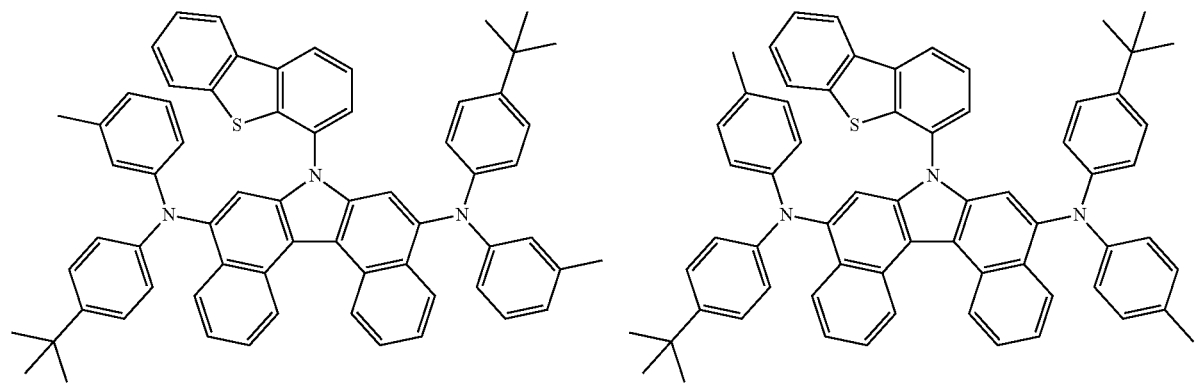

-continued
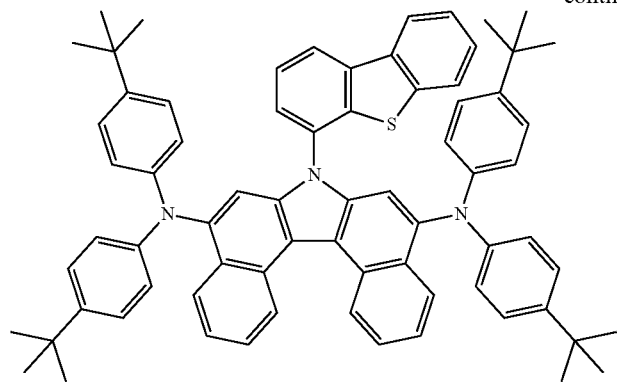
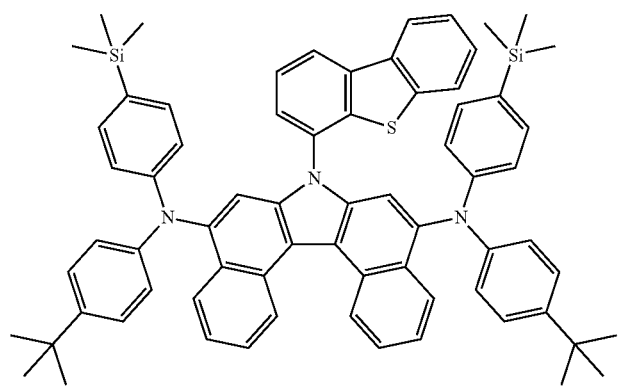
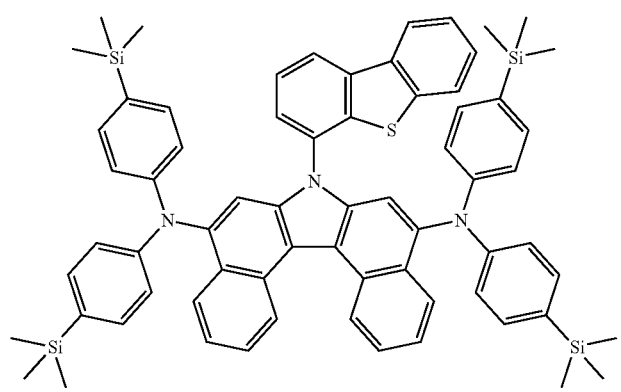
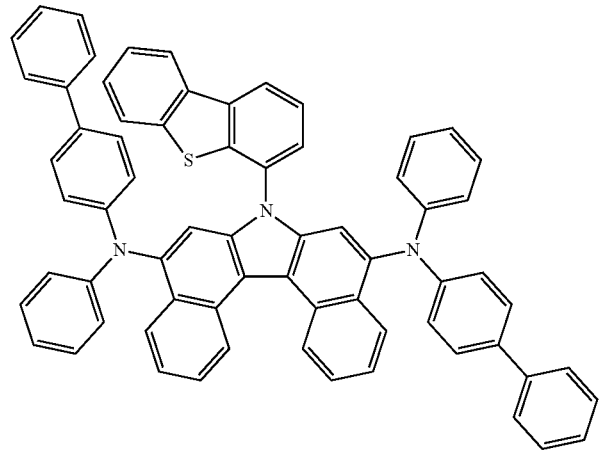

-continued
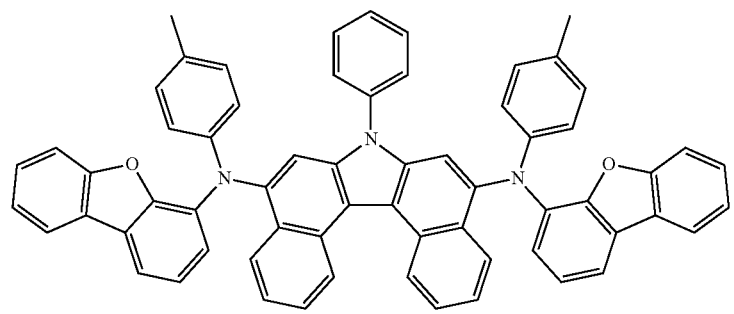
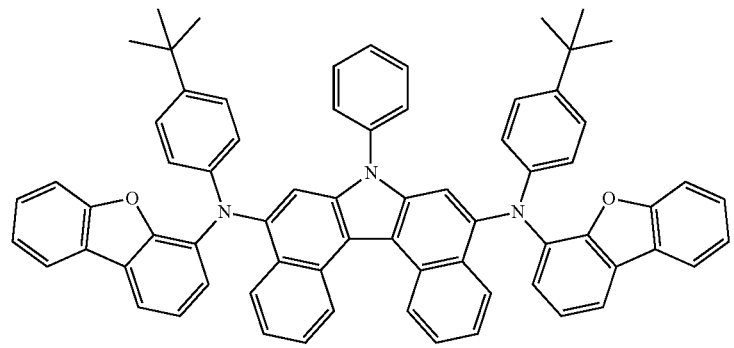
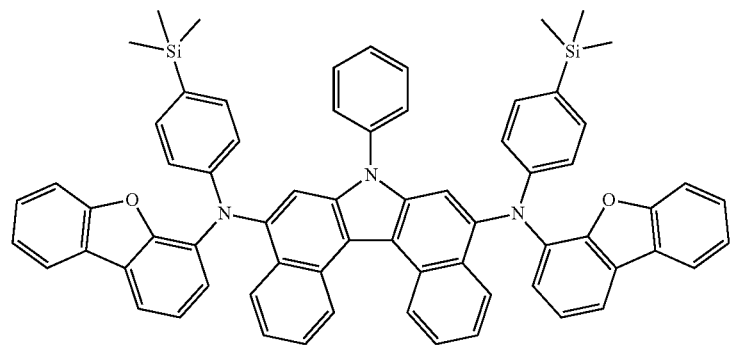
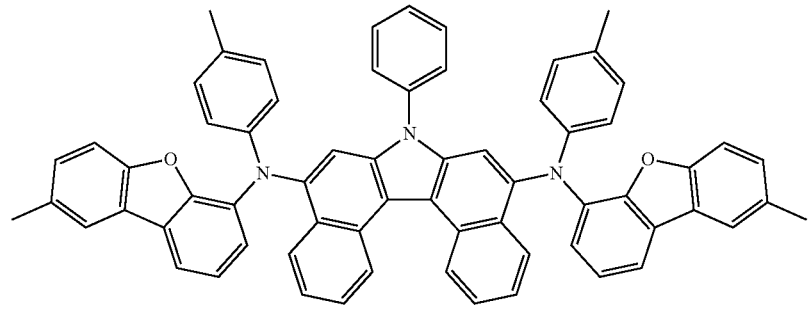
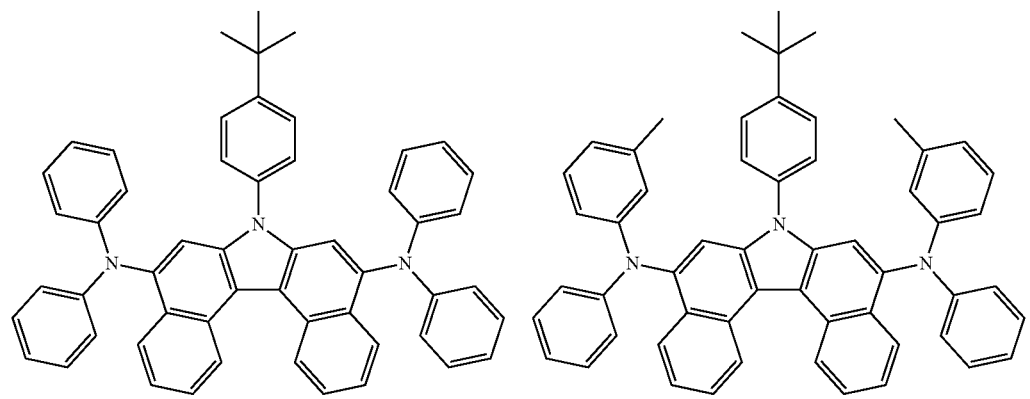

167 168
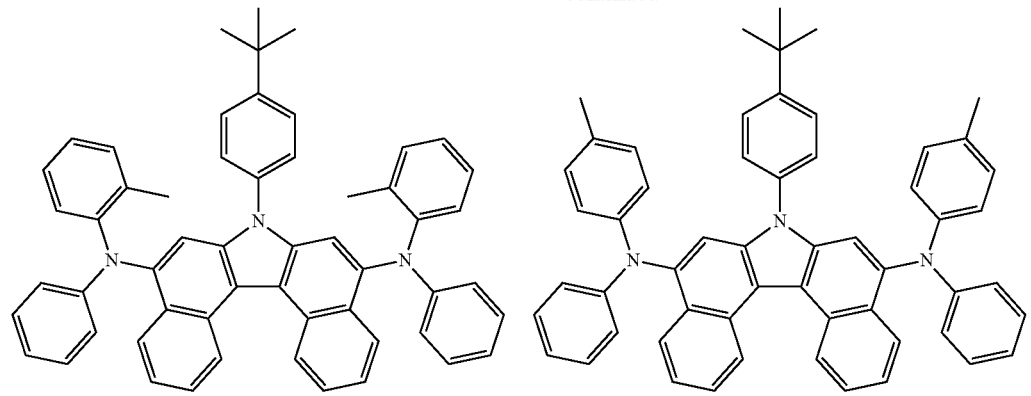
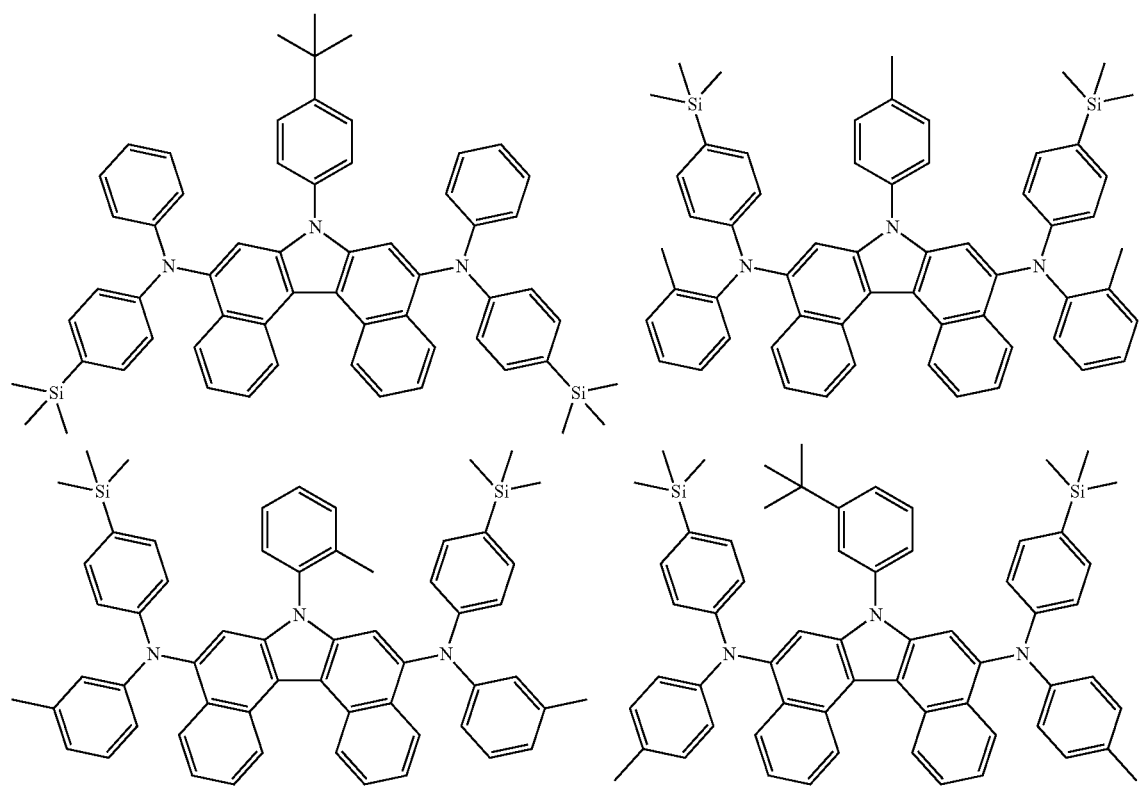
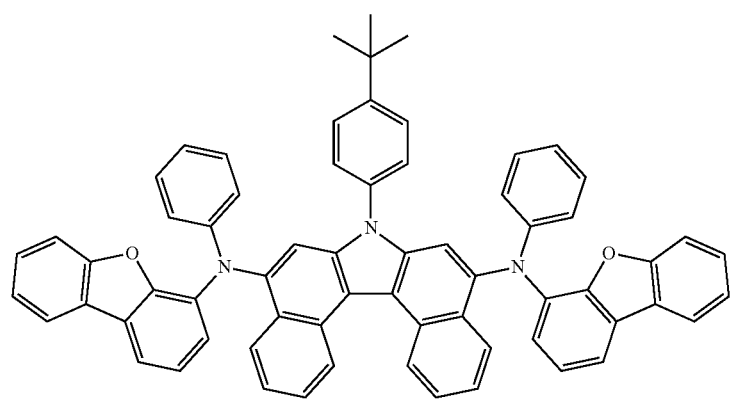

-continued
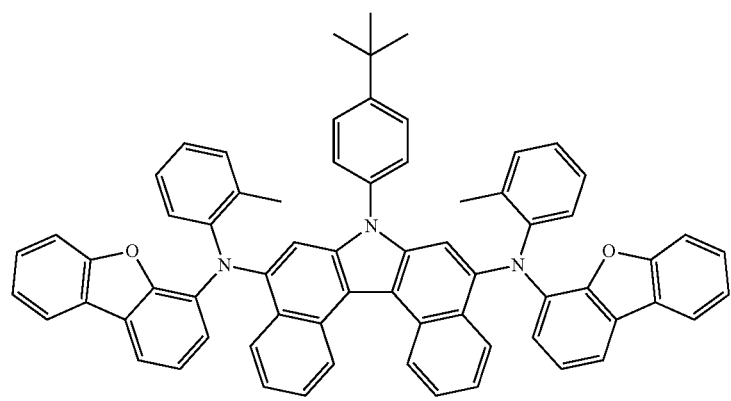
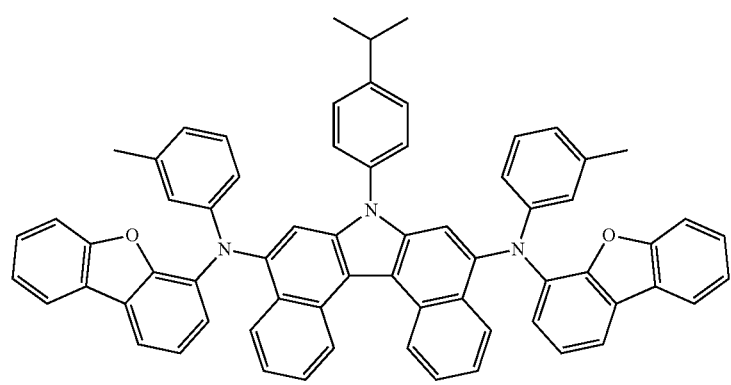
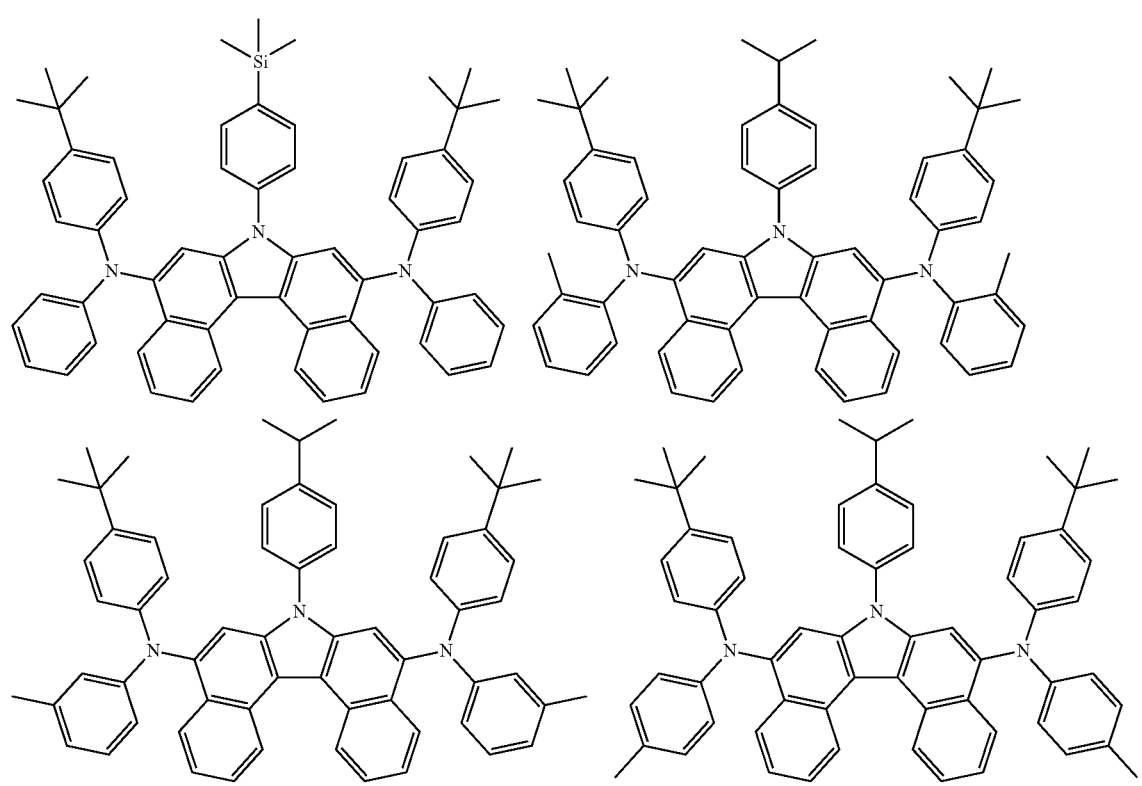

-continued
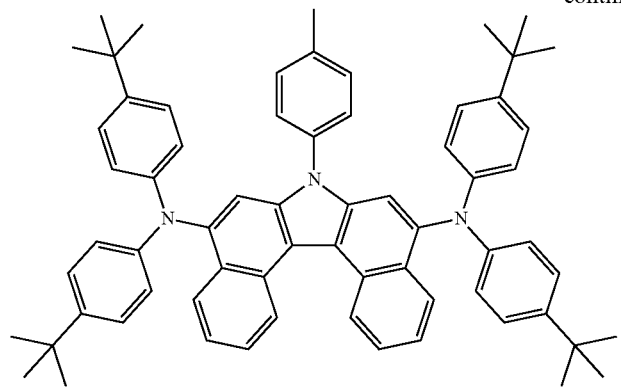
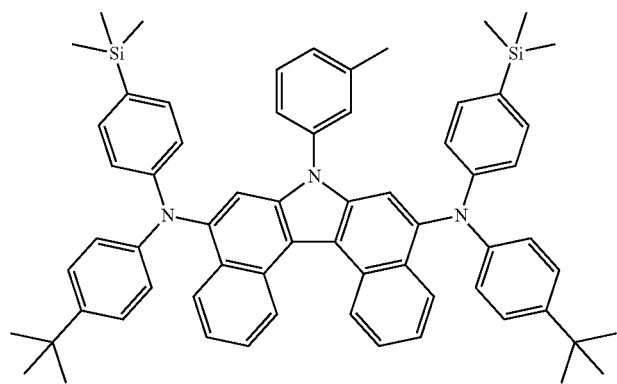
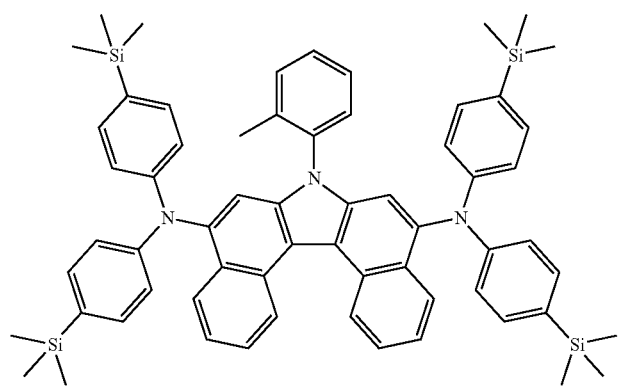
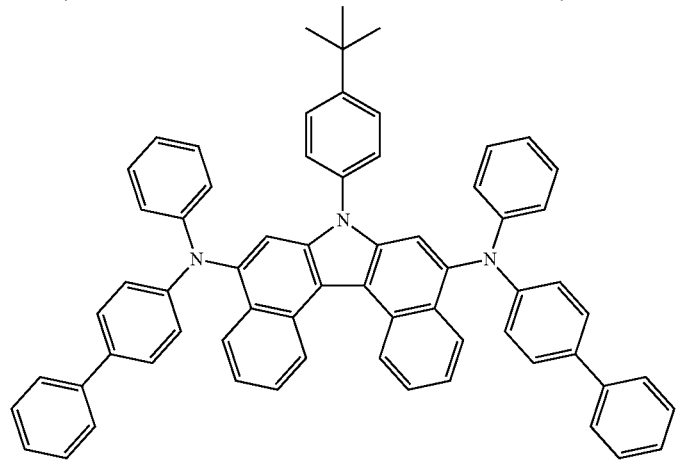

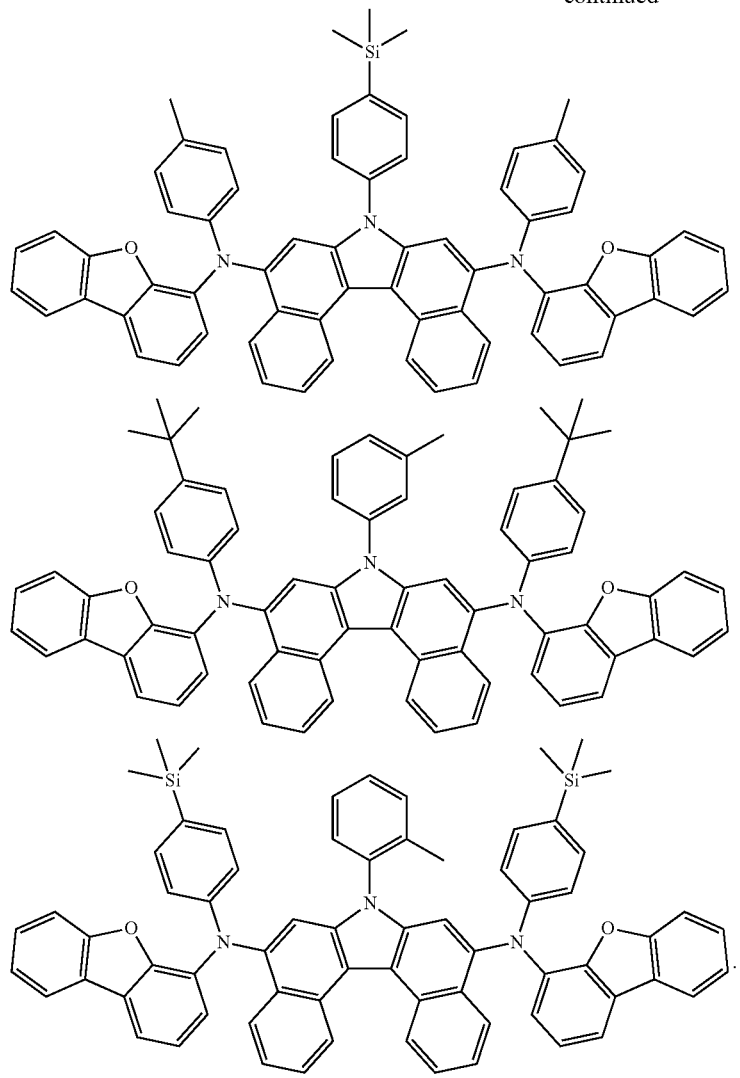

6. An organic light emitting device comprising:
a first electrode;
a second electrode provided opposite to the first electrode; and
one or more organic material layers provided between the first electrode and the second electrode,
wherein one or more layers of the organic material layers include the compound of claim 1.

7. The organic light emitting device of claim 6, wherein the organic material layer includes a light emitting layer, and the light emitting layer includes the compound.

8. The organic light emitting device of claim 6, wherein the organic material layer includes an electron injection layer, an electron transfer layer, or an electron injection and transfer layer, and the electron injection layer, the electron transfer layer, or the electron injection and transfer layer includes the compound.

9. The organic light emitting device of claim 6, wherein the organic material layer includes a hole injection layer, a hole transfer layer, or a hole injection and transfer layer, and the hole injection layer, the hole transfer layer, or the hole injection and transfer layer includes the compound.

10. The organic light emitting device of claim 6, wherein the organic material layer includes a light emitting layer, and the light emitting layer includes the compound as a blue dopant.

11. The organic light emitting device of claim 10, wherein the light emitting layer further includes a compound including anthracene as a host.

12. The organic light emitting device of claim 11, wherein the host is a compound of Chemical Formula A:

[Chemical Formula A]

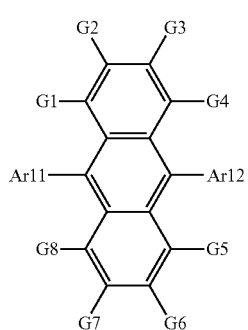

wherein in Chemical Formula A:
  Ar11 and Ar12 are the same as or different from each other, and each independently is a substituted or unsubstituted aryl group; or a substituted or unsubstituted heterocyclic group; and
  G1 to G8 are the same as or different from each other, and each independently is hydrogen a substituted or unsubstituted monocyclic aryl group, or a substituted or unsubstituted polycyclic aryl group.

13. The organic light emitting device of claim 12, wherein Chemical Formula A is selected from among the following compounds:

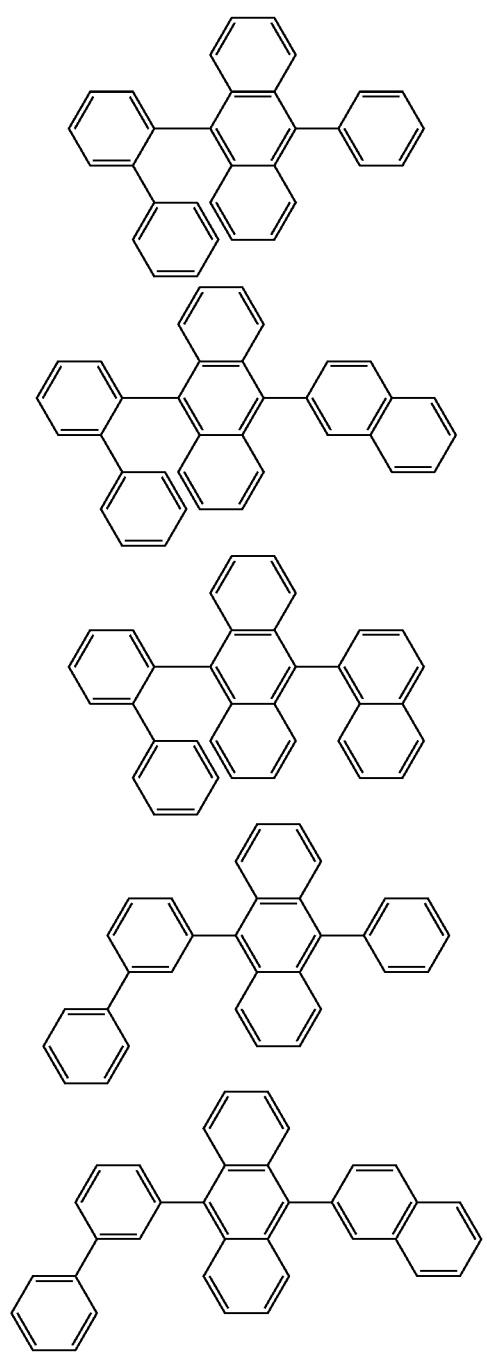
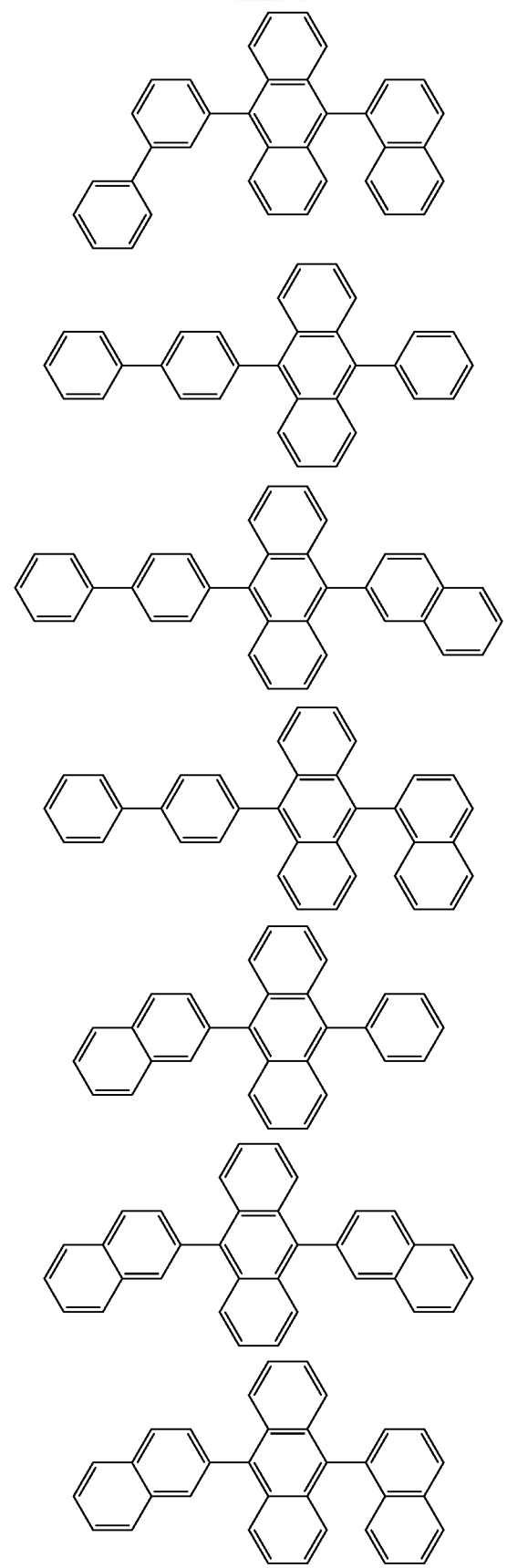

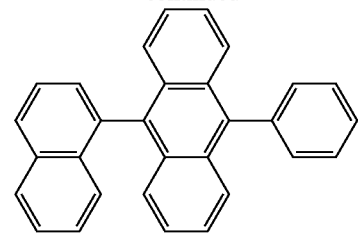
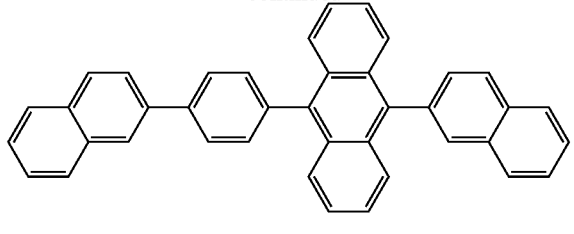
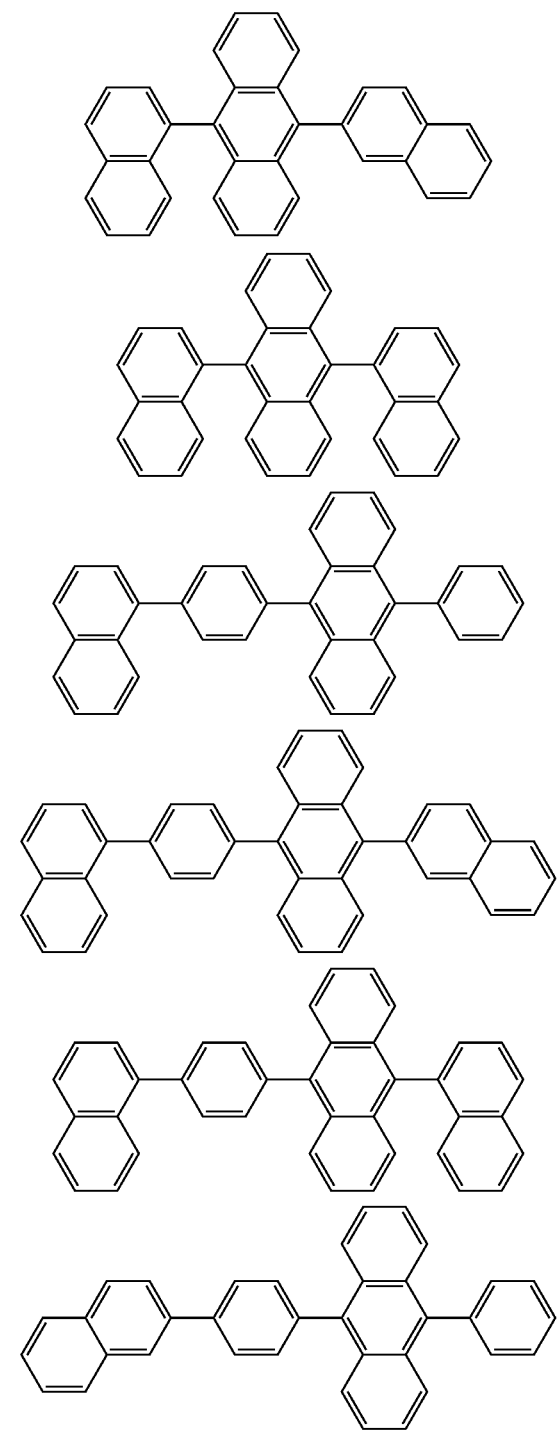
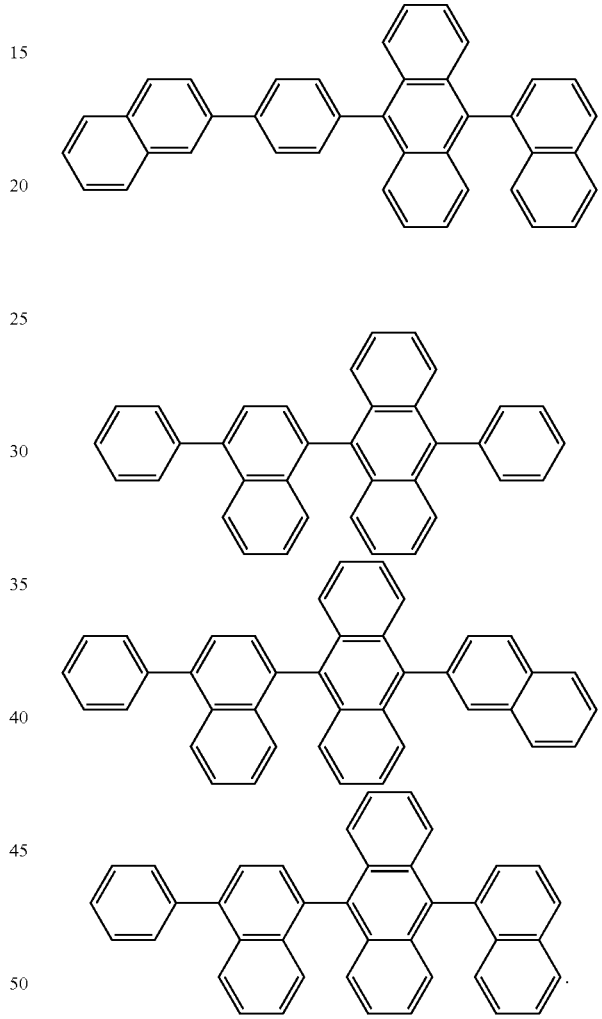

14. An organic light emitting device comprising:
a first electrode;
a second electrode provided opposite to the first electrode; and
one or more organic material layers provided between the first electrode and the second electrode,
wherein:
the organic material layers include a light emitting layer, and the light emitting layer includes a compound of the following Chemical Formula 1 as a blue dopant, and
the light emitting layer further includes a compound including anthracene as a host, wherein the host is a compound of the following Chemical Formula A-1:

[Chemical Formula A-1]

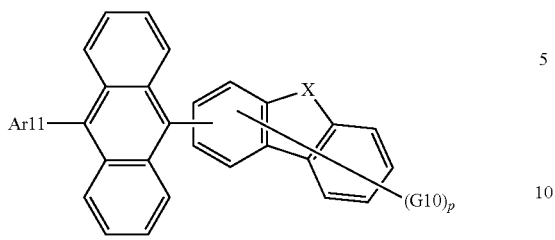

wherein, in Chemical Formula 1:

Ar1 is a substituted or unsubstituted aryl group having 6 to 30 carbon atoms, or a substituted or unsubstituted heterocyclic group having 2 to 30 carbon atoms;

Ar2 and Ar4 are the same as each other, and Ar3 and Ar5 are the same as each other;

Ar2 to Ar5 are each a substituted or unsubstituted aryl group, or a substituted or unsubstituted heterocyclic group;

R1 and R2 are the same as or different from each other, and each independently is hydrogen, deuterium, a halogen group, a cyano group, a substituted or unsubstituted alkyl group, a substituted or unsubstituted alkoxy group, a substituted or unsubstituted aryl group, or a substituted or unsubstituted heterocyclic group; and n and m are each an integer of 0 to 5, and when n is 2 or greater, the R1s are the same as or different from each other, and when m is 2 or greater, the R2s are the same as or different from each other;

[Chemical Formula A-1]

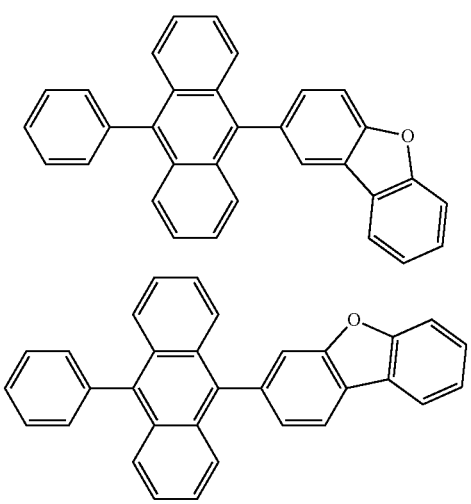

wherein in Chemical Formula A-1:

Ar11 is a substituted or unsubstituted aryl group;

X is O or S;

G10 is hydrogen, a substituted or unsubstituted aryl group, or a substituted or unsubstituted heterocyclic group, or adjacent two or more G10s bond to each other to form a ring; and p is an integer of 0 to 4, and when p is 2 or greater, the G10s are the same as or different from each other.

15. The organic light emitting device of claim 14, wherein Chemical Formula A-1 is selected from among the following compounds:

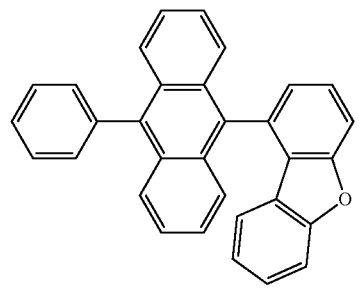

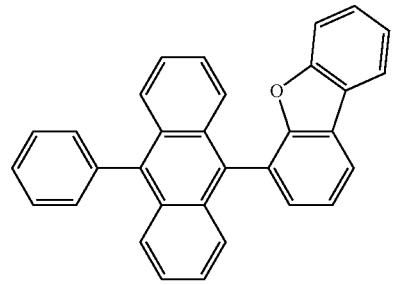

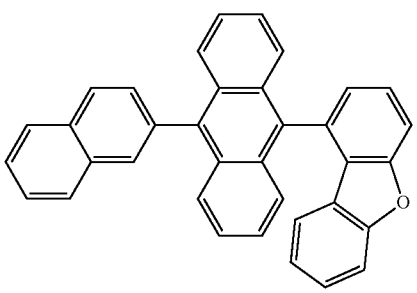

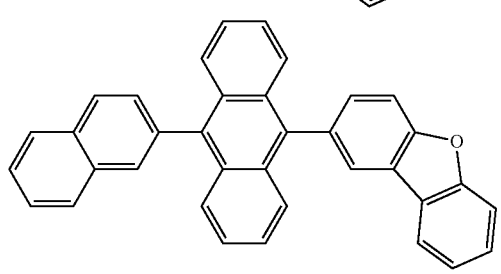

181
-continued
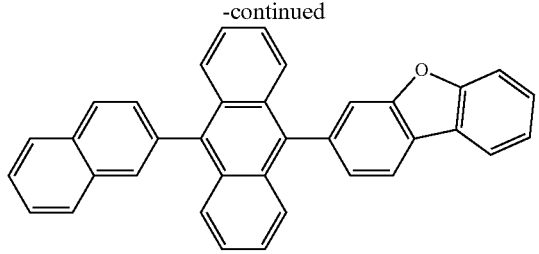
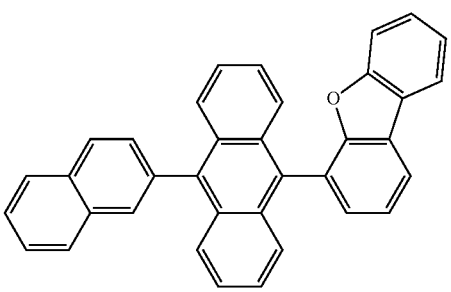
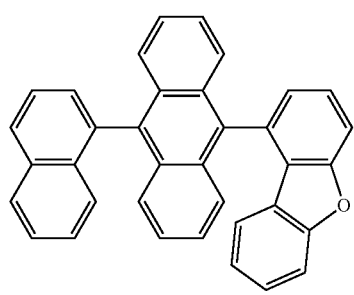
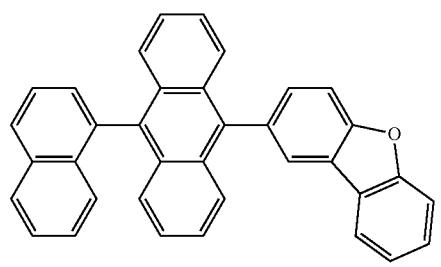
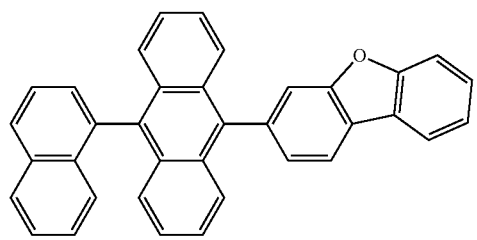
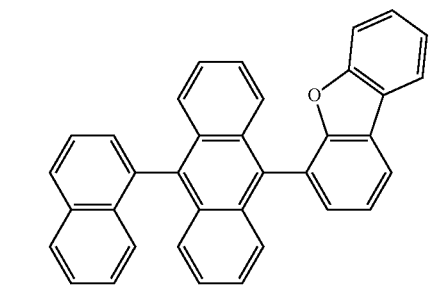
182
-continued
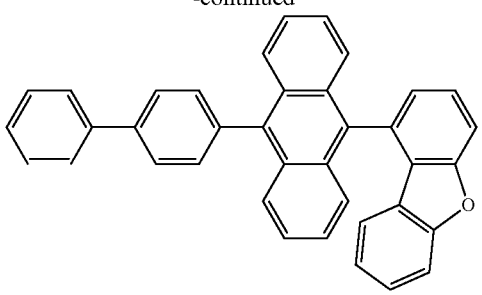
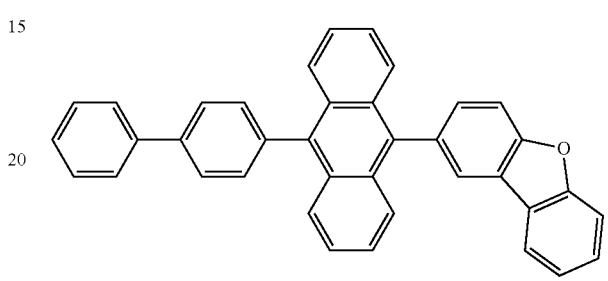
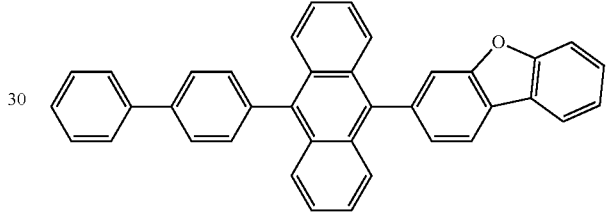
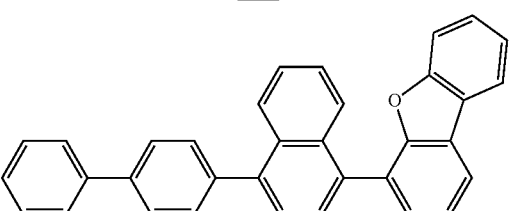
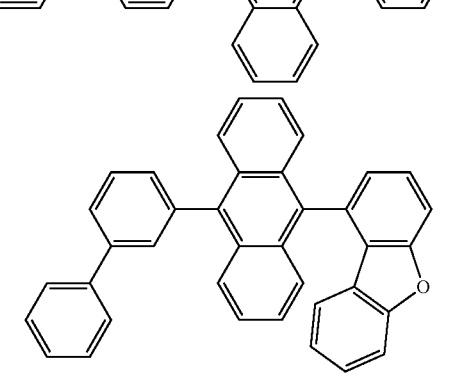
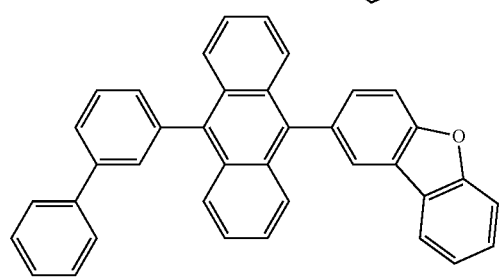

-continued
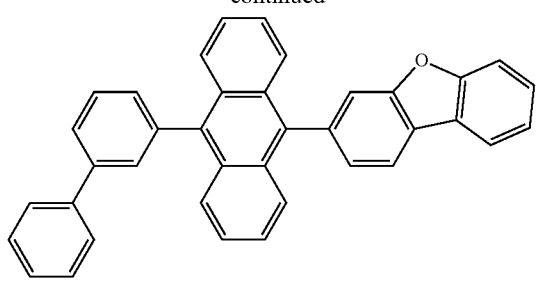
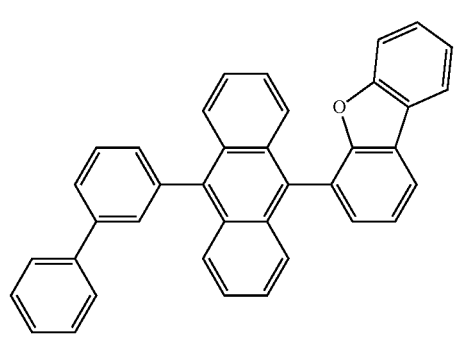
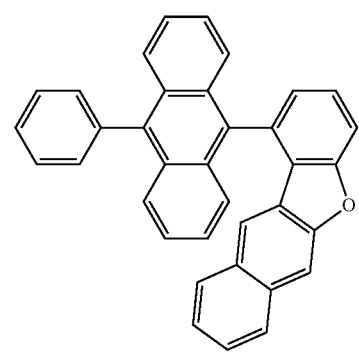
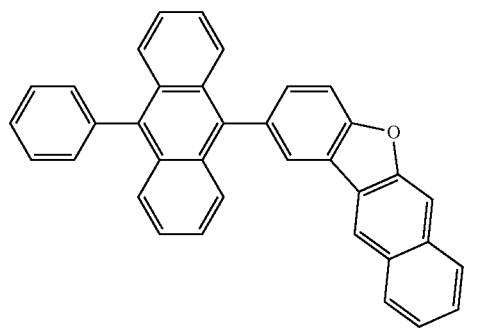
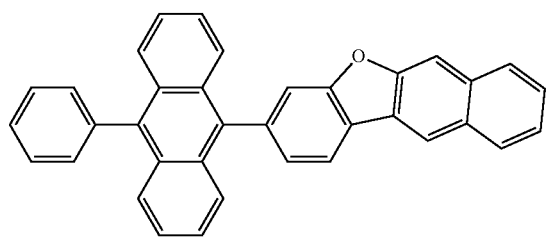
-continued
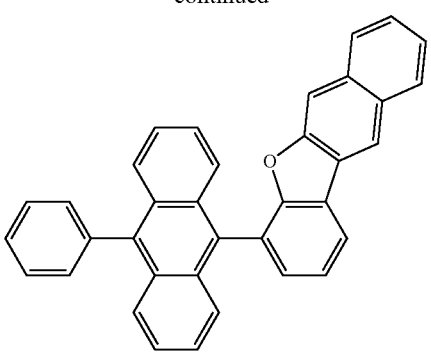
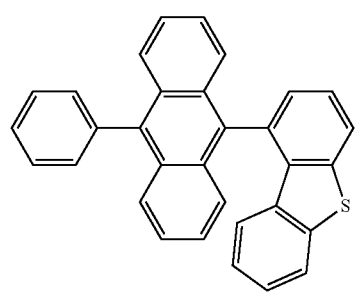
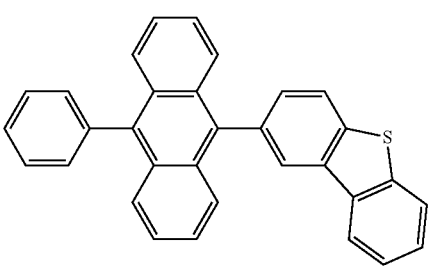
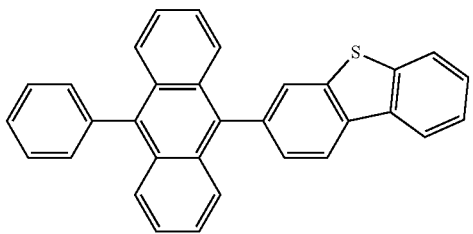
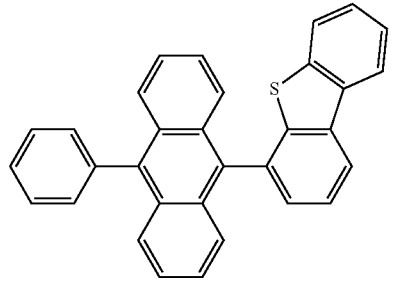
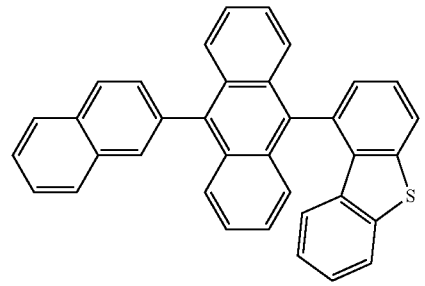

-continued
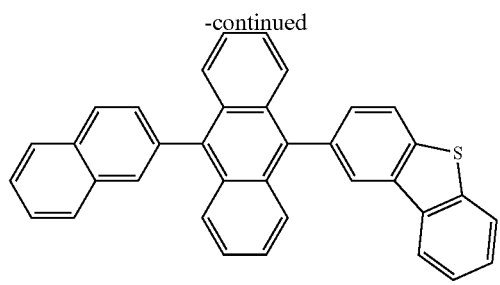
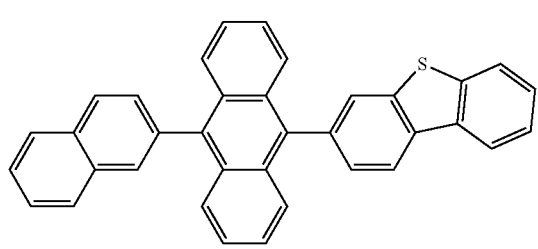
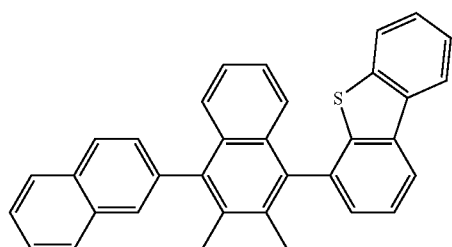
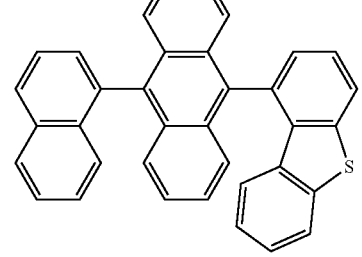
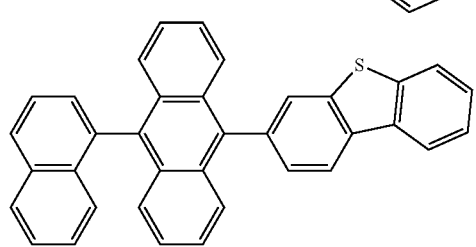
-continued
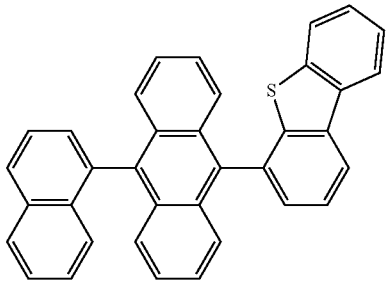
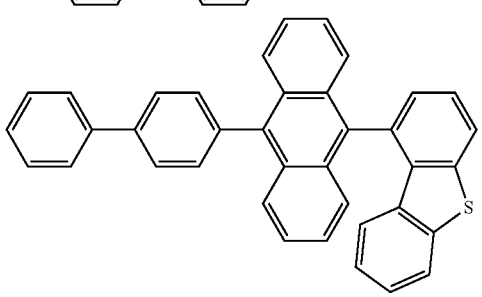
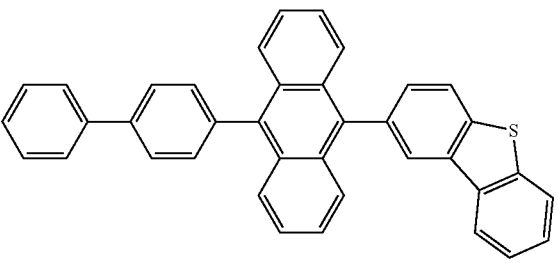
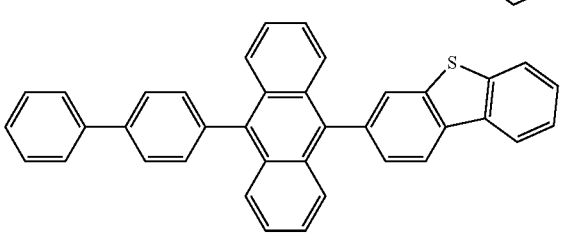
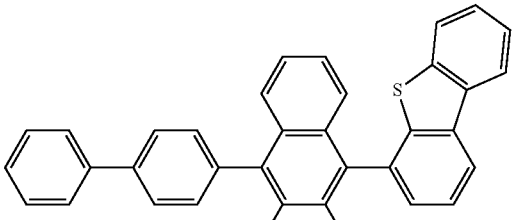
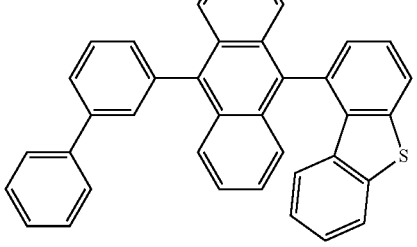

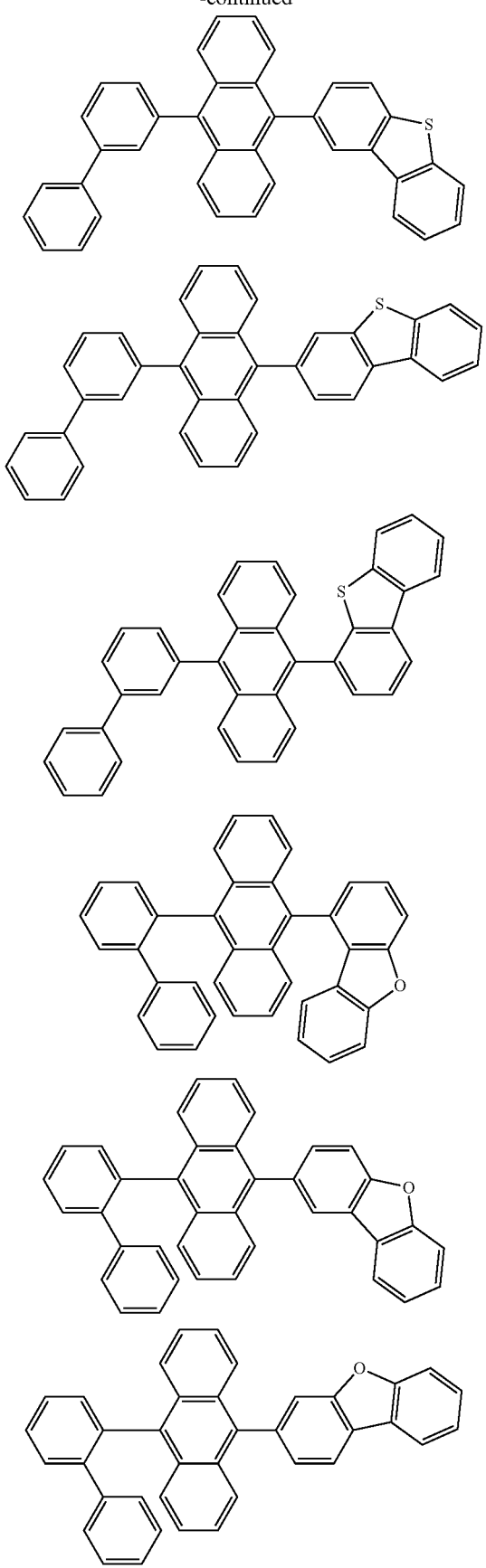
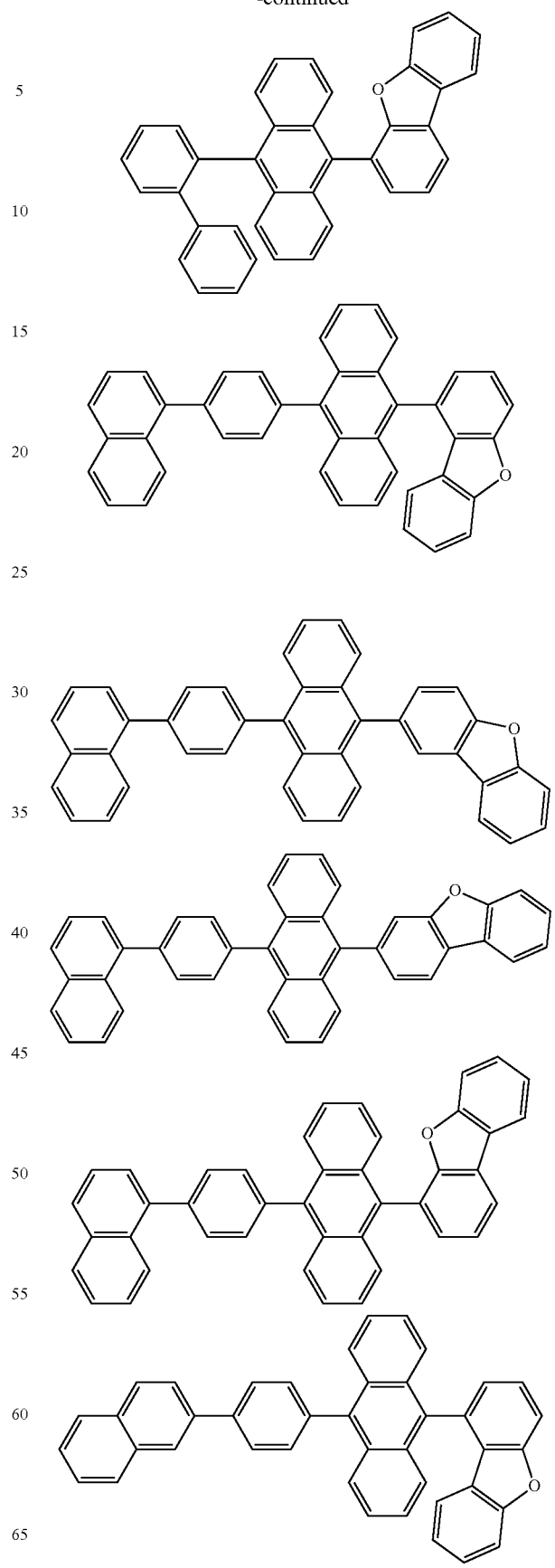

-continued
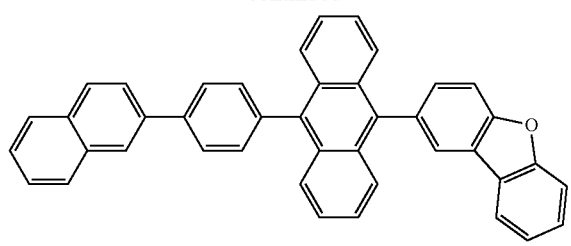
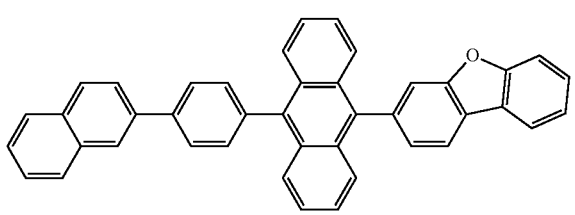
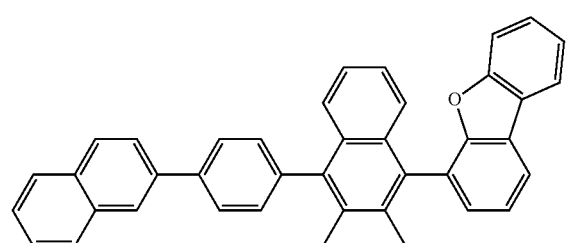
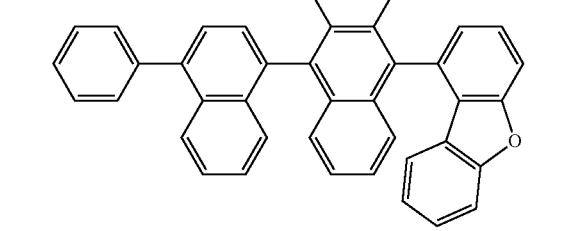
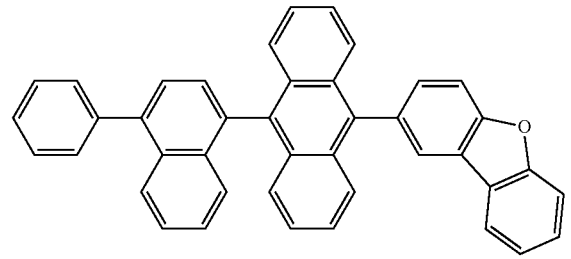
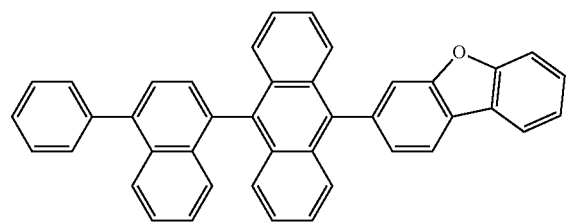
-continued
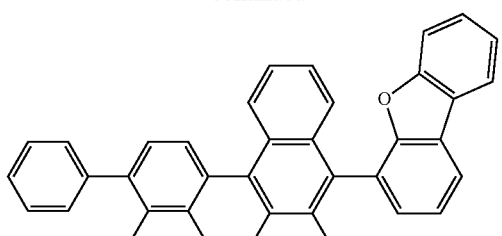
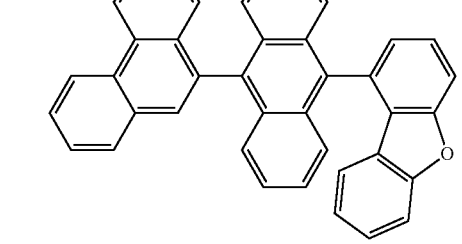
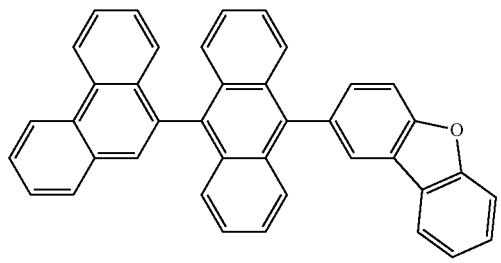
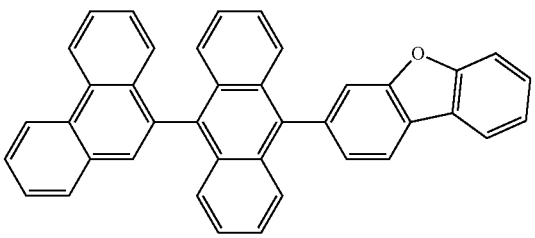
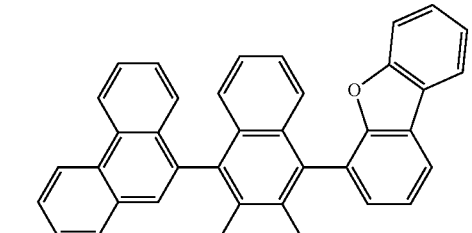
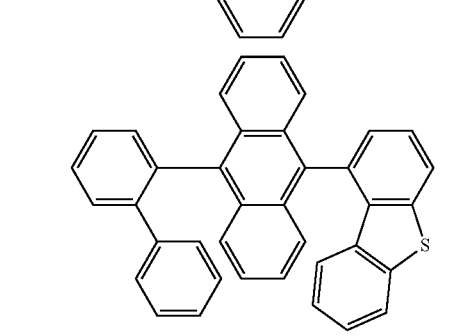

191
-continued
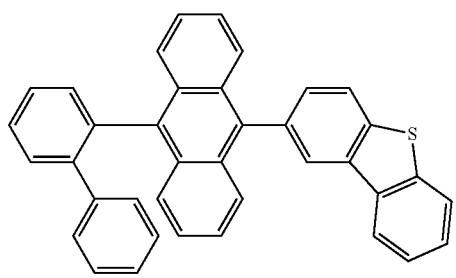
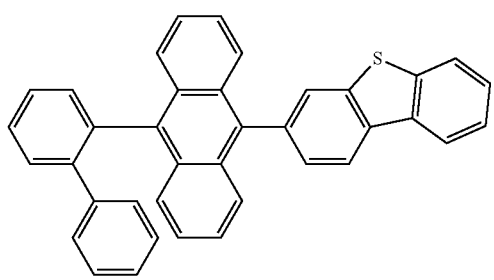
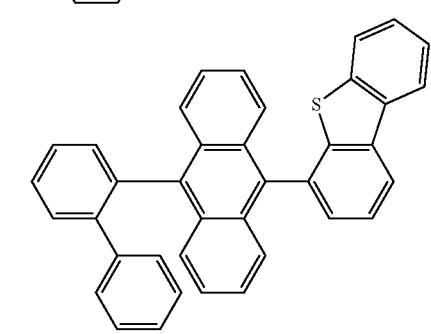
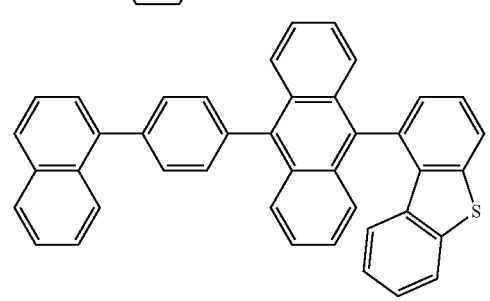
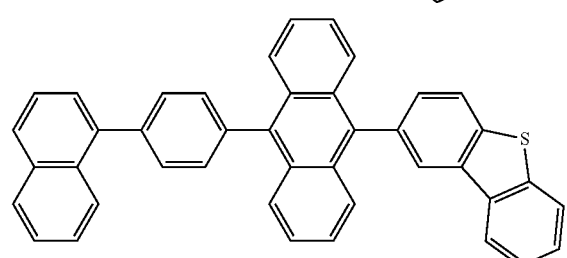
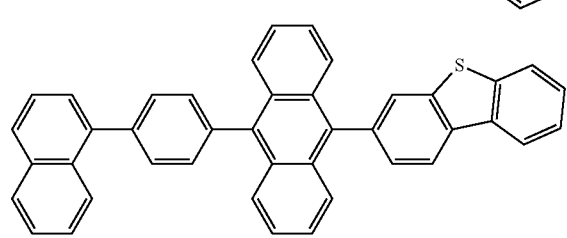
192
-continued
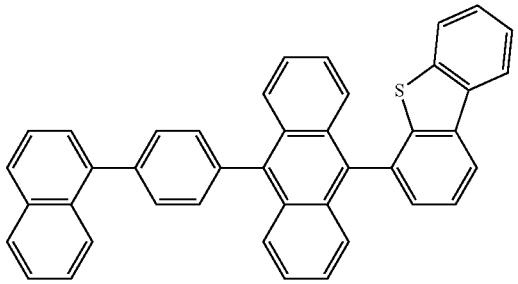
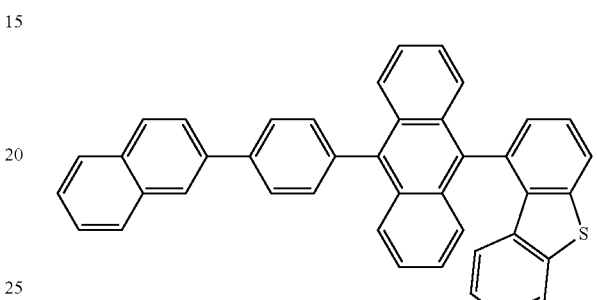
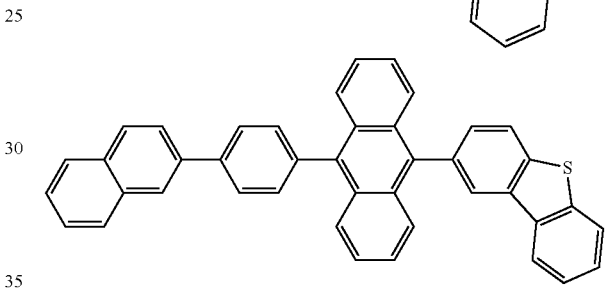
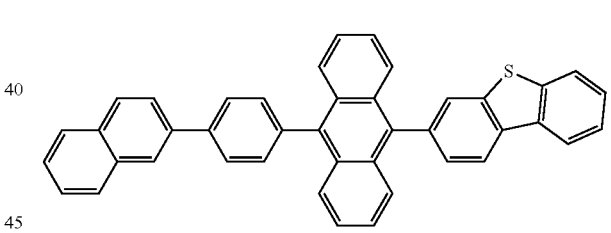
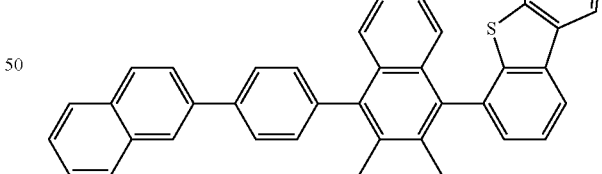
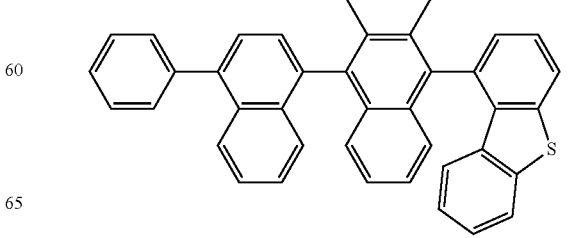

-continued
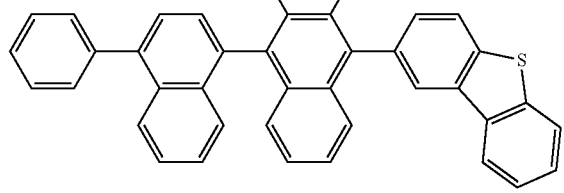
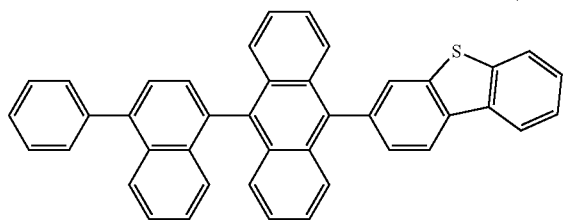
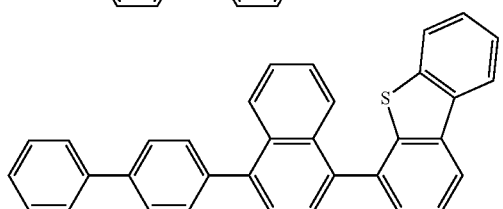
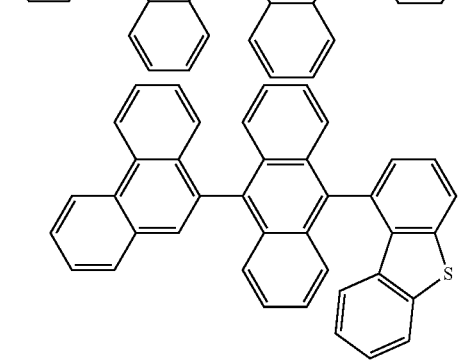
-continued
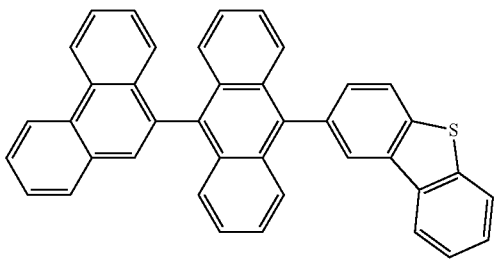
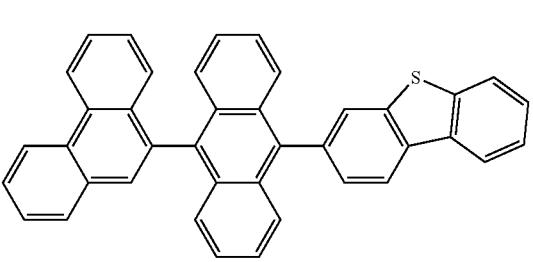
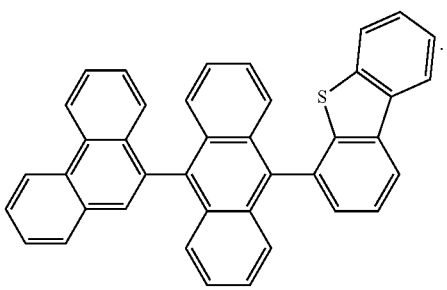
* * * * *

UNITED STATES PATENT AND TRADEMARK OFFICE
CERTIFICATE OF CORRECTION

| | | |
|---|---|---|
| PATENT NO. | : 11,396,494 B2 | Page 1 of 1 |
| APPLICATION NO. | : 16/624554 | |
| DATED | : July 26, 2022 | |
| INVENTOR(S) | : Sang Duk Suh et al. | |

It is certified that error appears in the above-identified patent and that said Letters Patent is hereby corrected as shown below:

In the Claims

In Claim 14, at Column 179, at Lines 1-13, please replace Chemical Formula A-1 with Chemical Formula 1:

Chemical Formula 1

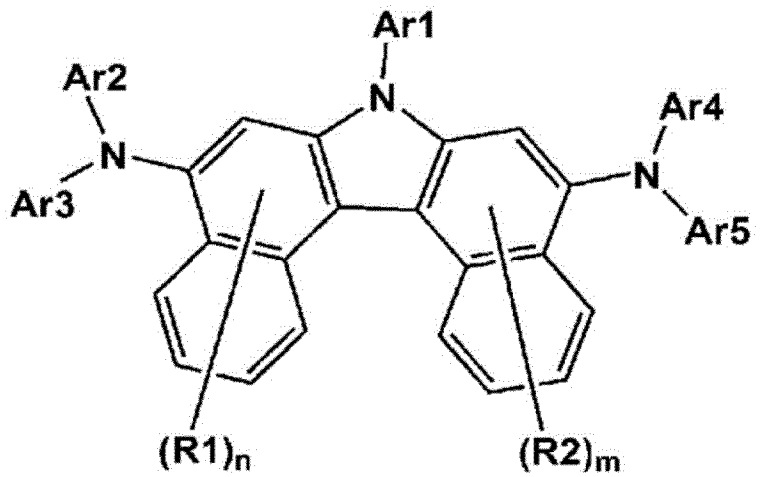

Signed and Sealed this
Thirtieth Day of August, 2022

Katherine Kelly Vidal
*Director of the United States Patent and Trademark Office*